US011453868B2

United States Patent
Svendsen et al.

(10) Patent No.: US 11,453,868 B2
(45) Date of Patent: *Sep. 27, 2022

(54) VARIANTS AND COMPOSITIONS COMPRISING VARIANTS WITH HIGH STABILITY IN PRESENCE OF A CHELATING AGENT

(71) Applicant: NOVOZYMES A/S, Bagsvaerd (DK)

(72) Inventors: Allan Svendsen, Hoersholm (DK); Annette Helle Johansen, Copenhagen Oe (DK); Mads Bjoernvad, Virum (DK); Frank W. Rasmussen, Roskilde (DK); Michael Skjoet, Roskilde (DK); Signe Eskildsen Larsen, Lyngby (DK); Jens Oebro, Copenhagen NV (DK); Svend Kaasgaard, Skovlunde (DK); Lars Beier, Lyngby (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/204,244

(22) Filed: Mar. 17, 2021

(65) Prior Publication Data

US 2021/0317431 A1  Oct. 14, 2021

Related U.S. Application Data

(63) Continuation of application No. 16/834,010, filed on Mar. 30, 2020, now abandoned, which is a continuation of application No. 16/362,955, filed on Mar. 25, 2019, now Pat. No. 10,655,116, which is a continuation of application No. 15/708,669, filed on Sep. 19, 2017, now Pat. No. 10,240,135, which is a continuation of application No. 13/024,770, filed on Feb. 10, 2011, now Pat. No. 9,896,673.

(60) Provisional application No. 61/303,345, filed on Feb. 11, 2010.

(30) Foreign Application Priority Data

Feb. 10, 2010 (EP) .................................. 10153180

(51) Int. Cl.
*C12N 9/28* (2006.01)

(52) U.S. Cl.
CPC .................................. *C12N 9/2417* (2013.01)

(58) Field of Classification Search
None
See application file for complete search history.

(56) References Cited

U.S. PATENT DOCUMENTS

| | | | |
|---|---|---|---|
| 6,093,562 A | 7/2000 | Bisgaard-Frantzen | |
| 6,197,565 B1 | 3/2001 | Svendsen | |
| 6,204,232 B1 | 3/2001 | Borchert | |
| 6,361,989 B1 | 3/2002 | Svendsen | |
| 6,410,295 B1 | 6/2002 | Andersen | |
| 8,343,907 B2 | 1/2013 | Bianchetti | |
| 9,896,673 B2 | 2/2018 | Svendsen | |
| 10,017,752 B2 * | 7/2018 | Andersen | C12P 19/14 |
| 10,030,239 B2 * | 7/2018 | Gjermansen | C12N 9/54 |
| 10,240,135 B2 | 3/2019 | Svendsen | |
| 10,655,116 B2 | 5/2020 | Svendsen | |
| 2013/0059315 A1 | 3/2013 | Svendsen | |
| 2020/0270593 A1 * | 8/2020 | Svendsen | C12N 9/2417 |
| 2021/0317431 A1 * | 10/2021 | Svendsen | C12N 9/2417 |

FOREIGN PATENT DOCUMENTS

| | | |
|---|---|---|
| WO | 95/26397 A1 | 10/1995 |
| WO | 96/23873 A1 | 8/1996 |
| WO | 99/23211 A1 | 5/1999 |
| WO | 00/60058 A2 | 10/2000 |
| WO | 00/60060 A2 | 10/2000 |
| WO | 2000/060058 A2 | 10/2000 |
| WO | 01/88107 A2 | 11/2001 |
| WO | 02/10355 A2 | 2/2002 |
| WO | 02/092797 A2 | 11/2002 |
| WO | 2006/002643 A2 | 12/2006 |
| WO | 99/19467 A1 | 4/2009 |
| WO | 2009/061379 A2 | 5/2009 |
| WO | 2011/100410 A2 | 8/2011 |

OTHER PUBLICATIONS

Declerck et al, 2000, J Mol Biol 301, 1041-1057.
EBI Access No. ABB76644 (2002).
Tsukamoto et al, 1988, Biochem Biophys Res Comm 151(1), 25-31.
Anonymous, PCT/DK2005/000469 (Published Dec. 27, 2005).

* cited by examiner

*Primary Examiner* — Hope A Robinson
(74) *Attorney, Agent, or Firm* — Yoshimi Barron

(57) ABSTRACT

The present invention relates to variants of an alpha-amylase having improved stability to chelating agents relative to its parent enzyme, compositions comprising the variants, nucleic acids encoding the variants, methods of producing the variants, and methods for using the variants.

23 Claims, No Drawings

Specification includes a Sequence Listing.

US 11,453,868 B2

VARIANTS AND COMPOSITIONS COMPRISING VARIANTS WITH HIGH STABILITY IN PRESENCE OF A CHELATING AGENT

CROSS-REFERENCE TO RELATED APPLICATIONS

This application is a continuation of U.S. application Ser. No. 16/834,010, which is a continuation of U.S. application Ser. No. 16/362,955 filed Mar. 25, 2019, now U.S. Pat. No. 10,655,116, which is a continuation of U.S. application Ser. No. 15/708,669 Sep. 19, 2017, U.S. Pat. No. 10,240,135, which claims priority or the benefit under 35 U.S.C. 1120 of U.S. application Ser. No. 13/024,770 filed Feb. 10, 2011, now U.S. Pat. No. 9,896,673, which claims priority or the benefit under 35 U.S.C. 119 of European application no. 10153180.4 filed Feb. 10, 2010 and U.S. provisional application No. 61/303,345 filed Feb. 11, 2010, the contents of which are fully incorporated herein by reference.

REFERENCE TO A SEQUENCE LISTING

This application contains a Sequence Listing in computer readable form. The computer readable form is incorporated herein by reference.

FIELD OF THE INVENTION

The present invention relates to variants of an alpha-amylase having improved stability to chelating agents relative to its parent enzyme, compositions comprising the variants, nucleic acids encoding the variants, methods of producing the variants, and methods for using the variants.

BACKGROUND OF THE INVENTION

Alpha-amylases (alpha-1,4-glucan-4-glucanohydrolases, E.C. 3.2.1.1) constitute a group of enzymes, which catalyses hydrolysis of starch and other linear and branched 1,4-gluosidic oligo- and polysaccharides.

There is a long history of industrial application of alpha-amylases in e.g. detergent, baking, brewing, starch liquefaction and saccharification such as in preparation of high fructose syrups or as part of ethanol production from starch. Many of these and other applications of alpha-amylases utilize alpha-amylases derived from microorganisms, in particular bacterial alpha-amylases.

Among the first bacterial alpha-amylases to be used were an alpha-amylase from *B. licheniformis*, also known as Termamyl, which has been extensively characterized and the crystal structure has been determined for this enzyme. Alkaline amylases, such as the alpha-amylase derived from *Bacillus* sp. as disclosed in WO 95/26397, form a particular group of alpha-amylases that have found use in detergents. Many of these known bacterial amylases have been modified in order to improve their functionality in a particular application.

Termamyl and many highly efficient alpha-amylases required calcium for activity. The crystal structure for Termamyl was found that four calcium atoms were bound in the alpha-amylase structure coordinated by negatively charged amino acid residues. In other alpha-amylases the amount of calcium ions bound in the structure might be different. This requirement for calcium is a disadvantage in applications where strong chelating compounds are present, such as in detergents or during ethanol production from whole grains.

As mentioned above it is well known that a number of enzymes are dependent on calcium or other metal ions such as magnesium or zinc for both activity and stability, hence it is a challenge to develop enzymes which are both stable and show good performance in compositions comprising a chelating agent, e.g. detergents containing chelating agents or compositions for use in the production of biofuel wherein the plant material or the starch-containing material has a natural content of chelating agents such as e.g. phytic acid. Chelating agents are e.g. added or incorporated to reduce the water hardness during wash, protect bleaching agents that may also be present, and chelating agents also have a direct effect on the removal of some stains. The stability of a calcium dependent enzyme in a detergent can sometimes be improved by addition of calcium to the detergent, but often this will then destroy the stain removing effect. Furthermore, addition of calcium to a liquid detergent may present problems with the formulation, i.e. the physical stability of the detergent.

SUMMARY OF THE INVENTION

It would therefore be beneficial to provide compositions and variants of alpha-amylases which are stable towards chelating agents and which preferably have retained or increased wash performance compared to the parent alpha-amylase.

Thus a first aspect of the invention relates to a composition comprising a variant of a parent alpha-amylase, wherein the variant comprises a substitution at one or more positions selected from the group consisting of 195, 193, 197, 198, 200, 203, 206, 210, 212, 213 and 243, using the numbering according to SEQ ID NO: 6, and further comprising at least one chelating agent wherein said chelating agent at a concentration below 10 mM is capable of reducing the concentration of free calcium ions from 2.0 mM to 0.10 mM when measured at 21° C. and pH 8.0.

Another aspect relates to a composition comprising a variant of a parent alpha-amylase, wherein the variant comprises a substitution at one or more positions selected from the group comprising 195, 193, 197, 198, 200, 203, 206, 210, 212, 213 and 243, using the numbering according to SEQ ID NO:6, and further comprising at least one chelating agent wherein said chelating agent is capable of reducing the free calcium ion concentration from 2.0 mM to 0.10 mM at a chelating agent concentration less than 0.9 times the concentration of citrate capable of reducing the free calcium ion concentration from 2.0 mM to 0.10 mM, when measured at 21° C. and pH 8.0.

The invention further relates to a method for preparing a polypeptide comprising:
  (a) providing an amino acid sequence of a parent polypeptide having amylase activity;
  (b) selecting one or more amino acids occupying one or more positions corresponding to positions 195, 197, 198, 200, 203, 206, 210, 212, 213, 243 and further selecting one or more position corresponding to positions 116, 118, 129, 133, 142, 146, 147, 149, 151, 152, 169, 174, 186, 235, 244, 303, 320, 339, 359, 418, 431, 434, 447, 458 of the mature polypeptide of SEQ ID NO:6;
  (c) modifying the sequence by substituting or deleting the selected amino acid residue or inserting one or more amino acid residues adjacent to the selected amino acid residue;
  (d) producing a variant polypeptide having the modified sequence;

(e) testing the variant polypeptide for amylase activity and stability; and (f) selecting a variant polypeptide having amylase activity and increased stability relative to the parent polypeptide in the presence of a chelating agent wherein said chelating agent at a concentration below 10 mM is capable of reducing the concentration of free calcium ions from 2.0 mM to 0.10 mM at 21° C. and pH 8.0.

In a preferred aspect the invention relates to a variant of a parent alpha-amylase comprising an alteration at one or more positions corresponding to positions selected from the group consisting of 195, 197, 198, 200, 203, 206, 210, 212, 213 and 243 and further comprising an alteration at one or more positions corresponding to positions selected from the group consisting of 116, 118, 129, 133, 142, 146, 147, 149, 151, 152, 169, 174, 186, 235, 244, 303, 320, 339, 359, 418, 431, 434, 447 and 458 wherein (a) the alteration(s) are independently
  (i) an insertion of an amino acid immediately downstream and adjacent of the position,
  (ii) a deletion of the amino acid which occupies the position, and/or
  (iii) a substitution of the amino acid which occupies the position,
(b) the variant has alpha-amylase activity; and
(c) each position corresponds to a position of the amino acid sequence of the enzyme having the amino acid sequence of SEQ ID NO: 6.

In another aspect the invention relates to a variant of a parent alpha-amylase comprising at least one, at least two, or at least three deletions in amino acid region of 181, 182, 183, or 184 and further comprising an alteration at one or more positions selected from the group consisting of 195, 197, 198, 200, 203, 206, 210, 212, 213 and 243 and further comprising an alteration at one or more positions selected from the group consisting of 116, 118, 129, 133, 142, 146, 147, 149, 151, 152, 169, 174, 186, 235, 244, 303, 320, 339, 359, 418, 431, 434, 447 and 458 wherein (a) the alteration(s) are independently
  (i) an insertion of an amino acid immediately downstream and adjacent of the position,
  (ii) a deletion of the amino acid which occupies the position, and/or
  (iii) a substitution of the amino acid which occupies the position,
(b) the variant has alpha-amylase activity; and
(c) each position corresponds to a position of the amino acid sequence of the enzyme having the amino acid sequence of SEQ ID NO: 6.

The invention further relates to an isolated nucleotide sequence encoding the variant of the invention and recombinant host cell comprising the nucleotide sequence encoding the variants according to the invention.

DETAILED DESCRIPTION OF THE INVENTION

Definitions

Alpha-Amylases (alpha-1,4-glucan-4-glucanohydrolases, E.C. 3.2.1.1) constitute a group of enzymes, which catalyze hydrolysis of starch and other linear and branched 1,4-glucosidic oligo- and polysaccharides. Alpha-amylases are known derived from a wide selection of organisms including Bacteria, such as from species of the genus *Bacillus* e.g. *Bacillus licheniformis*; from species of fungi, such as *Aspergillus oryzae* (TAKA-amylase) or *Aspergillus niger*; from plants such as barley and from mammals.

Wild-Type Enzyme: The term "wild-type" alpha-amylase denotes an alpha-amylase expressed by a naturally occurring microorganism, such as a bacterium, yeast or filamentous fungus found in nature. The terms "wild-type enzyme" and "parent enzyme" can be used interchangeably when the parent enzyme is not a variant enzyme.

Variant Enzyme: The term "variant" is defined herein as a polypeptide having alpha-amylase activity comprising an alteration, such as a substitution, insertion, and/or deletion, of one or more (or one or several) amino acid residues at one or more (or one or several) specific positions of the parent or wild type alpha-amylase. Preferably less than 50 modifications, more preferred less than 30 modifications. The altered alpha-amylase is obtained through human intervention by modification of the parent alpha-amylase.

Parent Enzyme: The term "parent" alpha-amylase as used herein means an alpha-amylase to which modifications are made to produce the variant alpha-amylases of the present invention. This term also refers to the polypeptide with which a variant of the invention is compared. The parent may be a naturally occurring (wild type) polypeptide, or it may even be a variant thereof, prepared by any suitable means. For instance, the parent protein may be a variant of a naturally occurring polypeptide which has been modified or altered in the amino acid sequence. Thus the parent alpha-amylase may have one or more (or one or several) amino acid substitutions, deletions and/or insertions. Thus the parent alpha-amylase may be a variant of a parent alpha-amylase. A parent may also be an allelic variant which is a polypeptide encoded by any of two or more alternative forms of a gene occupying the same chromosomal locus.

Improved property: The term "improved property" is defined herein as a characteristic associated with a variant that is improved compared to the parent alpha-amylase. Such improved properties include, but are not limited to, increased amylolytic activity e.g. when measured in EnzChek assay or the PNP-G7 assay as described in Examples section herein, increased wash performance such as soil performance e.g. performance to starch containing soils, stain removal, anti-greying, stability e.g. thermostability, pH stability, or stability in the presence of builders, incl. chelants, stability in powder, liquid or gel detergent formulations or dishwashing compositions, altered temperature-dependent performance and activity profile, pH activity, substrate specificity, product specificity, and chemical stability. Wash performance and/or dish wash performance may be measured as described below under "Materials and Methods" in the present application. Preferably the variants of the invention include a combination of improved properties such as improved stability, improved wash performance, improved dish wash performance and/or improved activity in detergent. Improved stability includes both stability during storage in a concentrated detergent product and stability in the diluted detergent during wash. The improved property includes improved wash or dish wash performance at low temperature.

Activity: In the present context the term "activity" is the amylolytic activity measured by the number of 1,4-alpha-D-glycosidic linkages hydrolysed in polysaccharides containing three or more 1,4-alpha-linked D-glucose units as e.g. in starch per unit of time and per unit of enzyme protein at specified conditions, e.g. the activity obtained at specified conditions per mL of an enzyme sample of g of an enzyme protein. The activity can be measured in e.g. EnzChek assay or a PNP-G7 assay as described below under "Material and Methods". In the present application the term "activity" is used interchangeably with "amylolytic activity". The term "specific activity" is often used to describe the maximal activity obtained per mL (or g) of an enzyme protein.

Improved chemical stability: The term "improved chemical stability" is defined herein as a variant enzyme displaying retention of enzymatic activity after a period of incubation in the presence of a chemical or chemicals, either naturally occurring or synthetic, which reduces the enzymatic activity of the parent enzyme. Improved chemical stability may also result in variants better able to catalyze a reaction in the presence of such chemicals. In a particular aspect of the invention the improved chemical stability is an improved stability in a detergent, in particular in a liquid detergent. The improved detergent stability is in particular an improved stability of the alpha-amylase activity when an alpha-amylase variant of the present invention is mixed into a liquid detergent formulation comprising a chelating agent, the liquid also includes gels or a paste. The liquid detergent formulation may refer to concentrated detergent which is added during a laundry or automated dish wash process or a dilute detergent such as a wash solution, i.e. an aqueous solution to which the concentrated detergent is added.

In the present invention liquid detergents are particular useful as liquid laundry detergents.

Stability: The term "stability" includes storage stability and stability during use, e.g. during a wash process or another industrial process, and reflects the stability of the amylase as a function of time e.g. how much activity is retained when the amylase is kept in solution in particular in a detergent solution. For example, the alpha-amylase variant may have a residual activity, i.e. how much activity is retained, above 70% after 18 hours at 31° C. The stability is influenced by many factors e.g. pH, temperature, detergent composition e.g. amount and type of builder, surfactants etc. The amylase stability is measured using either the EnzCheck assay or the PNP-G7 assay described in under "Materials and Methods".

Improved stability: The term "improved stability" is defined herein as a variant enzyme displaying an increased stability which is higher than the stability of the parent alpha-amylase, e.g. by having a residual activity above 70% or having at least 10 pp improvement in residual activity relative to parent after 18 hours at pH 8 in the presence of 1.5% (w/v) DTPA at 31° C. when measured in the EnzCheck assay as described under "Materials and Methods". The percentage point (pp) improvement in residual activity of the variant relative to the parent is calculated as the difference between the residual activity of the variant and that of the parent as described under "Materials and Methods".

Builder: Builders may be classified by the test described by M. K. Nagarajan et al., JAOCS, Vol. 61, no. 9 (September 1984), pp. 1475-1478 to determine the minimum builder level required to lower the water hardness at pH 8 from 2.0 mM (as $CaCO_3$) to 0.10 mM in a solution. The builder may particularly be chelating agent that forms water-soluble complexes with e.g. calcium and magnesium ions.

Chelating agents or chelators are chemicals which form molecules with certain metal ions, inactivating the ions so that they cannot react with other elements thus a binding agent that sup-presses chemical activity by forming chelates. Chelation is the formation or presence of two or more separate bindings between a ligand and a single central atom. The ligand may be any organic compound, a silicate or a phosphate. In the present context the term "chelating agents" comprises chelants, chelating agent, chelating agents, complexing agents, or sequestering agents that forms water-soluble complexes with metal ions such as calcium and magnesium. The chelate effect describes the enhanced affinity of chelating ligands for a metal ion compared to the affinity of a collection of similar nonchelating ligands for the same metal. Chelating agents having binding capacity with metal ions, in particular calcium ($Ca^{2+}$) ions, and has been used widely in detergents and compositions in general for wash, such as laundry or dish wash. Chelating agents have however shown themselves to inhibit enzymatic activity. The term chelating agent is used in the present application interchangeably with "complexing agent" or "chelating agent" or "chelant".

Since most alpha-amylases are calcium sensitive the presence of chelating agents these may impair the enzyme activity. The calcium sensitivity of alpha-amylases can be determined by incubating a given alpha-amylase in the presence of a strong chelating agent and analyze the impact of this incubation on the activity of the alpha-amylase in question. A calcium sensitive alpha-amylase will lose a major part or all of its activity during the incubation.

Characterizing chelating agents: As mentioned the chelate effect or the chelating effect describes the enhanced affinity of chelating ligands for a metal ion compared to the affinity of a collection of similar nonchelating ligands for the same metal. However, the strength of this chelate effect can be determined by various types of assays or measure methods thereby differentiating or ranking the chelating agents according to their chelating effect (or strength).

In a preferred assay the chelating agents may be characterized by their ability to reduce the concentration of free calcium ions ($Ca^{2+}$) from 2.0 mM to 0.10 mM or less at pH 8.0, e.g. by using a test based on the method described by M. K. Nagarajan et al., JAOCS, Vol. 61, no. 9 (September 1984), pp. 1475-1478. An example of characterization of chelating agents using the Nagarajan et. al. based method is described in example 2a. Preferably, a the chelating agent according to the invention encompass chelating agents able to reduce the concentration of free calcium ions from 2.0 mM to 0.1 mM or less at a concentration below 10 mM, preferably below 9.5 mM, preferably below 9 mM, preferably below 8.5 mM, preferably below 8 mM, preferably below 7.5 mM, preferably below 7 mM, preferably below 6.5 mM, preferably below 6 mM, preferably below 5.5 mM, preferably, preferably below 5 mM, preferably below 4.5 mM, below 4 mM, preferably below 3.5 mM, preferably below 3 mM, preferably below 2.5 mM, preferably below 2 mM, preferably below 1.5 mM or preferably below 1 mM, when measured in pH 8.0 at 21° C.

Preferably, the chelating agent according to the invention encompasses chelating agents able to reduce the concentration of free calcium ions from 2.0 mM to 0.1 mM at a concentration below 10 mM, preferably below 9.5 mM, preferably below 9 mM, preferably below 8.5 mM, preferably below 8 mM, preferably below 7.5 mM, preferably below 7 mM, preferably below 6.5 mM, preferably below 6 mM, preferably below 5.5 mM, preferably, preferably below 5 mM, preferably below 4.5 mM, below 4 mM, preferably below 3.5 mM, preferably below 3 mM, preferably below 2.5 mM, preferably below 2 mM, preferably below 1.5 mM or preferably below 1 mM, when measured in 80 mM potassium chloride and 49 mM EPPS ((4-(2-hydroxyethyl)piperazine-1-propanesulfonic acid)), at pH 8 at 21° C. In a particular preferred embodiment the chelating agent is able to reduce the concentration of free calcium ions from 2.0 mM to 0.1 mM when measured in 80 mM potassium chloride and 49 mM EPPS, at pH 8 and 21° C. and using a calcium ion selective electrode for the determination of the free calcium concentration, as described under "Materials and Methods". Thus preferably, the chelating agents encompass chelating agents which are able to reduce the concentration of free calcium ions from 2.0 mM to 0.10 mM at a concentration below 10 mM, preferably below 9.5 mM, preferably below 9.0 mM, preferably below 8.5 mM, preferably below 8.0 mM, preferably below 7.5 mM, preferably below 7.0 mM, preferably below 6.5 mM, preferably below 6.0 mM, preferably below 5.5 mM, preferably, preferably below 5.0 mM, preferably below 4.5 mM, below 4.0 mM, preferably below 3.5 mM, preferably below 3.0 mM, preferably below 2.5 mM, preferably below 2.0 mM, preferably below 1.5 mM or preferably below 1.0 mM when tested at pH 8.0 and 21° C., as described under "Materials and Methods".

In a particularly preferred embodiment the chelating agents is able to reduce the concentration of free calcium ions from 2.0 mM to 0.10 mM when measured in 80 mM potassium chloride and 49 mM EPPS at pH 8 and 21° C. at a concentration of 9 mM to 0.5 mM, preferably 9 mM to 1 mM, preferably 8 mM to 1 mM, preferably 7 mM to 1 mM, preferably 6 mM to 1 mM, preferably 5 mM to 1 mM, preferably 4 mM to 1 mM, preferably 3 mM to 1 mM, preferably 2 mM to 1 mM, preferably 9.0 mM to 1.5 mM, preferably 8.0 mM to 1.5 mM, preferably 7.0 mM to 1.5 mM, preferably 6.0 mM to 1.5 mM, preferably 5.0 mM to 1.5 mM, preferably 4.0 mM to 1.5 mM, preferably 3.0 to 1.5 mM, preferably 2.5 mM to 1.0 mM, preferably 2.0 mM to 1.1 mM, preferably 1.85 mM to 1.0 mM.

The reduction in free calcium ion concentration from 2.0 mM $Ca^{2+}$ to 0.10 mM, corresponds to reducing the water hardness from 200 ppm (as $CaCO_3$, in the form of $Ca(HCO_3)_2$ in the presence of acidic $CO_2$) to 10 ppm. The minimum builder level is calculated from the sodium salt of the chelant and on a 100% dry chelant basis.

The chelating effect of the chelating agent can also be measured relative to citrate. The concentration of the citrate able to reduce the amount of free calcium ion concentration from 2.0 mM to 0.10 mM is assigned the value of 1 and the results of the chelating agents are compared to this value. The preferred chelating agent according to the invention is capable of reducing the free calcium concentration from 2.0 mM to 0.10 mM at a concentration below 0.9, such as below 0.8, such as below 0.7, such as below 0.6, such as below 0.5, such as below 0.4, such as below 0.3, such as below 0.2, such as below 0.1 times lower compared to the concentration of citrate, when measured at pH 8.0 and 21° C. The preferred chelating agent according to the invention is capable of reducing the free calcium concentration from 2.0 mM to 0.10 mM at a concentration below 0.9, such as below 0.8, such as below 0.7, such as below 0.6, such as below 0.5, such as below 0.4, such as below 0.3, such as below 0.2, such as below 0.1 times lower compared to the concentration of citrate, when measured in pH 8.0 at 21° C. using a calcium ion selective electrode for the determination of the free calcium concentration when measured in 80 mM potassium chloride and 49 mM EPPS at 21° C. and pH 8.0.

In a particularly preferred embodiment the chelating agent is able to reduce the concentration of free calcium ions from 2.0 mM to 0.10 mM at a chelating agent concentration below 1.0 to 0.1, such as below 0.9 to 0.1, such as below 0.8 to 0.1, such as below 0.7 to 0.1, such as below 0.6 to 0.1, such as below 0.5 to 0.1, such as below 0.4 to 0.1, such as below 0.35 to 0.1, such as below 0.3 to 0.1 times lower compared to the concentration of citrate able to reduce the concentration of free calcium ions from 2.0 mM to 0.10 mM, when measured at pH 8.0 and 21° C.

Thus a preferred embodiment of the invention concerns a composition comprising a variant of a parent alpha-amylase wherein the variant comprise a substitution at one or more positions in the range 193 to 213, using the numbering according to SEQ ID NO: 6, and further comprising at least one chelating agent wherein said chelating agent is capable of reducing the free calcium ion concentration from 2.0 mM to 0.10 mM at a chelating agent concentration less than 0.9 times the concentration of citrate capable of reducing the free calcium ion concentration from 2.0 mM to 0.10 mM, when measured at 21° C. and pH 8.

A further embodiment of the invention relates to a composition comprising a variant of a parent alpha-amylase wherein the variant alpha-amylase comprises a substitution at one or more positions selected from the group consisting of 193, 195, 197, 198, 200, 203, 206, 210, 212 and 213, using the numbering according to SEQ ID NO: 6, and further comprising at least one chelating agent wherein said chelating agent at a concentration below 10 mM is capable of reducing the concentration of free calcium ions from 2.0 mM to 0.10 mM when measured at 21° C. and pH 8.0.

A further embodiment of the invention relates to a composition comprising a variant of a parent alpha-amylase wherein the variant alpha-amylase comprises a substitution at one or more positions selected from the group consisting of 193, 195, 197, 198, 200, 203, 206, 210, 212 and 213, using the numbering according to SEQ ID NO: 6, and further comprising at least one chelating agent wherein said chelating agent at a concentration below 10 mM is capable of reducing the concentration of free calcium ions from 2.0 mM to 0.10 mM when measured at 21° C. and pH 8.0, and optionally a cleaning adjunct.

A further embodiment of the invention relates to a composition comprising a variant of a parent alpha-amylase wherein the variant alpha-amylase comprises an amino acid sequence which is at least 70% identical to SEQ ID NO: 6 and further comprises a substitution at one or more positions selected from the group consisting of 193, 195, 197, 198, 200, 203, 206, 210, 212 and 213, using the numbering according to SEQ ID NO: 6, and further comprising at least one chelating agent wherein said chelating agent at a concentration below 10 mM is capable of reducing the concentration of free calcium ions from 2.0 mM to 0.10 mM when measured at 21° C. and pH 8.0.

Thus the chelating agent according to the invention is able to reduce the free calcium ion concentration from 2.0 mM to 0.10 mM at a concentration lower than the concentration of citrate necessary to reduce the free calcium ion concentration from 2.0 mM to 0.10 mM at the same conditions.

Alternatively the strength of the complex formed between the chelating agent and metal ions such as calcium and/or magnesium, is expressed as the log K value (equilibrium or binding or dissociating or stability constant). This constant may be measured at a given pH, at a given temperature and at a given ionic strength.

As mentioned above the strength of the complex formed between the chelating agent and the metal ions e.g. calcium and/or magnesium may be expressed as the log K value (equilibrium or binding or dissociating or stability constant), the constant may be measured by isothermal titration calorimetry (ITC) as described in A. Nielsen et al., Anal. Biochem. Vol. 314, (2003), pp 227-234 and from the K value, the log K can be calculated as the logarithm of the K value (base 10). The log K value measured by this method will depend on the temperature, pH, ion strength, so it is important when comparing log K values, that they are determined at similar, preferably the same, conditions. Furthermore, by introducing a standard as reference, such as citrate, impacts from variations in the experiments can be reduced. Preferably log K is determined as described under "Materials and Methods" of the present application thus in one embodiment of the invention the chelating agent in the composition according to the invention has a log K of at least 3, such as at least 4, such as at least 5, such as at least 6, such as at least 7, such as at least 8, such as at least 9, such as at least 10, such as at least 11, when the log K is measured at pH 10 and 19° C. as described under "Materials and Methods". The log K value of the chelating agent in the compositions according to the invention may also be in the range 3-11, such as 3-10, such as 3-9, such as 3-8, such as 4-11, such as 5-11 such as 6-11, such as 4-10, such as 5-10, such as 4-9, such as 5-9, such as 4-8, in particularly 5-8. Preferably, the log K of the chelating agent in the composition according to the invention is a factor of at least 1, such as at least 1.33, such as at least 1.67, such as at least 2, such as at least 2.33, such as at least 2.67, such as at least 3, such as at least 3.33, such as at least 3.67 times the log K of citrate determined as described under "Materials and Methods". The chelating agent in the compositions according to the invention may also be in the range of a factor 1-3.67, such as 1-3.33, such as 1-3.00, such as 1-2.67, such as 1.33-3.67, such as 1.33-3.33, such as 1.33-3.00, such as 1.33-2.67, such as 1.67-3.67, such as 1.67-3.33, such as 1.67-3, in particular 1.67-2.67 times the log K of citrate determined as described under "Materials and Methods".

Useful chelating agents may be, but are not limited to, the following: N-(1,2-dicarboxy-ethyl)-D,L-aspartic acid (IDS), N-(2-hydroxyethyl)iminodiacetic acid (EDG), aspartic acid-N-monoacetic acid (ASMA), aspartic acid-N,N-diacetic acid (ASDA), aspartic acid-N— monopropionic acid (ASMP), iminodisuccinic acid (IDA), N— (2-sulfomethyl) aspartic acid (SMAS), N-(2-sulfoethyl) aspartic acid (SEAS), N-(2-sulfomethyl) glutamic acid (SMGL), N-(2-sulfoethyl) glutamic acid (SEGL), N-methyliminodiacetic acid (MIDA), α-alanine-N,N-di-acetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N, N-diacetic acid (TUDA), sulfomethyl-N,N-diacetic acid (SM DA), N-(hydroxyethyl)-ethylidenediaminetriacetate (HEDTA), diethanolglycine (DEG), aminotris(methylenephosphonic acid) (ATMP).

The preferred chelating agent may contain an amino group and may be, e.g., an amino-polycarboxylate or a phosphonate. It may be a monomeric molecule comprising one, two or three amino groups (typically secondary or tertiary amino groups), and it may contain two, three, four or five carboxyl groups or even more carboxyl groups. The chelating agents may be phosphorus containing or without phosphor. There are many ways of grouping chelating agents one way might be as follows:

Chelating agents may be carboxylates or be based on carboxylate groups like EDTA (ethylene diamine tetraacetate), NTA (2,2',2"-nitrilotriacetate), citrate, 2-hydroxypropan-1,2,3-tricarboxylate, DTPA (diethylenetriaminepentaacetic acid), MGDA (methylglycinediacetic acid or N,N'-bis(carboxymethyl)alanine), EGTA (ethylene glycol tetraacetic acid), EDDS (ethylenediamine-N,N'-disuccinic acid), GLDA (L-Glutamic acid, N,N-diacetic acid), Poly-carboxylates such as PAA [poly(acrylic acid)], PAA/PMA [copoly(acrylic acid/maleic acid)].

Chelating agents containing phosphorous may be polyphosphates or phosphonates, such as Sodium tripolyphosphate (STP), HEDP (1-Hydroxyethylidene-1,1-Diphosphonic Acid), EDTMP [bis(phosphonomethyl)amino] methylphosphonic acid] or (ethylenediamine tetra(methylene phosphonic acid)), EDTMPA (ethylenediaminetetramethylenetetraphosphonic acid), DTPMP (diethylenetriamine penta (methylene phosphonic acid), DTMPA (diethylenetriaminepenta(methylenehosphonic acid)). The chelating agents may contain nitrogen such as in EDTA, NTA, DTPA, PDTA, GLDA, MGDA, EDDS, EDTMP, EDTMPA, and DTPMP or ASMA, ASDA, ASMP, IDA, SMAS, SEAS, SMGL, SEGL, MIDA, α-ALDA, SEDA, ISDA, PHDA, ANDA, SLDA, TUDA, SMDA, HEDTA, DEG, ATMP, or mixtures thereof.

Thus, the preferred chelating agents may be but are not limited to the following: ethylene-diamine-tetra-acetic acid (EDTA), diethylene triamine penta methylene phosphonic acid (DTMPA, DTPMP), hydroxy-ethane diphosphonic acid (HEDP), ethylenediamine N,N'-disuccinic acid (EDDS), methyl glycine di-acetic acid (MGDA), diethylene triamine penta acetic acid (DTPA), propylene diamine tetraacetic acid (PDTA), 2-hydroxypyridine-N-oxide (HPNO), methyl glycine diacetic acid (MGDA), glutamic acid N,N-diacetic acid (N,N-dicarboxymethyl glutamic acid tetrasodium salt (GLDA) and nitrilotriacetic acid (NTA) or mixtures thereof. The chelating agents may be present in their acid form or a salt, preferably the chelating agents may be present as a sodium, ammonium or potassium salt.

Further chelating agents may be chelating agents which originate from plant material, such as e.g. starch-containing material as described in detail below. Examples of such natural chelating agents are, but are not limited to, phytic acid (also known as Inositol hexaphosphoric acid (IP6), or phytin, or phytate when in salt for), Inositol diphosphoric acid, Inositol triphosphoric or Inositol pentaphosphoric acid.

Chelating agent may be present in the composition in an amount from 0.0001 wt % to 20 wt %, preferably from 0.01 to 10 wt %, more preferably from 0.1 to 5 wt %.

Parent alpha-amylase: The parent alpha-amylase may in principle be any alpha-amylase for which it is desired to prepare a variant having improved stability during storage or in use, e.g. during wash or in a starch hydrolyzing process. The improved stability may thus be observed as a reduced loss of amylolytic activity during storage or as an increased activity and performance during use. Known alpha-amylases are derived from a wide selection of organisms including Bacteria, such as from species of the genus *Bacillus* e.g. *Bacillus licheniformis*; from species of fungi, such as *Aspergillus oryzae* (TAKA-amylase) or *Aspergillus niger*; from plants such as barley and from mammals. The parent alpha-amylase may in principle be any such alpha-amylase irrespective of the origin.

It is well known that a number of alpha-amylases produced by *Bacillus* spp. are highly identical on the amino acid level. Because of the substantial identity found between these alpha-amylases, they are considered to belong to the same class of alpha-amylases, namely the class of "Termamyl-like alpha-amylases".

Accordingly, in the present context, the term "Termamyl-like" alpha-amylase" is intended to indicate an alpha-amylase, in particular *Bacillus* alpha-amylase, which, at the amino acid level, exhibits a substantial identity i.e. at least 60% to the *B. licheniformis* alpha-amylase having the amino acid sequence shown in SEQ ID NO: 20 (Termamyl™), herein.

Termamyl-Like Alpha-Amylases

The identity of a number of known *Bacillus* alpha-amylases can be found in the below Table 1:

TABLE 1

| | SEQ ID NO | Percent identity | | | | | | |
|---|---|---|---|---|---|---|---|---|
| | | #707 | AP1378 | BAN | BSG | SP690 | SP722 | AA560 | Termamyl |
| #707 | 8 | 100.0 | 86.4 | 66.9 | 66.5 | 87.6 | 86.2 | 95.5 | 68.1 |
| AP1378 | 18 | 86.4 | 100.0 | 67.1 | 68.1 | 95.1 | 86.6 | 86.0 | 69.4 |
| BAN | 14 | 66.9 | 67.1 | 100.0 | 65.6 | 67.1 | 68.8 | 66.9 | 80.7 |
| BSG | 16 | 66.5 | 68.1 | 65.6 | 100.0 | 67.9 | 67.1 | 66.3 | 65.4 |
| SP690 | 12 | 87.6 | 95.1 | 67.1 | 67.9 | 100.0 | 87.2 | 87.0 | 69.2 |
| SP722 | 6 | 86.2 | 86.6 | 68.8 | 67.1 | 87.2 | 100.0 | 86.8 | 70.8 |
| AA560 | 10 | 95.5 | 86.0 | 66.9 | 66.3 | 87.0 | 86.8 | 100.0 | 68.3 |
| Termamyl | 20 | 68.1 | 69.4 | 80.7 | 65.4 | 69.2 | 70.8 | 68.3 | 100.0 |

For instance, the *B. licheniformis* alpha-amylase comprising the amino acid sequence shown in SEQ ID NO: 20 (commercially available as Termamyl™) has been found to be about 81% homologous with the *B. amyloliquefaciens* alpha-amylase comprising the amino acid sequence shown in SEQ ID NO: 14 (BAN) and about 65% homologous with the *B. stearothermophilus* alpha-amylase comprising the amino acid sequence shown in SEQ ID NO: 16 (BSG). Further homologous alpha-amylases include SP722 and SP690 disclosed in WO 95/26397 and further depicted in SEQ ID NO: 6 and SEQ ID NO: 12, respectively, herein. Other amylases are the AA560 alpha-amylase derived from *Bacillus* sp. and shown in SEQ ID NO: 10, and the SP707 or #707 alpha-amylase derived from *Bacillus* sp., shown in SEQ ID NO: 8 and described by Tsukamoto et al., Biochemical and Biophys-ical Research Communications, 151 (1988), pp. 25-31. Further homolog alpha-amylase is the KSM AP1378 alpha-amylase is disclosed in WO 97/00324 (from KAO Corporation) SEQ ID NO: 18. Yet another homolog alpha-amylase is the SP.7-7 alpha-amylase with SEQ ID NO: 22. Another suitable parent amylase is the K 38 SEQ ID NO: 2 or the *B. circulans* amylase with SEQ ID NO: 4 and SEQ ID NO: 24, described in WO2005/001064.

Still further interesting alpha-amylases include the alpha-amylase produced by the *B. licheniformis* strain described in EP 0252666 (ATCC 27811), and the alpha-amylases identified in WO 91/00353 and WO 94/18314. Other commercial Termamyl-like alpha-amylases are comprised in the products sold under the following tradenames: OPTITHERM™ and TAKATHERM™ (Solvay); MAXAMYL™ (available from Gist-brocades/Genencor), SPEZYM® AA and SPEZYME® DELTA AA (available from Genencor), and KEISTASE™ (available from Daiwa), Dex lo, GC 521 (available from Genencor) and Ultraphlow (from Enzyme Biosystems), PURASTAR™ ST 5000E, PURASTAR™ HPAM L, POWERASE®, Spezyme FRED, GC358, CLEARFLOW® AA(from Danisco), or the alpha-amylase TS-23 (SEQ ID NO: 26 (Lin et al, J.App.Microbiol. 1997, 82, 325-334).

The non-Termamyl-like alpha-amylase may, e.g., be a fungal alpha-amylase, a mammalian or a plant alpha-amylase or a bacterial alpha-amylase (different from a Termamyl-like alpha-amylase). Specific examples of such alpha-amylases include the *Aspergillus oryzae* TAKA alpha-amylase, the *A. niger* acid alpha-amylase, the *Bacillus subtilis* alpha-amylase, the porcine pancreatic alpha-amylase and a barley alpha-amylase. All of these alpha-amylases have elucidated structures, which are markedly different from the structure of a typical Termamyl-like alpha-amylase as referred to herein.

The fungal alpha-amylases mentioned above, i.e., derived from *A. niger* and *A. oryzae*, are highly identical on the amino acid level and generally considered to belong to the same family of alpha-amylases. The fungal alpha-amylase derived from *Aspergillus oryzae* is commercially available under the trade name Fungamyl™

Parent Hybrid Alpha-Amylases

The parent alpha-amylase may be a hybrid alpha-amylase, i.e., an alpha-amylase, which comprises a combination of partial amino acid sequences derived from at least two alpha-amylases.

The parent hybrid alpha-amylase may be one, which on the basis of amino acid homology and/or immunological cross-reactivity and/or DNA hybridization (as defined above) can be determined to belong to the Termamyl-like alpha-amylase family. In this case, the hybrid alpha-amylase is typically composed of at least one part of a Termamyl-like alpha-amylase and part(s) of one or more other alpha-amylases selected from Termamyl-like alpha-amylases or non-Termamyl-like alpha-amylases of microbial (bacterial or fungal) and/or mammalian origin.

Thus, the parent hybrid alpha-amylase may comprise a combination of partial amino acid sequences deriving from at least two Termamyl-like alpha-amylases, or from at least one Termamyl-like and at least one non-Termamyl-like bacterial alpha-amylase, or from at least one Termamyl-like and at least one fungal alpha-amylase. The Termamyl-like alpha-amylase from which a partial amino acid sequence derives may be any of those Termamyl-like, alpha-amylases referred to herein.

In one embodiment the parent Termamyl-like alpha-amylase is a hybrid Termamyl-like alpha-amylase identical to the *Bacillus licheniformis* alpha-amylase shown in SEQ ID NO: 20, except that the N-terminal 35 amino acid residues (of the mature protein) is replaced with the N-terminal 33 amino acid residues of the mature protein of the *Bacillus amyloliquefaciens* alpha-amylase shown in SEQ ID NO: 14 said hybrid may further have the following mutations: H156Y+A181T+N190F+A209V+Q264S (using the numbering in SEQ ID NO: 6) referred to as LE174. In another embodiment LE174 further comprising the mutations G48A, T49I, G107A, I201F, referred to as LE399. In one embodiment the parent is SEQ ID NO: 16 with the mutations I181*+G182*+N195F.

In a preferred aspect of the invention the parent alpha-amylase is an alpha-amylase, which has the amino acid sequence shown in SEQ ID NO: 2, 4, 6, 8, 10, 12, 14, 16, 18, 20, 22, 24 or 26 herein. In another preferred aspect the parent alpha-amylase is an alpha-amylase, which displays 60%, preferred at least 65%, preferred at least 70%, preferred at least 75% preferred at least 80%, preferred at least 81%, preferred at least 82%, preferred at least 83%, preferred at least 84% preferred at least 85%, preferred at least 86%, preferred at least 87%, preferred at least 88%, preferred at least 89%, especially preferred at least 90%, especially preferred at least 91%, especially preferred at least 92%, especially preferred at least 93%, especially preferred at least 94%, even especially more preferred at least 95% homology, more preferred at least 96%, more preferred at least 97%, more preferred at least 98%, more preferred at least 99% of the mature polypeptide of SEQ ID NO: 2, 4, 6, 8, 10, 12, 14, 16, 18, 20, 22, 24 or 26.

In one aspect, the parent alpha-amylases have an amino acid sequence that differs (e.g., deletion, insertion or substitution) by one or several amino acids, preferably ten amino acids, more preferably by nine, eight, seven, six, five amino acids, more preferably by four amino acids, even more preferably by three amino acids, most preferably by two amino acids, and even most preferably by one amino acid from the mature polypeptide of SEQ ID NO: 2, 4, 6, 8, 10, 12, 14, 16, 18, 20, 22, 24 or 26.

The parent alpha-amylase may be an alpha-amylase which displays immunological cross-reactivity with an antibody raised against an alpha-amylase having one of the amino acid sequences selected from the group consisting of SEQ ID NO: 2, 4, 6, 8, 10, 12, 14, 16, 18, 20, 22, 24 and 26. In a preferred embodiment, the parent alpha-amylase is one wherein the antibody raised against the parent alpha-amylase displays an affinity or avidity for an alpha-amylase having one of the amino acid sequences shown in SEQ ID NO: 2, 4, 6, 8, 10, 12, 14, 16, 18, 20, 22, 24 or 26 in a competitive assay technique such as e.g. ELISA or BiaCore, respectively, or that displays an affinity or avidity that is comparable to that of the parent alpha-amylase, and wherein the antibody raised against the alpha-amylase having one of the amino acid sequences shown in SEQ ID NO: 2, 4, 6, 8, 10, 12, 14, 16, 18, 20, 22, 24 or 26 displays in said competitive assay technique an affinity or avidity for the parent alpha-amylase that is comparable with the affinity or avidity for the alpha-amylase having one of the amino acid sequences shown in SEQ ID NO: 2, 4, 6, 8, 10, 12, 14, 16, 18, 20, 22, 24 or 26. In further embodiments, the parent alpha-amylase is one which has an affinity or avidity which is at least 70%, preferred at least 75% preferred at least 80%, preferred at least 85%, preferred at least 90%, preferred at least 95%, preferred at least 100%, preferred at least 110%, preferred at least 120%, especially preferred at least 125% of the affinity or avidity of the alpha-amylase having one of the amino acid sequences shown in SEQ ID NO: 2, 4, 6, 8, 10, 12, 14, 16, 18, 20, 22, 24 or 26.

The parent alpha-amylase may also be an alpha-amylase which is encoded by a DNA sequence which hybridizes to the DNA sequence encoding the above-specified alpha-amylases, which are apparent from SEQ ID NO: 1, 3, 5, 7, 9, 11, 13, 15, 17, 19, 21, 23 or 25 of the present application. Thus one embodiment concerns a variant alpha-amylase of a parent alpha-amylase, where the parent alpha-amylase is:

(A) derived from a strain of *B. licheniformis, B. amyloliquefaciens, B. stearothermophilus, Bacillus* sp. or KSM AP1378, (B) selected from the group having amino acid sequences as shown in SEQ ID NO: 2, 4, 6, 8, 10, 12, 14, 16, 18, 20, 22, 24 or 26, (C) having a sequence identity to one of SEQ ID NO: 2, 4, 6, 8, 10, 12, 14, 16, 18, 20, 22, 24 or 26 of at least 70%, preferably at least 80%, more preferably at least about 90%, even more preferably at least 95%, even more preferably at least 97%, and even more preferably at least 99%, or (D) encoded by a nucleic acid sequence, which hybridizes under low, preferably medium, preferred high stringency conditions, with the nucleic acid sequence of one of SEQ ID NO: 1, 3, 5, 7, 9, 11, 13, 15, 17, 19, 21, 23 or 25.

In one aspect, the parent polypeptide having amylolytic enhancing activity is (a) a polypeptide comprising an amino acid sequence having at least 60% identity with the mature polypeptide of SEQ ID NO: 2, 4, 6, 8, 10, 12, 14, 16, 18, 20, 22, 24 or 26; (b) a polypeptide encoded by a polynucleotide that hybridizes under at least low stringency conditions with (i) the mature polypeptide coding sequence of SEQ ID NO: 1, 3, 5, 7, 9, 11, 13, 15, 17, 19, 21, 23 or 25, (ii) the genomic DNA sequence comprising the mature polypeptide coding sequence of SEQ ID NO: 1, 3, 5, 7, 9, 11, 13, 15, 17, 19, 21, 23 or 25, or (iii) a full-length complementary strand of (i) or (ii); or (c) a polypeptide encoded by a polynucleotide comprising a nucleotide sequence having at least 60% identity with the mature polypeptide coding sequence of SEQ ID NO: 1, 3, 5, 7, 9, 11, 13, 15, 17, 19, 21, 23 or 25.

When a particular variant of a parent alpha-amylase is referred to—in a conventional manner—by reference to modification (e.g., deletion or substitution) of specific amino acid residues in the amino acid sequence of a specific alpha-amylase, it is to be understood that variants of another alpha-amylase modified in the equivalent position(s) (as determined from the best possible amino acid sequence alignment between the respective amino acid sequences) are encompassed thereby.

In a particular aspect of the invention the parent alpha-amylase is a variant of a naturally occurring (wild type), prepared by any suitable means. For instance, the parent alpha-amylase may be a variant of a naturally occurring alpha-amylase which has been modified or altered in the amino acid sequence.

The parent alpha-amylase may be a substantially homologous parent alpha-amylase which may have one or more (several) amino acid substitutions, deletions and/or insertions. These changes are preferably of a minor nature, that is conservative amino acid substitutions as described below and other substitutions that do not significantly affect the three-dimensional folding or activity of the protein or polypeptide; small deletions, typically of one to about 30 amino acids; and small amino- or carboxyl-terminal extensions, such as an amino-terminal methionine residue, a small linker peptide of up to about 20-25 residues, or a small extension that facilitates purification (an affinity tag), such as a polyhistidine tract, or protein A (Nilsson et al., 1985, EMBO J. 4: 1075; Nilsson et al., 1991, Methods Enzymol. 198: 3. See, also, in general, Ford et al., 1991, Protein Expression and Purification 2: 95-107.

Although the changes described above preferably are of a minor nature, such changes may also be of a substantive nature such as fusion of larger polypeptides of up to 300 amino acids or more both as amino- or carboxyl-terminal extensions.

When a particular variant of a parent alpha-amylase (variant of the invention) is referred to—in a conventional manner—by reference to modification (e.g., deletion or substitution) of specific amino acid residues in the amino acid sequence of a specific parent alpha-amylase, it is to be understood that variants of another parent alpha-amylase modified in the equivalent position(s) (as determined from the best possible amino acid sequence alignment between the respective amino acid sequences) are encompassed thereby.

Homology (Sequence Identity)

The homology may be determined as the degree of identity between the two sequences indicating a derivation of the first sequence from the second. For purposes of the present invention, the degree of sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the —nobrief option) is used as the percent identity and is calculated as follows:

(Identical Residues×100)/(Length of Alignment–
Total Number of Gaps in Alignment)

For purposes of the present invention, the degree of sequence identity between two de-oxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the —nobrief option) is used as the percent identity and is calculated as follows:

(Identical Deoxyribonucleotides×100)/(Length of
Alignment–Total Number of Gaps in Alignment).

The homology or sequence identity may also be determined as the degree of identity between the two sequences indicating a derivation of the first sequence from the second. The homology may suitably be determined by means of older computer programs known in the art such as GAP provided in the GCG program package. Thus, Gap GCGv8 may be used with the default scoring matrix for identity and the following default parameters: GAP creation penalty of 5.0 and GAP extension penalty of 0.3, respectively for nucleic acidic sequence comparison, and GAP creation penalty of 3.0 and GAP extension penalty of 0.1, respectively, for protein sequence comparison. GAP uses the method of Needleman and Wunsch, (1970), J. Mol. Biol. 48, p. 443-453, to make alignments and to calculate the identity.

A structural alignment between e.g. Termamyl and an alpha-amylase may be used to identify equivalent/corresponding positions in other alpha-amylases. One method of obtaining said structural alignment is to use the Pile Up programme from the GCG package using default values of gap pen-alties, i.e., a gap creation penalty of 3.0 and gap extension penalty of 0.1. Other structural alignment methods include the hydrophobic cluster analysis (Gaboriaud et al., (1987), FEBS LETTERS 224, pp. 149-155) and reverse threading (Huber, T; Torda, A E, PROTEIN SCIENCE Vol. 7, No. 1 pp. 142-149 (1998). Properties of the alpha-amylases, i.e., the immunological cross reactivity, may be assayed using an antibody raised against, or reactive with, at least one epitope of the relevant Ter-mamyl-like alpha-amylase. The antibody, which may either be monoclonal or polyclonal, may be produced by methods known in the art, e.g., as described by Hudson et al., Practical Immunology, Third edition (1989), Blackwell Scientific Publications. The immunological cross-reactivity may be determined using assays known in the art, examples of which are Western Blotting or radial immu-nodiffusion assay, e.g., as described by Hudson et al., 1989.

Hybridisation

In one aspect, the parent polypeptide having amylolytic activity is encoded by a polynucleotide that hybridizes under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, 3, 5, 7, 9, 11, 13, 15, 17, 19, 21, 23 or 25, (ii) the genomic DNA sequence comprising the mature polypeptide coding sequence of SEQ ID NO: 1, (iii) a subsequence of (i) or (ii), or (iv) a full-length complementary strand of (i), (ii), or (iii) (J. Sambrook, E.F. Fritsch, and T. Maniatis, 1989, *Molecular Cloning*, A Laboratory Manual, 2d edition, Cold Spring Harbor, N.Y.). The subsequence may encode a polypeptide fragment having amylolytic activity. In one aspect, the complementary strand is the full-length complementary strand of the mature polypeptide coding sequence of SEQ ID NO: 1, 3, 5, 7, 9, 11, 13, 15, 17, 19, 21, 23 or 25.

An oligonucleotide probe used in the characterization of the alpha-amylase in accordance with the desired property which may be alpha-amylase activity may suitably be prepared on the basis of the full or partial nucleotide or amino acid sequence of the alpha-amylase in question.

Suitable conditions for testing hybridization involve pre-soaking in 5×SSC (standard sodium citrate, 1×SSC corresponds to 0.1650 M NaCl) and prehybridizing for 1 hour at ~40° C. in a solution of 20% formamide, 5×Denhardt's solution, 50 mM sodium phosphate, pH 6.8, and 50 mg of denatured sonicated calf thymus DNA, followed by hybridization in the same solution supplemented with 100 mM ATP (adenosine triphosphate) for 18 hours at ~40° C., followed by three times washing of the filter in 2×SSC, 0.2% SDS (sodium dodecylsulfate) at 40° C. for 30 minutes (low stringency), preferred at 50° C. (medium stringency), more preferably at 65° C. (high stringency), even more preferably at ~75° C. (very high stringency). More details about the hybridization method can be found in Sambrook et al., Molecular_Cloning: A Laboratory Manual, 2nd Ed., Cold Spring Harbor, 1989.

In the present context, "derived from" is intended not only to indicate an alpha-amylase produced or producible by a strain of the organism in question, but also an alpha-amylase encoded by a DNA sequence isolated from such strain and produced in a host organism transformed with said DNA sequence. Finally, the term is intended to indicate an alpha-amylase, which is encoded by a DNA sequence of synthetic and/or cDNA origin and which has the identifying characteristics of the alpha-amylase in question. The term is also intended to indicate that the parent alpha-amylase may be a variant of a naturally occurring alpha-amylase, i.e. a variant, which is the result of a modification (insertion, substitution, deletion) of one or more amino acid residues of the naturally occurring alpha-amylase.

Methods for Preparing Alpha-Amylase Variants

Several methods for introducing mutations into genes are known in the art. After a brief discussion of the cloning of alpha-amylase-encoding DNA sequences, methods for generating mutations at specific sites within the alpha-amylase-encoding sequence will be discussed.

Cloning a DNA Sequence Encoding an Alpha-Amylase

The DNA sequence encoding a parent alpha-amylase may be isolated from any cell or microorganism producing the alpha-amylase in question, using various methods well known in the art. First, a genomic DNA and/or cDNA library should be constructed using chromosomal DNA or messenger RNA from the organism that produces the alpha-amylase to be studied. Then, if the amino acid sequence of the alpha-amylase is known, homologous, labeled oligonucleotide probes may be synthesized and used to identify alpha-amylase-encoding clones from a genomic library prepared from the organism in question. Alternatively, a labeled oligonucleotide probe containing sequences homologous to a known alpha-amylase gene could be used as a probe to identify alpha-amylase-encoding clones, using hybridization and washing conditions of lower stringency.

Yet another method for identifying alpha-amylase-encoding clones would involve inserting fragments of genomic DNA into an expression vector, such as a plasmid, transforming alpha-amylase-negative bacteria with the resulting genomic DNA library, and then plating the transformed bacteria onto agar containing a substrate for alpha-amylase, thereby allowing clones expressing the alpha-amylase to be identified.

Alternatively, the DNA sequence encoding the enzyme may be prepared synthetically by established standard methods, e.g., the phosphoroamidite method described by S.L. Beaucage and M. H. Caruthers, 1981, Tetrahedron Letters 22: 1859 or the method described by Matthes et al., 1984, EMBO J. 3 801-805. In the phosphoroamidite method, oligonucleotides are synthesized, e.g., in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al., 1988, Science Vol. 239 no. 4839 pp. 487-491.

Site-Directed Mutagenesis

Once an alpha-amylase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the alpha-amylase-encoding sequence, is created in a vector carrying the alpha-amylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al., 1984, *Biotechnology* 2, pp. 636-639. U.S. Pat. No. 4,760,025 disclose the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method for introducing mutations into alpha-amylase-encoding DNA sequences is described in Nelson and Long (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Random Mutagenesis

Random mutagenesis is suitably performed either as localised or region-specific random mutagenesis in at least three parts of the gene translating to the amino acid sequence shown in question, or within the whole gene.

The random mutagenesis of a DNA sequence encoding a parent alpha-amylase may be conveniently performed by use of any method known in the art.

In relation to the above, a further aspect of the present invention relates to a method for generating a variant of a parent alpha-amylase, e.g., wherein the variant exhibits an altered starch affinity relative to the parent, the method comprising:

(a) subjecting a DNA sequence encoding the parent alpha-amylase to random mutagenesis, (b) expressing the mutated DNA sequence obtained in step (a) in a host cell, and (c) screening for host cells expressing an alpha-amylase variant which has an altered starch affinity relative to the parent alpha-amylase.

Step (a) of the above method of the invention is preferably performed using doped primers. For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents. The mutagenizing agent may, e.g., be one, which induces transitions, transversions, inversions, scrambling, deletions, and/or insertions.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues. When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties. When the mutagenesis is performed by the use of an oligonucleotide, the oligonucleotide may be doped or spiked with the three non-parent nucleotides during the synthesis of the oligonucleotide at the positions, which are to be changed. The doping or spiking may be done so that codons for unwanted amino acids are avoided. The doped or spiked oligonucleotide can be incorporated into the DNA encoding the alpha-amylase enzyme by any published technique, using e.g., PCR, LCR or any DNA polymerase and ligase as deemed appropriate. Preferably, the doping is carried out using "constant random doping", in which the percentage of wild type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints. The doping scheme may be made by using the DOPE program, which, inter alia, ensures that introduction of stop codons is avoided. When PCR-generated mutagenesis is used, either a chemically treated or non-treated gene encoding a parent alpha-amylase is subjected to PCR under conditions that increase the misincorporation of nucleotides (Deshler 1992, Genetic Analysis: Biomolecular Engineering, 9(4), pp 103-106; Leung et al., 1989, Technique, Vol. 1, pp. 11-15). A mutator strain of E. coli (Fowler et al., 1974, Molec. Gen. Genet., 133, pp. 179-191), S. cereviseae or any other microbial organism may be used for the random mutagenesis of the DNA encoding the alpha-amylase by, e.g., transforming a plasmid containing the parent glycosidase into the mutator strain, growing the mutator strain with the plasmid and isolating the mutated plasmid from the mutator strain. The mutated plasmid may be subsequently transformed into the expression organism. The DNA sequence to be mutagenized may be conveniently present in a genomic or cDNA library prepared from an organism expressing the parent alpha-amylase. Alternatively, the DNA sequence may be present on a suitable vector such as a plasmid or a bacteriophage, which as such may be incubated with or otherwise exposed to the mutagenising agent. The DNA to be mutagenized may also be present in a host cell either by being integrated in the genome of said cell or by being present on a vector harboured in the cell. Finally, the DNA to be mutagenized may be in isolated form. It will be understood that the DNA sequence to be subjected to random mutagenesis is preferably a cDNA or a genomic DNA sequence. In some cases it may be convenient to amplify the mutated DNA sequence prior to performing the expression step b) or the screening step c). Such amplification may be performed in accordance with methods known in the art, the presently preferred method being PCR-generated amplification using oligonucleotide primers prepared on the basis of the DNA or amino acid sequence of the parent enzyme. Subsequent to the incubation with or exposure to the mutagenising agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment. Examples of suitable host cells are the following: gram positive bacteria such as Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis, Streptomyces lividans or Streptomyces murinus; and gram-negative bacteria such as E. coli. The mutated DNA sequence may further comprise a DNA sequence encoding functions permitting expression of the mutated DNA sequence.

Localised Random Mutagenesis

The random mutagenesis may be advantageously localised to a part of the parent alpha-amylase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized or region-specific, random mutagenesis is conveniently performed by use of PCR generated mutagenesis techniques as described above or any other suitable technique known in the art. Alternatively, the DNA sequence encoding the part of the DNA sequence to be modified may be isolated, e.g., by insertion into a suitable vector, and said part may be subsequently subjected to mutagenesis by use of any of the mutagenesis methods discussed above.

Alternative Methods of Providing Alpha-Amylase Variants

Alternative methods for providing variants of the invention include gene-shuffling method known in the art including the methods e.g., described in WO 95/22625 (from Affymax Technologies N.V.) and WO 96/00343 (from Novo Nordisk A/S).

Expression of Alpha-Amylase Variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding an alpha-amylase variant of the invention may be any vector, which may conveniently be subjected to recombinant DNA procedures, and the choice of vector will often depend on the host cell into which it is to be introduced. Thus, the vector may be an autonomously replicating vector, i.e., a vector, which exists as an extrachromosomal entity, the replication of which is independent of chromosomal replication, e.g., a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the DNA sequence encoding an alpha-amylase variant of the invention, especially in a bacterial host, are the promoter of the lac operon of E. coli, the Streptomyces coelicoloragarase gene dagA promoters, the promoters of the Bacillus licheniformis alpha-amylase gene (amyL), the promoters of the Bacillus stearothermophilus maltogenic amylase gene (amyM), the promoters of the Bacillus amyloliquefaciens alpha-amylase (amyQ), the promoters of the Bacillus subtilis xylA and xylB genes etc. For transcription in a fungal host, examples of useful promoters are those derived from the gene encoding A. oryzae TAKA amylase, Rhizomucor miehei aspartic proteinase, A. niger neutral alpha-amylase, A. niger acid stable alpha-amylase, A. niger glucoamylase, Rhizomucor miehei lipase, A. oryzae alkaline protease, A. oryzae triose phosphate isomerase or A. nidulans acetamidase.

The expression vector of the invention may also comprise a suitable transcription terminator and, in eukaryotes, polyadenylation sequences operably connected to the DNA sequence encoding the alpha-amylase variant of the invention. Termination and polyadenylation sequences may suitably be derived from the same sources as the promoter.

The vector may further comprise a DNA sequence enabling the vector to replicate in the host cell in question.

Examples of such sequences are the origins of replication of plasmids pUC19, pACYC177, pUB110, pE194, pAMB1 and pIJ702.

The vector may also comprise a selectable marker, e.g., a gene the product of which comple-ments a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise *Aspergillus* selection markers such as amdS, argB, niaD and sC, a marker giving rise to hygromycin resistance, or the selection may be accomplished by co-transformation, e.g., as described in WO 91/17243.

While intracellular expression may be advantageous in some respects, e.g., when using certain bacteria as host cells, it is generally preferred that the expression is extracellular. In general, the *Bacillus* alpha-amylases mentioned herein comprise a pre-region permitting secretion of the expressed protease into the culture medium. If desirable, this pre-region may be replaced by a different preregion or signal sequence, conveniently accomplished by substitution of the DNA sequences encoding the respective preregions.

The procedures used to ligate the DNA construct of the invention encoding an alpha-amylase variant, the promoter, terminator and other elements, respectively, and to insert them into suitable vectors containing the information necessary for replication, are well known to persons skilled in the art (cf., for instance, Sambrook et al., Molecular Cloning: A Laboratory Manual, 2nd Ed., Cold Spring Harbor, 1989).

The cell of the invention, either comprising a DNA construct or an expression vector of the invention as defined above, is advantageously used as a host cell in the recombinant production of an alpha-amylase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g., a bacterial or a fungal (including yeast) cell.

Examples of suitable bacteria are gram-positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis,* or *Streptomyces lividans* or *Streptomyces murinus*, or gramne-gative bacteria such as *E. coli*. The transformation of the bacteria may, for instance, be effected by protoplast transformation or by using competent cells in a manner known per se.

The yeast organism may favourably be selected from a species of *Saccharomyces* or *Schizosaccharomyces*, e.g., *Saccharomyces cerevisiae*. The filamentous fungus may advantageously belong to a species of *Aspergillus*, e.g., *Aspergillus oryzae* or *Aspergillus niger*. Fungal cells may be transformed by a process involving protoplast formation and transformation of the protoplasts followed by regeneration of the cell wall in a manner known per se. A suitable procedure for transformation of *Aspergillus* host cells is described in EP 238 023.

In yet a further aspect, the present invention relates to a method of producing an alpha-amylase variant of the invention, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the alpha-amylase variant of the invention. Suitable media are available from commercial suppliers or may be prepared according to published recipes (e.g., as described in catalogues of the American Type Culture Collection).

The alpha-amylase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Conventions for Designation of Variants

Using the numbering system originating from the amino acid sequence of the alpha-amylase disclosed in SEQ ID NO: 6 aligned with the amino acid sequence of a number of other alpha-amylases, it is possible to indicate the position of an amino acid residue in an alpha-amylase in regions of structural homology.

In describing the various alpha-amylase variants of the present invention, the nomenclature described below is adapted for ease of reference. In all cases, the accepted IUPAC single letter or triple letter amino acid abbreviation is employed.

In the present description and claims, the conventional one-letter and three-letter codes for amino acid residues are used. For ease of reference, alpha-amylase variants of the invention are described by use of the following nomenclature:

Original amino acid(s): position(s): substituted amino acid(s)

According to this nomenclature, for instance the substitution of alanine for asparagine in position 30 is shown as:
 Ala30Asn or A30N
a deletion of alanine in the same position is shown as:
 Ala30* or A30*
and insertion of an additional amino acid residue after position 30, such as lysine, is shown as:
 Ala30AlaLys or A30AK A deletion of a consecutive stretch of amino acid residues, such as amino acid residues 30-33, is indicated as (30-33)* or A (A30-N33). Deletion of a single amino acid residue may simply be disclosed as 30*.

Where a specific alpha-amylase contains a "deletion" in comparison with other alpha-amylases and an insertion is made in such a position this is indicated as:
 *36Asp or *36D
for insertion of an aspartic acid in position 36.

Multiple mutations may be separated by plus signs or with a space, i.e.:
 Ala30Asn+Glu34Ser or A30N+E34S
 Ala30Asn Glu34Ser or A30N E34S
representing mutations in positions 30 and 34 substituting alanine and glutamic acid for asparagine and serine, respectively.

Alternatively multiple mutations may be separated by commas or semicolons, i.e.:
Ala30Asn, Glu34Ser or A30N, E34S
Even more simplified multiple mutations may be separated by a space e.g.
Alternatively multiple mutations may be separated by commas or semicolons, i.e.:
Ala30Asn Glu34Ser or A30N E34S
When one or more alternative amino acid residues may be inserted in a given position it is indicated as
  A30N,E or
  A30N or A30E
Alternatively one or more alternative amino acid residues may be inserted in a given position it is indicated as:
A30 [N, E] or A30 [N E], alternatively A30 {N, E} or A30 {N E}
For simplicity alternative amino acid which could be substituted at a certain position may be indicated as:
A30 N, E, H, L or V Furthermore, when a position suitable for modification is identified herein without any specific modification being suggested, it is to be understood that any amino acid residue may be substituted for the amino acid residue present in the position. Thus, for instance, when a modification of an alanine in position 30 is mentioned, but not specified, it is to be understood that the alanine may be deleted or substituted for any other amino acid, i.e., any one of:
R, N, D, A, C, Q, E, G, H, I, L, K, M, F, P, S, T, W, Y, V.
Further, "A30X" means any one of the following substitutions:
A30R, A30N, A30D, A30O, A30Q, A30E, A30G, A30H, A30I, A30L, A30K, A30M, A30F, A30P, A30S, A30T, A30W, A30Y, or A30V; or in short: A30R,N,D,C,Q,E,G,H,I,L,K,M,F,P,S,T,W,Y,V.
Or e.g. A30 [R, N, D, C, Q, E, G, H, I, L, K, M, F, P, S, T, W, Y, V]

The skilled person would know that using numbering e.g. according to SEQ ID NO 6 means using SEQ ID NO: 6 for countering not that the parent necessarily is SEQ ID NO: 6 but simply that the positions to be altered are defined according to SEQ ID NO: 6. Therefore, another way of describing the specific substitutions is to indicate the amino acid to be altered with an X. Thus X30N means that any amino acid present at position 30 could be substituted with N reflecting that different alpha-amylase can be used as parent alpha-amylase.

Thus, the nomenclature "X30N" or "X30V" means that any amino acid which might be at position 30 in the parent alpha-amylase is substituted by an asparagine or a valine.
Characteristics of Amino Acid Residues
Charged Amino Acids:
Asp, Glu, Arg, Lys, His
Negatively Charged Amino Acids (with the Most Negative Residue First):
Asp, Glu
Positively Charged Amino Acids (with the Most Positive Residue First):
Arg, Lys, His
Neutral Amino Acids:
Gly, Ala, Val, Leu, Ile, Phe, Tyr, Trp, Met, Cys, Asn, Gln, Ser, Thr, Pro
Hydrophobic Amino Acid Residues (with the Most Hydrophobic Residue Listed Last):
Gly, Ala, Val, Pro, Met, Leu, Ile, Tyr, Phe, Trp,
Hydrophilic amino acids (with the most hydrophilic residue listed last):
Thr, Ser, Cys, Gln, Asn This nomenclature is particularly relevant to modifications involving substituting, inserting or deleting amino acid residues having specific common properties. Such modifications are referred to as conservative amino acid modification(s). Examples of conservative modifications are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid modifications, which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as the reverse (Taylor, 1986, Journal of Theoretical Biology 119: 205-218.

Variants of the Invention

In a preferred embodiment the variants comprise alteration(s) in one or more, or one or several, amino acid residues in the region 193 to 213 of the parent alpha-amylase. In a particularly preferred embodiment the variant comprising at least one, at least two, or at least three deletions in amino acid region of 181, 182, 183, or 184 and further an altering at one or more, or one or several, amino acid residues in the region 193 to 213, wherein the numbering corresponds to the mature polypeptide of SEQ ID NO: 6, i.e. using numbering according to SEQ ID NO: 6. The inventors have found that such alterations provides variants having an increased stability in compositions comprising a chelating agent, in particular when the chelating agents capable of reducing the concentration of free calcium ions from 2.0 mM to 0.10 mM at a concentration below 10 mM, preferably below 9.5 mM, preferably below 9.0 mM, preferably below 8.5 mM, preferably below 8.0 mM, preferably below 7.5 mM, preferably below 7.0 mM, preferably below 6.5 mM, preferably below 6.0 mM, preferably below 5.5 mM, preferably, preferably below 5.0 mM, preferably below 4.5 mM, below 4.0 mM, preferably below 3.5 mM, preferably below 3.0 mM, preferably below 2.5 mM, preferably below 2.0 mM, preferably below 1.5 mM or preferably below 1.0 mM when measured at 21° C. and pH 8.0, as described in the below under "Materials and Methods".

A first aspect of the invention relates to a composition comprising a variant of a parent alpha-amylase, wherein the variant comprises a substitution at one or more positions in the range 193 to 213, using the numbering according to SEQ ID NO: 6, and further comprising at least one chelating agent wherein said chelating agent at a concentration below 10 mM is capable of reducing the concentration of free calcium ions from 2.0 mM to 0.10 mM when measured at 21° C. and pH 8.0.

A first aspect of the invention relates to a composition comprising a variant of a parent alpha-amylase, wherein the variant comprises a substitution at one or more positions in the range 193 to 213, using the numbering according to SEQ ID NO: 6, and further comprising at least one chelating agent wherein said chelating agent at a concentration below 10 mM is capable of reducing the concentration of free calcium ions from 2.0 mM to 0.10 mM when measured at 21° C. and pH 8.0, and optionally a cleaning adjunct.

A second aspect provides a composition comprising a variant of a parent alpha-amylase wherein the variant alpha-amylase comprises an amino acid sequence which is at least 70%, such as at least 75%, such as at least 80%, such as at least 85%, such as at least 90%, such as at least 95%, such as at least 100% identical to SEQ ID NO: 6, 8, 10, 12, 18, and 22 and further comprises a substitution at one or more positions selected from the group comprising 195, 193, 197, 198, 200, 203, 206, 210, 212 213 and 243 using the numbering according to SEQ ID NO: 6, and further comprising at least one chelating agent wherein said chelating agent at a concentration below 10 mM is capable of reducing the concentration of free calcium ions from 2.0 mM to 0.10 mM when measured at 21° C. and pH 8.0.

A further aspect provides a composition comprising a variant which comprises a substitution at one or more positions selected from the group comprising 195, 193, 197, 198, 200, 203, 206, 210, 212, 213 and 243 (using the numbering according to SEQ ID NO: 6) wherein said composition further comprises at least one chelating agent wherein said chelating agent at a concentration below 10 mM is capable of reducing the concentration of free calcium ions from 2.0 mM to 0.10 mM when measured at 21° C. and pH 8.0.

A further aspect provides a composition comprising a variant which comprises a substitution at one or more positions selected from the group comprising 195, 193, 197, 198, 200, 203, 206, 210, 212, 213 and 243 (using the numbering according to SEQ ID NO: 6) and wherein the variant comprise an amino acid sequence having at least 70% identity to amino acid sequence from the group consisting of SEQ ID NO: 2, 4, 6, 8, 10, 12, 14, 16, 18, 20, 22, 24 and 26, preferably SEQ ID NO: 14, 16 or 20, preferably SEQ ID NO: 6, SEQ ID NO: 8, SEQ ID NO: 10, SEQ ID NO: 12, SEQ ID NO: 18, or SEQ ID NO: 22 and wherein said composition further comprises at least one chelating agent wherein said chelating agent at a concentration below 10 mM is capable of reducing the concentration of free calcium ions from 2.0 mM to 0.10 mM when measured at 21° C. and pH 8.0.

A further aspect provides a composition comprising a variant which comprises a substitution at one or more positions selected from the group comprising 195, 193, 197, 198, 200, 203, 206, 210, 212, 213 and 243 (using the numbering according to SEQ ID NO: 6) and wherein the variant comprise an amino acid sequence having at least 70% identity to amino acid sequence from the group consisting of SEQ ID NO: 14, SEQ ID NO: 16 or SEQ ID NO: 20 and wherein said composition further comprises at least one chelating agent wherein said chelating agent at a concentration below 10 mM is capable of reducing the concentration of free calcium ions from 2.0 mM to 0.10 mM when measured at 21° C. and pH 8.0.

A third aspect relates to a composition wherein the chelating agent at a concentration below 10 mM is capable of reducing the concentration of free calcium ions from 2.0 mM to 0.10 mM when measured in 80 mM potassium chloride and 49 mM EPPS at 21° C. and pH 8.0.

A third aspect relates to a composition wherein the chelating agent at a concentration below 10 mM is capable of reducing the concentration of free calcium ions from 2.0 mM to 0.10 mM when measured in the assay described under "Materials and Methods".

Thus in a preferred aspect of the invention the variant comprises at least one substitution at one or more position in the range corresponding to positions 193 to 213 of the mature polypeptide of SEQ ID NO: 6. The terms "using the numbering according to" or "corresponding to" are used interchangeably in the application and refers to the numbering system used in the present application. Thus position 195 is the amino acid corresponding to position 195 in SEQ ID NO: 6. Thus it is to be understood that variants of other parent alpha-amylases modified in the equivalent position(s) (as determined from the best possible amino acid sequence alignment between the respective amino acid sequences) are encompassed thereby. When there are deletions the countering is made as if no deletions were present.

In a particularly preferred embodiment the composition comprises a variant, which variant comprises an altering at one or more positions corresponding to positions selected from the group consisting of 193, 195, 197, 198, 200, 203, 206, 210, 212, 213 and 243 and an altering at one or more positions corresponding to positions selected from the group consisting of 116, 118, 129, 133, 134, 142, 146, 147, 149, 151, 152, 169, 174, 186, 235, 244, 303, 320, 339, 359, 418, 431, 434, 447, 458 (using numbering according to SEQ ID NO: 6).

In a particularly preferred embodiment the composition comprises a variant, which variant comprises at least one, at least two, or at least three deletions in amino acid region of 181, 182, 183, or 184 and further an alteration at one or more, or one or several, positions corresponding to positions selected from the group consisting of 193, 195, 197, 198, 200, 203, 206, 210, 212, 213 and 243 and an altering at one or more, or one or several, positions corresponding to positions selected from the group consisting of 116, 118, 129, 133, 134, 142, 146, 147, 149, 151, 152, 169, 174, 186, 235, 244, 303, 320, 339, 359, 418, 431, 434, 447, 458 (using numbering according to SEQ ID NO: 6).

In one aspect of the present invention the composition comprises a variant of a parent alpha-amylase comprising at least one, at least two, or at least three deletions in amino acid region of 181, 182, 183, or 184 and further comprises a substitution at one or more, or one or several, positions selected from the group consisting of 193, 195, 197, 198, 200, 203, 206, 210, 212, 213 and 243, using the numbering according to SEQ ID NO: 6, and wherein the variant has an amino acid sequence having a degree of identity of at least 70%, preferred at least 75%, preferred at least 80%, preferred at least 81%, preferred at least 82%, preferred at least 83%, preferred at least 84%, preferred at least 85%, preferred at least 86%, preferred at least 87%, preferred at least 88%, preferred at least 89%, especially preferred at least 90%, preferred at least 91%, preferred at least 92%, preferred at least 93%, preferred at least 94%, preferred at least 95%, preferred at least 96%, preferred at least 97%, preferred at least 98%, preferred at least 99% identity to the amino acid sequence of the parent alpha-amylase, which may be any of the sequences with SEQ ID NO: 2, 4, 6, 8, 10, 12, 14, 16, 18, 20, 22, 24 or 26, preferably SEQ ID NO: 14, 16 or 20, preferably SEQ ID NO: 6, 8, 10, 12, 18, or 22, and wherein the variant has at least 70% residual activity, preferably at least 75% residual activity, preferably at least 80% residual activity, preferably at least 85% residual activity, preferably at least 90% residual activity, preferably at least 95% residual activity, preferably at least 100% residual activity, preferably at least 105% residual activity, preferably at least 110% residual activity or has a residual activity which is at least 5, 10, 20, 30, 40, 50, 60, 70, 80, 90, 100 pp improved compared to the residual activity of the parent alpha-amylase, when the residual activity is determined after 18 hours at pH 8 and 31° C. as described in the EnzChek or the PNP-G7 assay (see under "Materials and Methods" for details) in the presence of a chelating agent wherein said chelating agent at a concentration below 10 mM is capable of reducing the concentration of free calcium ions from 2.0 mM to 0.10 mM when measured at 21° C. and pH 8.0, as described below.

The composition according to the invention preferably comprising an alpha-amylase wherein the parent alpha-amylase is modified by at least one of the following substitutions: position 193 is [G, A, S, T, or M]; position 195 is [F, W, Y, L, I, or V]; position 197 is [F, W, Y, L, I, or V]; position 198 is [Q or N]; position 200 is [F, W, Y, L, I, or V]; position 203 is [F, W, Y, L, I,or V]; position 206 is [F, W, Y, N, L, I, V, or H]; position 210 is [F, W, Y, L, I,or V]; position 212 is [F, W, Y, L, I, or V] or position 213 is [G, A, S, T, or M] wherein the positions corresponds to the position of the mature polypeptide with SEQ ID NO: 6 and further comprising at least one chelating agent wherein said chelating agent at a concentration below 10 mM is capable of reducing the concentration of free calcium ions from 2.0 mM to 0.10 mM when measured at 21° C. and pH 8.0, as described under "Materials and Methods".

The composition according to the invention preferably comprising an alpha-amylase variant, wherein the variant comprising at least one, at least two, or at least three deletions in amino acid region of 181, 182, 183, or 184 and wherein the parent alpha-amylase further is modified by at least one of the following substitutions: 193 is [G, A, S, T, or M]; position 195 is [F, W, Y, L, I, or V]; position 197 is [F, W, Y, L, I, or V]; position 198 is [Q or N]; position 200 is [F, W, Y, L, I, or V]; position 203 is [F, W, Y, L, I, or V]; position 206 is [F, W, Y, N, L, I, V, or H]; position 210 is [F, W, Y, L, I, or V]; position 212 is [F, W, Y, L, I, or V], position 213 is [G, A, S, T, or M] or position 243 is [F, W, Y, L, I or V] wherein the positions corresponds to the position of the mature polypeptide with SEQ ID NO: 6 and further comprising at least one chelating agent wherein said chelating agent at a concentration below 10 mM is capable of reducing the concentration of free calcium ions from 2.0 mM to 0.10 mM when measured at 21° C. and pH 8.0, as described under "Materials and Methods".

In particular the invention concerns a composition comprising an alpha-amylase wherein the amino acid sequence is modified by at least one of the following substitutions: 193 is T; position 195 is F or Y; position 197 is F or L; position 198 is N; position 200 is F; position 203 is F; position 206 is F, L or Y; position 210 is Y; position 212 is V; position 213 is A position 243 is F, wherein the positions corresponds to the position of the mature polypeptide with SEQ ID NO: 6 and further comprising at least one chelating agent wherein said chelating agent at a concentration below 10 mM is capable of reducing the concentration of free calcium ions from 2.0 mM to 0.10 mM when measured in at 21° C. and pH 8.0, as described under "Materials and Methods".

In a further aspect the composition comprises an alpha-amylase variant, wherein said variant comprises a substitution at two or more, or two or several, positions selected from the group consisting of 193, 195, 197, 198, 200, 203, 206, 210, 212, 213 and 243, wherein the positions correspond to positions of the mature polypeptide of SEQ ID NO: 6 and further comprising at least one chelating agent wherein said chelating agent at a concentration below 10 mM is capable of reducing the concentration of free calcium ions from 2.0 mM to 0.10 mM when measured at 21° C. and pH 8.0, as described under "Materials and Methods".

In yet a further aspect the composition comprises an alpha-amylase variant, wherein the variant comprises at least two or more, or at least three or more, deletions in amino acid region of 181, 182, 183, or 184 and further comprises a substitution at two or more positions selected from the group consisting of 193, 195, 197, 198, 200, 203, 206, 210, 212, 213 and 243 wherein the positions correspond to positions of the mature polypeptide of SEQ ID NO: 6 and further comprising at least one chelating agent wherein said chelating agent at a concentration below 10 mM is capable of reducing the concentration of free calcium ions from 2.0 mM to 0.10 mM when measured at 21° C. and pH 8.0, as described under "Materials and Methods", and wherein the variant has at least 70% residual activity, preferably at least 75% residual activity, preferably at least 80% residual activity, preferably at least 85% residual activity, preferably at least 90% residual activity, preferably at least 95% residual activity, preferably at least 100% residual activity, preferably at least 105% residual activity, preferably at least 110% residual activity or has a residual activity which is at least 5, 10, 20, 30, 40, 50, 60, 70, 80, 90, 100 pp improved compared to the residual activity of the parent alpha-amylase, when the residual activity is determined after 18 hours at pH 8 and 31° C. as described in the EnzChek or the PNP-G7 assay (see under "Materials and Methods" for details) in the presence of a chelating agent wherein said chelating agent at a concentration below 10 mM is capable of reducing the concentration of free calcium ions from 2.0 mM to 0.10 mM when measured at 21° C. and pH 8.0, as described below.

In preferred embodiments the at least two deletions in amino acid region of 181, 182, 183, or 184 is selected from the group consisting of 181*+182*; 181*+183*, 182*+183*; 181*+184*, 182*+184* and 183*+184*.

In an even further aspect, the composition comprises an alpha-amylase variant, wherein the variant comprises at least two, or at least three deletions in amino acid region of 181, 182, 183, or 184 and further comprises a substitution at two or more positions selected from the group consisting of 193, 195, 197, 198, 200, 203, 206, 210, 212, 213 and 243 wherein the positions correspond to positions of the mature polypeptide of SEQ ID NO: 6 and an altering at one or more, or one or several, positions corresponding to positions selected from the group consisting of 116, 118, 129, 133, 134, 142, 146, 147, 149, 151, 152, 169, 174, 186, 235, 244, 303, 320, 339, 359, 418, 431, 434, 447, 458 (using numbering according to SEQ ID NO: 6), and further comprising at least one chelating agent wherein said chelating agent at a concentration below 10 mM is capable of reducing the concentration of free calcium ions from 2.0 mM to 0.10 mM when measured at 21° C. and pH 8.0, as described under "Materials and Methods".

In one aspect of the invention, the composition comprises at least one chelating agent wherein said chelating agent at a concentration below 10 mM is capable of reducing the concentration of free calcium ions from 2.0 mM to 0.10 mM when measured at 21° C. and pH 8.0 and one or more, or one or several, of the following amylase variants; SP722+ R181*G182* N195F; SP722+G182* D183* N195F; SP722+D183* G184* N195F; SP722+R181* G182* N195F M202L; SP722+G182 D183* N195F M202L; SP722+D183* G184* N195F M202L; SP722+D183* G184* N195F V206L Y243F; SP722+D183* G184* N195F V206YY243F; SP722+R181* G182* L118K N195F R458K; SP722+G182* D183* L118K N195F H458K; SP722+D183* G184* L118K N195F H458K; SP722+D183* G184* G133E G149R N195Y Y203F V206L. AA560+R181* G182* N195F; AA560+G182* D183* N195F; AA560+D183* G184* N195F; AA560+D183* G184* I206Y; AA560+D183* G184* Y243F; AA560+ D183* G184* V206L, Y243F; AA560+D183* G184* N195F V206L; AA560+D183* G184* N195F Y243F;

AA560+D183* G184* N195F V206L Y243F; AA560+ D183* G184* N195F V206Y Y243F; AA560+R181* G182* N195F M202L; AA560+G182* D183* N195F M202L; AA560+D183* G184* N195F M202L; AA560+ R181* G182* R118K N195F R320K R458K; AA560+ G182* D183* R118K N195F R320K R458K; AA560+ D183* G184* R118K N195F R320K R458K; AA560+ D183* G184* R118K N195F I206L R320K R458K; AA560+D183* G184* R118K N195F I206Y R320K R458K; AA560+D183* G184* R118K N195F Y243F R320K R458K; AA560+D183* G184* R118K N195F I206L Y243F R320K R458K.

SP707+R181* G182* N195F; SP707+G182* H183* N195F; SP707+H183* G184* N195F; SP707+H183* G184* I206Y; SP707+H183* G184* N195F I206Y; SP707+H183* G184* N195F Y243F; SP707+H183* G184* I206Y Y243F; SP707+H183* G184* N195F I206LY243F; SP707+H183* G184* N195F I206Y Y243F; SP707+R181* G182* N195F M202L; SP707+G182* H183* N195F M202L; SP707+H183* G184* N195F M202L; SP707+R181* G182* R118K N195F R320K R458K; 5P707+G182* H183* R118K N195F R320K R458K; 5P707+H183* G184* R118K N195F R320K R458K;

SP690+R181* G182* N195F; SP690+G182* T183* N195F; SP690+T183* G184* N195F; SP690+H183* G184* V206Y; SP690+H183* G184* N195F V206Y; SP690+H183* G184* N195F Y243F; SP690+H183* G184* V206Y Y243F; SP690+H183* G184* N195F V206L Y243F; SP690+H183* G184* N195F V206Y Y243F; SP690+R181* G182* N195F M202L; SP690+ G182* T183* N195F M202L; SP690+T183* G184* N195F M202L; SP690+R181* G182* R118K N195F R320K R458K; SP690+G182* T183* R118K N195F R320K R458K; SP690+T183* G184* R118K N195F R320K R458K.

In useful embodiments, the composition according to the invention comprises an amylase which is a variant of a parent alpha-amylase, wherein the parent alpha-amylase is that of SEQ ID NO:6, and the variant comprises the deletions D183* and G184* and one of the following sets of mutations: (a) N195F+H210Y; (b) N195F+V206L,H,Y; (c) N195F+V206L, F+H210Y; (d) N195F+V206Y+Y243F; (e) N195F+Y243F; (f) S193T+V206L; (g) G133E+G149R+ N195Y+Y203F+V206L; (h) V206L,Y; (i) Y243F; (j) N195F+V206L+Y243F; (k) N195F; or (l) V206F+Y243F.

Another embodiment of the invention relates to a composition, wherein the residual activity of the variant is at least 70%, such as at least 75%, such as at least 80%, such as at least 85%, such as at least 90%, such as at least 95%, such as at least 100%, such as at least 105%, such as at least 110%, such as at least 115% residual activity compared to the parent alpha-amylase in the presence of a chelating agent wherein said chelating agent at a concentration below 10 mM, preferably below 9.5 mM, preferably below 9 mM, preferably below 8.5 mM, preferably below 8 mM, preferably below 7.5 mM, preferably below 7 mM, preferably below 6.5 mM, preferably below 6 mM, preferably below 5.5 mM, preferably, preferably below 5 mM, preferably below 4.5 mM, below 4 mM, preferably below 3.5 mM, preferably below 3 mM, preferably below 2.5 mM, preferably below 2 mM, preferably below 1.5 mM or preferably below 1 mM is capable of reducing the concentration of free calcium ions from 2.0 mM to 0.10 mM when measured at 21° C. and pH 8.0, as described under "Materials and Methods" and when residual activity is determined after 18 hours at pH 8 at 31° C. as described in the EnzChek or the PNP-G7 assay described under "Materials and Methods".

A further embodiment of the invention relates to a composition, wherein the residual activity of the variant is at least 5, 10, 20, 30, 40, 50, 60, 70, 80, 90, 100 pp improved compared to the residual activity of the parent alpha-amylase in the presence of a chelating agent wherein said chelating agent at a concentration below 10 mM, preferably below 9.5 mM, preferably below 9 mM, preferably below 8.5 mM, preferably below 8 mM, preferably below 7.5 mM, preferably below 7 mM, preferably below 6.5 mM, preferably below 6 mM, preferably below 5.5 mM, preferably, preferably below 5 mM, preferably below 4.5 mM, below 4 mM, preferably below 3.5 mM, preferably below 3 mM, preferably below 2.5 mM, preferably below 2 mM, preferably below 1.5 mM or preferably below 1 mM is capable of reducing the concentration of free calcium ions from 2.0 mM to 0.10 mM when measured at 21° C. and pH 8.0, as described under "Materials and Methods" and when residual activity is determined after 18 hours at pH 8 at 31° C. as described in the EnzChek or the PNP-G7 assay described under "Materials and Methods". The percentage point (pp) improvement in residual activity of the variant relative to the parent is calculated as the difference between the residual activity of the variant and that of the parent.

Thus in a particular aspect of the invention the composition comprises a chelating agent selected from the group consisting of: phosphorous-containing, non-phosphorous containing, carboxylate containing, nitrogen containing or non-nitrogen containing chelating agents, preferred chelating agents are as EDTA, MGDA, EGTA, DTPA, DTPMP, HEDP and mixtures thereof.

In a preferred aspect of the invention the variant comprises a substitution at one or more positions selected from the group consisting of 195, 193, 197, 198, 200, 203, 206, 210, 212 and 213 wherein the positions correspond to positions of the mature polypeptide of SEQ ID NO: 6.

In a particularly preferred aspect of the invention the variant comprising at least one, at least two, or at least three deletions in amino acid region of 181, 182, 183, or 184 and further comprises a substitution at one or more positions selected from the group consisting of 195, 193, 197, 198, 200, 203, 206, 210, 212 213 and 243 wherein the positions correspond to positions of the mature polypeptide of SEQ ID NO: 6. In preferred embodiments the at least two deletions in the amino acid region of 181, 182, 183, or 184 is selected from the group consisting of 181*+182*; 181*+183*, 182*+ 183*; 181*+184*, 182*+184* and 183*+184*.

In another preferred aspect of the invention the variant comprises a substitution at one or more positions selected from the group consisting of 195, 193, 197, 198, 200, 203, 206, 210, 212, 213 and 243 and further comprises a substitution at one or more, or one or several, positions selected from the group consisting of 116, 118, 129, 133, 134, 142, 146, 147, 149, 151, 152, 169, 174, 186, 235, 244, 303, 320, 339, 359, 418, 431, 434, 447, 458 wherein the positions correspond to positions of the mature polypeptide of SEQ ID NO: 6.

In a yet preferred aspect of the invention the variant comprising at least one, at least two, or at least three deletions in amino acid region of 181, 182, 183, or 184 and further comprises a substitution at one or more positions selected from the group consisting of 195, 193, 197, 198, 200, 203, 206, 210, 212, 213 and 243 and further comprises a substitution at one or more positions selected from the group consisting of 116, 118, 129, 133, 134, 142, 146, 147, 149, 151, 152, 169, 174, 186, 235, 244, 303, 320, 339, 359, 418, 431, 434, 447, 458 wherein the positions correspond to positions of the mature polypeptide of SEQ ID NO: 6.

In a further aspect the variant comprises a substitution at two or more positions selected from the group consisting of 116, 118, 129, 133, 134, 142, 146, 147, 149, 151, 152, 169, 174, 186, 193, 195, 197, 198, 200, 203, 206, 210, 212, 213, 235, 243, 244, 303, 320, 339, 359, 418, 431, 434, 447 and 458 wherein the positions correspond to positions of the mature polypeptide of SEQ ID NO: 6.

In yet a further aspect the variant comprising at least one, at least two, or at least three deletions in amino acid region of 181, 182, 183, or 184 and further comprises a substitution at two or more positions selected from the group consisting of 116, 118, 129, 133, 134, 142, 146, 147, 149, 151, 152, 169, 174, 186, 193, 195, 197, 198, 200, 203, 206, 210, 212, 213, 235, 243, 244, 303, 320, 339, 359, 418, 431, 434, 447 and 458 wherein the positions correspond to positions of the mature polypeptide of SEQ ID NO: 6.

Preferably, the variants comprising alterations at one or more of the above identified positions have an increased stability in compositions comprising a chelating agent, e.g. in detergent, preferably in liquid detergent as compared to the parent alpha-amylase.

Thus, the variants according to the invention have in a preferred embodiment improved stability relative to its parent amylase in the presence of one or more chelating agents. In a preferred aspect the variants according to the invention have improved stability relative to its parent amylase in the presence of one or more chelating agents and low calcium concentration. In yet a preferred aspect the variants according to the invention have improved stability relative to its parent amylase in presence of a chelating agent wherein said chelating agent at a concentration below 10 mM is capable of reducing the concentration of free calcium ions from 2.0 mM to 0.10 mM when measured at 21° C. and pH 8.0.

In a particular aspect the variant comprising at least one, at least two, or at least three deletions in amino acid region of 181, 182, 183, or 184 and further comprising a substitution at one or more position selected from the group consisting of 193, 195, 197, 198, 200, 203, 206, 210, 212, 213 and 243 and a substitution at one or more positions selected from the group consisting of 116, 118, 129, 133, 134, 142, 146, 147, 149, 151, 152, 169, 174, 186, 235, 244, 303, 320, 338, 359, 418, 431, 434, 447 and 458 wherein the positions correspond to positions of the mature polypeptide of SEQ ID NO: 6 and wherein the variant further has at least 60%, such as at least 65%, such as at least 70%, such as at least 75%, such as at least 80%, such as at least 85%, such as at least 90%, such as at least 95%, such as at least 100% residual activity in the presence of a chelating agent wherein said chelating agent at a concentration below 10 mM, preferably below 9.5 mM, preferably below 9 mM, preferably below 8.5 mM, preferably below 8 mM, preferably below 7.5 mM, preferably below 7 mM, preferably below 6.5 mM, preferably below 6 mM, preferably below 5.5 mM, preferably, preferably below 5 mM, preferably below 4.5 mM, below 4 mM, preferably below 3.5 mM, preferably below 3 mM, preferably below 2.5 mM, preferably below 2 mM, preferably below 1.5 mM or preferably below 1 mM is capable of reducing the concentration of free calcium ions from 2.0 mM to 0.10 mM at 21° C. and pH 8.0, as described below, and when residual activity is determined after 18 hours at pH 8, at 31° C. as described in the EnzChek assay or the PNP-G7 assay described under "Materials and Methods". In preferred embodiments the at least two deletions in the amino acid region of 181, 182, 183, or 184 is selected from the group consisting of 181*+182*; 181*+183*, 182*+183*; 181*+184*, 182*+184* and 183*+184*.

In a another particular aspect the variant comprises a substitution at one or more positions selected from the group consisting of 193, 195, 197, 198, 200, 203, 206, 210, 212, 213 and 243 and further comprising a substitution at one or more positions selected from the group consisting of 116, 118, 129, 133, 134, 142, 146, 147, 149, 151, 152, 169, 174, 186, 235, 244, 303, 320, 339, 359, 418, 431, 434, 447 and 458 wherein the positions correspond to positions of the mature polypeptide of SEQ ID NO: 6 and wherein the variant further has at least 60%, such as at least 65%, such as at least 70%, such as at least 75%, such as at least 80%, such as at least 85%, such as at least 90%, such as at least 95%, such as at least 100% residual activity or has a residual activity which is at least 5, 10, 20, 30, 40, 50, 60, 70, 80, 90, 100 pp improved compared to the residual activity of the parent alpha-amylase in the presence of a chelating agent wherein said chelating agent at a concentration below 10 mM, preferably below 9.5 mM, preferably below 9 mM, preferably below 8.5 mM, preferably below 8 mM, preferably below 7.5 mM, preferably below 7 mM, preferably below 6.5 mM, preferably below 6 mM, preferably below 5.5 mM, preferably, preferably below 5 mM, preferably below 4.5 mM, below 4 mM, preferably below 3.5 mM, preferably below 3 mM, preferably below 2.5 mM, preferably below 2 mM, preferably below 1.5 mM or preferably below 1 mM is capable of reducing the concentration of free calcium ions from 2.0 mM to 0.10 mM when measured at 21° C. and pH 8.0, as described under "Materials and Methods" and when residual activity is determined after 18 hours at pH 8 in the presence of DTPA at 31° C. as described in the EnzChek assay or the PNP-G7 assay described under "Materials and Methods".

The variants according to the invention have the benefit of being more stable towards strong chelating agents relative to their parent alpha-amylase however at the same time they have maintained the performance properties of the parent alpha-amylase such as wash performance or dish wash performance. In a preferred embodiment the variants according to the invention have the benefit of being more stable towards chelating agents wherein said chelating agent at a concentration below 10 mM is capable of reducing the concentration of free calcium ions from 2.0 mM to 0.10 mM when measured in 80 mM potassium chloride and 49 mM EPPS, at 21° C. and pH 8.0, as described under "Materials and Methods". These preferred chelating agents may be selected from, but are not restricted to, the EDTA, MGDA, EGTA, DTPA, DTPMP HEDP and mixtures thereof.

Thus, the variants of the invention have increased stability in the presence of chelating agents binding metal ions in particular calcium ions compared to their parent alpha-amylase. In detergents it is common to include chelating agents because of the beneficial effect of the laundering process, but the increased stability may also be at conditions where plant material including natural chelating agents such as phytate or citrate is present. In particular a strong chelating agents will compete with the calcium sensitive alpha-amylases for the calcium ions and will to some extend be able to deprive the alpha-amylase for the calcium ions bound in their structure with the consequence that the stability or activity of the alpha-amylase is reduced.

Thus, the variants of the invention have improved stability and/or activity in the presence of chelating agents, such as EDTA, MGDA, EGTA, DTPA, DTPMP HEDP and mixtures thereof, compared to their parent alpha-amylase.

In addition to increased stability towards chelating agents relative to the parent alpha-amylase the variants of the present invention have retained or improved wash performance when compared to the parent alpha-amylase. The improved wash performance can be measured in AMSA or in a wash performance test using beakers as described under "Materials and Methods".

Thus, in a particular embodiment of the invention the variant has at least 60% such as at least 65% residual activity, preferably at least 70% residual activity, preferably at least 75% residual activity, preferably at least 80% residual activity, preferably at least 85% residual activity, preferably at least 90% residual activity, preferably at least 95% residual activity or has a residual activity which is at least 5, 10, 20, 30, 40, 50, 60, 70, 80, 90, 100 pp improved compared to the residual activity of the parent alpha-amylase, when the residual activity is determined after 18 hours at pH 8 and 31° C. as described in the EnzChek or the PNP-G7 assay (see under "Materials and Methods" for details) in the presence of a chelating agent wherein said chelating agent at a concentration below 10 mM is capable of reducing the concentration of free calcium ions from 2.0 mM to 0.10 mM when measured at 21° C. and pH 8.0, as described below and wherein the variant further has at least 40%, such as at least 50%, such as at least 55%, such as at least 60%, such as at least 65%, such as at least 70%, such as at least 75%, such as at least 80%, such as at least 85%, such as at least 90%, such as at least 95%, such as at least 100% improved wash performance compared to the parent alpha-amylase when measured in AMSA or in a wash performance test using beakers as described under "Materials and Methods".

In a preferred aspect of the invention the composition comprises a variant having at least 60%, such as at least 65%, such as at least 70%, such as at least 75%, such as at least 80%, such as at least 85%, such as at least 90%, such as at least 95%, such as at least 100% residual activity compared to the parent alpha-amylase in the presence of a chelating agent wherein said chelating agent at a concentration below 10 mM, preferably below 9.5 mM, preferably below 9 mM, preferably below 8.5 mM, preferably below 8 mM, preferably below 7.5 mM, preferably below 7 mM, preferably below 6.5 mM, preferably below 6 mM, preferably below 5.5 mM, preferably, preferably below 5 mM, preferably below 4.5 mM, below 4 mM, preferably below 3.5 mM, preferably below 3 mM, preferably below 2.5 mM, preferably below 2 mM, preferably below 1.5 mM or preferably below 1 mM is capable of reducing the concentration of free calcium ions from 2.0 mM to 0.10 mM when measured at 21° C. and pH 8.0, as described in example 2a and when residual activity is determined after 18 hours at pH 8 at 31° C. as described in the EnzChek or the PNP-G7 assay described under "Materials and Methods".

Thus, in a particular aspect of the invention the composition comprises a chelating agent selected from the group consisting of: phosphorous-containing, non-phosphorous containing, nitrogen containing or non-nitrogen containing chelating agents, preferred chelating agents are EDTA, MGDA, EGTA, DTPA, DTPMP, HEDP and mixtures thereof.

In a preferred aspect the variants according to the invention have an amino acid sequence having a degree of identity of at least 60%, preferred at least 65%, preferred at least 70%, preferred at least 75%, preferred at least 80%, preferred at least 81%, preferred at least 82%, preferred at least 83%, preferred at least 84%, preferred at least 85%, preferred at least 86%, preferred at least 87%, preferred at least 88%, preferred at least 89%, especially preferred at least 90%, preferred at least 91%, preferred at least 92%, preferred at least 93%, preferred at least 94%, preferred at least 95%, preferred at least 96%, preferred at least 97%, preferred at least 98%, preferred at least 99% identity to the amino acid sequence of the parent alpha-amylase, which may be any of the sequences with SEQ ID NO: 2, 4, 6, 8, 10, 12, 14, 16, 18, 20, 22, 24 or 26, preferably, SEQ ID NO: 6, 8, 10, 12, 18, or 22, preferably SEQ ID NO:14, 16 or 20, preferably SEQ ID NO: 6, 8, 10 or 12.

In one aspect of the present invention, the variants of a parent alpha-amylase comprise a substitution at one or more positions selected from the group consisting of 193, 195, 197, 198, 200, 203, 206, 210, 212 213 and 243, using the numbering according to SEQ ID NO: 6, and wherein the variant have an amino acid sequence having a degree of identity of at least 60%, preferred at least 65%, preferred at least 70%, preferred at least 75%, preferred at least 80%, preferred at least 81%, preferred at least 82%, preferred at least 83%, preferred at least 84%, preferred at least 85%, preferred at least 86%, preferred at least 87%, preferred at least 88%, preferred at least 89%, especially preferred at least 90%, preferred at least 91%, preferred at least 92%, preferred at least 93%, preferred at least 94%, preferred at least 95%, preferred at least 96%, preferred at least 97%, preferred at least 98%, preferred at least 99% identity to the amino acid sequence of the parent alpha-amylase, which may be any of the sequences with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect of the present invention, the variants of a parent alpha-amylase comprising at least one, at least two, or at least three deletions in amino acid region of 181, 182, 183, or 184 and further comprises a substitution at one or more positions selected from the group consisting of 193, 195, 197, 198, 200, 203, 206, 210, 212 213 and 243, using the numbering according to SEQ ID NO: 6, and wherein the variant has an amino acid sequence having a degree of identity of at least 60%, preferred at least 65%, preferred at least 70%, preferred at least 75%, preferred at least 80%, preferred at least 81%, preferred at least 82%, preferred at least 83%, preferred at least 84%, preferred at least 85%, preferred at least 86%, preferred at least 87%, preferred at least 88%, preferred at least 89%, especially preferred at least 90%, preferred at least 91%, preferred at least 92%, preferred at least 93%, preferred at least 94%, preferred at least 95%, preferred at least 96%, preferred at least 97%, preferred at least 98%, preferred at least 99% identity to the amino acid sequence of the parent alpha-amylase, which may be any of the sequences with SEQ ID NO: 2, 4, 6, 8, 10, 12, 14, 16, 18, 20, 22, 24 or 26, preferably SEQ ID NO: 14, 16 or 20, preferably SEQ ID NO: 6, 8, 10, 12, 18, or 22, preferably SEQ ID NO: 6, 8, 10 or 12.

In one further aspect of the present invention, the variant comprises at least one, at least two, or at least three deletions in amino acid region of 181, 182, 183, or 184 and further comprises a substitution at one or more positions selected from the group consisting of 193, 195, 197, 198, 200, 203, 206, 210, 212, 213 and 243, using the numbering according to SEQ ID NO: 6, and wherein the variant has an amino acid sequence having a degree of identity of at least 60%, preferred at least 65%, preferred at least 70%, preferred at least 75%, preferred at least 80%, preferred at least 81%, preferred at least 82%, preferred at least 83%, preferred at least 84%, preferred at least 85%, preferred at least 86%, preferred at least 87%, preferred at least 88%, preferred at least 89%, especially preferred at least 90%, preferred at least 91%, preferred at least 92%, preferred at least 93%, preferred at least 94%, preferred at least 95%, preferred at least 96%, preferred at least 97%, preferred at least 98%, preferred at least 99% identity to the amino acid sequence shown in SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18 or 22, preferably SEQ ID NO: 6, 8, 10 or 12.

In another aspect of the invention the variant comprises a substitution at one or more positions 193, 195, 197, 198, 200, 203, 206, 210, 212, 213 or 243 and a substitution at one or more positions 116, 118, 129, 133, 134, 142, 146, 147, 149, 151, 152, 169, 174, 186, 235, 244, 303, 320, 339, 359, 418, 431, 434, 447, 458, using the numbering according to SEQ ID NO: 6, and wherein the variant have an amino acid sequence having a degree of identity of at least 60%, preferred at least 65%, preferred at least 70%, preferred at least 75%, preferred at least 80%, preferred at least 81%, preferred at least 82%, preferred at least 83%, preferred at least 84%, preferred at least 85%, preferred at least 86%, preferred at least 87%, preferred at least 88%, preferred at least 89%, especially preferred at least 90%, preferred at least 91%, preferred at least 92%, preferred at least 93%, preferred at least 94%, preferred at least 95%, preferred at least 96%, preferred at least 97%, preferred at least 98%, preferred at least 99% identity to the amino acid sequence of the parent alpha-amylase, which may be any of the sequences with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In another aspect of the invention the variant comprising at least one, at least two, or at least three deletions in amino acid region of 181, 182, 183, or 184 and further comprises a substitution at one or more positions 193, 195, 197, 198, 200, 203, 206, 210, 212, 213 or 243 and a substitution at one or more positions 116, 118, 129, 133, 134, 142, 146, 147, 149, 151, 152, 169, 174, 186, 235, 244, 303, 320, 339, 359, 418, 431, 434, 447, 458, using the numbering according to SEQ ID NO: 6, and wherein the variant have an amino acid sequence having a degree of identity of at least 60%, preferred at least 65%, preferred at least 70%, preferred at least 75%, preferred at least 80%, preferred at least 81%, preferred at least 82%, preferred at least 83%, preferred at least 84%, preferred at least 85%, preferred at least 86%, preferred at least 87%, preferred at least 88%, preferred at least 89%, especially preferred at least 90%, preferred at least 91%, preferred at least 92%, preferred at least 93%, preferred at least 94%, preferred at least 95%, preferred at least 96%, preferred at least 97%, preferred at least 98%, preferred at least 99% identity to the amino acid sequence of the parent alpha-amylase, which may be any of the sequences with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the number of amino acid substitutions in the variants of the present invention is below 10 substitutions, such as below 9 substitutions, such as below 8 substitutions, such as below 7 substitutions, such as below 6 substitutions, such as below 5 substitutions, such as below 4 substitutions, such as below 3 substitutions, such as below 2 substitutions, and/or wherein the number of deletions is below 10 deletions, such as below 9 deletions, such as below 8 deletions, such as below 7 deletions, such as below 6 deletions, such as below 5 deletions, such as below 4 deletions, such as below 3 deletions, such as below 2 deletions, such as below 1 deletion or the variant may comprise no deletions and/or wherein the number of insertions is below 10 insertions, such as below 9 insertions, such as below 8 insertions, such as below 7 insertions, such as below 6 insertions, such as below 5 insertions, such as below 4 insertions, such as below 3 insertions, such as below 2 insertions, such as below 1 insertions or the variant may comprise no insertions compared to the parent alpha-amylase which may be any of the sequences with SEQ ID NO: 2, 4, 6, 8, 10, 12, 14, 16, 18, 20, 22, 24 or 26, preferably SEQ ID NO: 6, 8, 10, 12, 18, or 22, preferably SEQ ID NO:14, 16 or 20, preferably SEQ ID NO: 6, 8, 10 or 12.

In one aspect, the variant comprises a substitution at a position corresponding to position 193. In another aspect, the variant comprises a substitution at a position corresponding to position 193 with [G, A, T or M] of the mature polypeptide of SEQ ID NO: 6. In one particular embodiment the variant comprises the substitution S193T of the mature polypeptide of SEQ ID NO: 6. In another aspect, the variant comprising at least one, at least two, or at least three deletions in amino acid region of 181, 182, 183, or 184 and further comprises the substitution S193T, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprises a substitution at position 195, in a preferred aspect the variant comprises a substitution at position 195 with [F, W, Y, L, I or V], in another preferred aspect, the variant comprises F at position 195, in yet another preferred aspect, the variant comprises the substitution N195F, wherein the parent is any of the mature polypeptides with SEQ ID NO: 6, 8, 10 or 12. In another aspect, the variant comprises Y as a substitution at position 195. In another aspect, the variant comprises the substitution N195Y, wherein the parent alpha-amylase is any of the mature polypeptides with SEQ ID NO: 2, 4, 6, 8, 10, 12, 14, 16, 18, 20, 22, 24 or 26, preferably SEQ ID NO: 14, 16 or 20, preferably SEQ ID NO: 6, 8, 10, 12, 18, or 22, preferably SEQ ID NO: 6, 8, 10 or 12.

In one aspect, the variant of a parent alpha-amylase comprising at least one, at least two, or at least three deletions in amino acid region of 181, 182, 183, or 184 and further comprises a substitution at position 195, in a preferred aspect the variant comprises a substitution at position 195 with [F, W, Y, L, I or V], in another preferred aspect, the variant comprises F at position 195, in yet another preferred aspect, the variant comprises the substitution N195F, wherein the parent is any of the mature polypeptides with SEQ ID NO: 2, 4, 6, 8, 10, 12, 14, 16, 18, 20, 22, 24 or 26, preferably SEQ ID NO: 6, 8, 10, 12, 18, or 22, preferably SEQ ID NO: 6, 8, 10 or 12. In another aspect, the variant comprises Y as a substitution at position 195. In another aspect, the variant comprising at least one, at least two, or at least three deletions in amino acid region of 181, 182, 183, or 184 and further comprises the substitution N195Y, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprises a substitution at position 197, in a preferred aspect the variant comprises a substitution at position 197 with [F, W, Y, L, I or V], in another preferred aspect, the variant comprises F at position 197, in yet another preferred aspect, the variant comprises the substitution N197F, wherein the parent is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12. In another aspect, the variant comprises L as a substitution at position 197. In another aspect, the variant comprising at least one, at least two, or at least three deletions in amino acid region of 181, 182, 183, or 184 and further comprises the substitution N197L, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprising at least one, at least two, or at least three deletions in amino acid region of 181, 182, 183, or 184 and further comprises a substitution at position 197, in a preferred aspect the variant comprises a substitution at position 197 with [F, W, Y, L, I or V], in another preferred aspect, the variant comprises F at position 197, in yet another preferred aspect, the variant comprises the substitution N197F, wherein the parent is any of the mature polypeptides with SEQ ID NO: 6, 8, 10 or 12. In another aspect, the variant comprises L as a substitution at position 197. In another aspect, the variant comprising at least one, at least two, or at least three deletions in amino acid region of 181, 182, 183, or 184 and further comprises the substitution N197L, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprises a substitution at position 198, in a preferred aspect the variant comprises a substitution at position 198 with [Q, N, D, E, R, K or H], in another preferred aspect, the variant comprises N at position 198, in yet another preferred aspect, the variant comprises the substitution Y198N, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, 20 or 22, preferably SEQ ID NO: 6, 8, 10 or 12.

In one aspect, the variant of a parent alpha-amylase comprising at least one, at least two, or at least three deletions in amino acid region of 181, 182, 183, or 184 and further comprises a substitution at position 198, in a preferred aspect the variant comprises a substitution at position 198 with [Q, N, D, E, R, K or H], in another preferred aspect, the variant comprises F at position 198, in yet another preferred aspect, the variant comprises the substitution Y198N, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprises a substitution at position 200, in a preferred aspect the variant comprises a substitution at position 200 with [F, W, Y, L, I or V], in another preferred aspect, the variant comprises F at position 200, in yet another preferred aspect, the variant comprises the substitution Y200F, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprising at least one, at least two, or at least three deletions in amino acid region of 181, 182, 183, or 184 and further comprises a substitution at position 200, in a preferred aspect the variant comprises a substitution at position 200 with [F, W, Y, L, I or V], in another preferred aspect, the variant comprises F at position 200, in yet another preferred aspect, the variant comprises the substitution Y200F, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprises a substitution at position 203, in a preferred aspect the variant comprises a substitution at position 203 with [F, W, Y, L, I or V], in another preferred aspect, the variant comprises F at position 203, in yet another preferred aspect, the variant comprises the substitution Y203F, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprising at least one, at least two, or at least three deletions in amino acid region of 181, 182, 183, or 184 and further comprises a substitution at position 203, in a preferred aspect the variant comprises a substitution at position 203 with [F, W, Y, L, I or V], in another preferred aspect, the variant comprises F at position 203, in yet another preferred aspect, the variant comprises the substitution Y203F, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprises a substitution at position 206, in a preferred aspect the variant comprises a substitution at position 206 with [F, W, Y, N, L, I, V, H, Q, D, or E], in another preferred aspect, the variant comprises F at position 206, in yet another preferred aspect, the variant comprises Y at position 206, in still another aspect the variant comprises L at position 206, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one particular embodiment the variant comprises the substitution V206Y of the mature polypeptide of SEQ ID NO: 6 or 12. In another particular embodiment the variant comprises the substitution I206Y of the mature polypeptide of SEQ ID NO: 8 or 10.

In one particular embodiment the variant comprises the substitution V206F of the mature polypeptide of SEQ ID NO: 6 or 12. In another particular embodiment the variant comprises the substitution I206F of the mature polypeptide of SEQ ID NO: 8 or 10.

In one particular embodiment the variant comprises the substitution V206L of the mature polypeptide of SEQ ID NO: 6 or 12. In another particular embodiment the variant comprises the substitution I206L of the mature polypeptide of SEQ ID NO: 8 or 10.

In one particular embodiment the variant comprises the substitution V206H of the mature polypeptide of SEQ ID NO: 6 or 12. In another particular embodiment the variant comprises the substitution I206H of the mature polypeptide of SEQ ID NO: 8 or 10.

In one aspect, the variant of a parent alpha-amylase comprising at least one, at least two, or at least three deletions in amino acid region of 181, 182, 183, or 184 and further comprises a substitution at position 206, in a preferred aspect the variant comprises a substitution at position 206 with [F, W, Y, N, L, I, V, H, Q, D, or E], in another preferred aspect, the variant comprises F at position 206, in another preferred aspect, the variant comprises Y at position 206.

In one particular embodiment the variant comprising at least one, at least two, or at least three deletions in amino acid region of 181, 182, 183, or 184 and further comprises the substitution V206Y of the mature polypeptide of SEQ ID NO: 6 or 12. In another particular embodiment the variant comprising at least one, at least two, or at least three deletions in amino acid region of 181, 182, 183, or 184 and further comprises the substitution I206Y of the mature polypeptide of SEQ ID NO: 8 or 10.

In one particular embodiment the variant comprising at least one, at least two, or at least three deletions in amino acid region of 181, 182, 183, or 184 and further comprises the substitution V206L of the mature polypeptide of SEQ ID NO: 6 or 12. In another particular embodiment the variant comprising at least one, at least two, or at least three deletions in amino acid region of 181, 182, 183, or 184 and further comprises the substitution I206L of the mature polypeptide of SEQ ID NO: 8 or 10.

In one particular embodiment the variant comprising at least one, at least two, or at least three deletions in amino acid region of 181, 182, 183, or 184 and further comprises the substitution V206H of the mature polypeptide of SEQ ID NO: 6 or 12. In another particular embodiment the variant comprising at least one, at least two, or at least three deletions in amino acid region of 181, 182, 183, or 184 and further comprises the substitution I206H of the mature polypeptide of SEQ ID NO: 8 or 10

In one aspect, the variant of a parent alpha-amylase comprises a substitution at position 210, in a preferred aspect the variant comprises a substitution at position 210 with [F, W, Y, L, I or V], in another preferred aspect, the variant comprises Y at position 210, in yet another preferred aspect, the variant comprises the substitution H210Y, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprising at least one, at least two, or at least three deletions in amino acid region of 181, 182, 183, or 184 and further comprises a substitution at position 210, in a preferred aspect the variant comprises a substitution at position 210 with [F, W, Y, L, I or V], in another preferred aspect, the variant comprises Y at position 210, in yet another preferred aspect, the variant comprises the substitution H210Y, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprises a substitution at position 212, in a preferred aspect the variant comprises a substitution at position 212 with [F, W, Y, L, I or V], in another preferred aspect, the variant comprises V at position 212, in yet another preferred aspect, the variant comprises the substitution E212V, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprising at least one, at least two, or at least three deletions in amino acid region of 181, 182, 183, or 184 and further comprises a substitution at position 212, in a preferred aspect the variant comprises a substitution at position 212 with [F, W, Y, L, I or V], in another preferred aspect, the variant comprises V at position 212, in yet another preferred aspect, the variant comprises the substitution E212V, wherein the parent alpha-amylase is any of the mature polypeptides with SEQ ID NO: 2, 4, 6, 8, 10, 12, 14, 16, 18, 20, 22, 24 or 26, preferably SEQ ID NO: 6, 8, 10, 12, 18, or 22, preferably SEQ ID NO: 6, 8, 10 or 12.

In one aspect, the variant of a parent alpha-amylase comprises a substitution at position 213, in a preferred aspect the variant comprises a substitution at position 213 with [G, A, S, T or M], in another preferred aspect, the variant comprises A at position 213, in yet another preferred aspect, the variant comprises the substitution V213A, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprising at least one, at least two, or at least three deletions in amino acid region of 181, 182, 183, or 184 and further comprises a substitution at position 213, in a preferred aspect the variant comprises a substitution at position 213 with [G, A, S, T or M], in another preferred aspect, the variant comprises A at position 213, in yet another preferred aspect, the variant comprises the substitution V213A, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprises a substitution at position 243, in a preferred aspect the variant comprises a substitution at position 243 with [F, W, Y, L, I or V], in another preferred aspect, the variant comprises F at position 243, in yet another preferred aspect, the variant comprises the substitution Y243F, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In one aspect, the variant of a parent alpha-amylase comprising at least one, at least two, or at least three deletions in amino acid region of 181, 182, 183, or 184 and further comprises a substitution at position 243, in a preferred aspect the variant comprises a substitution at position 243 with [F, W, Y, L, I or V], in another preferred aspect, the variant comprises A at position 243, in yet another preferred aspect, the variant comprises the substitution Y243F, wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In another aspect, the variant comprises substitutions at positions 193 and 195. In another aspect, the variant comprises substitutions at positions 193 and 195 with [F, W, Y, L, I, V, N, G, A, T, M or Q]. In another aspect, the variant comprises T and F as substitutions at positions 193 and 195, respectively. In another aspect, the variant comprises the substitutions S193T+N195F of the mature polypeptide of SEQ ID NO: 6. In another aspect, the variant comprises T and Y as substitutions at positions 193 and 195, respectively. In another aspect, the variant comprises the substitutions S193T+N195Y of the mature polypeptide of SEQ ID NO: 6.

In another aspect, the variant of a parent alpha-amylase comprising at least one, at least two, or at least three deletions in amino acid region of 181, 182, 183, or 184 and further comprises substitutions at positions 193 and 195. In another aspect, the variant comprising at least one, at least two, or at least three deletions in amino acid region of 181, 182, 183, or 184 and further comprises substitutions at positions 193 and 195 with [F, W, Y, L, I, V, N, G, A, T, M or Q]. In another aspect, the variant comprises T and F as substitutions at positions 193 and 195, respectively. In another aspect, the variant comprising at least one, at least two, or at least three deletions in amino acid region of 181, 182, 183, or 184 and further comprises the substitutions S193T+N195F of the mature polypeptide of SEQ ID NO: 6. In another aspect, the variant comprises T and Y as substitutions at positions 193 and 195, respectively. In another aspect, the variant comprising at least one, at least two, or at least three deletions in amino acid region of 181, 182, 183, or 184 and further comprises the substitutions S193T+N195Y of the mature polypeptide of SEQ ID NO: 6.

In another aspect, the variant of a parent alpha-amylase comprises a substitution at positions 195 and 198, using the numbering of SEQ ID NO: 6. In another aspect, the variant comprises a substitution at positions 195 and 198 with [F, W, Y, L, I, V, N or Q]. In another aspect, the variant comprises F and N as substitutions at positions 195 and 198, respectively. In another aspect, the variant comprises the substitutions N195F+Y198N wherein the parent is any of the mature polypeptides with SEQ ID NO: 6, 8, 10 or 12. In another aspect, the variant comprises Y and N as substitutions at positions 195 and 198, respectively. In another aspect, the variant comprises the substitutions N195Y+Y198N wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In another aspect, the variant of a parent alpha-amylase comprising at least one, at least two, or at least three deletions in amino acid region of 181, 182, 183, or 184 and further comprises a substitution at positions 195 and 198, using the numbering of SEQ ID NO: 6. In another aspect, the variant comprising at least one, at least two, or at least three deletions in amino acid region of 181, 182, 183, or 184 and further comprises substitutions at positions 195 and 198 with [F, W, Y, L, I, V, N or Q]. In another aspect, the variant comprises F and N as substitutions at positions 195 and 198, respectively. In another aspect, the variant comprising at least one, at least two, or at least three deletions in amino acid region of 181, 182, 183, or 184 and further comprises the substitutions N195F+Y198N wherein the parent is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12. In another aspect, the variant comprises Y and N as substitutions at positions 195 and 198, respectively. In another aspect, the variant comprising at least one, at least two, or at least three deletions in amino acid region of 181, 182, 183, or 184 and further comprises the substitutions N195Y+Y198N wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In another aspect, the variant of a parent alpha-amylase comprises a substitution at positions 195 and 206 using numbering according to SEQ ID NO: 6. In another aspect, the variant comprises a substitution at positions 195 and 206 with [F, W, Y, V, I, L, C, N, S, T, D, E or H]. In another aspect, the variant comprises F and L as substitutions at positions 195 and 206, respectively. In another aspect, the variant comprises the substitutions N195F+V206 [F, Y, L, H, or N] of the mature polypeptide of SEQ ID NO: 6 or 12. In another aspect, the variant comprises the substitutions N195F+I206[F, Y, L, or H] of the mature polypeptide of SEQ ID NO: 8 or 10. In another aspect, the variant comprises Y and L as substitutions at 195 and 206, respectively. In another aspect, the variant comprises the substitutions N195Y+V206 [F, Y, L, H, or N] of the mature polypeptide of SEQ ID NO: 6 or 12. In another aspect, the variant comprises the substitutions N195Y+I206 [F, Y, L, H, or N] of the mature polypeptide of SEQ ID NO: 8 or 10.

In another aspect, the variant of a parent alpha-amylase comprising at least one, at least two, or at least three deletions in amino acid region of 181, 182, 183, or 184 and further comprises substitutions at positions 195 and 206 using the numbering according to SEQ ID NO: 6. In another aspect, the variant comprising at least one, at least two, or at least three deletions in amino acid region of 181, 182, 183, or 184 and further comprises substitutions at positions 195 and 206 with [F, W, Y, V, I, L, C, N, S, T, D, E or H]. In another aspect, the variant comprises F and L as substitutions at positions 195 and 206, respectively. In another aspect, the variant comprising at least one, at least two, or at least three deletions in amino acid region of 181, 182, 183, or 184 and further comprises the substitutions N195F+V206 [For Y] of the mature polypeptide of SEQ ID NO: 6 or 12. In another aspect, the variant comprising at least one, at least two, or at least three deletions in amino acid region of 181, 182, 183, or 184 and further comprises the substitutions N195F+I206 [F, Y, L, H, or N] of the mature polypeptide of SEQ ID NO: 8 or 10. In another aspect, the variant comprises Y and L as substitutions at positions 195 and 206, respectively. In another aspect, the variant comprising at least one, at least two, or at least three deletions in amino acid region of 181, 182, 183, or 184 and further comprises the substitutions N195Y+V206 [F, Y, L, H, or N] of the mature polypeptide of SEQ ID NO: 6 or 12. In another aspect, the variant comprising at least one, at least two, or at least three deletions in amino acid region of 181, 182, 183, or 184 and further comprises the substitutions N195Y+I206F of the mature polypeptide of SEQ ID NO: 8 or 10.

In another aspect, the variant of a parent alpha-amylase comprises substitutions at positions 195 and 210 using the numbering according to SEQ ID NO: 6. In another aspect, the variant comprises a substitution at positions 195 and 210 with [F, W, Y, V, I, L, C, N, S, T or H]. In another aspect, the variant comprises F and Y as substitutions at positions 195 and 210, respectively. In another aspect, the variant comprises the substitutions N195F+H210Y wherein the parent is any of the mature polypeptides with SEQ ID NO: 6, 8, 10 or 12. In another aspect, the variant comprises Y as substitution at positions 195 and 210. In another aspect, the variant comprises the substitutions N195Y+H210Y wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In another aspect, the variant of a parent alpha-amylase comprising at least one, at least two, or at least three deletions in amino acid region of 181, 182, 183, or 184 and further comprises substitutions at positions 195 and 210 using the numbering according to SEQ ID NO: 6. In another aspect, the variant comprising at least one, at least two, or at least three deletions in amino acid region of 181, 182, 183, or 184 and further comprises substitutions at positions 195 and 210 with [F, W, Y, V, I, L, C, N, S, T or H]. In another aspect, the variant comprises F and Y as substitutions at positions 195 and 210, respectively. In another aspect, the variant comprising at least one, at least two, or at least three deletions in amino acid region of 181, 182, 183, or 184 and further comprises the substitutions N195F+H210Y wherein the parent alpha-amylase is any of the mature polypeptides with SEQ ID NO: 6, 8, 10, 12, 18, or 22, preferably SEQ ID NO: 6, 8, 10 or 12. In another aspect, the variant comprises Y as substitution at positions corresponding to positions 195 and 210. In another aspect, the variant comprising at least one, at least two, or at least three deletions in amino acid region of 181, 182, 183, or 184 and further comprises the substitutions N195Y+H210Y wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In another aspect, the variant parent alpha-amylase comprises substitutions at positions corresponding to positions 198 and 206 using numbering according to SEQ ID NO: 6. In another aspect, the variant comprises substitutions at positions 198 and 206 with [N, Q, L, I, F, Y, C, N, S, T, D, E or H]. In another aspect, the variant comprises N and [F or Y] as substitutions at positions 198 and 206, respectively. In another aspect, the variant comprises the substitutions Y198N+V206 [F, Y, L, H, or N] of the mature polypeptide of SEQ ID NO: 6 or 12. In another aspect, the variant comprises the substitutions Y198N+I206 [F, Y, L, H or N] of the mature polypeptide of SEQ ID NO: 8 or 10.

In another aspect, the variant parent alpha-amylase comprising at least one, at least two, or at least three deletions in amino acid region of 181, 182, 183, or 184 and further comprises substitutions at positions corresponding to positions 198 and 206 using numbering according to SEQ ID NO: 6. In another aspect, the variant comprising at least one, at least two, or at least three deletions in amino acid region of 181, 182, 183, or 184 and further comprises substitutions at positions 198 and 206 with [N, Q, L, 1, F, Y, C, N, S, T, D, E or H]. In another aspect, the variant comprises N and [For Y] as substitutions at positions 198 and 206, respectively. In another aspect, the variant comprising at least one, at least two, or at least three deletions in amino acid region of 181, 182, 183, or 184 and further comprises the substitutions Y198N+V206 [F, Y, L, H, or N] of the mature polypeptide of SEQ ID NO: 6 or 12. In another aspect, the variant comprising at least one, at least two, or at least three deletions in amino acid region of 181, 182, 183, or 184 and further comprises the substitutions Y198N+1206 [F, Y, L, H or N] of the mature polypeptide of SEQ ID NO: 8 or 10.

In another aspect, the variant of a parent alpha-amylase comprises substitutions at positions 206 and 213, using the numbering according to SEQ ID NO: 6. In another aspect, the variant comprises a substitution at positions 206 and 213 with [D, E, L, 1, V, F, Y, W, G, A, S, T or M]. In another aspect, the variant comprises [F or Y] and A as substitutions at positions 206 and 210, respectively. In another aspect, the variant comprises the substitutions V206F or Y+V213A of the mature polypeptide of SEQ ID NO: 6 or 12. In another aspect, the variant comprises the substitutions 1206 [F, Y, L, H, or N]+V213A of the mature polypeptide of SEQ ID NO: 8 or 10.

In another aspect, the variant of a parent alpha-amylase comprising at least one, at least two, or at least three deletions in amino acid region of 181, 182, 183, or 184 and further comprises substitutions at positions 206 and 213, using the numbering according to SEQ ID NO: 6. In another aspect, the variant comprising at least one, at least two, or at least three deletions in amino acid region of 181, 182, 183, or 184 and further comprises substitutions at positions 206 and 213 with [D, E, L, 1, V, F, Y, W, G, A, S, T or M]. In another aspect, the variant comprises [F or Y] and A as substitutions at positions 206 and 210, respectively. In another aspect, the variant comprising at least one, at least two, or at least three deletions in amino acid region of 181, 182, 183, or 184 and further comprises the substitutions V206 [F, Y, L, H, or N], V213A of the mature polypeptide of SEQ ID NO: 6 or 12. In another aspect, the variant comprising at least one, at least two, or at least three deletions in amino acid region of 181, 182, 183, or 184 and further comprises the substitutions 1206 [F, Y, L, H, or N]+V213A of the mature polypeptide of SEQ ID NO: 8 or 10.

In another aspect, the variant of a parent alpha-amylase comprises substitutions at positions 195 and 243 using the numbering according to SEQ ID NO: 6. In another aspect, the variant comprises a substitution at positions 195 and 243 with [F, W, Y, L, 1 or V]. In another aspect, the variant comprises F as substitutions at positions 195 and 243, respectively. In another aspect, the variant comprises the substitutions N195F+Y243F, wherein the parent alpha-amylase is any of the mature polypeptides with SEQ ID NO: 6, 8, 10 or 12. In another aspect, the variant comprises Y and F as substitutions at positions 195 and 243, respectively. In another aspect, the variant comprises the substitutions N195Y+Y243F wherein the parent alpha-amylase is any of the mature polypeptides with SEQ ID NO: 6, 8, 10 or 12.

In another aspect, the variant of a parent alpha-amylase comprising at least one, at least two, or at least three deletions in amino acid region of 181, 182, 183, or 184 and further comprises substitutions at positions corresponding to positions 195 and 243. In another aspect, the variant comprising at least one, at least two, or at least three deletions in amino acid region of 181, 182, 183, or 184 and further comprises substitutions at positions 195 and 243 with [F, W, Y, L, 1 or V]. In another aspect, the variant comprises F as substitutions at positions 195 and 243, respectively. In another aspect, the variant comprising at least one, at least two, or at least three deletions in amino acid region of 181, 182, 183, or 184 and further comprises the substitutions N195F+Y243F wherein the parent alpha-amylase is any of the mature polypeptides with SEQ ID NO: 6, 8, 10 or 12. In another aspect, the variant comprises Y and F as substitutions at positions 195 and 243, respectively. In another aspect, the variant comprising at least one, at least two, or at least three deletions in amino acid region of 181, 182, 183, or 184 and further comprises the substitutions N195Y+Y243F wherein the parent alpha-amylase is any of the mature polypeptides with SEQ ID NO: 2, 4, 6, 8, 10, 12, 14, 16, 18, 20, 22, 24 or 26, preferably SEQ ID NO: 6, 8, 10, 12, 18, or 22, preferably SEQ ID NO: 6, 8, 10 or 12.

In another aspect, the variant of a parent alpha-amylase comprises substitutions at positions 206 and 243 using the numbering according to SEQ ID NO: 6. In another aspect, the variant comprises a substitution at positions 206 and 243 with [H, D, E, N, F, W, Y, L, I or V]. In another aspect, the variant comprises L and F as substitutions at positions 206 and 243, respectively. In another aspect, the variant comprises the substitutions V206 [F, Y, L, H, or N]+Y243F of the mature polypeptide of SEQ ID NO: 6 or 12. In another aspect, the variant comprises the substitutions V206 [F, Y, L, H, or N]+Y243F of the mature polypeptide of SEQ ID NO: 8 or 10.

In another aspect, the variant of a parent alpha-amylase comprising at least one, at least two, or at least three deletions in amino acid region of 181, 182, 183, or 184 and further comprises substitutions at positions 206 and 243 using the numbering according to SEQ ID NO: 6. In another aspect, the variant comprising at least one, at least two, or at least three deletions in amino acid region of 181, 182, 183, or 184 and further comprises substitutions at positions 206 and 243 with [H, D, E, N, F, W, Y, L, I or V]. In another aspect, the variant comprises L and F as substitutions at positions 206 and 243, respectively. In another aspect, the variant comprising at least one, at least two, or at least three deletions in amino acid region of 181, 182, 183, or 184 and further comprises the substitutions V206 [F, Y, L, H, or N]+Y243F of the mature polypeptide of SEQ ID NO: 6 or 12. In another aspect, the variant comprising at least one, at least two, or at least three deletions in amino acid region of 181, 182, 183, or 184 and further comprises the substitutions V206 [F, Y, L, H, or N]+Y243F of the mature polypeptide of SEQ ID NO: 8 or 10. In another aspect, the variant of a parent alpha-amylase comprises substitutions at positions 193, 195, and 197 using the numbering according to SEQ ID NO: 6. In another aspect, the variant comprises a substitution at positions 193, 195, and 197 with [F, W, Y, L, I or V]. In another aspect, the variant comprises T and F as substitutions at positions corresponding to positions 193, 195, and 197, respectively. In another aspect, the variant comprises the substitutions S193T+N195F+N197F wherein the parent alpha-amylase is any of the mature polypeptides with SEQ ID NO: 2, 4, 6, 8, 10, 12, 14, 16, 18, 20, 22, 24 or 26, preferably SEQ ID NO: 6, 8, 10, 12, 18, or 22, preferably SEQ ID NO: 6, 8, 10 or 12. In another aspect, the variant comprises T, F and L as substitutions at positions 193, 195, and 197, respectively. In another aspect, the variant comprises the substitutions S193T+N195F+N197L wherein the parent alpha-amylase is any of the mature polypeptides with SEQ ID NO: 2, 4, 6, 8, 10, 12, 14, 16, 18, 20, 22, 24 or 26, preferably SEQ ID NO: 6, 8, 10, 12, 18, or 22, preferably SEQ ID NO: 6, 8, 10 or 12. In another aspect, the variant comprises T, Y and F as substitutions at positions corresponding to positions 193, 195, and 197, respectively. In another aspect, the variant comprises the substitutions S193T+N195Y+N197F wherein the parent alpha-amylase is any of the mature polypeptides with SEQ ID NO: 2, 4, 6, 8, 10, 12, 14, 16, 18, 20, 22, 24 or 26, preferably SEQ ID NO: 6, 8, 10, 12, 18, or 22, preferably SEQ ID NO: 6, 8, 10 or 12. In another aspect, the variant comprises T, Y and L as substitutions at positions corresponding to positions 193, 195, and 197, respectively. In another aspect, the variant comprises the substitutions S193T+N195Y+N197L wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, 20 or 22, preferably SEQ ID NO: 6, 8, 10 or 12.

In another aspect, the variant comprising at least one, at least two, or at least three deletions in amino acid region of 181, 182, 183, or 184 and further comprises substitutions at positions 193, 195, and 197 using the numbering according to SEQ ID NO: 6. In another aspect, the variant comprising at least one, at least two, or at least three deletions in amino acid region of 181, 182, 183, or 184 and further comprises substitutions at positions 193, 195, and 197 with [F, W, Y, L, I or V]. In another aspect, the variant comprises T and F as substitutions at positions 193, 195, and 197, respectively. In another aspect, the variant comprising at least one, at least two, or at least three deletions in amino acid region of 181, 182, 183, or 184 and further comprises the substitutions S193T+N195F+N197F wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12. In another aspect, the variant comprises T, F and L as substitutions at positions 193, 195, and 197, respectively. In another aspect, the variant comprising at least one, at least two, or at least three deletions in amino acid region of 181, 182, 183, or 184 and further comprises the substitutions S193T+N195F+N197L, wherein the parent alpha-amylase is any of the mature polypeptides with SEQ ID NO: 2, 4, 6, 8, 10, 12, 14, 16, 18, 20, 22, 24 or 26, preferably SEQ ID NO: 6, 8, 10, 12, 18, or 22, preferably SEQ ID NO:14, 16 or 20, preferably SEQ ID NO: 6, 8, 10 or 12. In another aspect, the variant comprises T, Y and F as substitutions at positions 193, 195, and 197, respectively. In another aspect, the variant comprising at least one, at least two, or at least three deletions in amino acid region of 181, 182, 183, or 184 and further comprises the substitutions S193T+N195Y+N197F wherein the parent alpha-amylase is any of the mature polypeptides with SEQ ID NO: 6, 8, 10 or 12. In another aspect, the variant comprises T, Y and L as substitutions at positions 193, 195, and 197, respectively. In another aspect, the variant comprising at least two, or at least three deletions in amino acid region of 181, 182, 183, or 184 and further comprises the substitutions S193T+N195Y+N197L wherein the parent alpha-amylase is any of the mature polypeptides with SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 18, or 22, preferably SEQ ID NO: 6, 8, 10 or 12.

In another aspect, the variant of a parent alpha-amylase comprises substitutions at positions 195, 206 and 243 using the numbering according to SEQ ID NO: 6. In another aspect, the variant comprises substitutions at positions 195, 206 and 243 with [D, E, L, I, F, V, Y, C, N, S, T or H]. In another aspect, the variant comprises F, Y and F as substitutions at positions 195, 206, and 243, respectively. In another aspect, the variant comprises the substitutions N195F+V206Y+Y243F of the mature polypeptide of SEQ ID NO: 6 or 12. In another aspect, the variant comprises the substitutions N195F+I206Y+Y243F of the mature polypeptide of SEQ ID NO: 8 or 10. In another aspect, the variant comprises Y, Y and F as substitutions at positions 195, 206, and 243, respectively. In another aspect, the variant comprises the substitutions N195Y+V206Y+Y243F of the mature polypeptide of SEQ ID NO: 6 or 12. In another aspect, the variant comprises the substitutions N195Y+I206Y+Y243F of the mature polypeptide of SEQ ID NO: 8 or 10.

In another aspect, the variant of a parent alpha-amylase comprises substitutions at positions 195, 206 and 243 using the numbering according to SEQ ID NO: 6. In another aspect, the variant comprises substitutions at positions 195, 206 and 243 with [D, E, L, I, F, V, Y, C, N, S, T or H]. In another aspect, the variant comprises F, L and F as substitutions at positions 195, 206, and 243, respectively. In another aspect, the variant comprises the substitutions N195F+V206L+Y243F of the mature polypeptide of SEQ ID NO: 6 or 12. In another aspect, the variant comprises the substitutions N195F+I206L+Y243F of the mature polypeptide of SEQ ID NO: 8 or 10. In another aspect, the variant comprises Y, L and F as substitutions at positions 195, 206, and 243, respectively. In another aspect, the variant comprises the substitutions N195Y+V206L+Y243F of the mature polypeptide of SEQ ID NO: 6 or 12. In another aspect, the variant comprises the substitutions N195Y+I206L+Y243F of the mature polypeptide of SEQ ID NO: 8 or 10.

In another aspect, the variant of a parent alpha-amylase comprises substitutions at positions 195, 206 and 243 using the numbering according to SEQ ID NO: 6. In another aspect, the variant comprises substitutions at positions 195, 206 and 243 with [D, E, L, I, F, V, Y, C, N, S, T or H]. In another aspect, the variant comprises F, N and F as substitutions at positions 195, 206, and 243, respectively. In another aspect, the variant comprises the substitutions N195F+V206N+Y243F of the mature polypeptide of SEQ ID NO: 6 or 12. In another aspect, the variant comprises the substitutions N195F+I206N+Y243F of the mature polypeptide of SEQ ID NO: 8 or 10. In another aspect, the variant comprises Y, N and F as substitutions at positions 195, 206, and 243, respectively. In another aspect, the variant comprises the substitutions N195Y+V206N+Y243F of the mature polypeptide of SEQ ID NO: 6 or 12. In another aspect, the variant comprises the substitutions N195Y+I206N+Y243F of the mature polypeptide of SEQ ID NO: 8 or 10.

In another aspect, the variant of a parent alpha-amylase comprises substitutions at positions 195, 206 and 243 using the numbering according to SEQ ID NO: 6. In another aspect, the variant comprises substitutions at positions 195, 206 and 243 with [D, E, L, I, F, V, Y, C, N, S, T or H]. In another aspect, the variant comprises F, H and F as substitutions at positions 195, 206, and 243, respectively. In another aspect, the variant comprises the substitutions N195F+V206H+Y243F of the mature polypeptide of SEQ ID NO: 6 or 12. In another aspect, the variant comprises the substitutions N195F+I206H+Y243F of the mature polypeptide of SEQ ID NO: 8 or 10. In another aspect, the variant comprises Y, H and F as substitutions at positions 195, 206, and 243, respectively. In another aspect, the variant comprises the substitutions N195Y+V206H+Y243F of the mature polypeptide of SEQ ID NO: 6 or 12. In another aspect, the variant comprises the substitutions N195Y+I206H+Y243F of the mature polypeptide of SEQ ID NO: 8 or 10.

In another aspect, the variant of a parent alpha-amylase comprises substitutions at positions 195, 206 and 243 using the numbering according to SEQ ID NO: 6. In another aspect, the variant comprises substitutions at positions 195, 206 and 243 with [D, E, L, I, F, V, Y, C, N, S, T or H]. In another aspect, the variant comprises F, F and F as substitutions at positions 195, 206, and 243, respectively. In another aspect, the variant comprises the substitutions N195F+V206F+Y243F of the mature polypeptide of SEQ ID NO: 6 or 12. In another aspect, the variant comprises the substitutions N195F+I206F+Y243F of the mature polypeptide of SEQ ID NO: 8 or 10. In another aspect, the variant comprises Y, F and F as substitutions at positions 195, 206, and 243, respectively. In another aspect, the variant comprises the substitutions N195Y+V206F+Y243F of the mature polypeptide of SEQ ID NO: 6 or 12. In another aspect, the variant comprises the substitutions N195Y+I206F+Y243F of the mature polypeptide of SEQ ID NO: 8 or 10.

In another aspect, the variant of a parent alpha-amylase comprising at least one, at least two, or at least three deletions in amino acid region of 181, 182, 183, or 184 and further comprises substitutions at positions 195, 206 and 243, using the numbering according to SEQ ID NO: 6. In another aspect, the variant comprising at least one, at least two, or at least three deletions in amino acid region of 181, 182, 183, or 184 and further comprises substitutions at positions 195, 206 and 243 with [D, E, L, I, F, V, Y, C, N, S, T or H]. In another aspect, the variant comprises F, Y and F as substitutions at positions 195, 206, and 243, respectively. In another aspect, the variant comprising at least one, at least two, or at least three deletions in amino acid region of 181, 182, 183, or 184 and further comprises the substitutions N195F+V206Y+Y243F of the mature polypeptide of SEQ ID NO: 6 or 12. In another aspect, the variant comprising at least one, at least two, or at least three deletions in amino acid region of 181, 182, 183, or 184 and further comprises the substitutions N195F+I206Y+Y243F of the mature polypeptide of SEQ ID NO: 8 or 10. In another aspect, the variant comprises Y, Y and F as substitutions at positions 195, 206, and 243, respectively. In another aspect, the variant comprising at least one, at least two, or at least three deletions in amino acid region of 181, 182, 183, or 184 and further comprises the substitutions N195Y+V206Y+Y243F of the mature polypeptide of SEQ ID NO: 6 or 12. In another aspect, the variant comprising at least one, at least two, or at least three deletions in amino acid region of 181, 182, 183, or 184 and further comprises the substitutions N195Y+I206Y+Y243F of the mature polypeptide of SEQ ID NO: 8 or 10.

In another aspect, the variant of a parent alpha-amylase comprising at least one, at least two, or at least three deletions in amino acid region of 181, 182, 183, or 184 and further comprises substitutions at positions 195, 206 and 243, using the numbering according to SEQ ID NO: 6. In another aspect, the variant comprising at least one, at least two, or at least three deletions in amino acid region of 181, 182, 183, or 184 and further comprises substitutions at positions 195, 206 and 243 with [D, E, L, I, F, V, Y, C, N, S, T or H]. In another aspect, the variant comprises F, L and F as substitutions at positions 195, 206, and 243, respectively. In another aspect, the variant comprising at least one, at least two, or at least three deletions in amino acid region of 181, 182, 183, or 184 and further comprises the substitutions N195F+V206L+Y243F of the mature polypeptide of SEQ ID NO: 6 or 12. In another aspect, the variant comprising at least one, at least two, or at least three deletions in amino acid region of 181, 182, 183, or 184 and further comprises the substitutions N195F+I206L+Y243F of the mature polypeptide of SEQ ID NO: 8 or 10. In another aspect, the variant comprises Y, L and F as substitutions at positions 195, 206, and 243, respectively. In another aspect, the variant comprising at least one, at least two, or at least three deletions in amino acid region of 181, 182, 183, or 184 and further comprises the substitutions N195Y+V206L+Y243F of the mature polypeptide of SEQ ID NO: 6 or 12. In another aspect, the variant comprising at least one, at least two, or at least three deletions in amino acid region of 181, 182, 183, or 184 and further comprises the substitutions N195Y+I206L+Y243F of the mature polypeptide of SEQ ID NO: 8 or 10.

In another aspect, the variant of a parent alpha-amylase comprising at least one, at least two, or at least three deletions in amino acid region of 181, 182, 183, or 184 and further comprises substitutions at positions 195, 206 and 243, using the numbering according to SEQ ID NO: 6. In another aspect, the variant comprising at least one, at least two, or at least three deletions in amino acid region of 181, 182, 183, or 184 and further comprises substitutions at positions 195, 206 and 243 with [D, E, L, I, F, V, Y, C, N, S, T or H]. In another aspect, the variant comprises F, N and F as substitutions at positions 195, 206, and 243, respectively. In another aspect, the variant comprising at least one, at least two, or at least three deletions in amino acid region of 181, 182, 183, or 184 and further comprises the substitutions N195F+V206N+Y243F of the mature polypeptide of SEQ ID NO: 6 or 12. In another aspect, the variant comprising at least one, at least two, or at least three deletions in amino acid region of 181, 182, 183, or 184 and further comprises the substitutions N195F+I206N+Y243F of the mature polypeptide of SEQ ID NO: 8 or 10. In another aspect, the variant comprises Y, N and F as substitutions at positions 195, 206, and 243, respectively. In another aspect, the variant comprising at least one, at least two, or at least three deletions in amino acid region of 181, 182, 183, or 184 and further comprises the substitutions N195Y+V206N+Y243F of the mature polypeptide of SEQ ID NO: 6 or 12. In another aspect, the variant comprising at least one, at least two, or at least three deletions in amino acid region of 181, 182, 183, or 184 and further comprises the substitutions N195Y+I206N+Y243F of the mature polypeptide of SEQ ID NO: 8 or 10.

In another aspect, the variant of a parent alpha-amylase comprising at least one, at least two, or at least three deletions in amino acid region of 181, 182, 183, or 184 and further comprises substitutions at positions 195, 206 and 243, using the numbering according to SEQ ID NO: 6. In another aspect, the variant comprising at least one, at least two, or at least three deletions in amino acid region of 181, 182, 183, or 184 and further comprises substitutions at positions 195, 206 and 243 with [D, E, L, I, F, V, Y, C, N, S, T or H]. In another aspect, the variant comprises F, H and F as substitutions at positions 195, 206, and 243, respectively. In another aspect, the variant comprising at least one, at least two, or at least three deletions in amino acid region of 181, 182, 183, or 184 and further comprises the substitutions N195F+V206H+Y243F of the mature polypeptide of SEQ ID NO: 6 or 12. In another aspect, the variant comprising at least one, at least two, or at least three deletions in amino acid region of 181, 182, 183, or 184 and further comprises the substitutions N195F+I206H+Y243F of the mature polypeptide of SEQ ID NO: 8 or 10. In another aspect, the variant comprises Y, H and F as substitutions at positions 195, 206, and 243, respectively. In another aspect, the variant comprising at least one, at least two, or at least three deletions in amino acid region of 181, 182, 183, or 184 and further comprises the substitutions N195Y+V206H+Y243F of the mature polypeptide of SEQ ID NO: 6 or 12. In another aspect, the variant comprising at least one, at least two, or at least three deletions in amino acid region of 181, 182, 183, or 184 and further comprises the substitutions N195Y+I206H+Y243F of the mature polypeptide of SEQ ID NO: 8 or 10.

In another aspect, the variant of a parent alpha-amylase comprising at least one, at least two, or at least three deletions in amino acid region of 181, 182, 183, or 184 and further comprises substitutions at positions 195, 206 and 243, using the numbering according to SEQ ID NO: 6. In another aspect, the variant comprising at least one, at least two, or at least three deletions in amino acid region of 181, 182, 183, or 184 and further comprises substitutions at positions 195, 206 and 243 with [D, E, L, I, F, V, Y, C, N, S, T or H]. In another aspect, the variant comprises F, F and F as substitutions at positions 195, 206, and 243, respectively. In another aspect, the variant comprising at least one, at least two, or at least three deletions in amino acid region of 181, 182, 183, or 184 and further comprises the substitutions N195F+V206F+Y243F of the mature polypeptide of SEQ ID NO: 6 or 12. In another aspect, the variant comprising at least one, at least two, or at least three deletions in amino acid region of 181, 182, 183, or 184 and further comprises the substitutions N195F+I206F+Y243F of the mature polypeptide of SEQ ID NO: 8 or 10. In another aspect, the variant comprises Y, F and F as substitutions at positions 195, 206, and 243, respectively. In another aspect, the variant comprising at least one, at least two, or at least three deletions in amino acid region of 181, 182, 183, or 184 and further comprises the substitutions N195Y+V206F+Y243F of the mature polypeptide of SEQ ID NO: 6 or 12. In another aspect, the variant comprising at least one, at least two, or at least three deletions in amino acid region of 181, 182, 183, or 184 and further comprises the substitutions N195Y+I206F+Y243F of the mature polypeptide of SEQ ID NO: 8 or 10.

In one aspect of the invention the variant comprising at least one, at least two, or at least three deletions in amino acid region of 181, 182, 183, or 184 and one or more of the following substitutions N195 [F or Y], N197 [F or L], Y198N, Y200F, Y203F, I206 [H, L, N, F, or Y], H210Y, E212 [V or G], V213A and a substitution at one or more positions M116T, Q129L, G133E, E134Y, K142R, P146S, G147E, G149R, N151R, Y152H, Q169E, N174R, G186R, Y243F, S244Q, G303V, R320N, R359I, N418D, A447V of the mature polypeptide sequence of SEQ ID NO: 10 or an amino acid sequence having a degree of identity of at least 60%, preferred at least 65%, preferred at least 70%, preferred at least 75% preferred at least 80%, preferred at least 81%, preferred at least 82%, preferred at least 83%, preferred at least 84% preferred at least 85%, preferred at least 86%, preferred at least 87%, preferred at least 88%, preferred at least 89%, especially preferred at least 90%, especially preferred at least 91%, especially preferred at least 92%, especially preferred at least 93%, especially preferred at least 94%, even especially more preferred at least 95% homology, more preferred at least 96%, more preferred at least 97%, more preferred at least 98%, more preferred at least 99% to the amino acid sequence with SEQ ID NO: 10.

In another aspect of the invention the variant comprising at least one, at least two, or at least three deletions in amino acid region of 181, 182, 183, or 184 and one or more of the following substitutions N195 [F or Y], N197 [F or L], Y198N, Y200F, Y203F, I206 [F, Y, L, H, or N], H210Y, E212 [V or G], V213A and a substitution at one or more positions M116T, Q129L, G133E, E134Y, P146S, G147E, G149R, T151R, Y152H, Q169E, N174R, A186R, Y243F, S244Q, G303V, R320N, R359I, N418D, A447V of the mature polypeptide sequence of SEQ ID NO: 8 or an amino acid sequence having a degree of identity of at least 60%, preferred at least 65%, preferred at least 70%, preferred at least 75% preferred at least 80%, preferred at least 81%, preferred at least 82%, preferred at least 83%, preferred at least 84% preferred at least 85%, preferred at least 86%, preferred at least 87%, preferred at least 88%, preferred at least 89%, especially preferred at least 90%, especially preferred at least 91%, especially preferred at least 92%, especially preferred at least 93%, especially preferred at least 94%, even especially more preferred at least 95% homology, more preferred at least 96%, more preferred at least 97%, more preferred at least 98%, more preferred at least 99% to the amino acid sequence with SEQ ID NO: 8.

In one aspect of the invention the variant comprising at least one, at least two, or at least three deletions in amino acid region of 181, 182, 183, or 184 and one or more of the following substitutions N195 [F or Y], N197 [F or L], Y198N, Y200F, Y203F, V206 [F, Y, L, H, or N], H210Y, E212 [V or G], V213A, or Y243F and a substitution at one or more positions I116T, Q129L, G133E, E134Y, K142R, P146S, G147E, G149R, N151R, Y152H, Q169E, Q174R, A186R, S244Q, G303V, K320N, R359I, N418D, A447V of the mature polypeptide sequence of SEQ ID NO: 6 or an amino acid sequence having a degree of identity of at least 60%, preferred at least 65%, preferred at least 70%, preferred at least 75% preferred at least 80%, preferred at least 81%, preferred at least 82%, preferred at least 83%, preferred at least 84% preferred at least 85%, preferred at least 86%, preferred at least 87%, preferred at least 88%, preferred at least 89%, especially preferred at least 90%, especially preferred at least 91%, especially preferred at least 92%, especially preferred at least 93%, especially preferred at least 94%, even especially more preferred at least 95% homology, more preferred at least 96%, more preferred at least 97%, more preferred at least 98%, more preferred at least 99% to the amino acid sequence with SEQ ID NO: 6.

In one aspect of the invention the variant comprising at least one, at least two, or at least three deletions in amino acid region of 181, 182, 183, or 184 and one or more of the following substitutions N195 [F or Y], N197 [F or L], Y198N, Y200F, Y203F, V206 [F, Y, L, H, or N], H210Y, E212 [V or G], V213A or Y243F and a substitution at one or more positions I116T, Q129L, G133E, E134Y, K142R, P146S, G147E, G149R, N151R, Y152H, Q169E, Q174R, A186R, S244Q, G303V, K320N, R359I, N418D, A447V of the mature polypeptide sequence of SEQ ID NO: 12 or an amino acid sequence having a degree of identity of at least 60%, preferred at least 65%, preferred at least 70%, preferred at least 75%, preferred at least 80%, preferred at least 81%, preferred at least 82%, preferred at least 83%, preferred at least 84%, preferred at least 85%, preferred at least 86%, preferred at least 87%, preferred at least 88%, preferred at least 89%, especially preferred at least 90%, especially preferred at least 91%, especially preferred at least 92%, especially preferred at least 93%, especially preferred at least 94%, even especially more preferred at least 95% homology, more preferred at least 96%, more preferred at least 97%, more preferred at least 98%, more preferred at least 99% to the amino acid sequence with SEQ ID NO: 12.

Thus one aspect of the invention concern variants of a parent alpha-amylase comprising an alteration at one or more positions selected from the group consisting of 195, 197, 198, 200, 203, 206, 210, 212, 213 and 243 and further comprising an alteration at one or more positions selected from the group consisting of 116, 118, 129, 133, 134, 142, 146, 147, 149, 151, 152, 169, 174, 186, 235, 244, 303, 320, 359, 418, 431, 434, 447 and 458 wherein
(a) the alteration(s) are independently
 (i) an insertion of an amino acid immediately downstream of the position,
 (ii) a deletion of the amino acid which occupies the position, and/or
 (iii) a substitution of the amino acid which occupies the position,
(b) the variant has alpha-amylase activity; and
(c) each position corresponds to a position of the amino acid sequence of the enzyme having the amino acid sequence of SEQ ID NO:6.

Thus one aspect of the invention concern variants of a parent alpha-amylase comprising at least one, at least two, or at least three deletions in amino acid region of 181, 182, 183, or 184 and an alteration at one or more positions selected from the group consisting of 195, 197, 198, 200, 203, 206, 210, 212, 213, 243 and further comprising an alteration at one or more positions selected from the group consisting of 116, 118, 129, 133, 134, 142, 146, 147, 149, 151, 152, 169, 174, 186, 235, 244, 303, 320, 339, 359, 418, 431, 434, 447 and 458 wherein
(a) the alteration(s) are independently
 (i) an insertion of an amino acid immediately downstream and adjacent of the position, (ii) a deletion of the amino acid which occupies the position, and/or
 (iii) a substitution of the amino acid which occupies the position,
(b) the variant has alpha-amylase activity; and
(c) each position corresponds to a position of the amino acid sequence of the enzyme having the amino acid sequence of SEQ ID NO:6.

Preferably the variant comprises an amino acid sequence which has a degree of identity of at least 70%, preferably at least 75%, more preferably at least 80%, more preferably at least 85%, even more preferably at least 90%, most preferably at least 95%, and even most preferably at least about 97% to the amino acid sequence of one of SEQ ID NO: 2, 4, 6, 8, 10, 12, 14, 16, 18, 20, 22, 24 or 26, preferably SEQ ID NO:14, 16 or 20, preferably SEQ ID NO: 6, 8, 10, 12, 14, 16, 18, 22, or 20.

Preferably, the variants comprising alterations at one or more of the above identified positions have an increased stability in compositions comprising a chelating agent such as industrial compositions, e.g. detergent, preferably in liquid detergent as compared to the parent alpha-amylase.

The inventors have found that these variants have an improved stability relative to the parent alpha-amylase in compositions comprising a chelating agent wherein said chelating agent at a concentration below 10 mM is capable of reducing the concentration of free calcium ions from 2.0 mM to 0.10 mM, at 21° C. and pH 8.0, as described under "Materials and Methods".

Thus another aspect the invention relates to a method for preparing a polypeptide comprising;
 (a) providing an amino acid sequence of a parent polypeptide having amylase activity;
 (b) selecting one or more amino acid which occupies one or more position corresponding to positions 195, 197, 198, 200, 203, 206, 210, 212, 213, 243, and further selecting one or more position corresponding to positions 116, 118, 129, 133, 134, 142, 146, 147, 149, 151, 152, 169, 174, 186, 235, 244, 303, 320, 339, 359, 418, 431, 434, 447, 458 of the mature polypeptide of SEQ ID NO: 6;

(c) modifying the sequence by substituting or deleting the selected amino acid residue or inserting one or more amino acid residues downstream and adjacent to the selected amino acid residue;
(d) producing a variant polypeptide having the modified sequence;
(e) testing the variant polypeptide for amylase activity and stability; and
(f) selecting a variant polypeptide having amylase activity and increased stability relative to the parent polypeptide in the presence of a chelating agent wherein said chelating agent at a concentration below 10 mM is capable of reducing the concentration of free calcium ions from 2.0 mM to 0.10 mM at 21° C. and pH 8.0.

Preferably the variants comprises alterations at three positions, more preferred four positions even more preferred five positions and most preferred six positions, in a particularly preferred embodiment the variant comprising at least one, at least two, or at least three deletions in amino acid region of 181, 182, 183, or 184 and further one or more substitution at one or more positions corresponding to positions in the parent alpha-amylase selected from the group consisting of 193, 195, 197, 198, 200, 203, 206, 210, 212, 213, 243 (using numbering according to SEQ ID NO: 6).

Thus a preferred aspect relates to a variant of a parent alpha-amylase comprising at least one, at least two, or at least three deletions in amino acid region of 181, 182, 183, or 184 an alteration at one or more positions selected from the group consisting of 195, 197, 198, 200, 203, 206, 210, 212, 213, 243 and further comprising an alteration at one or more positions selected from the group consisting of 116, 118, 129, 133, 134, 142, 146, 147, 149, 151, 152, 169, 174, 186, 235, 244, 303, 320, 339, 359, 418, 413, 434, 447, 458 wherein
(a) the alteration(s) are independently
  (i) an insertion of an amino acid immediately downstream and adjacent of the position,
  (ii) a deletion of the amino acid which occupies the position, and/or
  (iii) a substitution of the amino acid which occupies the position,
(b) the variant has alpha-amylase activity; and
(c) each position corresponds to a position of the amino acid sequence of the enzyme having the amino acid sequence of SEQ ID NO:6.

In a preferred embodiment the variant alpha-amylase have one or more (several) amino acid deletions and/or substitutions and/or insertions. In a particularly preferred embodiment the variant alpha-amylases include an alpha-amylase, which has the amino acid sequence shown in SEQ ID NO: 6 herein and which further comprise the following alteration: D183*+G184* (deletion at position 183 and 184), this variant show good performance in detergents and have improved stability in the presence of chelating agents.

In a preferred embodiment the variant alpha-amylase comprises SP707 (SEQ ID NO: 8) including any of SP707+R181* G182*, SP707+G182* H183*, SP707+H183* G184*.

In another preferred embodiment the variant alpha-amylase comprises SP722 (SEQ ID NO: 6) including any of SP722+R181* G182*, SP722+G182* D183*, SP722+D183* G184*.

In yet another preferred embodiment the variant alpha-amylase comprises AA560 (SEQ ID NO: 10) including any of AA560+R181* G182*, AA560+G182* D183*, AA560+D183* G184*.

In another preferred embodiment the parent alpha-amylase comprises SP690 (SEQ ID NO: 12) including any of SP690+R181* G182*; SP690+G182* T183*; SP690+T183* G184*.

"SP722+R181* G182* means the Bacillus spp. alpha-amylase SP722 has been mutated by deletions in positions R181 and G182 wherein the numbering corresponds to SEQ.ID NO: 6.

Thus in one aspect of the invention the variant alpha-amylase comprises any one of the following: SP722, SP690, SP707 or AA560 including any of:
SP722+R181*G182*, SP722+G182*+D183*, SP722+D183*+G184*; SP722+R181*G182* N195F; SP722+G182* D183* N195F; SP722+D183* G184* N195F; SP722+R181*G182* M202L; SP722+G182* D183* M202L; SP722+D183* G184* M202L; SP722+R181* G182* N195F M202L; SP722+G182 D183* N195F M202L; SP722+D183* G184* N195F M202L; SP722+D183* G184* N195F V206LY243F; SP722+D183* G184* N195F V206YY243F SP722+D183* G184* N195F V206F Y243F; SP722+R181* G182* R181Q; SP722+G182* D183* R181Q; SP722+D183* G184* R181Q; SP722+R181* G182* L118K N195F H458K; SP722+G182* D183* L118K N195F H458K; SP722+D183* G184* L118K N195F H458K; SP722+D183* G184* G133E G149R N195Y Y203F V206L.
AA560+R181* G182*, AA560+G182* D183*, AA560+D183* G184*; AA560+R181* G182* N195F; AA560+G182* D183* N195F; AA560+D183* G184* N195F; AA560+D183* G184* I206Y; AA560+D183* G184* Y243F; AA560+D183* G184* I206L Y243F; AA560+D183* G184* N195F I206L; AA560+D183* G184* N195F Y243F; AA560+D183* G184* N195F I206L, Y243F; AA560+D183* G184* N195F I206Y Y243F; AA560+D183* G184* N195F I206F; AA560+R181* G182* M202L; AA560+G182* D183* M202L; AA560+D183* G184* M202L; AA560+R181* G182* N195F M202L; AA560+G182* D183* N195F M202L; AA560+D183* G184* N195F M202L; AA560+R181* G182* R118K N195F R320K T458K; AA560+G182* D183* R118K N195F R320K T458K; AA560+D183* G184* R118K N195F R320K T458K; AA560+D183* G184* R118K N195F I206L R320K R458K; AA560+D183* G184* R118K N195F I206Y R320K R458K; AA560+D183* G184* R118K N195F Y243F R320K R458K; AA560+D183* G184* R118K N195F I206L Y243F R320K R458K.
SP707+R181* G182*, SP707+G182* H183*, SP707+H183* G184*; SP707+R181* G182* N195F; SP707+G182* H183* N195F; SP707+H183* G184* N195F I206L, Y243F; SP707+H183* G184* N195F I206Y Y243F; SP707+H183* G184* N195F I206F Y243F; SP707+H183* G184* N195F; SP707+R181* G182* M202L; SP707+G182* H183* M202L; SP707+D183* G184* M202L; SP707+R181* G182* N195F M202L; SP707+G182* H183* N195F M202L; SP707+H183* G184* N195F M202L; SP707+R181* G182* R181Q; SP707+G182* H183* R181Q; SP707+H183* G184* R181Q; SP707+R181* G182* R118K N195F R320K R458K; SP707+G182* H183* R118K N195F R320K R458K; SP707+H183* G184* R118K N195F R320K R458K;
SP690+R181* G182*, SP690+G182* T183*, SP690+T183* G184*; SP690+R181* G182* N195F; SP690+G182* T183* N195F; SP690+T183* G184* N195F; SP690+T183* G184* N195F V206L, Y243F; SP690+T183* G184* N195F V206Y Y243F; SP690+T183* G184* N195F V206F Y243F SP690+R181* G182* M202L; SP690+G182* T183* M202L; SP690+T183* G184*

M202L; SP690+R181* N195F M202L; SP690+ G182* T183* N195F M202L; SP690+T183* G184* N195F M202L; SP690+R181* G182* R118K N195F R320K R458K; SP690+G182* T183* R118K N195F R320K R458K; SP690+T183* G184* R118K N195F R320K R458K.

"SP722+R181* G182* N195F" means the *Bacillus* spp. alpha-amylase SP722 has been mutated as follows: deletions in positions R181 and G182 and a substitution from Asn (N) to Phe (F) in position 195 wherein the numbering corresponds to SEQ.ID NO: 6 (Counting as if the deleted positions are still present i.e. the numbering does not shift down by two when deleting two positions).

In a particular preferred embodiment of the invention the alterations are selected from the following substitutions:

X193A, C, E, F, G, H, I, K, L, M, N, P, Q, R, S, T, V, W, X, Y, preferably S193T;
X195A, C, E, F, G, H, I, K, L, M, N, P, Q, R, S, T, V, W, X, Y, preferably N195 [For Y];
X197A, C, D, E, F, G, H, I, K, L, N, P, Q, R, S, T, V, W, X, Y, preferably N197 [F or L];
X198A, C, E, F, G, H, I, K, L, M, N, P, Q, R, S, T, V, W, X, Y, preferably Y198N;
X200A, C, D, E, F, G, H, I, L, M, N, P, Q, R, S, T, V, W, X, Y, preferably Y200F;
X203A, C, D, E, F, G, H, I, K, L, M, N, P, Q, R, T, V, W, X, Y, preferably Y203F.
X206A, C, D, E, F, G, H, I, K, L, N, P, Q, R, S, T, V, W, X, Y, preferably V206 [F, Y, L, H, or N];
X210A, C, E, F, G, H, I, K, L, M, N, P, Q, R, S, T, V, W, X, Y, preferably H210Y;
X212A, C, D, E, F, G, H, I, L, M, N, P, Q, R, S, T, V, W, X, Y, preferably E212 [V or G]; and
X213A, C, D, E, F, G, H, I, K, L, M, N, P, Q, R, S, T, V, W, X, Y, preferably V213A.
X243A, C, D, E, F, G, I, K, L, M, N, P, Q, R, S, T, V, W, Y, preferably Y243F In another preferred embodiment the variants comprises alterations at three positions, more preferred four positions, more preferred five positions and more preferred six positions, in a particularly preferred embodiment the variant comprising at least one, at least two, or at least three deletions in amino acid region of 181, 182, 183, or 184 and further an altering at one or more positions corresponding to positions selected from the group consisting of 193, 195, 197, 198, 200, 203, 206, 210, 212, 213, 243 and an altering at one or more positions corresponding to positions selected from the group consisting of 116, 129, 133, 142, 146, 147, 149, 151, 152, 169, 174, 186, 244, 303, 320, 359, 418, 447 (using numbering according to SEQ ID NO: 6).

Thus in a particular preferred embodiment of the invention the alterations are selected from the following substitutions:

X116A, C, D, E, F, G, H, I, K, L, M, P, Q, R, S, T, V, W, Y, preferably N116T
X118A, C, D, E, F, G, H, I, K, L, M, P, Q, R, S, T, V, W, Y, preferably R118K
X129A, C, D, E, F, G, H, I, K, L, M, N, P, Q, R, S, T, V, W, Y, preferably Q129L
X133A, C, D, E, F, H, I, K, L, M, N, P, Q, R, S, T, V, W, Y, preferably G133E
X134A, C, D, E, F, G, H, I, L, M, N, P, Q, R, S, T, V, W, Y, preferably D134Y
X142A, C, D, E, F, H, I, K, L, M, N, P, Q, R, S, T, V, W, Y, preferably K142R
X146A, C, E, F, G, H, I, K, L, M, N, P, Q, R, S, T, V, W, Y, preferably P146S
X147A, C, D, E, F, G, H, I, K, L, M, N, P, Q, R, S, T, W, Y, preferably G147E
X149A, C, D, E, F, G, I, K, L, M, N, P, Q, R, S, T, V, W, Y, preferably G149R
X151A, C, D, E, F, G, H, I, K, L, M, P, Q, R, S, T, V, W, Y, preferably T151R
X152A, C, D, E, F, G, H, I, K, L, M, P, Q, R, S, T, V, W, Y, preferably Y152H
X169A, C, E, F, G, H, I, K, L, M, N, P, Q, R, S, T, V, W, Y, preferably Q169E
X174C, D, E, F, G, H, I, K, L, M, N, P, Q, R, S, T, V, W, Y, preferably Q174R
X186A, C, D, E, F, G, H, I, K, L, M, N, P, Q, R, S, T, W, Y, preferably A186R
X235A, C, D, E, F, G, H, I, K, L, M, P, Q, R, S, T, V, W, Y, preferably I235N
X244A, C, D, E, F, G, I, K, L, M, N, P, Q, R, S, T, V, W, Y, preferably S244Q
X303A, C, D, E, F, G, H, I, K, L, M, P, Q, R, S, T, V, W, Y, preferably G303V
X320A, C, E, F, G, H, I, K, L, M, N, P, Q, R, S, T, V, W, Y, preferably K320N
X339A, C, D, E, F, G, H, I, K, L, M, P, Q, R, S, T, V, W, Y, preferably S339P
X359C, D, E, F, G, H, I, K, L, M, N, P, Q, R, S, T, V, W, Y, preferably R359I
X418A, C, D, E, F, G, H, I, K, L, M, P, Q, R, S, T, V, W, Y, preferably N418D
X431A, C, D, E, F, G, H, I, K, L, M, P, Q, R, S, T, V, W, Y, preferably S431T
X434A, C, D, E, F, G, H, I, K, L, M, P, Q, R, S, T, V, W, Y, preferably P434T
X447A, C, E, F, G, H, I, K, L, M, N, P, Q, R, S, T, V, W, Y, preferably A447V
X458A, C, D, E, F, G, H, I, K, L, M, P, Q, R, S, T, V, W, Y, preferably R458K In a particular preferred embodiment the variant further comprising at least one, at least two, or at least three deletions in amino acid region of 181, 182, 183, or 184.

In a preferred embodiment, the number of amino acid substitutions in the variants of the present invention is preferably 17 substitutions, more preferably 16 substitutions, more preferably 15 substitutions, more preferably 14 substitutions, more preferably 13 substitutions, more preferably 12 substitutions, more preferably 11 substitutions, more preferably 10 substitutions, more preferably 9 substitutions, more preferably 8 substitutions, more preferably 7 substitutions, more preferably 6 substitutions, more preferably 5 substitutions, more preferably 4 substitutions, even more preferably 3 substitutions, and most preferably 2 substitution. In another preferred embodiment, the number of amino acid substitutions in the variants of the present invention consists of preferably 17 substitutions, more preferably 16 substitutions, more preferably 15 substitutions, more preferably 14 substitutions, more preferably 13 substitutions, more preferably 12 substitutions, more preferably 11 substitutions, more preferably 10 substitutions, more preferably 9 substitutions, more preferably 8 substitutions, more preferably 7 substitutions, more preferably 6 substitutions, more preferably 5 substitutions, more preferably 4 substitutions, even more preferably 3 substitutions, and most preferably 2 substitution.

In particular preferred embodiment the variants according to the present invention comprises a combinations of different alterations. Thus in an preferred embodiment the variant according to the present invention comprising at least one, at least two, or at least three deletions in amino acid region of 181, 182, 183, or 184, preferably deletion at position 183 and 184 and further comprises one of the following combinations of alterations substitutions at positions 186 and 195; substitutions at positions 174 and 212; substitutions at positions 206 and 212; substitutions at positions 206, 212 and 304; substitutions at positions 206, 212, 304 and 447; substitutions at positions 116 and 133; substitutions at positions 235 and 339; substitutions at positions 193 and 206; substitutions at positions 116, 133 and 142; substitutions at positions 116, 133, 142 and 198; substitutions at positions 116, 133, 142, 198 and 206; substitutions at positions 133 and 195; substitutions at positions 133, 195 and 198; substitutions at positions 133, 195, 198 and 200; substitutions at positions 116 and 195; substitutions at positions 116, 195 and 198; substitutions at positions 142 and 146; substitutions at positions 142, 146 and 149; substitutions at positions 142, 146, 149 and 195; substitutions at positions 142, 146, 149, 195 and 198; substitutions at positions 142, 146, 149, 195, 198 and 206; substitutions at positions 151 and 210; substitutions at positions 151, 210 and 320; substitutions at positions 186, 195, 212 and 213; substitutions at positions 151, 210, 320 and 359; substitutions at positions 151, 210, 320, 359 and 418; substitutions at positions 147 and 149; substitutions at positions 147, 149 and 169; substitutions at positions 147, 149, 169 and 198; substitutions at positions 147, 149, 169, 198 and 203; substitutions at positions 147, 149, 169, 198, 203 and 206; substitutions at positions 133 and 149; substitutions at positions 133, 149 and 195; substitutions at positions 133, 149, 195 and 198; substitutions at positions 133, 149, 195, 198 and 203; substitutions at positions 147 and 152; substitutions at positions 147, 152 and 169; substitutions at positions 147, 152, 169 and 198; substitutions at positions 147, 152, 169, 198 and 206; substitutions at positions 195 and 206; substitutions at positions 195 and 243; substitutions at positions 195 and 210; substitutions at positions 206 and 210; substitutions at positions 186 and 195; substitutions at positions 195 and 206; substitutions at positions 195, 206 and 243; substitutions at positions 206 and 243; substitutions at positions 133 and 149; substitutions at positions 133, 149 and 198; substitutions at positions 133, 149, 198 and 206; substitutions at positions 116 and 133; substitutions at positions 116, 133 and 147; substitutions at positions 116, 133, 147 and 152; substitutions at positions 116, 133, 147, 152 and 198; substitutions at positions 116, 133, 147, 152, 198 and 203; substitutions at positions 116, 133, 147, 152, 198, 203 and 206; substitutions at positions 147 and 149; substitutions at positions 147, 149 and 195; substitutions at positions 147, 149, 195 and 198; substitutions at positions 147, 149, 195, 198 and 206; substitutions at positions 133 and 142; substitutions at positions 133, 142 and 195; substitutions at positions 133, 142, 195 and 198; substitutions at positions 133 and 149; substitutions at positions 133, 149 and 152; substitutions at positions 133, 149, 152 and 195; substitutions at positions 133, 149, 152, 195 and 198; substitutions at positions 133, 149, 152, 195, 198 and 206; substitutions at positions 116 and 129; substitutions at positions 116, 129 and 142; substitutions at positions 116, 129, 142 and 195; substitutions at positions 116, 129, 142, 195 and 198; substitutions at positions 116, 129, 142, 195, 198 and 203; substitutions at positions 116, 129, 142, 195, 198, 203 and 206; substitutions at positions 133 and 149; substitutions at positions 133, 149 and 152; substitutions at positions 133, 149, 152 and 195; substitutions at positions 133, 149, 152, 195 and 198; substitutions at positions 133, 149, 152, 195, 198 and 203; substitutions at positions 133, 149, 152, 195, 198, 203 and 206; substitutions at positions 116 and 133; substitutions at positions 116, 133 and 149; substitutions at positions 116, 133, 149 and 198; substitutions at positions 116, 133, 149, 198 and 203; substitutions at positions 116, 133, 149, 198, 203 and 206; substitutions at positions 195 and 198; substitutions at positions 195, 198 and 203; substitutions at positions 195, 198, 203 and 206; substitutions at positions 133, 149, 195, 203, and 206.

In another particular preferred embodiment the variants according to the present invention comprises a combinations of different alterations. Thus in an preferred embodiment the variant according to the present invention comprising at least one, at least two, or at least three deletions in amino acid region of 181, 182, 183, or 184, preferably deletion at position 183 and 184 and further comprises one of the following combinations of alterations substitutions at positions 186 with [R, T, K, H, E, D, Q, or N] and 195 with [F, W, Y, L, I, or oV]; substitutions at positions 174 with [R, K, H, E, D, Q, or N] and 212 with [F, W, Y, L, I, or V]; substitutions at positions 206 with [D, E, F, W, Y, L, I, V, N, Q, or H] and 212 with [F, W, Y, L, I, or V]; substitutions at positions 206 with [F, W, Y, L, I, V, N, Q, or H], 212 with [F, W, Y, L, I, or V] and 304 with [F, W, Y, L, I, or V]; substitutions at positions 206 with [F, W, Y, L, I, V, N, Q, or H], 212 with [F, W, Y, L, I, or V], 304 with [F, W, Y, L, I, or V] and 447 with [F, W, Y, L, I, or V]; substitutions at positions 116 with [G, A, S, T, or M] and 133 with [E or D]; substitutions at positions 235 with [N or L] and 339 with [P]; substitutions at positions 193 with [G, A, T or M] and 206 with [F, W, Y, L, I, V, N, Q, or H]; substitutions at positions 116 with [G, A, S, T, or M], 133 with [E or D] and 142 with [R, K, H, Q, or N]; substitutions at positions 116 with [G, A, S, T, or M], 133 with [E or D], 142 with [R, K, H, Q, or N] and 198 with [Q or N]; substitutions at positions 116 with [G, A, S, T, or M], 133 with [E or D], 142 with [R, K, H, Q, or N], 198 with [Q or N] with [Q or N] and 206 with [F, W, Y, L, I, V, N, Q, or H]; substitutions at positions 133 with [E or D] and 195 with [F, W, Y, L, I, or V]; substitutions at positions 133 with [E or D], 195 with [F, W, Y, L, I, or V] and 198 with [Q or N]; substitutions at positions 186 with [R, T, K, H, E, D, Q, or N], 195, with [F, W, Y, L, I, or V], 212 with [F, W, Y, L, I, or V] and 213; with [A]; substitutions at positions 133 with [E or D], 195 with [F, W, Y, L, I, or V], 198 with [Q or N] and 200 with [F, W, Y, L, I, or V]; substitutions at positions 116 with [G, A, S, T, or M] and 195 with [F, W, Y, L, I, or V]; substitutions at positions 116 with [G, A, S, T, or M], 195 with [F, W, Y, L, I, or V] and 198 with [Q or N]; substitutions at positions 142 with [R, K, H, Q, or N] and 146 with [G, A, S, T, or M]; substitutions at positions 142 with [R, K, H, Q, or N], 146 with [G, A, S, T, or M] and 149 with [R, K, H, Q, or N]; substitutions at positions 142 with [R, K, H, Q, or N], 146 with [G, A, S, T, or M], 149 with [R, K, H, Q, or N] and 195 with [F, W, Y, L, I, or V]; substitutions at positions 142 with [R, K, H, Q, or N], 146 with [G, A, S, T, or M], 149 with [R, K, H, Q, or N], 195 with [F, W, Y, L, I, or V] and 198 with [Q, or N]; substitutions at positions 142 with [R, K, H, Q, or N], 146 with [G, A, S, T, or M], 149 with [R, K, H, Q, or N], 195 with [F, W, Y, L, I, or V], 198 with [Q, N] and 206 with [F, W, Y, L, I, V, N, Q, or H]; substitutions at positions 151 with [R] and 210 with [F, W, Y, L, I, or V]; substitutions at positions 151 with [R], 210 with [F, W, Y, L, I, or V] and 320 with [Q, or N]; substitutions at positions 151 with [R], 210 with [F, W, Y, L, I, or V], 320 with [Q, N] and 359 with [F, W, Y, L, I, or V]; substitutions at positions 151 with [R], 210 with [F, W, Y, L, I, or V], 320 with [Q, or N], 359 with [F, W, Y, L, I, or V] and 418 with [E, or D]; substitutions at positions 147 with

[E, or D] and 149 with [R, K, H, Q, or N]; substitutions at positions 147 with [E, or D], 149 with [R, K, H, Q, or N] and 169 with [E, or D]; substitutions at positions 147 with [E, or D], 149 with [R, K, H, Q, or N], 169 with [E, or D] and 198 with [Q, or N]; substitutions at positions 147 with [E, or D], 149 with [R, K, H, Q, or N], 169 with [E, or D], 198 with [Q, or N] and 203 with [F, W, Y, L, I, or V]; substitutions at positions 147 with [E, or D], 149 with [R, K, H, Q, or N], 169 with [E, or D], 198 with [Q, or N], 203 with [F, W, Y, L, I, or V] and 206 with [F, W, Y, L, I, V, N, Q, or H]; substitutions at positions 133 with [E, or D] and 149 with [R, K, H, Q, or N]; substitutions at positions 133 with [E, or D], 149 with [R, K, H, Q, or N] and 195 with [F, W, Y, L, I, or V]; substitutions at positions 133 with [E, or D], 149 with [R, K, H, Q, or N], 195 with [F, W, Y, L, I, or V] and 198 with [Q, or N]; substitutions at positions 133 with [E, or D], 149 with [R, K, H, Q, or N], 195 with [F, W, Y, L, I, or V], 198 with [Q, or N] and 203 with [F, W, Y, L, I, or V]; substitutions at positions 147 with [E, or D] and 152 with [R, K, H, Q, or N]; substitutions at positions 147 with [E, or D], 152 with [R, K, H, Q, or N] and 169 with [E, or D]; substitutions at positions 147 with [E, or D], 152 with [R, K, H, Q, or N], 169 with [E, or D] and 198 with [Q, or N]; substitutions at positions 147 with [E, or D], 152 with [R, K, H, Q, or N], 169 with [E, or D], 198 with [Q, or N] and 206 with [F, W, Y, L, I, V, N, Q, or H]; substitutions at positions 195 with [F, W, Y, L, I, or V] and 206 with [F, W, Y, L, I, V, N, Q, or H]; substitutions at positions 195 with [F, W, Y, L, I, or V] and 243 with [F, W, Y, L, I, or V]; substitutions at positions 195 with [F, W, Y, L, I, or V] and 210 with [F, W, Y, L, I, or V]; substitutions at positions 206 with [F, W, Y, L, I, V, N, Q, or H] and 210 with [F, W, Y, L, I, or V]; substitutions at positions 186 with [R, T, K, H, E, D, Q, or N] and 195 with [F, W, Y, L, I, or V]; substitutions at positions 195 with [F, W, Y, L, I, or V] and 206 with [F, W, Y, L, I, V, N, Q, or H]; substitutions at positions 195 with [F, W, Y, L, I, or V], 206 and 243 with [F, W, Y, L, I, or V]; substitutions at positions 206 and 243 with [F, W, Y, L, I, or V]; substitutions at positions 133 with [E, or D] and 149 with [R, K, H, Q, or N]; substitutions at positions 133 with [E, or D], 149 with [R, K, H, Q, or N] and 198 with [Q, or N]; substitutions at positions 133 with [E, or D], 149 with [R, K, H, Q, or N], 198 with [Q, or N] and 206; substitutions at positions 116 with [G, A, S, T, or M] and 133 with [E, or D]; substitutions at positions 116 with [G, A, S, T, or M], 133 with [E, or D] and 147 with [E, or D]; substitutions at positions 116 with [G, A, S, T, or M], 133 with [E, or D], 147 with [E, or D] and 152 with [R, K, H, Q, or N]; substitutions at positions 116 with [G, A, S, T, or M], 133 with [E, or D], 147 with [E, or D], 152 with [R, K, H, Q, or N] and 198 with [Q, or N]; substitutions at positions 116 with [G, A, S, T, or M], 133 with [E, or D], 147 with [E, or D], 152 with [R, K, H, Q, or N], 198 with [Q, or N] and 203 with [F, W, Y, L, I, or V]; substitutions at positions 116 with [G, A, S, T, or M], 133 with [E, or D], 147 with [E, or D], 152 with [R, K, H, Q, or N], 198 with [Q, or N], 203 with [F, W, Y, L, I, or V] and 206; substitutions at positions 147 with [E, or D] and 149 with [R, K, H, Q, or N]; substitutions at positions 147 with [E, or D], 149 with [R, K, H, Q, or N] and 195 with [F, W, Y, L, I, or V]; substitutions at positions 147 with [E, or D], 149 with [R, K, H, Q, or N], 195 with [F, W, Y, L, I, or V] and 198 with [Q, or N]; substitutions at positions 147 with [E, or D], 149 with [R, K, H, Q, or N], 195 with [F, W, Y, L, I, or V], 198 with [Q, or N] and 206; substitutions at positions 133 with [E, or D] and 142 with [R, K, H, Q, or N]; substitutions at positions 133 with [E, or D], 142 with [R, K, H, Q, or N] and 195 with [F, W, Y, L, I, or V]; substitutions at positions 133 with [E, or D], 142 with [R, K, H, Q, or N], 195 with [F, W, Y, L, I, or V] and 198 with [Q, or N]; substitutions at positions 133 with [E, or D] and 149 with [R, K, H, Q, or N]; substitutions at positions 133 with [E, or D], 149 with [R, K, H, Q, or N] and 152 with [R, K, H, Q, or N]; substitutions at positions 133 with [E, or D], 149 with [R, K, H, Q, or N], 152 with [R, K, H, Q, or N] and 195 with [F, W, Y, L, I, or V]; substitutions at positions 133 with [E, or D], 149 with [R, K, H, Q, or N], 152 with [R, K, H, Q, or N], 195 with [F, W, Y, L, I, or V] and 198 with [Q, or N]; substitutions at positions 133 with [E, or D], 149 with [R, K, H, Q, or N], 152 with [R, K, H, Q, or N], 195 with [F, W, Y, L, I, or V], 198 with [Q, or N] and 206; substitutions at positions 116 with [G, A, S, T, or M] and 129 with [F, W, Y, L, I, or V]; substitutions at positions 116 with [G, A, S, T, or M], 129 with [F, W, Y, L, I, or V] and 142 with [R, K, H, Q, or N]; substitutions at positions 116 with [G, A, S, T, or M], 129 with [F, W, Y, L, I, or V], 142 with [R, K, H, Q, or N] and 195 with [F, W, Y, L, I, or V]; substitutions at positions 116 with [G, A, S, T, or M], 129 with [F, W, Y, L, I, or V], 142 with [R, K, H, Q, or N], 195 with [F, W, Y, L, I, or V] and 198 with [Q, or N]; substitutions at positions 116 with [G, A, S, T, or M], 129 with [F, W, Y, L, I, or V], 142 with [R, K, H, Q, or N], 195 with [F, W, Y, L, I, or V], 198 with [Q, or N] and 203 with [F, W, Y, L, I, or V]; substitutions at positions 116 with [G, A, S, T, or M], 129 with [F, W, Y, L, I, or V], 142 with [R, K, H, Q, or N], 195 with [F, W, Y, L, I, or V], 198 with [Q, or N], 203 with [F, W, Y, L, I, or V] and 206; substitutions at positions 133 with [E, or D] and 149 with [R, K, H, Q, or N]; substitutions at positions 133 with [E, or D], 149 with [R, K, H, Q, or N] and 152 with [R, K, H, Q, or N]; substitutions at positions 133 with [E, or D], 149 with [R, K, H, Q, or N], 152 with [R, K, H, Q, or N] and 195 with [F, W, Y, L, I, or V]; substitutions at positions 133 with [E, or D], 149 with [R, K, H, Q, or N], 152 with [R, K, H, Q, or N], 195 with [F, W, Y, L, I, or V] and 198 with [Q, or N]; substitutions at positions 133 with [E, or D], 149 with [R, K, H, Q, or N], 152 with [R, K, H, Q, or N], 195 with [F, W, Y, L, I, or V], 198 with [Q, or N] and 203 with [F, W, Y, L, I, or V]; substitutions at positions 133 with [E, or D], 149 with [R, K, H, Q, or N], 152 with [R, K, H, Q, or N], 195 with [F, W, Y, L, I, or V], 198 with [Q, or N], 203 with [F, W, Y, L, I, or V] and 206; substitutions at positions 116 with [G, A, S, T, or M] and 133 with [E, or D]; substitutions at positions 116 with [G, A, S, T, or M], 133 with [E, or D] and 149 with [R, K, H, Q, or N]; substitutions at positions 116 with [G, A, S, T, or M], 133 with [E, or D], 149 with [R, K, H, Q, or N] with [R, K, H, Q, or N] and 198 with [Q, or N]; substitutions at positions 116 with [G, A, S, T, or M], 133 with [E, or D], 149 with [R, K, H, Q, or N], 198 with [Q, or N] and 203 with [F, W, Y, L, I, or V]; substitutions at positions 116 with [G, A, S, T, or M], 133 with [E, or D], 149 with [R, K, H, Q, or N], 198 with [Q, or N], 203 with [F, W, Y, L, I, or V] and 206; substitutions at positions 195 with [F, W, Y, L, I, or V] and 198 with [Q, or N]; substitutions at positions 195 with [F, W, Y, L, I, or V], 198 with [Q, or N] and 203 with [F, W, Y, L, I, or V]; substitutions at positions 195 with [F, W, Y, L, I, or V], 198 with [Q, or N], 203 with [F, W, Y, L, I, or V] and 206 with [F, W, Y, L, I, V, N, Q, or H]; substitutions at positions 133 with [E, or D], 149 with [R, K, H, Q, or N], 195 with [F, W, Y, L, I, or V], 203 with [F, W, Y, L, I, or V], and 206 with [F, W, Y, L, I, V, N, Q, or H].

Particular useful variants according to the invention includes (using the numbering of SEQ ID NO: 6): D183* G184* N195L; D183* G184* N197F; D183* G184* N197L; D183* G184* Y243F; D183* G184* N195F, D183* G184* N277F; D183* G184* 5431T; D183* G184* P434T; D183* G184* 1235N S339P; D183* G184* L351F; D183* G184* A186R, N195F; D183* G184* H210Y; D183* G184* V206Y; D183* G184* V206L; D183* G184* V206F; D183* G184* V213A Q174R; D183* G184* E212V; D183* G184* V206F E212G G304V A447V; N116T G133E K142R D183* G184* Y198N V206Y; G133E D183* G184* N195Y Y198N Y200F; D183* G184* A186D N195F E212V V213A; N116T D183* G184* N195Y Y198N; K142R P146S G149K D183* G184* N195YY198N V206I; D134Y D183* G184*; T151R D183* G184* H210Y K320N R359I N418D Q490H; G147E G149R Q169E D183* G184* Y198N Y203F V206Y; G133E G149R D183* G184* N195Y Y198N Y203F V206Y; G147E Y152H Q169E D183* G184* Y198N V206Y; D183* G184* N195F V206Y; D183* G184* N195F V206L; D183* G184* N195F V206F; D183* G184* V206L Y243F; D183* G184* V206F Y243F; D183* G184* N195F Y243F; D183* G184* N195F H210Y; D183* G184* V206Y H210Y; D183* G184* V213A; D183* G184* S193T; D183* G184* A186T N195F; D183* G184* N195F V206Y Y243F; D183* G184* N195F V206L Y243F; D183* G184* N195F V206Y Y243F; D183* G184* N195F V206F Y243F; D183* G184* V206Y Y243F; D183* G184* N195Y; G133D G149R D183* G184* Y198N V206Y; N116T G133E G147E Y152H D183* G184* Y198N Y203F V206Y; G147E G149R D183* G184* N195F Y198N V206Y; G133E K142R D183* G184* N195F Y198N; G133E G149R Y152H D183* G184* N195Y Y198N V206Y; N116T Q129L K142R D183* G184* N195Y Y198N Y203F V206Y; G133E G149R Y152H D183* G184* N195Y Y198N Y203F V206Y; N116T G133E G149R G182* D183* Y198N Y203F V206Y, D183* G184* S193T V206L, D183* G184* G133E G149R N195Y Y203F V206L In a preferred embodiment variants according to the invention includes, SP722SP722+D183* G184* N195L; SP722SP722+D183* G184* N197F; SP722SP722+D183* G184* N197L; SP722SP722+D183* G184* Y243F; SP722SP722+D183* G184* N195F, SP722SP722+D183* G184* N277F; SP722+D183* G184* S431T; SP722+D183* G184* P434T; SP722+D183* G184* 1235N S339P; SP722+D183* G184* L351F; SP722+D183* G184* A186D N195F E212V V213A; SP722+D183* G184* A186R N195F; SP722+D183* G184* H210Y; SP722+D183* G184* V206Y; SP722+D183* G184* V206L, SP722+D183* G184* V206F; SP722+D183* G184* V213A Q174R; SP722+D183* G184* E212V; SP722+D183* G184* V206Y E212G G304V A447V; SP722+N116T G133E K142R D183* G184* Y198N V206Y; SP722+G133E D183* G184* N195Y Y198N Y200F; SP722+N116T D183* G184* N195YY198N; SP722+K142R P146S G149K D183* G184* N195YY198N V206I; SP722+D134Y D183* G184*; SP722+T151R D183* G184* H210Y K320N R359I N418D; SP722+G147E G149R Q169E D183* G184* Y198N Y203F V206Y; SP722+G133E G149R D183* G184* N195Y Y198N Y203F V206Y; SP722+G147E Y152H Q169E D183* G184* Y198N V206Y; SP722+D183* G184* N195F V206Y; SP722+D183* G184* N195F V206F; SP722+D183* G184* N195F V206L; SP722+D183* G184* I206L Y243F; SP722+D183* G184* I206F Y243F; SP722+D183* G184* N195F Y243F; SP722+D183* G184* N195F H210Y; SP722+D183* G184* V206Y H210Y; SP722+D183* G184* V213A; SP722+D183* G184* S193T; SP722+D183* G184* A186T N195F; SP722+D183* G184* N195F V206Y Y243F; SP722+D183* G184* V206Y Y243F; SP722+D183* G184* N195Y; SP722+G133D G149R D183* G184* Y198N V206Y; SP722+N116T G133E G147E Y152H D183* G184* Y198N Y203F V206Y; SP722+G147E G149R D183* G184* N195F Y198N V206Y; SP722+G133E K142R D183* G184* N195F Y198N; SP722+G133E G149R Y152H D183* G184* N195Y Y198N V206Y; SP722+N116T Q129L K142R D183* G184* N195Y Y198N Y203F V206Y; SP722+G133E G149R Y152H D183* G184* N195Y Y198N Y203F V206Y; SP722+N116T G133E G149R G182* D183* Y198N Y203F V206Y, SP722+D183* G184* G133E G149R N195Y Y203F V206L.

In one preferred embodiment the variants are selected from the following: SP722+D183* G184* N195F V206L Y243F; SP722+D183* G184* N195F V206Y Y243F; SP722+D183* G184* N195F V206N Y243F; SP722+D183* G184* N195F V206F Y243F; SP722+D183* G184* N195F V206H; SP722+D183* G184* N195F V206Y; SP722+D183* G184* V206F Y243F; SP722+D183* G184* N195F V206L H210Y; SP722+D183* G184* S193T V206L; SP722+D183* G184* G133E G149R N195Y Y203F V206L.

In another preferred embodiment variants according to the invention includes, SP707+H183* G184* N195L; SP707+H183* G184* N197F; SP707+H183* G184* N197L; SP707+H183* G184* Y243F; SP707+H183* G184* N195F, SP707+H183* G184* N277F; SP707+H183* G184* A186D N195F E212V V213A; SP707+H183* G184* S431T; SP707+H183* G184* A434T; SP707+H183* G184* I235N A339P; SP707+H183* G184* L351F, SP707+H183* G184* A186R, N195F; SP707+H183* G184* H210Y; SP707+H183* G184* I206Y; SP707+H183* G184* I206L, SP707+H183* G184* I206F; SP707+H183* G184* V213A Q174R; SP707+H183* G184* E212V; SP707+H183* G184* I206Y E212G G304V A447V; SP707+M116T G133E H183* G184* Y198N I206Y; SP707+G133E H183* G184* N195Y Y198N Y200F; SP707+M116T H183* G184* N195Y Y198N; SP707+P146S G149K H183* G184* N195Y Y198N V206I; SP707+E134Y H183* G184*; SP707+T151R H183* G184* H210Y R320N R359I N418D; SP707+G147E G149R Q169E H183* G184* Y198N Y203F I206Y; SP707+H183* G184* G149R N195Y Y198N Y203F I206Y; SP707+G147E Q169E H183* G184* Y198N I206Y; SP707+H183* G184* N195F I206Y; SP707+H183* G184* N195F I206L; SP707+H183* G184* N195F I206F; SP707+H183* G184* N195F Y243F; SP707+H183* G184* N195F H210Y; SP707+H183* G184* I206Y H210Y; SP707+H183* G184* V213A; SP707+H183* G184* S193T; SP707+H183* G184* A186T N195F; SP707+H183* G184* N195F I206Y Y243F; SP707+H183* G184* N195F I206F Y243F; SP707+H183* G184* N195F I206L Y243F; SP707+H183* G184* N195F I206Y Y243F SP707+H183* G184* I206Y Y243F; SP707+H183* G184*I206L Y243F; SP707+H183* G184*I206F Y243F; SP707+H183* G184* N195Y; SP707+G133D G149R H183* G184* Y198N I206Y; SP707+M116T G133E G147E H183* G184* Y198N Y203F I206Y; SP707+G147E G149R+H183* G184* N195F Y198N I206Y; SP707+G133E H183* G184* N195F Y198N; SP707+G133E G149R H183* G184* N195Y Y198N I206Y; SP707+M116T Q129L H183* G184* N195Y Y198N Y203F I206Y; SP707+G133E G149R H183* G184* N195Y Y198N Y203F I206Y; SP707+M116T G133E G149R G182* H183* Y198N Y203F I206Y; SP707+D183* G184* R118K N195F R320K R458K; SP707+D183* G184* R118K N195F I206L R320K R458K; SP707+D183* G184* R118K N195F I206Y R320K R458K; SP707+D183* G184* R118K N195F Y243F R320K R458K; SP707+D183* G184* R118K N195F I206L Y243F R320K R458K.

In a preferred embodiment variants according to the invention includes, AA560+D183* G184* N195L; AA560+ D183* G184* N197F; AA560+D183* G184* N197L; AA560+D183* G184* Y243F; AA560+D183* G184* N195F, AA560+D183* G184* N277F; AA560+D183* G184* S431T; AA560+D183* G184* A434T; AA560+ D183* G184* I235N A339P; AA560+D183* G184* L351F; D183* G184* G186D N195F E212V V213A AA560+D183* G184* G186R, N195F; AA560+D183* G184* H210Y; AA560+D183* G184* I206Y; AA560+ D183* G184* I206L; AA560+D183* G184* I206F; AA560+D183* G184* V213A Q174R; AA560+D183* G184* E212V; AA560+D183* G184* I206Y E212G G304V A447V; AA560+M116T G133E K142R D183* G184* Y198N I206Y; AA560+G133E D183* G184* N195Y Y198N Y200F; AA560+M116T D183* G184* N195Y Y198N; AA560+K142R P146S G149K D183* G184* N195Y Y198N I206I; AA560+E134Y D183* G184*; AA560+T151R D183* G184* H210Y R320N R359I N418D; AA560+G147E G149R Q169E D183* G184* Y198N Y203F I206Y; AA560+G133E G149R D183* G184* N195Y Y198N Y203F I206Y; AA560+ G147E Y152H Q169E D183* G184* Y198N I206Y; AA560+D183* G184* N195F I206Y; AA560+D183* G184* N195F I206L; AA560+D183* G184* N195F I206F; AA560+D183* G184* I206L Y243F; AA560+D183* G184* I206F Y243F; AA560+D183* G184* N195F Y243F; AA560+D183* G184* N195F H210Y; AA560+ D183* G184* I206Y H210Y; AA560+D183* G184* V213A; AA560+D183* G184* S193T; AA560+D183* G184* G186T N195F; AA560+D183* G184* N195F I206Y Y243F, AA560+D183* G184* N195F I206L Y243F; AA560+D183* G184* N195F I206Y Y243F AA560+ D183* G184* I206Y Y243F; AA560+D183* G184* I206L Y243F; AA560+D183* G184* N195Y; AA560+G133D G149R D183* G184* Y198N I206Y; AA560+M116T G133E G147E Y152H D183* G184* Y198N Y203F I206Y; AA560+G147E G149R D183* G184* N195F Y198N I206Y; AA560+G133E K142R D183* G184* N195F Y198N; AA560+G133E G149R Y152H D183*G184*N195YY198NI206Y; AA560+M116TQ129L K142R D183*G184* N195Y Y198N Y203F I206Y; AA560+G133E G149R Y152H D183* G184* N195Y Y198N Y203F I206Y; AA560+M116T G133E G149R G182* D183* Y198N Y203F I206Y; AA560+D183* G184* R118K N195F R320K R458K; AA560+D183* G184* R118K N195F I206L R320K R458K; AA560+D183* G184* R118K N195F I206Y R320K R458K; AA560+ D183* G184* R118K N195F Y243F R320K R458K; AA560+D183* G184* R118K N195F I206L Y243F R320K R458K.

In a preferred embodiment variants according to the invention includes,
SP690+T183* G184* N195L; SP690+T183* G184* N197F; SP690+T183* G184* N197L; SP690+T183* G184* Y243F; SP690+T183* G184* N195F, SP690+T183* G184* N277F; SP690+T183* G184* S431T; SP690+T183* G184* P434T; SP690+T183* G184* I235N A339P; SP690+T183* G184* L351F; SP690+T183* G184* A186D N195F E212V V213A; SP690+T183* G184* A186R N195F; SP690+T183* G184* H210Y; SP690+T183* G184* V206Y; SP690+T183* G184* V206L, SP690+ T183* G184* V206F; SP690+T183* G184* V213A Q174R; SP690+T183* G184* E212V; SP690+T183* G184* V206Y E212G G304V A447V; SP690+N116T G133E K142R T183* G184* Y198N V206Y; SP690+ G133E T183* G184* N195Y Y198N Y200F; SP690+ N116T T183* G184* N195Y Y198N; SP690+K142R P146S G149K T183* G184* N195Y Y198N V206I; SP690+E134Y T183* G184*; SP690+N151R T183* G184* H210Y K320N R359I N418D; SP690+G147E G149R Q169E T183* G184* Y198N Y203F V206Y; SP690+ G133E G149R T183* G184* N195Y Y198N Y203F V206Y; SP690+G147E Y152H Q169E T183* G184* Y198N V206Y; SP690+T183* G184* N195F V206Y; SP690+T183* G184* N195F V206F; SP690+T183* G184* N195F V206L; SP690+T183* G184* I206L Y243F; SP690+T183* G184* I206F Y243F; SP690+T183* G184* N195F Y243F; SP690+T183* G184* N195F H210Y; SP690+T183* G184* V206Y H210Y; SP690+T183* G184* V213A; SP690+T183* G184* S193T; SP690+ T183* G184* A186T N195F; SP690+T183* G184* N195F V206Y Y243F; SP690+T183* G184* V206Y Y243F; SP690+T183* G184* N195Y; SP690+G133D G149R T183* G184* Y198N V206Y; SP690+N116T G133E G147E Y152H T183* G184* Y198N Y203F V206Y; SP690+G147E G149R T183* G184* N195F Y198N V206Y; SP690+G133E K142R T183* G184* N195F Y198N; SP690+G133E G149R Y152H T183*G184*N195YY198N V206Y; SP690+N116TQ129L K142R T183*G184*N195Y Y198N Y203F V206Y; SP690+G133E G149R Y152H T183* G184* N195Y Y198N Y203F V206Y; SP690+N116T G133E G149R G182* T183* Y198N Y203F V206Y, SP690+T183* G184* G133E G149R N195Y Y203F V206L, SP690+T183* G184* R118K N195F R320K R458K; 5P690+T183* G184* N118K N195F V206L R320K R458K; 5P690+ T183* G184* N118K N195F V206Y R320K R458K; SP690+T183* G184* N118K N195F Y243F R320K R458K; SP690+T183* G184* N118K N195F V206L Y243F R320K R458K; SP690+T183* G184* N195F V206L Y243F; SP690+T183* G184* N195F V206Y Y243F; SP690+T183* G184* N195F V206N Y243F; SP690+T183* G184* N195F V206F Y243F; SP690+T183* G184* N195F V206H; SP690+T183* G184* N195F V206Y; SP690+T183* G184* V206F Y243F; SP690+ T183* G184* N195F V206L H210Y; SP690+T183* G184* S193T V206L; SP690+T183* G184* G133E G149R N195Y Y203F V206L.

In a preferred embodiment, variants according to the invention includes a variant of a parent alpha-amylase, wherein the parent alpha-amylase is that of SEQ ID NO:6, and the variant comprises the deletions D183* and G184* and one of the following sets of mutations: (a) N195F+ H210Y; (b) N195F+V206L,H,Y; (c) N195F+V206L, F+H210Y; (d) N195F+V206Y+Y243F; (e) N195F+Y243F; (f) S193T+V206L; (g) G133E+G149R+N195Y+Y203F+ V206L; (h) V206L,Y; (i) Y243F; (j) N195F+V206L+ Y243F; (k) N195F; or (l) V206F+Y243F.

Detergent Compositions: According to the invention, the above alpha-amylase variants may typically be a component of a detergent composition, e.g., a laundry detergent composition or a dishwashing detergent composition. In a special embodiment of the invention the composition further comprises a strong chelating agent or complexing agent. Thus one aspect of the invention concerns a composition comprising a variant of a parent alpha-amylase comprising a substitution at one or more position in the range corresponding to positions 193 to 213 of the mature polypeptide of SEQ ID NO: 6 and further comprising a chelating agent wherein said chelating agent at a concentration below 10 mM is capable of reducing the concentration of free calcium ions from 2.0 mM to 0.10 mM when measured at 21° C. and pH 8.0, as described under "Materials and Methods".

In another embodiment the composition comprises a chelating agent selected from, but not limited, to the following: The chelating agent may contain an amino group and may be, e.g., an amino-polycarboxylate or a phosphonate. It may be a monomeric molecule comprising one, two or three amino groups (typically secondary or tertiary amino groups), and it may contain two, three, four or five or even more carboxyl groups. Chelating agents may be but are not limited to the following: ethylene-diamine-tetra-acetic acid (EDTA), diethylene triamine penta methylene phosphonic acid (DTPMP), hydroxy-ethane diphosphonic acid (HEDP), ethylenediamine N,N'-disuccinic acid (EDDS), methyl glycine di-acetic acid (MGDA), diethylene triamine penta acetic acid (DTPA), propylene diamine tetracetic acid (PDTA), 2-hydroxypyridine-N-oxide (HPNO), or ethylenedinitrilotertrakis (methylenephosphonic acid) N,N,-dioxide, methyl glycine diacetic acid (MGDA), glutamic acid N,N-diacetic acid (N,N-dicarboxymethyl glutamic acid tetrasodium salt, (GLDA) and nitrilotriacetic acid (NTA) or mixtures thereof. The chelating agents are typically present at a level of from 0.1% to 75% by weight in a detergent.

The detergent composition of the present invention may further comprise a cleaning/detergent adjunct, which is not a chelating agent as defined above, preferably comprising a mixture of components. Typically the cleaning adjunct will be present in the composition in an amount from 0.001 to 99.9 wt %, more typically from 0.01 to 80 wt % cleaning adjunct. Suitable cleaning adjuncts comprise: surfactants, builders, bleaches, bleach catalysts, colorants, bleach boosters, dye transfer agents, deposition aids, dispersants, additional enzymes, and enzyme stabilizers, catalytic materials, bleach activators, hydrogen peroxide, sources of hydrogen peroxide, optical brighteners, photoactivators, fluorescers, fabric hueing agents, fabric conditioners, preformed peracids, polymeric dispersing agents, clay soil removal/anti-redeposition agents, filler salts, hydrotropes, brighteners, suds suppressors, structure elasticizing agents, fabric softeners, hydro-lyzable surfactants, preservatives, anti-oxidants, anti-shrinkage agents, germicides, fungicides, anti-tarnish, anti-corrosion agents, alkalinity sources, solubilizing agents, carriers, processing aids, pigments, dyes, perfumes and pH control agents. For example, these may include: bleach ingredients such as imine bleach boosters; sources of hydrogen peroxide such as percarbonate and/or perborate, especially percarbonate coated with material such as carbonate and/or sulphate salt, silicate salt, borosilicate, and any mixture thereof; pre-formed peracid, including pre-formed peracid in encapsulated form; transition metal catalysts; suds suppressors or suppressor systems such as silicone based suds suppressors and/or fatty acid based suds suppressors; fabric-softeners such as clay, silicone and/or quaternary ammonium compounds; flocculants such as polyethylene oxide; dye transfer inhibitors such as polyvinylpyrrolidone, poly 4-vinylpyridine N-oxide and/or co-polymer of vinylpyrrolidone and vinylimidazole; fabric integrity components such as oligomers produced by the condensation of imidazole and epichlorhydrin; soil dispersants and soil anti-redeposition aids such as alkoxylated polyamines and ethoxylated ethyleneimine polymers; anti-redeposition components such as polyesters; carboxylate polymers such as maleic acid polymers or co-polymers of maleic and acrylic acid; perfumes such as perfume microcapsules, starch encapsulated accords, perfume spray-on; soap rings; aesthetic particles; dyes; fillers such as sodium sulphate, although it is preferred for the composition to be substantially free of fillers; silicate salt such as sodium silicate, including 1.6R and 2.0R sodium silicate, or sodium metasilicate; co-polyesters of di-carboxylic acids and diols; cellulosic polymers such as methyl cellulose, carboxymethyl cellulose, hydroxyethoxycellulose, or other alkyl or alkyl-alkoxy cellulose; solvents such as 1,2 propanediol, mono-ethanolamine; diethylene glycol, ethanol, and any mixture thereof; hydrotropes such as sodium cumene sulphonate, sodium xylene sulphonate, sodium toluene sulphonate, and any mixtures; organic acids such as citric acid; and any combination thereof.

Accordingly, the composition may further contain builders, such as builders based on carbonate, bicarbonate or silicates which may be Zeolittes, such as Zeolit A, Zeolit MAP (Miximum Aluminium type P). Zeolites, useable in laundry preferably has the formula $Na_{12}(AlO_2)_{12}(SiO_2)_{12}.27H_2O$ and the particle size is usually between 1-10 μm for zeolit A and 0.7-2 um for zeolit MAP. Other builders are Sodium metasilicate ($Na_2SiO_3.nH_2O$ or $Na_2Si_2O_5.n\,H_2O$) strong alkaline and preferably used in dish wash. In preferred embodiments, the amount of a detergent builder may be above 5%, above 10%, above 20%, above 30%, above 40% or above 50%, and may be below 80%, 65%. In a dishwash detergent, the level of builder is typically 40-65%, particularly 50-65% or even 75-90%.

In another preferred aspect the composition comprises one or more surfactants, which may be non-ionic including semi-polar and/or anionic and/or cationic and/or zwitterionic and/or ampholytic and/or semi-polar nonionic and/or mixtures thereof. The surfactants are typically present at a level of from 0.1% to 60% by weight, while in alternative embodiments, the level is from about 1 percent to about 50 percent, while in still further embodiments, the level is from about 5 percent to about 40 percent, by weight of the detergent composition.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonyl-phenol ethoxylate, alkylpolygly-coside, alkyldimethylamine-oxide, ethoxylated fatty acid monoethanol-amide, fatty acid monoeth-anolamide, polyhydroxy alkyl fatty acid amide, or N-acyl N-alkyl derivatives of glucosamine ("glu-cam ides").

Further suitable anionic surfactants are soaps and those containing sulfate or sulfonate groups. Surfactants of the sulfonate type that come into consideration are (C9-C13-alkyl)benzenesulfonates and olefinsulfonates, the latter being understood to be mixtures of alkenesulfonates and hydroxyalkanesulfonates and -disulfonates, as obtained, for example, by sulfonation of C12-C18 monoolefins having a terminally or internally located double bond. Also suitable are (C12-C18)alkanesulfonates and esters of alpha-sulfo fatty acids (ester sulfonates), for example the alpha-sulfonated methyl esters of hydrogenated coconut, palm kernel or tallow fatty acids, typically produced by saponification of triglycerides from the plant or animal oils followed by methylation and sulfonation, may be used.

Further suitable anionic surfactants are sulfonated fatty acid glycerol esters comprising mono-, di- and tri-esters and mixtures thereof.

Alk(en)yl sulfates to which preference is given are the alkali metal salts and the sodium salts of sulfuric acid monoesters of C12-C18 fatty alcohols, for example from coconut fatty alcohol, tallow fatty alcohol, lauryl, myristyl, cetyl or stearyl alcohol, or of C10-C20 oxo alcohols and sulfuric acid monoesters of secondary alcohols having that chain length. From the point of view of washing technology, special preference is given to C12-C16 alkyl sulfates and C12-C15 alkyl sulfates and also to C14-C15 alkyl sulfates. Suitable anionic surfactants are also alkane-2,3-diylbis(sulfates) that are prepared, for example, in accordance with U.S. Pat. No. 3,234,258 or 5,075,041.

Also suitable are the sulfuric acid monoesters of straight-chain or branched C7-C21 alcohols ethoxylated with from 1 to 6 mole of ethylene oxide, such as 2-methyl-branched C9-C11 alcohols with, on average, 3.5 mole of ethylene oxide (EO) or C12-C18 fatty alcohols with from 1 to 4 EO. Because of their high foaming characteristics, they are normally used in washing and cleaning compositions only at relatively low levels, for example at levels of from 1% to 5% by weight.

Anionic surfactants may also include diesters, and/or salts of monoesters, of sulfosuccinic acid with C8-C18 fatty alcohol residues or mixtures thereof. Special preference is given to sulfosuccinates in which the fatty alcohol residues have a narrow chain length distribution. It is likewise also possible to use alk(en)yl sulfosuccinates having preferably from 8 to 18 C-atoms in the alk(en)yl chain, or salts thereof.

Further anionic surfactants that come into consideration are fatty acid derivatives of amino acids, for example of methyltaurine (taurides) and/or of methylglycine (sarcosides). Further anionic surfactants that come into consideration are soaps. Saturated fatty acid soaps such as the salts of lauric acid, myristic acid, palmitic acid, stearic acid, hydrogenated erucic acid and behenic acid and soap mixtures derived from natural fatty acids, for example coconut, palm kernel or tallow fatty acids. The anionic surfactants, including the soaps, may be present in the form of their sodium, potassium or ammonium salts and in the form of soluble salts of organic bases such as mono-, di- or triethanolamine. The anionic surfactants may be present in the form of their sodium or potassium salts. As non-ionic surfactants, preferably alkoxylated, advantageously ethoxylated and/or propoxylated, especially primary alcohols having from 8 to 18 C-atoms and, on average, from 1 to 12 moles of ethylene oxide (EO) and/or from 1 to 10 moles of propylene oxide (PO) per mole of alcohol are used. Special preference is given to C8-C16 alcohol alkoxylates, advantageously ethoxylated and/or propoxylated C10-C15 alcohol alkoxylates, especially C12-C14 alcohol alkoxylates, having a degree of ethoxylation between 2 and 10, or between 3 and 8, and/or a degree of propoxylation between 1 and 6, or between 1.5 and 5. The alcohol residue may be preferably linear or, especially in the 2-position, methyl-branched, or may comprise a mixture of linear and methyl-branched chains, as are usually present in oxo alcohols. Special preference is given, however, to alcohol ethoxylates derived from linear alcohols of natural origin that contain from 12 to 18 C-atoms, for example coconut, palm and tallow fatty alcohol or oleyl alcohol, and on average from 2 to 8 EO per mole of alcohol. The ethoxylated alcohols include, for example, C12-C14 alcohols with 3 EO or 4 EO, C9-C11 alcohols with 7 EO, C13-C15 alcohols with 3 EO, 5 EO, 7 EO or 8 EO, C12-18 alcohols with 3 EO, 5 EO or 7 EO, mixtures thereof, such as mixtures of C12-C14 alcohol with 3 EO and C12-C18 alcohol with 5 EO. The mentioned degrees of ethoxylation and propoxylation represent statistical averages which, for a specific product, can be a whole number or a fractional number. Preferred alcohol ethoxylates and propoxylates have a restricted homologue distribution (narrow range ethoxylates/propoxylates, NRE/NRP). In addition to those non-ionic surfactants, fatty alcohol ethoxylates having more than 12 EO may also be used. Examples thereof are tallow fatty alcohol ethoxylate with 14 EO, 25 EO, 30 EO or 40 EO.

Also suitable are alkoxylated amines, which are ethoxylated and/or propoxylated, especially primary and secondary amines having from 1 to 18 C-atoms per alkyl chain and, on average, from 1 to 12 moles of ethylene oxide (EO) and/or from 1 to 10 moles of propylene oxide (PO) per mole of amine.

In addition, as further non-ionic surfactants, there may also be used alkyl polyglycosides of the general formula $R_1O(G)_x$, wherein $R_1$ is a primary straight-chain or methyl-branched (especially methyl-branched in the 2-position) alkyl group having from 8 to 22, preferably from 12 to 18, C-atoms and the symbol 'G' indicates a glycose (monosaccharide) unit having 5 or 6 C-atoms; preferably G is glucose. The degree of oligomerisation x, which indicates the average number of glycose units, will generally lie between 1 and 10; x is preferably from 1.2 to 1.4.

A further class of used non-ionic surfactants, which are used either as sole non-ionic surfactant or in combination with other non-ionic surfactants, comprises alkoxylated, preferably ethoxylated or ethoxylated and propoxylated fatty acid alkyl esters, having from 1 to 4 C-atoms in the alkyl chain, especially fatty acid methyl esters, as described, for example, in JP58/217598.

Non-ionic surfactants of the amine oxide type, for example N-(coco alkyl)-N,N-dimethylamine oxide and N-(tallow-alkyl)-N,N-bis(2-hydroxyethyl)amine oxide, and of the fatty acid alkanolamide or ethoxylated fatty acid alkanolamide type may also be suitable.

In a more preferred embodiment, the surfactant is sodium dodecyl sulfate, quaternary ammonium compounds, alkyl pyridinium iodides, TWEEN™ 80 (polysorbate 80), TWEEN™ 85 (polyoxyethylene sorbitan trioleate), TRITON™ X-100 (2-[4-(2,4,4-trimethylpentan-2-yl)phenoxy]ethanol), Brij 56, biological surfactants, rhamnolipid, surfactin, visconsin, or sulfonates.

In some embodiments the invention relates to a composition wherein the concentration of the at least one surfactant is from 0 to 500, from 0.00001 to 100, from 0.0001 to 50, from 0.0001 to 40, from 0.001 to 30, from 0.01 to 20, from 0.1 to 15, from 1 to 10 milligram per gram textile in the wash.

In some embodiments the invention relates to a composition, wherein the concentration of the at least one surfactant is from 0 to 50, from 0.0001 to 40, from 0.001 to 30, from 0.01 to 20 from 0.1 to 10, or from 1 to 5 g per L solution.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be for-mutated for hand or machine dishwashing operations. The detergent may be a powder, or granulated form, or it may be in the form of a liquid, gel or paste or in the form of a unit dose product such as a tablet or pouch, including multi-compartment pouches, or the detergent can be in the form of a sheet.

The detergent composition may comprise one or more other enzymes such as a protease, a lipase, a peroxidase, another amylolytic enzyme, e.g., another alpha-amylase, glucoamylase, maltogenic amylase, CGTase and/or a cellulase, mannanase (such as MANNAWAY™ from Novozymes, Denmark), pectinase, pectine lyase, cutinase, and/or laccase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

Proteases: Suitable proteases include metalloproteases and/or serine proteases, including neutral or alkaline microbial serine proteases, such as subtilisins (EC 3.4.21.62). Suitable proteases include those of animal, vegetable or microbial origin. In one aspect, such suitable protease may be of microbial origin. The suitable proteases include chemically or genetically modified mutants of the aforementioned suitable proteases. In one aspect, the suitable protease may be a serine protease, such as an alkaline microbial protease or/and a trypsin-type protease. Examples of suitable neutral or alkaline proteases include:

(a) subtilisins (EC 3.4.21.62), including those derived from Bacillus, such as Bacillus lentus, B. alkalophilus, B. subtilis, B. amyloliquefaciens, Bacillus pumilus and Bacillus gibsonii described in U.S. Pat. No. 6,312,936 B1, U.S. Pat. Nos. 5,679,630, 4,760,025, 7,262,042 and WO09/021867.

(b) trypsin-type or chymotrypsin-type proteases, such as trypsin (e.g., of porcine or bovine origin), including the Fusarium protease described in WO 89/06270 and the chymotrypsin proteases derived from Cellumonas described in WO 05/052161 and WO 05/052146.

(c) metalloproteases, including those derived from Bacillus amyloliquefaciens described in WO 07/044993A2.

Preferred proteases include those derived from Bacillus gibsonii or Bacillus Lentus.

Suitable commercially available protease enzymes include those sold under the trade names ALCALASE®, SAVINASE®, PRIMASE®, DURAZYM®, POLARZYME®, KANNASE®, LIQUANASE®, LIQUANASE ULTRA®, SAVINASE ULTRA®, OVOZYME®, NEUTRASE®, EVER-LASE® and ESPERASE® by Novozymes A/S (Denmark), those sold under the tradename MAX-ATASE®, MAXACAL®, MAXAPEM®, PROPERASE®, PURAFECT®, PURAFECT PRIME®, PURAFECT OX®, FN3®, FN4®, EXCELLASE® and PURAFECT OXP® by Genencor International, those sold under the tradename OPTICLEAN® and OPTIMASE® by Solvay Enzymes, those available from Henkel/Kemira, namely BLAP (sequence shown in FIG. 29 of U.S. Pat. No. 5,352,604 with the following mutations S99D+S101 R+S103A+V104I+G159S, hereinafter referred to as BLAP), BLAP R (BLAP with S3T+V4I+V199M+V205I+L217D), BLAP X (BLAP with S3T+V4I+V205I) and BLAP F49 (BLAP with S3T+V4I+A194P+V199M+V205I+L217D)—all from Henkel/Kemira; and KAP (Bacillus alkalophilus subtilisin with mutations A230V+S256G+S259N) from Kao.

Lipases: Suitable lipases include those of bacterial or fungal origin. Chemically modified or protein engineered mutants are included. Examples of useful lipases include lipases from Humicola (synonym Thermomyces), e.g., from H. lanuginosa (T. lanuginosus) as described in EP 258 068 and EP 305 216 or from H. insolens as described in WO 96/13580, a Pseudomonas lipase, e.g., from P. alcaligenes or P. pseudoalcaligenes (EP 218 272), P. cepacia (EP 331 376), P. stutzeri (GB 1,372,034), P. fluorescens, Pseudomonas sp. strain SD 705 (WO 95/06720 and WO 96/27002), P. wisconsinensis (WO 96/12012), a Bacillus lipase, e.g., from B. subtilis (Dartois et al. (1993), Biochemica et Biophysica Acta, 1131, 253-360), B. stearothermophilus (JP 64/744992) or B. pumilus (WO 91/16422).

The lipase may be a "first cycle lipase" such as those described in U.S. Pat. No. 6,939,702 B1 and US PA 2009/0217464. In one aspect, the lipase is a first-wash lipase, preferably a variant of the wild-type lipase from Thermomyces lanuginosus comprising T231R and N233R mutations. The wild-type sequence is the 269 amino acids (amino acids 23-291) of the Swissprot accession number Swiss-Prot O59952 (derived from Thermomyces lanuginosus (Humicola lanuginosa)). Preferred lipases would include those sold under the tradenames Lipex®, Lipolex® and Lipoclean®. Cellulases: Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g., the fungal cellulases produced from Humicola insolens, Myceliophthora thermophila and Fusarium oxysporum disclosed in U.S. Pat. Nos. 4,435,307, 5,648,263, 5,691,178, 5,776,757 and WO 89/09259.

Cellulases: Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g., the fungal cellulases produced from Humicola insolens, Myceliophthora thermophila and Fusarium oxysporum disclosed in U.S. Pat. Nos. 4,435,307, 5,648,263, 5,691,178, 5,776,757 and WO 89/09259.

Especially suitable cellulases are the alkaline or neutral cellulases having colour care ben-efits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include CELLUZYME®, and CAREZYME® (Novozymes A/S), CLAZINASE®, and PURADAX HA® (Genencor International Inc.), and KAC-500(B)® (Kao Corporation).

Peroxidases/Oxidases: Suitable peroxidases/oxidases include those of plant, bac-terial or fungal origin. Chemically modified or protein engineered mutants are included. Examples of useful peroxidases include peroxidases from Coprinus, e.g., from C. cinereus, and variants thereof as those described in WO 93/24618, WO 95/10602, and WO 98/15257.

Commercially available peroxidases include GUARDZYME® (Novozymes A/S).

Other enzymes: Other preferred enzymes include pectate lyases sold under the tradenames PECTAWASH®, PECTAWAY® and mannanases sold under the tradenames MANNAWAY® (all from Novozymes A/S, Bagsvaerd, Denmark), and PURABRITE® (Genencor International Inc., Palo Alto, Calif.).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, e.g., granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonyl-phenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste, a gel, a liquid, a powder—form all-purpose, a "heavy-duty" washing agent, a paste-form all-purpose, a heavy-duty liquid type, a liquid fine-fabric, a hand dishwashing agent, a light duty dishwashing agent, a high-foaming type. a machine dishwashing agent, a various tablet, a dishwash granular, a dish wash liquid, a rinse-aid type. The composition can also be in unit dose packages, including those known in the art and those that are water soluble, water insoluble and/or water permeable. A liquid detergent may be aqueous, typically containing up to 70% water and 0-30% organic solvent, or non-aqueous or a solution containing more than 0.5 g/L of the detergent composition. The composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. The detergent may be a powder, or granulated form, or it may be in the form of a liquid, gel or paste or in the form of a unit dose product such as a tablet or pouch, including multi-compartment pouches, or the detergent can be in the form of a sheet.

The composition may comprise a fabric hueing agent. Suitable fabric hueing agents include dyes, dye-clay conjugates, and pigments that preferably satisfy the requirements of Test Method 1, described herein below. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example:

(1) Tris-Azo Direct Blue Dyes of the Formula

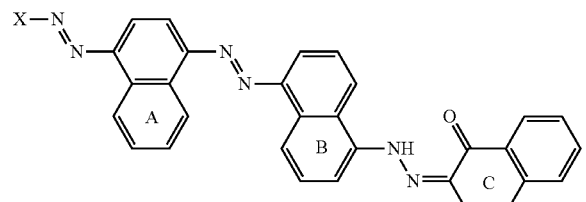

where at least two of the A, B and C napthyl rings are substituted by a sulfonate group, the C ring may be substituted at the 5 position by an $NH_2$ or NHPh group, X is a benzyl or naphthyl ring substituted with up to 2 sulfonate groups and may be substituted at the 2 position with an OH group and may also be substituted with an $NH_2$ or NHPh group.

(2) Bis-Azo Direct Violet Dyes of the Formula:

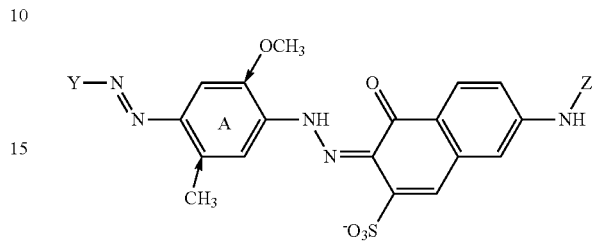

where Z is H or phenyl, the A ring is preferably substituted by a methyl and methoxy group at the positions indicated by arrows, the A ring may also be a naphthyl ring, the Y group is a benzyl or naphthyl ring, which is substituted by sulfate group and may be mono or disubstituted by methyl groups.

(3) Blue or Red Acid Dyes of the Formula

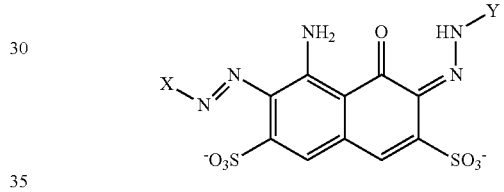

where at least one of X and Y must be an aromatic group. In one aspect, both the aromatic groups may be a substituted benzyl or naphthyl group, which may be substituted with non water-solubilising groups such as alkyl or alkyloxy or aryloxy groups, X and Y may not be substituted with water solubilising groups such as sulfonates or carboxylates. In another aspect, X is a nitro substituted benzyl group and Y is a benzyl group (4) Red Acid Dyes of the Structure

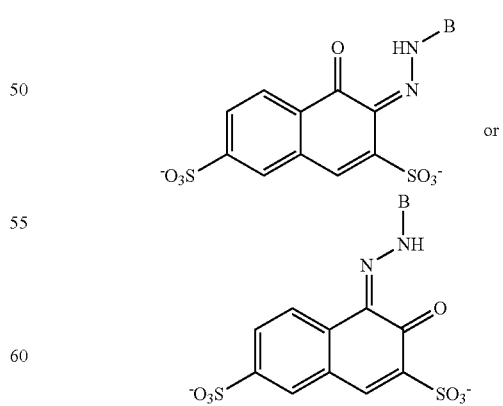

where B is a naphthyl or benzyl group that may be substituted with non water solubilising groups such as alkyl or alkyloxy or aryloxy groups, B may not be substituted with water solubilising groups such as sulfonates or carboxylates.

(5) Dis-Azo Dyes of the Structure

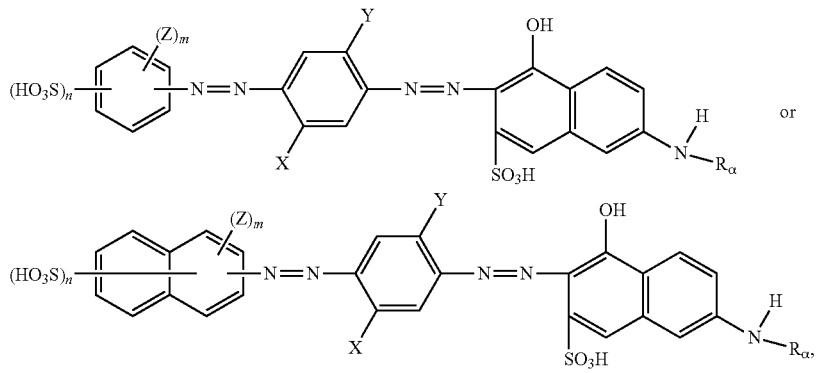

wherein X and Y, independently of one another, are each hydrogen, $C_1$-$C_4$ alkyl or $C_1$-$C_4$-alkoxy, R□ is hydrogen or aryl, Z is $C_1$-$C_4$ alkyl; $C_1$-$C_4$-alkoxy; halogen; hydroxyl or carboxyl, n is 1 or 2 and m is 0, 1 or 2, as well as corresponding salts thereof and mixtures thereof (6) Triphenylmethane Dyes of the Following Structures

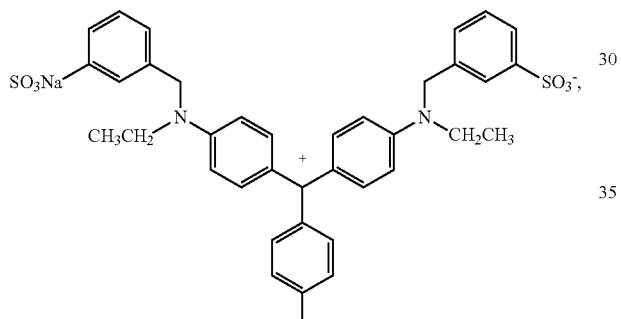

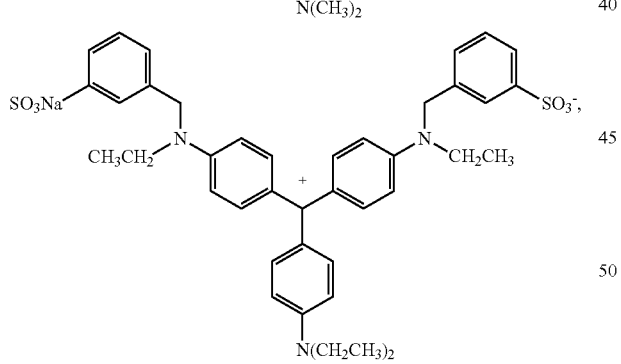

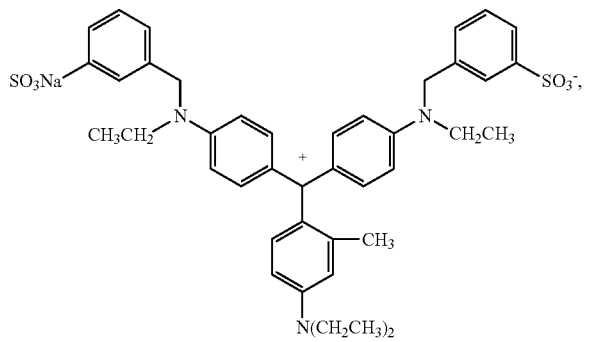

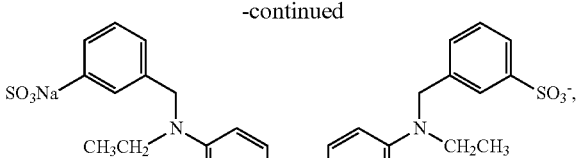

-continued

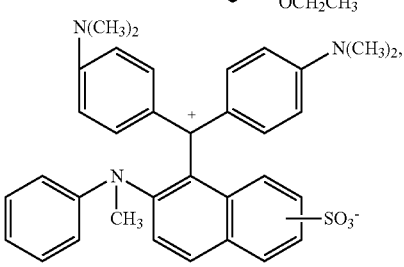

and/or and mixtures thereof. In another aspect, suitable small molecule dyes include small molecule dyes selected from the group consisting of Colour Index (Society of Dyers and Colourists, Bradford, UK) numbers Direct Violet 9, Direct Violet 35, Direct Violet 48, Direct Violet 51, Direct Violet 66, Direct Blue 1, Direct Blue 71, Direct Blue 80, Direct Blue 279, Acid Red 17, Acid Red 73, Acid Red 88, Acid Red 150, Acid Violet 15, Acid Violet 17, Acid Violet 24, Acid Violet 43, Acid Red 52, Acid Violet 49, Acid Blue 15, Acid Blue 17, Acid Blue 25, Acid Blue 29, Acid Blue 40, Acid Blue 45, Acid Blue 75, Acid Blue 80, Acid Blue 83, Acid Blue 90 and Acid Blue 113, Acid Black 1, Basic Violet 1, Basic Violet 3, Basic Violet 4, Basic Violet 10, Basic Violet 35, Basic Blue 3, Basic Blue 16, Basic Blue 22, Basic Blue 47, Basic Blue 66, Basic Blue 75, Basic Blue 159 and mixtures thereof. In another aspect, suitable small molecule dyes include small molecule dyes selected from the group consisting of Colour Index (Society of Dyers and Colourists, Bradford, UK) numbers Acid Violet 17, Acid Violet 43, Acid Red 52, Acid Red 73, Acid Red 88, Acid Red 150, Acid Blue 25, Acid Blue 29, Acid Blue 45, Acid Blue 113, Acid Black 1, Direct Blue 1, Direct Blue 71, Direct Violet 51 and mixtures thereof. In another aspect, suitable small molecule dyes include small molecule dyes selected from the group consisting of Colour Index (Society of Dyers and Colourists, Bradford, UK) numbers Acid Violet 17, Direct Blue 71, Direct Violet 51, Direct Blue 1, Acid Red 88, Acid Red 150, Acid Blue 29, Acid Blue 113 or mixtures thereof.

Suitable polymeric dyes include polymeric dyes selected from the group consisting of polymers containing conjugated chromogens (dye-polymer conjugates) and polymers with chromogens co-polymerized into the backbone of the polymer and mixtures thereof.

In another aspect, suitable polymeric dyes include polymeric dyes selected from the group consisting of fabric-substantive colorants sold under the name of LIQUITINT® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of LIQUITINT® (Milliken, Spartanburg, S.C., USA) Violet CT, carboxymethyl cellulose (CMC) conjugated with a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colourants, alkoxylated thiophene polymeric colourants, and mixtures thereof.

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, and a clay selected from the group consisting of Montmorillonite clay, Hectorite clay, Saponite clay and mixtures thereof. In still another aspect, suitable dye clay conjugates include dye clay conjugates selected from the group consisting of: Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green G1 C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green G1 C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green G1 C.I. 42040 conjugate, Saponite Basic Red R1 C.I. 45160 conjugate, Saponite C.I. Basic Black 2 conjugate and mixtures thereof.

Suitable pigments include pigments selected from the group consisting of flavanthrone, indanthrone, chlorinated indanthrone containing from 1 to 4 chlorine atoms, pyranthrone, dichlo-ropyranthrone, monobromodichloropyranthrone, dibromodichloropyranthrone, tetrabromopyranthrone, perylene-3,4,9,10-tetracarboxylic acid diimide, wherein the imide groups may be un-substituted or substituted by C1-C3-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof.

In another aspect, suitable pigments include pigments selected from the group consisting of Ultramarine Blue (C.I. Pigment Blue 29), Ultramarine Violet (C.I. Pigment Violet 15) and mixtures thereof.

The aforementioned fabric hueing agents can be used in combination (any mixture of fabric hueing agents can be used). Suitable fabric hueing agents can be purchased from Aldrich, Milwaukee, Wis., USA; Ciba Specialty Chemicals, Basel, Switzerland; BASF, Ludwigshafen, Germany; Dayglo Color Corporation, Mumbai, India; Organic Dyestuffs Corp., East Provi-dence, Rhode Island, USA; Dystar, Frankfurt, Germany; Lanxess, Leverkusen, Germany; Megazyme, Wicklow, Ireland; Clariant, Muttenz, Switzerland; Avecia, Manchester, UK and/or made in accordance with the examples contained herein. Suitable hueing agents are described in more detail in U.S. Pat. No. 7,208,459 B2.

Test Method 1

A protocol to define whether a dye or pigment material is a fabric hueing agent for the purpose of the invention is given here:

1.) Fill two tergotometer pots with 800 ml of Newcastle upon Tyne, UK, City Water (~12 grains per US gallon total hardness, supplied by Northumbrian Water, Pity Me, Durham, Co. Durham, UK).
2) Insert pots into tergotometer, with water temperature controlled at 30° C. and agitation set at 40 rpm for the duration of the experiment.
3) Add 4.8 g of IEC-B detergent (IEC 60456 Washing Machine Reference Base Detergent Type B), supplied by wfk, BrOggen-Bracht, Germany, to each pot.
4) After two minutes, add 2.0 mg active colorant to the first pot.
5) After one minute, add 50 g of flat cotton vest (supplied by Warwick Equest, Consett, County Durham, UK), cut into 5 cm×5 cm swatches, to each pot.
6) After 10 minutes, drain the pots and re-fill with cold Water (16° C.) having a water hardness of 14.4 English Clark Degrees Hardness with a 3:1 Calcium to Magnesium molar ratio.
7) After 2 minutes rinsing, remove fabrics.
8) Repeat steps 3-7 for a further three cycles using the same treatments.
9) Collect and line dry the fabrics indoors for 12 hours.

10) Analyse the swatches using a Hunter Miniscan spectrometer fitted with D65 illuminant and UVA cutting filter, to obtain Hunter a (red-green axis) and Hunter b (yellow-blue axis) values.

11) Average the Hunter a and Hunter b values for each set of fabrics. If the fabrics treated with colorant under assessment show an average difference in hue of greater than 0.2 units on either the a axis or b axis, it is deemed to be a fabric hueing agent for the purpose of the invention.

The composition may comprise an encapsulate. In one aspect, an encapsulate comprising a core, a shell having an inner and outer surface, said shell encapsulating said core.

In one aspect of said encapsulate, said core may comprise a material selected from the group consisting of perfumes; brighteners; dyes; insect repellants; silicones; waxes; flavors; vita-mins; fabric softening agents; skin care agents in one aspect, paraffins; enzymes; anti-bacterial agents; bleaches; sensates; and mixtures thereof; and said shell may comprise a material selected from the group consisting of polyethylenes; polyamides; polystyrenes; polyisoprenes; pol-ycarbonates; polyesters; polyacrylates; aminoplasts, in one aspect said aminoplast may comprise a polyureas, polyurethane, and/or polyureaurethane, in one aspect said polyurea may comprise polyoxymethyleneurea and/or melamine formaldehyde; polyolefins; polysaccharides, in one aspect said polysaccharide may comprise alginate and/or chitosan; gelatin; shellac; epoxy resins; vinyl polymers; water insoluble inorganics; silicone; and mixtures thereof.

In one aspect of said encapsulate, said core may comprise perfume.

In one aspect of said encapsulate, said shell may comprise melamine formaldehyde and/or cross linked melamine formaldehyde.

In a one aspect, suitable encapsulates may comprise a core material and a shell, said shell at least partially surrounding said core material, is disclosed. At least 75%, 85% or even 90% of said encapsulates may have a fracture strength of from about 0.2 MPa to about 10 MPa, from about 0.4 MPa to about 5 MPa, from about 0.6 MPa to about 3.5 MPa, or even from about 0.7 MPa to about 3M Pa; and a benefit agent leakage of from 0% to about 30%, from 0% to about 20%, or even from 0% to about 5%.

In one aspect, at least 75%, 85% or even 90% of said encapsulates may have a particle size of from about 1 microns to about 80 microns, about 5 microns to 60 microns, from about 10 microns to about 50 microns, or even from about 15 microns to about 40 microns.

In one aspect, at least 75%, 85% or even 90% of said encapsulates may have a particle wall thickness of from about 30 nm to about 250 nm, from about 80 nm to about 180 nm, or even from about 100 nm to about 160 nm.

In one aspect, said encapsulates' core material may comprise a material selected from the group consisting of a perfume raw material and/or optionally a material selected from the group consisting of vegetable oil, including neat and/or blended vegetable oils including caster oil, coconut oil, cottonseed oil, grape oil, rapeseed, soybean oil, corn oil, palm oil, linseed oil, safflower oil, olive oil, peanut oil, coconut oil, palm kernel oil, castor oil, lemon oil and mixtures thereof; esters of vegetable oils, esters, including dibutyl adipate, dibutyl phthalate, butyl benzyl adipate, benzyl octyl adipate, tricresyl phosphate, trioctyl phosphate and mixtures thereof; straight or branched chain hydrocarbons, including those straight or branched chain hydrocarbons having a boiling point of greater than about 80° C.; partially hydrogenated terphenyls, dialkyl phthalates, alkyl biphenyls, including monoisopropylbiphenyl, alkylated naphthalene, including dipropylnaph-thalene, petroleum spirits, including kerosene, mineral oil and mixtures thereof; aromatic solvents, including benzene, toluene and mixtures thereof; silicone oils; and mixtures thereof.

In one aspect, said encapsulates' wall material may comprise a suitable resin including the reaction product of an aldehyde and an amine, suitable aldehydes include, formaldehyde. Suitable amines include melamine, urea, benzoguanamine, glycoluril, and mixtures thereof. Suitable melamines include methylol melamine, methylated methylol melamine, imino melamine and mixtures thereof. Suitable ureas include dimethylol urea, methylated dimethylol urea, urea-res-orcinol, and mixtures thereof.

In one aspect, suitable formaldehyde scavengers may be employed with the encapsulates, for example, in a capsule slurry and/or added to a consumer product before, during or after the encapsulates are added to such consumer product.

Suitable capsules that can be made by following the teaching of USPA 2008/0305982 A1; and/or USPA 2009/0247449 A1. Alternatively, suitable capsules can be purchased from Appleton Papers Inc. of Appleton, Wis. USA.

In addition, the materials for making the aforementioned encapsulates can be obtained from Solutia Inc. (St Louis, Mo. U.S.A.), Cytec Industries (West Paterson, N.J. U.S.A.), sigma-Aldrich (St. Louis, Mo. U.S.A.), CP Kelco Corp. of San Diego, Calif., USA; BASF AG of Ludwigshafen, Germany; Rhodia Corp. of Cranbury, N.J., USA; Hercules Corp. of Wilmington, Del., USA; Agrium Inc. of Calgary, Alberta, Canada, ISP of New Jersey U.S.A., Akzo Nobel of Chicago, Ill., USA; Stroever Shellac Bremen of Bremen, Germany; Dow Chemical Company of Midland, Mich., USA; Bayer AG of Leverkusen, Germany; Sigma-Aldrich Corp., St. Louis, Mo., USA In one aspect, the composition may comprise an enzyme stabilizer selected from the group consisting of (a) inorganic salts selected from the group consisting of calcium salts, magnesium salts and mixtures thereof; (b) carbohydrates selected from the group consisting of oligo-saccharides, polysaccharides and mixtures thereof; (c) mass efficient reversible protease inhibitors selected from the group consisting of phenyl boronic acid and derivatives thereof; and (d) mixtures thereof.

In another embodiment, the composition comprises: (1) reversible protease inhibitors such as a boron containing compound; (2) 1-2 propane diol; (3) calcium formate and/or sodium formate; and (4) any combination thereof.

In one aspect, the composition may comprise a structurant selected from the group consisting of diglycerides and triglycerides, ethylene glycol distearate microcrystalline cel-lulose, cel-lulose-based materials, microfiber cellulose, biopolymers, xanthan gum, gellan gum, and mixtures thereof.

The detergent may comprise one or more polymers. Examples are carboxymethylcellu-lose, poly(vinyl-pyrrolidone), poly (ethylene glycol), poly(vinyl alcohol), poly (vinylpyridine-N-oxide), poly(vinylimidazole), polycarboxylates such as polyacrylates, maleic/acrylic acid copolymers and lauryl methacrylate/acrylic acid co-polymers.

The detergent may contain a bleaching system, which may comprise a $H_2O_2$ source such as perborate or percarbonate which may be combined with a peracid-forming bleach activator such as tetraacetylethylenediamine or nonanoyloxyben-zenesul-fonate. Alternatively, the bleaching system may comprise peroxyacids of, e.g., the amide, imide, or sulfone type. In general, when a bleaching agent is used, the compositions of the present invention may comprise from about 0.1% to about 50% or even from about 0.1% to about 25% bleaching agent by weight of the subject cleaning composition. The enzyme variants of the invention may be stabilized using conventional stabilizing agents or and protease inhibitors, e.g., a polyol such as propylene glycol or glycerol, a sugar or sugar alcohol, different salts such as NaCl and KCl; lactic acid, formic acid, boric acid, or a boric acid derivative, e.g., an aromatic borate ester, or a phenyl boronic acid derivative such as 4-formylphenyl boronic acid, or a peptide aldehyde such as di-, tri- or tetrapeptide aldehydes or aldehyde analogues (either of the form B1-B0-R wherein, R is H, CH3, CX3, CHX2, or CH2X (X=halogen), B0 is a single amino acid residue (preferably with an optionally substituted aliphatic or aromatic side chain); and B1 consists of one or more amino acid residues (preferably one, two or three), optionally comprising an N-terminal protection group, or as described in WO09118375, WO98/13459) or a protease inhibitor of the protein type such as RASI, BASI, WASI (bifunctional alpha-amylase/subtilisin inhibitors of rice, barley and wheat) or 012 or SSI.

The composition may be formulated as described in, e.g., WO 92/19709 and WO 92/19708 or U.S. Pat. No. 6,472,364. In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), Nickel (II), and oxovanadium (IV)).

The detergent may also contain other conventional detergent ingredients such as e.g. fabric conditioners including clays, foam boosters, suds suppressors, anti-corrosion agents, soil-suspending agents, anti-soil re-deposition agents, dyes, bactericides, optical brighteners, hydrotropes, tarnish inhibitors, organic solvents such as ethanol, or perfumes. Furthermore, the detergent could contain a pre-spotter or a booster, which is added to the wash to increase the general cleaning level, some of these additives may also be used as a pre-treatment agent applied to the textile before the washing step.

It is at present contemplated that in the detergent compositions any enzyme, in particular the enzyme of the invention, may be added in an amount corresponding to 0.001-100 mg of enzyme protein per liter of wash liquor, preferably 0.005-5 mg of enzyme protein per liter of wash liquor, more preferably 0.01-1 mg of enzyme protein per liter of wash liquor and in particular 0.1-1 mg of enzyme protein per liter of wash liquor. However, the detergent compositions of the present invention comprise at least 0.0001 to about 0.1% weight percent of pure enzyme protein, such as from about 0.0001% to about 0.01%, from about 0.001% to about 0.01% or from about 0.001% to about 0.01%. However, when using a formulated enzyme the detergent composition comprises from about 0.02% to about 20% weight percent, such as or from about 0.05% to about 15% weight, or from about 0.05 to about 20%, or from about 0.05% to about 5%, or from about 0.05% to about 3%.

The alpha-amylase variants of the invention may additionally be incorporated in the detergent formulations disclosed in WO 97/07202, which is hereby incorporated as reference.

The composition typically comprises other detergent ingredients. Suitable detergent ingredients include: bleach; imine bleach boosters; sources of hydrogen peroxide such as percarbonate and/or perborate, especially percarbonate coated with material such as carbonate and/or sulphate salt, silicate salt, borosilicate, and any mixture thereof; pre-formed peracid, including pre-formed peracid in encapsulated form; transition metal catalysts; suds suppressing systems such as silicone based suds suppressors and/or fatty acid based suds suppressors; brighteners; photobleach; fabric-softening agents such as clay, silicone and/or quaternary ammonium compounds; flocculants such as polyethylene oxide; dye transfer inhibitors such as polyvinylpyrrolidone, poly 4-vinylpyridine N-oxide and/or co-polymer of vinylpyrrolidone and vinylimidazole; fabric integrity components such as oligomers produced by the condensation of imidazole and epichlorhydrin; soil dispersants and soil anti-redeposition aids such as alkoxylated polyamines and ethoxylated ethyleneimine polymers; anti-redeposition components such as polyesters; carboxylate polymers such as maleic acid polymers or co-polymers of maleic and acrylic acid; perfumes such as perfume microcapsules, starch encapsulated accords, perfume spray-on; soap rings; aesthetic particles; dyes; fillers such as sodium sulphate, although it is preferred for the composition to be substantially free of fillers; silicate salt such as sodium silicate, including 1.6R and 2.0R sodium silicate, or sodium metasilicate; co-polyesters of di-carboxylic acids and diols; cellulosic polymers such as methyl cellulose, carboxymethyl cellulose, hydroxyethoxycellulose, or other alkyl or alkylalkoxy cellulose; solvents such as 1,2 propanediol, monoethanolamine; diethylene glycol, ethanol, and any mixture thereof; hydrotropes such as sodium cumene sulphonate, sodium xylene sulphonate, sodium toluene sulphonate, and any mixtures; organic acids such as citric acid; and any combination thereof.

Example Laundry Detergent Composition

The following are liquid laundry detergent compositions suitable for top-loading automatic washing machines (1 and 2) and front loading washing machines (3).

| Ingredient | Composition (wt % of composition) | | |
| --- | --- | --- | --- |
| | 1 | 2 | 3 |
| $C_{12-15}$ Alkylethoxy(1.8)sulfate | 14.7 | 11.6 | |
| $C_{11.8}$ Alkylbenzene sulfonate | 4.3 | 11.6 | 8.3 |
| $C_{16-17}$ Branched alkyl sulfate | 1.7 | 1.29 | |
| $C_{12-14}$ Alkyl -9-ethoxylate | 0.9 | 1.07 | |
| $C_{12}$ dimethylamine oxide | 0.6 | 0.64 | |
| Citric acid | 3.5 | 0.65 | 3 |
| $C_{12-18}$ fatty acid | 1.5 | 2.32 | 3.6 |
| Sodium Borate (Borax) | 2.5 | 2.46 | 1.2 |
| Sodium $C_{12-14}$ alkyl ethoxy 3 sulfate | | | 2.9 |
| $C_{14-15}$ alkyl 7-ethoxylate | | | 4.2 |
| $C_{12-14}$ Alkyl -7-ethoxylate | | | 1.7 |

| Ingredient | Composition (wt % of composition) | | |
|---|---|---|---|
| | 1 | 2 | 3 |
| Calcium formate | 0.09 | 0.09 | |
| A compound having the following general structure: bis((C$_2$H$_5$O)(C$_2$H$_4$O)$n$)(CH$_2$)—N$^+$—C$_x$H$_{2x}$—N$^+$—(CH$_3$)-bis((C$_2$H$_5$O)(C$_2$H$_4$O)$n$), wherein n = from 20 to 30, and x = from 3 to 8, or sulphated or sulphonated variants thereof | | | 1.2 |
| Random graft co-polymer[1] | | 1.46 | 0.5 |
| Ethoxylated Polyethylenimine [2] | 1.5 | 1.29 | |
| Diethylene triamine pentaacetic acid | 0.34 | 0.64 | |
| Diethylene triamine penta(methylene phosphonic acid) | | | 0.3 |
| Tinopal AMS-GX | | 0.06 | |
| Tinopal CBS-X | 0.2 | 0.17 | |
| Amphiphilic alkoxylated grease cleaning polymer [3] | 1.28 | 1 | 0.4 |
| Ethanol | 2 | 1.58 | 1.6 |
| Propylene Glycol | 3.9 | 3.59 | 1.3 |
| Diethylene glycol | 1.05 | 1.54 | |
| Polyethylene glycol | 0.06 | 0.04 | |
| Monoethanolamine | 3.05 | 2.41 | 0.4 |
| NaOH | 2.44 | 1.8 | |
| Sodium Cumene Sulphonate | | | 1 |
| Sodium Formate | | 0.11 | |
| Water, Aesthetics (Dyes, perfumes) and Minors (Enzymes, solvents, structurants) | Balance | balance | balance |

[1] Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.
[2] Polyethylenimine (MW = 600) with 20 ethoxylate groups per —NH.
[3] Amphiphilic alkoxylated grease cleaning polymer is a polyethylenimine (MW = 600) with 24 ethoxylate groups per —NH and 16 propoxylate groups per —NH Compositions 4-8 Automatic Dishwashing Gels

| | 4 (wt %) | 5 (wt %) | 6 (wt %) | 7 (wt %) | 8 (wt %) |
|---|---|---|---|---|---|
| Wetting agent[1] | 1.0 | 1.3 | 0.8 | 1 | 0.9 |
| Sodium Benzoate (33% active) | 0.61 | 0.61 | 0.61 | 0.6 | 0.6 |
| Xanthan gum | 1.0 | 0.8 | 1.2 | 1 | 1.1 |
| Sodium Sulphate | 10.0 | 10.0 | 10.0 | 8 | 10 |
| Perfume | 0.03 | 0.05 | 0.03 | 0.06 | 0.1 |
| Sodium Silicate | 0 | 0 | 0 | 0 | 2 |
| Citric Acid (50% active) | 12.5 | 0 | 11 | 0 | 12 |
| GLDA | 0 | 7 | 0 | 8 | 0 |
| Savinase Ultra XL(44 mg active/g)[2] | 0.7 | 0 | 0.3 | 0 | 0 |
| 4-Formyl-Phenyl Boronic Acid | 0 | 0 | 0.05 | 0 | 0 |
| Encapsulated Protease (10 mg/g) [3] | 0.0 | 2.0 | 0.0 | 0 | 0 |
| FN3 liquid (48 mg active/g) [4] | 0.0 | 0.0 | 0 | 0.6 | 0 |
| Protease Prill (123 mg active/g) [4] | 0 | 0 | 0 | 0 | 0.5 |
| Ethanol | 0.0 | 0.0 | 0 | 0.3 | 0 |
| Potassium Hydroxide (45% active) | 14.6 | 14.6 | 14.6 | 14 | 0 |
| Calcium Chloride (25% active) | 1.8 | 1.8 | 1.8 | 1.1 | 0.4 |
| Dye | 0.05 | 0.05 | 0.05 | 0.05 | 0.02 |
| Proxcel GXL ™ (19% active) [8] | 0.05 | 0.05 | 0.05 | 0.05 | 0.05 |
| Acusol ™ 820 [9] | 0.34 | 0.34 | 0.3 | 0.35 | 0.3 |
| Acusol ™ 425N (50% active) [9] | 3.0 | 3.0 | 3.5 | 2.5 | 2 |
| Amylases of this invention (25 mg/g active)[2] | 0.2 | 0.5 | 0.4 | 0.3 | 0.1 |
| Water & other adjunct ingredients | Balance to 100% | Balance to 100% | Balance to 100% | Balance to 100% | Balance to 100% |

[1] Sold under tradename Polytergent ® SLF-18 by BASF, Ludwigshafen, Germany.
[2] Sold by Novozymes A/S, Denmark.
[3] Encapsulated protease of this invention
[4] Sold by Genencor International, California, USA. Suitable protease prills are sold under the tradenames FN3 ® and Properase ®.
[6] Sold by Alco Chemical, Tennessee, USA.
[7] One such suitable polymer would be sold under the tradename AqualicTL by Nippon Shoku-bai, Japan.
[8] Sold by Arch Chemicals Incorporated, Smyrna, Georgia, USA
[9] Sold by Rohm and Haas, Philadelphia, Pennsylvania, USA
2.0R Silicate is supplied by PQ Corporation, Malvern, PA, USA.
Sodium Carbonate is supplied by Solvay, Houston, Texas, USA
Sodium percarbonate (2Na$_2$CO$_3$•3H$_2$O$_2$) supplied by Solvay, Houston, Texas, USA
Hydroxyethane di phosphonate (HEDP) is supplied by Dow Chemical, Midland, Michigan, USA Dishwash Detergent Compositions The enzyme of the invention may also be used in dish wash detergent compositions, including the following:

1) POWDER AUTOMATIC DISHWASHING COMPOSITION

| | |
|---|---|
| Nonionic surfactant | 0.4-2.5% |
| Sodium metasilicate | 0-20% |
| Sodium disilicate | 0-20% |
| Sodium triphosphate | 0-40% |
| Sodium carbonate | 0-20% |
| Sodium perborate | 2-9% |
| Tetraacetyl ethylene diamine (TAED) | 1-4% |
| Sodium sulfate | 5-33% |
| Enzymes | 0.0001-0.1% |

2) POWDER AUTOMATIC DISHWASHING COMPOSITION

| | |
|---|---|
| Nonionic surfactant (e.g. alcohol ethoxylate) | 1-2% |
| Sodium disilicate | 0-30% |
| Sodium carbonate | 10-50% |
| Sodium phosphonate | 0-5% |
| Trisodium citrate dehydrate | 0-30% |
| Nitrilotrisodium acetate (NTA) | 0-20% |
| Sodium perborate monohydrate | 5-10% |
| Tetraacetyl ethylene diamine (TAED) | 1-2% |
| Polyacrylate polymer (e.g. maleic acid/acrylic acid co-polymer) | 6-25% |
| Enzymes | 0.0001-0.1% |
| Perfume | 0.1-0.5% |
| Water | 5-10 |

3) POWDER AUTOMATIC DISHWASHING COMPOSITION

| | |
|---|---|
| Nonionic surfactant | 0.5-2.0% |
| Sodium disilicate | 0-40% |
| Sodium citrate | 0-55% |
| Sodium carbonate | 0-29% |
| Sodium bicarbonate | 0-20% |
| Sodium perborate monohydrate | 0-15% |
| Tetraacetyl ethylene diamine (TAED) | 0-6% |
| Maleic acid/acrylic acid copolymer | 0-5% |
| Clay | 0-3% |
| Polyamino acids | 0-20% |
| Sodium polyacrylate | 0-8% |
| Enzymes | 0.0001-0.1% |

4) POWDER AUTOMATIC DISHWASHING COMPOSITION

| | |
|---|---|
| Nonionic surfactant | 1-2% |
| Zeolite MAP | 15-42% |
| Sodium disilicate | 0-34% |
| Sodium citrate | 0-12% |
| Sodium carbonate | 0-20% |
| Sodium perborate monohydrate | 7-15% |
| Tetraacetyl ethylene diamine (TAED) | 0-3% |
| Polymer | 0-4% |
| Maleic acid/acrylic acid copolymer | 0-5% |
| Organic phosphonate | 0-4% |
| Clay | 0-2% |
| Enzymes | 0.0001-0.1% |
| Sodium sulfate | Balance |

5) POWDER AUTOMATIC DISHWASHING COMPOSITION

| | |
|---|---|
| Nonionic surfactant | 1-7% |
| Sodium disilicate | 0-30% |
| Trisodium citrate | 0-24% |
| Sodium carbonate | 12-20% |
| Monopersulfate (2 $KHSO_5 \cdot KHSO_4 \cdot K_2SO_4$) | 15-21% |
| Bleach stabilizer | 0.1-2% |
| Maleic acid/acrylic acid copolymer | 0-6% |
| Diethylene triamine pentaacetate, pentasodium salt | 0-2.5% |
| Enzymes | 0.0001-0.1% |
| Sodium sulfate, water | Balance |

6) POWDER AND LIQUID DISHWASHING COMPOSITION WITH CLEANING SURFACTANT System

| | |
|---|---|
| Nonionic surfactant | 0-1.5% |
| Octadecyl dimethylamine N-oxide dihydrate | 0-5% |
| 80:20 wt. C18/C16 blend of octadecyl dimethylamine N-oxide dihydrate and hexadecyldimethyl amine N-oxide dehydrate | 0-4% |
| 70:30 wt. C18/C16 blend of octadecyl bis (hydroxyethyl)amine N-oxide anhydrous and hexadecyl bis (hydroxyethyl)amine N-oxide anhydrous | 0-5% |
| $C_{13}$-$C_{15}$ alkyl ethoxysulfate with an average degree of ethoxylation of 3 | 0-10% |
| $C_{12}$-$C_{15}$ alkyl ethoxysulfate with an average degree of ethoxylation of 3 | 0-5% |
| $C_{13}$-$C_{15}$ ethoxylated alcohol with an average degree of ethoxylation of 12 | 0-5% |
| A blend of $C_{12}$-$C_{15}$ ethoxylated alcohols with an average degree of ethoxylation of 9 | 0-6.5% |
| A blend of $C_{13}$-$C_{15}$ ethoxylated alcohols with an average degree of ethoxylation of 30 | 0-4% |
| Sodium disilicate | 0-33% |
| Sodium tripolyphosphate | 0-46% |
| Sodium citrate | 0-28% |
| Citric acid | 0-29% |
| Sodium carbonate | 0-20% |
| Sodium perborate monohydrate | 0-11.5% |
| Tetraacetyl ethylene diamine (TAED) | 0-4% |
| Maleic acid/acrylic acid copolymer | 0-7.5% |
| Sodium sulfate | 0-12.5% |
| Enzymes | 0.0001-0.1% |

7) NON-AQUEOUS LIQUID AUTOMATIC DISHWASHING COMPOSITION

| | |
|---|---|
| Liquid nonionic surfactant (e.g. alcohol ethoxylates) | 2.0-10.0% |
| Alkali metal silicate | 0-15.0% |
| Alkali metal phosphate | 0-40.0% |
| Liquid carrier selected from higher glycols, polyglycols, polyoxides, glycolethers | 25.0-45.0% |
| Stabilizer (e.g. a partial ester of phosphoric acid and a $C_{16}$-$C_{18}$ alkanol) | 0.5-7.0% |
| Foam suppressor (e.g. silicone) | 0-1.5% |
| Enzymes | 0.0001-0.1% |

8) NON-AQUEOUS LIQUID DISHWASHING COMPOSITION

| | |
|---|---|
| Liquid nonionic surfactant (e.g. alcohol ethoxylates) | 2.0-10.0% |
| Sodium silicate | 0-15.0% |
| Alkali metal carbonate | 7.0-20.0% |
| Sodium citrate | 0-1.5% |
| Stabilizing system (e.g. mixtures of finely divided silicone and low molecular weight dialkyl polyglycol ethers) | 0.5-7.0% |
| Low molecule weight polyacrylate polymer | 5.0-15.0% |
| Clay gel thickener (e.g. bentonite) | 0-10.0% |

| | |
|---|---|
| Hydroxypropyl cellulose polymer | 0-0.6% |
| Enzymes | 0.0001-0.1% |
| Liquid carrier selected from higher lycols, polyglycols, polyoxides and glycol ethers | Balance |

9) THIXOTROPIC LIQUID AUTOMATIC DISHWASHING COMPOSITION

| | |
|---|---|
| $C_{12}$-$C_{14}$ fatty acid | 0-0.5% |
| Block co-polymer surfactant | 1.5-15.0% |
| Sodium citrate | 0-12% |
| Sodium tripolyphosphate | 0-15% |
| Sodium carbonate | 0-8% |
| Aluminium tristearate | 0-0.1% |
| Sodium cumene sulfonate | 0-1.7% |
| Polyacrylate thickener | 1.32-2.5% |
| Sodium polyacrylate | 2.4-6.0% |
| Boric acid | 0-4.0% |
| Sodium formate | 0-0.45% |
| Calcium formate | 0-0.2% |
| Sodium n-decydiphenyl oxide disulfonate | 0-4.0% |
| Monoethanol amine (MEA) | 0-1.86% |
| Sodium hydroxide (50%) | 1.9-9.3% |
| 1,2-Propanediol | 0-9.4% |
| Enzymes | 0.0001-0.1% |
| Suds suppressor, dye, perfumes, water | Balance |

10) LIQUID AUTOMATIC DISHWASHING COMPOSITION

| | |
|---|---|
| Alcohol ethoxylate | 0-20% |
| Fatty acid ester sulfonate | 0-30% |
| Sodium dodecyl sulfate | 0-20% |
| Alkyl polyglycoside | 0-21% |
| Oleic acid | 0-10% |
| Sodium disilicate monohydrate | 0-33% |
| Sodium citrate dehydrate | 0-33% |
| Sodium stearate | 0-2.5% |
| Sodium perborate monohydrate | 0-13% |
| Tetraacetyl ethylene diamine (TAED) | 0-8% |
| Maleic acid/acrylic acid copolymer | 4-8% |
| Enzymes | 0.0001-0.1% |

11) LIQUID AUTOMATIC DISHWASHING COMPOSITION CONTAINING PROTECTED BLEACH Particles

| | |
|---|---|
| Sodium silicate | 5-10% |
| Tetrapotassium pyrophosphate | 0-25% |
| Sodium triphosphate | 0-2% |
| Potassium carbonate | 4-8% |
| Protected bleach particles, e.g. chlorine | 5-10% |
| Polymeric thickener | 0.7-1.5% |
| Potassium hydroxide | 0-2% |
| Enzymes | 0.0001-0.1% |
| Water | Balance |

12) Automatic dishwashing compositions as described in 1), 2), 3), 4), 6) and 10), wherein perborate is replaced by percarbonate.

13) Automatic dishwashing compositions as described in 1)-6) which additionally contain a manganese catalyst. The manganese catalyst may, e.g., be one of the compounds described in "Efficient manganese catalysts for low-temperature bleaching", Nature, 369, 1994, pp. 637-639.

INDUSTRIAL APPLICATION

The present invention is also directed to methods for using the alpha-amylase variants.

The variant alpha-amylase are preferably incorporated into and/or used together with detergent compositions, for example in laundry detergent compositions, for example household laundry detergent compositions, especially liquid laundry detergent compositions. In particular the detergent comprises at least one chelating agent and the detergent composition typically comprises conventional detergent ingredients such as surfactants (anionic, cationic, nonionic, zwitterionic, amphoteric), builders, bleaches, polymers, other enzymes and other ingredients, e.g. as described in WO 2007/130562 and WO 2007/149806, which are hereby incorporated by reference in its entirety.

Owing to their activity at alkaline pH values, the α-amylases of the invention are well suited for use in a variety of industrial processes, in particular the enzyme finds potential applications as a component in washing, dishwashing and hard surface cleaning detergent compositions, but it may also be useful in the production of sweeteners, syrup such as glucose and the like, plastic precursors, a fermentation product, especially ethanol, butanol and methanol, and biogas such as methane or any other product originating from starch. Conditions for conventional starch-converting processes and liquefaction and/or saccharification processes are described in, for instance, U.S. Pat. No. 3,912,590 and EP patent publications Nos. EP 252,730 and EP 63,909.

The alpha-amylase variants of the invention may also be used in the production of lignocellulosic materials, such as pulp, paper and cardboard, from starch reinforced waste paper and cardboard, especially where repulping occurs at pH above 7 and where amylases can facilitate the disintegration of the waste material through degradation of the reinforcing starch. The alpha-amylase variants of the invention may also be useful in modifying starch where enzymatically modified starch is used in papermaking together with alkaline fillers such as calcium carbonate, kaolin and clays.

Thus the above described compositions may further comprise non-detergent components, a fermenting organism such as e.g. yeast preferably a strain of *Saccharomyces*, a plant material or starch-containing material such as e.g. tubers, roots, stems, whole grains, corns, cobs, wheat, barley, rye, milo, sago, cassava, tapioca, sorghum, rice peas, beans, or sweet potatoes, or mixtures thereof, or cereals, sugar-containing raw materials, such as molasses, fruit materials, sugar cane or sugar beet, potatoes, and cellulose-containing materials, such as wood or plant residues, or mixtures thereof.

The alpha-amylase variants of the invention may also be useful in textile desizing. In the textile processing industry, alpha-amylases are traditionally used as auxiliaries in the desizing process to facilitate the removal of starch-containing size which has served as a protective coating on weft yarns during weaving.

Complete removal of the size coating after weaving is important to ensure optimum results in the subsequent processes, in which the fabric is scoured, bleached and dyed. Enzymatic starch break-down is preferred because it does not involve any harmful effect on the fibre material.

In order to reduce processing cost and increase mill throughput, the desizing processing is sometimes combined with the scouring and bleaching steps. In such cases, non-enzymatic auxiliaries such as alkali or oxidation agents are typically used to break down the starch, because traditional alpha-amylases are not very compatible with high pH levels and bleaching agents. The non-enzymatic breakdown of the starch size does lead to some fibre damage because of the rather aggressive chemicals used.

Accordingly, it would be desirable to use the alpha-amylase variants of the invention as they have an improved performance in alkaline solutions. The alpha-amylase variants may be used alone or in combination with a cellulase when desizing cellulose-containing fabric or textile.

In one embodiment, the present invention relates to products for and/or methods relating to and/or use of the claimed compositions that are not for air care. In one embodiment, the present invention relates to products for and/or methods relating to and/or use of the claimed compositions that are not for car care. In one embodiment, the present invention relates to products for and/or methods relating to and/or use of the claimed compositions that are not for dishwashing. In one embodiment, the present invention relates to products for and/or methods relating to and/or use of the claimed compositions that are not for fabric conditioning (including softening). In one embodiment, the present invention relates to products for and/or methods relating to and/or use of the claimed compositions that are not for laundry detergency. In one embodiment, the present invention relates to products for and/or methods relating to and/or use of the claimed compositions that are not for laundry and rinse additive and/or care. In one embodiment, the present invention relates to products for and/or methods relating to and/or use of the claimed compositions that are not for hard surface cleaning and/or treatment and other cleaning for consumer or institutional use. In one embodiment, the present invention relates to products for and/or methods relating to and/or use of the claimed compositions that are not for air care, car care, dishwashing, fabric conditioning (including softening), laundry detergency, laundry and rinse additive and/or care, hard surface cleaning and/or treatment, and other cleaning for consumer or institutional use.

Materials and Methods
Enzymes:
SP722: SEQ ID NO: 6, available from Novozymes, and disclosed in WO 95/26397.
SP707 or #707: SEQ ID NO: 8
AA560: SEQ ID NO: 10
General Molecular Biology Methods:

Unless otherwise mentioned the DNA manipulations and transformations were performed using standard methods of molecular biology (Sambrook et al. (1989); Ausubel et al. (1995); Harwood and Cutting (1990).
Fermentation of Alpha-Amylases and Variants Fermentation may be performed by methods well known in the art or as follows. A *B. subtilis* strain harboring the relevant expression plasmid is streaked on a LB-agar plate with a relevant antibiotic, and grown overnight at 37° C.

The colonies are transferred to 100 ml BPX media supplemented with a relevant antibiotic (for instance 10 mg/l chloroamphinicol) in a 500 ml shaking flask.
Composition of BPX Medium:

| | |
|---|---|
| Potato starch | 100 g/l |
| Barley flour | 50 g/l |
| BAN 5000 SKB | 0.1 g/l |
| Sodium caseinate | 10 g/l |
| Soy Bean Meal | 20 g/l |
| $Na_2HPO_4$, 12 $H_2O$ | 9 g/l |
| Antifoaming agent | 0.1 g/l |

The culture is shaken at 37° C. at 270 rpm for 4 to 5 days.
Cells and cell debris are removed from the fermentation broth by centrifugation at 4500 rpm in 20-25 minutes.

Afterwards the supernatant is filtered to obtain a completely clear solution. The filtrate is concentrated and washed on an UF-filter (10000 cut off membrane) and the buffer is changed to 20 mM Acetate pH 5.5, e.g. by dialysis or gelfiltration. The UF-filtrate is applied on a S-sepharose F.F. (General Electric, Cation exchange, Matrix: Cross-linked agarose, functional group: —$OCH_2CHOHCH_2OCH_2CH_2CH_2SO_3$) and elution is carried out by step elution with 0.2 M NaCl in the same buffer. The eluate is dialysed against 10 mM Tris (2-amino-2-hydroxymethyl-propane-1,3-diol), pH 9.0 and applied on a Q-sepharose F.F. (General Electric, anion exchange, Matrix: cross-linked agarose, functional group: —$OCH_2CHOHCH_2OCH_2CHOHCH_2N+(CH_3)_3$), and eluted with a linear gra-dient from 0-0.3M NaCl over 6 column volumes. The fractions, which contain the activity (measured by the EnzCheck assay) are pooled, pH is adjusted to pH 7.5 and remaining color is removed by a treatment with 0.5% w/vol. active coal in 5 minutes. It may further be advantageous to add a further buffer exchange step, e.g. by dialysis or gelfiltration to a buffer system that does not affect the wash result in itself, e.g. to an EPPS-buffer, a glycine-buffer, an acetate buffer or the like, preferably with a small concentration of calcium (e.g. 0.1 mM) to stabilize the amylase during storage and about 0.01% TRITON™ X-100 to reduce risk of adsorption of enzyme protein to containers and pipettes.

Model Detergent
Composition of Model Detergent A:

| Compound | Amount g/100 g | % active ingredient |
|---|---|---|
| Surfactants | | |
| Na-LAS (92%) (Nacconol 90G) (anionic) (linear alkylbenzene sulfonate) | 10.87 | 10 |
| STEOL CS-370E (70%) (anionic), $CH_3(CH_2)_m$—$(OCH_2CH_2)_3$—$OSO_3$—, where m = 11-13 | 7.14 | 5 |
| Bio-soft N25-7 (99.5%) (non-ionic),: $CH_3(CH_2)_m$—$(OCH_2CH_2)_7$—OH, where and m = 11-14 | 5 | 5 |
| Oleic acid (fatty acid) | 2 | 2 |
| Solvents | | |
| $H_2O$ | 62 | 65 |
| Ethanol | 0.5 | 0.5 |
| STS (sodium p-toluene sulfonate (40%)) | 3.75 | 1.5 |
| Mono propylene glycol | 2 | 2 |
| Builder | | |
| Tri-sodium-citrate | 4 | 4 |
| Triethanolamine (TEA) | 0.5 | 0.5 |
| Stabilizer | | |
| Boric acid | 1.5 | 1.5 |
| Minors | | |
| 10N NaOH (for adjustment to pH 8.5) | 0.8 | 0.8 |

Composition of Model Detergent B:

| Compound | Amount g/100 g | % active ingredient |
|---|---|---|
| Surfactants | | |
| Na-LAS (92%) (Nacconol 90G) (anionic) | 10.87 | 10 |
| STEOL CS-370E (70%) (anionic) | 7.14 | 5 |
| Bio-soft N25-7 (99.5%) (non-ionic) | 5 | 5 |
| Oleic acid (fatty acid) | 2 | 2 |

-continued

| Compound | Amount g/100 g | % active ingredient |
|---|---|---|
| Solvents | | |
| H₂O | 62 | 65 |
| Ethanol | 0.5 | 0.5 |
| STS (sodium p-toluene sulfonate (40%) | 3.75 | 1.5 |
| Mono propylene glycol | 2 | 2 |
| Builder | | |
| Diethylene triamine penta acetic acid (DTPA) | 1.5 | 1.5 |
| Triethanolamine (TEA) | 0.5 | 0.5 |
| Stabilizer | | |
| Boric acid | 1.5 | 1.5 |
| Minors | | |
| 10N NaOH (for adjustment to pH 8.0) | 0.8 | 0.8 |

Assay for Measurement of Free Calcium Ions

The following assay may be used for the measurement of free calcium ions in solution, and thus for the determination of chelating agents (chelants) ability to reduce the concentration of free calcium ions ($Ca^{2+}$) from e.g. 2.0 mM to 0.10 mM at pH 8.

Assay Principle:

Various amounts of chelants are added to a solution of 2.0 mM Ca' and the free $Ca^{2+}$ concentration is determined by using a Calcium Ion Selective Electrode at fixed pH and temperature. The concentration of chelant necessary to reduce the concentration of free calcium from 2.0 mM to 0.10 mM can be determined from a plot of the free calcium concentration measured versus the concentration of chelant. In the present assay the concentration of chelant necessary to reduce the concentration of free calcium from 2.0 mM to 0.10 mM is measured at pH 8, at 21° C., in potassium chloride and 49 mM EPPS.

Solutions:

Electrolyte solution: 4 M potassium chloride in ultrapure water (Milli-Q water).

pH 8 buffer: 50 mM EPPS (4-(2-Hydroxyethyl)piperazine-1-propanesulfonic acid) adjusted to pH 8.0 using minimum amounts of 1 N sodium hydroxide.

Calcium stock solution: 25 mM $Ca^{2+}$ in pH 8 buffer, made from $CaCl_2.2H_2O$.

Chelant stock solution: 15 mM chelant (on a 100% dry chelator basis) in pH 8 buffer, re-adjusted to pH 8.0 using minimum amounts of 1 M NaOH or 1 M HCl.

Ultra pure water (Milli Q water) is used for preparation of all buffers and solutions.

Equipment:

Calcium Ion Selective Electrode from Thermo Scientific (cat. No. 9720BNWP) calibrated against a Calcium chloride standard solution. The electrode is calibrated as described by the guidelines following the electrode.

Procedure:

A series of vials are prepared, each containing 4 mL of the calcium stock solution (final concentration 2.0 mM), 1 mL electrolyte solution (final concentration 80 mM potassium chloride), chelant stock solution in various amounts (0-45 mL) and using the pH 8 buffer for adjusting the total volume to 50 mL. The final concentration of EPPS in the assay is 49 mM.

After mixing, the concentration of free $Ca^{2+}$ is measured by the calcium electrode. The free calcium concentration should be determined at a sufficient number of different chelant concentrations for each chelant tested, ensuring that the data set covers the entire range from 2.0 mM free calcium ions to a value below 0.10 mM or the final chelant concentration in the assay is higher than 10.0 mM. A suitable number of data points are 8 or more. The chelant concentration required to lower the initial 2.0 mM free calcium ions to 0.10 mM is obtained from a plot of the measured free calcium ion concentration versus chelator concentration by interpolation.

The solutions are equilibrated to the desired temperature, which in the present assay is 21° C.

Determination of log K

Chelating agents can also be characterized by the binding constant of the chelating agent (chelator) and calcium ions. This constant can be determined by ITC (isothermal titration calorimetry) as described by A D Nielsen, C C Fuglsang and P Westh, Analytical Biochemistry Vol. 314 (2003) page 227-234 and T Wiseman, S Williston, J F Brandts and L-N Lin, Analytical Biochemistry Vol. 179 (1989) page 131-137.

All glassware and plastic bottles used are washed with a 1% (w/w) EDTA solution and subsequently rinsed thoroughly in Chelex 100 treated ultrapure water (Milli-Q water). Solutions are stored in plastic bottles and kept at 5° C. until use.

Buffers:

20 mM HEPES (2-[4-(2-hydroxyethyl)-1-piperazinyl]-ethanesulfonic acid), pH 8 prepared with ultrapure water (Milli-Q water)

20 mM glycine, pH 10 prepared with ultrapure water (Milli-Q water)

Solutions:

125 µM chelant in 20 mM HEPES, pH 8 or 125 µM chelant in 20 mM glycine, pH 10

4 mM $CaCl_2$) in 20 mM HEPES, pH 8 or 4 mM $CaCl_2$) in 20 mM glycine, pH 10

Ultrapure water (Milli-Q water)

All buffers are passed through Chelex 100 columns (Sigma Aldrich C-7901, matrix 1% cross-linked polystyrene matrix active group iminodiacetic acid (sodium form) matrix attachment through methyl group to aromatic rings) to remove calcium ions. All solutions are degassed by stirring under vacuum before the experiments.

Instrument:

MCS-ITC (MicroCal Inc., Northampton, Mass., USA)

Procedure

The reference cell is filled with ultrapure water (Milli-Q water). The sample cell is filled with the chelant solution at the selected pH and the syringe is filled with the calcium solution at the selected pH. The solutions are equilibrated to the desired temperature, e.g. 19° C.

The chelator solution in the sample cell is then titrated with 30-40 aliquots of 8 µL of the calcium solution.

The obtained signals from the ITC are then integrated using the Origin software supplied by MicroCal Inc. To obtain the binding isotherms, regression routines are made using the same software package. These data are then fitted to a model using the routines embedded in the Origin software. Presently preferred is the "OneSites" model which gives the best fit for most of the commonly used chelating agents, i.e. the residuals are evenly distributed around zero. From the K value the log K is calculated as the logarithm (base 10) of the K value.

Assays for Determining Wash Performance

In order to assess the wash performance of the alpha-amylase variants in a detergent composition, washing experiments may be performed. The enzymes are tested using the Automatic Mechanical Stress Assay (AMSA) or the wash performing test using beakers. With the AMSA test the wash performance of a large quantity of small volume enzyme-detergent solutions can be examined. The AMSA plate has a number of slots for test solutions and a lid firmly squeezing the textile swatch to be washed against all the slot openings. During the washing time, the plate, test solutions, textile and lid are vigorously shaken to bring the test solution in contact with the textile and apply mechanical stress in a regular, periodic oscillating manner. For further description see WO 02/42740, especially the paragraph "Special method embodiments" at page 23-24.

General Wash Performance Description:

A test solution comprising water (15° dH), 0.8 g/L detergent, e.g. model detergent A or B as described above, or 50 mM HCO3-, and the enzyme of the invention, e.g. at concentration of 0, 0.2, 0.4, 0.8 and/or 1.2 mg enzyme protein/L, is prepared. Fabrics stained with starch (e.g. CS-28 from Center For Testmaterials BV, P.O. Box 120, 3133 KT, Vlaardingen, The Netherlands) is added and washed for 30 minutes at 20° C. After thorough rinse under running tap water and drying in the dark, the light intensity or reflectance values of the stained fabrics are subsequently measured as a measure for wash performance. The test with 0 mg enzyme protein/L is used as a blank to obtain a delta remission value. Preferably mechanical action is applied during the wash step, e.g. in the form of shaking, rotating or stirring the wash solution with the fabrics.

The AMSA wash performance experiments may be conducted under the experimental conditions specified below:

| | |
|---|---|
| Detergent | Model detergent A or B |
| Detergent dosage | 0.8 g/L |
| Test solution volume | 160 micro L |
| pH | As is |
| Wash time | 30 minutes |
| Temperature | 20° C. |
| Water hardness | 15° dH |
| Enzyme concentration in test solution | 0; 0.2; 0.4; 0.8; 1.2 mg/L |
| Test material | CS-28 (Rice starch on cotton) |

Water hardness was adjusted to 15° dH by addition of CaCl2, MgCl$_2$, and NaHCO$_3$ (Ca$^{2+}$:Mg$^{2+}$:HCO$_3^-$=4:1:7.5, molar basis) to the test system. After washing the textiles were flushed in tap water and dried in the dark.

The performance of the enzyme variant is measured as the brightness of the color of the textile washed with that specific amylase. Brightness can also be expressed as the intensity of the light reflected from the sample when illuminated with white light. When the sample is stained the intensity of the reflected light is lower, than that of a clean sample. Therefore, the intensity of the reflected light can be used to measure wash performance of an amylase.

Color measurements are made with a professional flatbed scanner (Kodak iQsmart, Kodak), which is used to capture an image of the washed textile.

To extract a value for the light intensity from the scanned images, 24-bit pixel values from the image are converted into values for red (r), green (g) and blue (b), also known as RGB value. The intensity value (Int) is calculated by adding the RGB values together as vectors and then taking the length of the resulting vector:

$$Int = \sqrt{r^2 + g^2 + b^2}.$$

Textiles: Textiles sample CS-28 (rice starch on cotton) can be obtained from Center For Test materials BV, P.O. Box 120, 3133 KT Vlaardingen, the Netherlands.

The wash performance test using beakers is an assay in a small scale model of a top loaded washing machine and used to evaluate the washing performance of amylases. The beaker wash performance test, using 250 mL beakers and a paddle stirrer providing oscillating rotational motion, 180° in each direction, with a frequency of 80 per minute, comprises the following steps: providing 100 mL wash solution (6° C., 15° dH, pH 8.0) containing 50 mM NaHCO$_3$ and 0.4 mg/L enzyme; adding two swatches of CS-28 (5×5 cm) and two swatches of EMPA 162 (5×5 cm) to the wash solution to start the wash; setting the agitation speed to 80 rpm; stopping the agitation after 60 minutes, rinsing the swatches under cold running tap water; drying the rinsed swatches in the dark over night; and evaluating the wash performance by measuring the remission of incident light at 460 nm using Color Eye as described below.

Equipment and Materials

Water bath (5° C.) with circulation; glass beakers (250 mL); one rotating arm per beaker with capacity of 100 mL of washing solution; test swatches: CS-28 (rice starch on cotton) from Center for Testmaterials BV, Vlaardingen, The Netherlands and EMPA 162 (rice starch on cotton/polyester) from EMPA Testmaterials AG, St. Gallen, Switzerland, the swatches are cut into 5×5 cm.

Wash solution: 50 mM NaHCO$_3$ buffer, pH 8.0, water hardness: 15° dH, Calcium:Magnesium ratio 4:1.

Amylase stock solution: 1 mg enzyme protein per mL.—A solution of 0.1% (w/v) Triton X-100 and 0.1 mM CaCl$_2$ in ultrapure water (MilliQ water) is used for dilution of amylase (amylase dilution buffer).

Color Eye Measurement

Wash performance is expressed as a delta remission value (ΔRem). Light reflectance evaluations of the swatches were done using a Macbeth Color Eye 7000 reflectance spectrophotometer with very small oval aperture, i.e. 0.7 cm$^2$ (~0.7×1.0 cm). The measurements were made without UV in the incident light and remission at 460 nm was extracted. The swatch to be measured was placed on top of another swatch of the same type before being measured to reduce reflection from the piston pushing the swatch up against the measuring opening. Delta remission values for individual swatches were calculated by subtracting the remission value of the swatch washed without added amylase (control) from the remission value of the swatch washed with amylase.

Assays for Measurement of Amylolytic Activity (Alpha-Amylase Activity)

EnzChek Assay

The amylase activity or residual amylase activity can be determined by the following EnzCheck assay. The substrate is a corn starch derivative, DQ™ starch (corn starch BODIPY FL conjugate), which is corn starch labeled with BODIPY® FL (4,4-difluoro-5,7-dimethyl-4-bora-3a,4a-diaza-s-indacene-3-propionic acid) dye to such a degree that the fluorescence is quenched. One vial containing approx. 1 mg lyophilized substrate is dissolved in 100 μL 50 mM sodium acetate pH 4.0. The vial is vortexed for 20 seconds and left at room temperature, in the dark, with occasional mixing until dissolved. Then 950 μL 10 mM sodium acetate, 0.01% (w/V) TRITON™ X100 ((polyethylene glycol p-(1, 1,3,3-tetramethylbutyl)-phenyl ether (C$_{14}$H$_{22}$O(C$_2$H$_4$O)$_n$ (n=9-10)), pH 5.0 is added, vortexed thoroughly and stored at room temperature, in the dark until ready to use. From 1 mL of this solution, the substrate working solution was prepared by mixing with 5 mL 50 mM HEPES, 0.01% (w/V) TRITON™ X100, 1 mM $CaCl_2$, pH 7.0.

The enzyme containing detergent is diluted to a concentration of 15 ng enzyme protein/ml (6826.7 times dilution) in 50 mM HEPES, 0.01% TRITON™ X100, 1 mM $CaCl_2$, pH 7.0. For the assay, 25 µL of the substrate working solution is mixed for 10 second with 25 µL of the diluted enzyme in a black 384 well microtiter plate. The fluorescence intensity is measured (exci-tation: 485 nm, emission: 555 nm) once every second minute for 30 minutes in each well at 25° C. and the $V_{max}$ is calculated as the slope of the plot of fluorescence intensity against time. The plot should be linear and the residual activity assay has to been adjusted so that the diluted reference enzyme solution is within the linear range of the activity assay.

In a few instances there is a significant interference from the detergent without amylase on the assay. In such cases alternative amylase assays can be used. Interference from a detergent on an amylase assay can be tested by adding a known amount of amylase to the detergent at two levels and then measure the activity of the two samples. If the difference in the measured activities corresponds to the differences in the levels between the added amylases, the assay can be used to determine the residual activity of the amylase after storage.

PNP-G7 Assay

The alpha-amylase activity may be determined by a method employing the PNP-G7 substrate. PNP-G7 which is an abbreviation for 4,6-ethylidene($G_7$)-p-nitrophenyl($G_1$)-α, D-maltaheptaoside, a blocked oligosaccharide which can be cleaved by an endo-amylase, such as an alpha-amylase. Following the cleavage, the alpha-Glucosidase included in the kit digest the hydrolysed substrate further to liberate a free PNP molecule which has a yellow color and thus can be measured by visible spectophometry at X=405 nm (400-420 nm.). Kits containing PNP-G7 substrate and alpha-Glucosidase is manufactured by Roche/Hitachi (cat. No. 11876473).

Reagents:

The G7-PNP substrate from this kit contains 22 mM 4,6-ethylidene-G7-PNP and 52.4 mM HEPES (2-[4-(2-hydroxyethyl)-1-piperazinyl]-ethanesulfonic acid), pH 7.0).

The alpha-Glucosidase reagent contains 52.4 mM HEPES, 87 mM NaCl, 12.6 mM $MgCl_2$, 0.075 mM $CaCl_2$, ≥4 kU/L alpha-glucosidase).

The substrate working solution is made by mixing 1 mL of the alpha-Glucosidase reagent with 0.2 mL of the G7-PNP substrate. This substrate working solution is made immediately before use.

Dilution buffer: 50 mM EPPS, 0.01% (w/v) TRITON™ X100 (polyethylene glycol p-(1,1,3,3-tetramethylbutyl)-phenyl ether ($C_{14}H_{22}O(C_2H_4O)$, (n=9-10))), 1 mM CaCl2), pH7.0.

Procedure:

The amylase sample to be analyzed was diluted in dilution buffer to ensure the pH in the diluted sample is 7. The assay was performed by transferring 20 µl diluted enzyme samples to 96 well microtiter plate and adding 80 µl substrate working solution. The solution was mixed and pre-incubated 1 minute at room temperature and absorption is measured every 20 sec. over 5 minutes at OD 405 nm.

The slope (absorbance per minute) of the time dependent absorption-curve is directly propor-tional to the specific activity (activity per mg enzyme) of the alpha-amylase in question under the given set of conditions. The amylase sample should be diluted to a level where the slope is below 0.4 absorbance units per minute.

Determination of Percentage Point (Pp)

The percentage point (pp) improvement in residual activity (stability) of the variant relative to the parent is calculated as the difference between the residual activity of the variant and the residual activity of the parent, i.e. the residual activity of the variant minus the residual activity of the parent.

EXAMPLES

Example 1: Preparation of Variants

The Amylase variants of SEQ ID NO: 6 (SP722) were prepared by standard procedures, in brief: Introducing random and/or site-directed mutations into the gene, transforming Bacillus subtilis host cells with the mutated genes, fermenting the transformed host cells (e.g. as described in Example 1 of WO 2004/111220), and purifying the amylase from the fermentation broth. The reference amylase (SEQ ID NO: 6) was produced recombinantly in Bacillus subtilis in a similar manner.

Example 2: Characterization of Chelating Agents

Example 2a

Measure of Free Calcium Ions

Chelating agents (chelants) may be ranked by their ability to reduce the concentration of free calcium ions ($Ca^{2+}$) from 2.0 mM to 0.10 mM at pH 8 developed from a method described by M. K. Nagarajan et al., JAOCS, Vol. 61, no. 9 (September 1984), pp. 1475-1478. The assay is described above under "Materials and Methods" for measuring of free calcium ions was used.Accordingly, the concentration of chelant necessary to reduce the water hardness from 2.0 mM to 0.10 mM was determined as described above. The experiment was carried out with the pH 8 buffer at 21° C.

The final concentrations of chelant used and the free $Ca^{2+}$ concentration measured are shown in table 2.1 below.

TABLE 2.1

Concentration of free $Ca^{2+}$ determined in a mixture of 2.0 mM $Ca^{2+}$ and various amounts of chelating agent at pH 8.

| mL Calcium stock solution | mL electrolyte solution | mL pH 8 buffer | mL chelant | mM chelant final concentration |
| --- | --- | --- | --- | --- |
| 4 | 1 | 45.0 | 0.0 | 0.00 |
| 4 | 1 | 44.0 | 1.0 | 0.30 |
| 4 | 1 | 43.0 | 2.0 | 0.60 |
| 4 | 1 | 41.0 | 4.0 | 1.20 |
| 4 | 1 | 39.0 | 6.0 | 1.80 |
| 4 | 1 | 38.5 | 6.5 | 1.95 |
| 4 | 1 | 38.0 | 7.0 | 2.10 |
| 4 | 1 | 37.5 | 7.5 | 2.25 |
| 4 | 1 | 37.0 | 8.0 | 2.40 |
| 4 | 1 | 36.5 | 8.5 | 2.55 |
| 4 | 1 | 36.0 | 9.0 | 2.70 |
| 4 | 1 | 35.5 | 9.5 | 2.85 |
| 4 | 1 | 35.0 | 10.0 | 3.00 |
| 4 | 1 | 32.5 | 12.5 | 3.75 |
| 4 | 1 | 30.0 | 15.0 | 4.50 |
| 4 | 1 | 25.0 | 20.0 | 6.00 |
| 4 | 1 | 20.0 | 25.0 | 7.50 |
| 4 | 1 | 15.0 | 30.0 | 9.00 |
| 4 | 1 | 10.0 | 35.0 | 10.50 |

From these data, the concentration of chelating agent necessary to reduce the free $Ca^{2+}$ concentration from 2.0 mM to below 0.10 mM were determined by interpolation.

A number of chelants were characterized using this assay and the chelator concentrations necessary to reduce the concentration of free calcium ions from 2.0 mM to 0.10 mM at pH 8.0 in 49 mM EPPS buffer and 80 mM potassium chloride are shown in Table 2.2.

TABLE 2.2

|  | mM | Relative to citrate |
|---|---|---|
| Citrate | 8.36 | 1.00 |
| EGTA | 2.60 | 0.33 |
| EDTA | 1.90 | 0.21 |
| HEDP | 1.60 | 0.20 |
| DTPA | 1.87 | 0.24 |
| DTPMP | 1.17 | 0.15 |
| MGDA | 2.56 | 0.33 |

Example 2b

Determination of log K

Alternatively the chelating agents can be characterized by the binding constant of the chelating agent (chelator) and calcium ions. This constant can be determined by ITC (isothermal titration calorimetry) as described by A D Nielsen, C C Fuglsang and P Westh, Analytical Biochemistry Vol. 314 (2003) page 227-234 and T Wiseman, S Williston, J F Brandts and L-N Lin, Analytical Biochemistry Vol. 179 (1989) page 131-137. The procedure for the determination of log K is described in detail above under "Materials and Methods".

Using this procedure for determination of log K, the following log K values for several chelating agents were determined at pH 10 (Table 2.3).

TABLE 2.3

|  | Log K | Log K relative to log K for citrate |
|---|---|---|
| Citrate | 3 | 1.00 |
| EGTA | 9 | 3.0 |
| EDTA | 8 | 2.7 |
| HEDP | 6 | 2.0 |
| DTPA | 7 | 2.7 |
| MGDA | 5 | 1.3 |

Example 3: Residual Activity after Incubation with Chelating Agent

EnzChek Assay

The amylase activity or residual amylase activity is in the present invention determined by the EnzCheck assay as described above. In general the residual amylase activity in model detergent B was determined after incubation at 31° C. for 18 hours the activity was then compared to the activity of a reference incubated at 4° C. for 18 hours as described above.

Test of the Stability of Amylase Variants in Detergent with 1.5% DTPA as Chelant For the determination of the amylase stability in detergent the enzymes to be tested were adjusted to a concentration of 0.6 mg/mL of enzyme protein by dilution in 20 mM HEPES, 0.1% (w/V) Triton X100, pH 8.0. If the starting amylase concentration is too low, it can be concentrated, by ultra filtration (UF) using a UF membrane with a cut off of 10 kDa.

25 µL of the amylase solution and 125 µL detergent (model detergent B) were transferred to a 96 well microtiter plate in 4 replicates. One small magnet (5×2 mm) was placed in each well, and the blend was mixed for 5 minutes at room temperature on a magnetic stirrer. Two identical plates were prepared. One of the plates was incubated at 4° C. for 18 hours (reference sample) and the other plate was incubated at 31° C. for 18 hours (31° C. sample).

Immediately after incubation, the samples on the plates were analyzed for amylase activity as described in the EnzCheck Assay for determination of residual amylase activity in detergents. It should be noted, that in order to reduce interference from other detergent ingredients than the enzyme on the assay, both reference and 31° C. sample were diluted to the same protein concentration. The activity of both the reference samples and the 31° C. samples were determined on same 384-well plate. It was ensured that the reference amylase was included on all test microtiter plates. The residual activity was calculated as $100*V_{max}(31° C.$ sample$)/V_{max}$(reference sample).

The result is shown in Table 3.1 using either SP722 or SP722+D183* G184* as reference amylase (parent). The percentage point (pp) improvement in residual activity of the variant relative to the parent is calculated as the difference between the residual activity of the variant and that of the parent.

TABLE 3.1

| Enzyme | Residual activity (%) | pp improvement in residual activity relative to parent SP722 | SP722 + D183* G184* |
|---|---|---|---|
| SP722 (parent) | 12 | 0 | — |
| SP722 + D183* G184* (parent) | 65 | 53 | 0 |
| SP722 + D183* G184* N195F | 88 | 76 | 23 |
| SP722 + D183* G184* N195L | 79 | 67 | 14 |
| SP722 + D183* G184* N197F | 95 | 83 | 30 |
| SP722 + D183* G184* N197L | 81 | 69 | 16 |
| SP722 + D183* G184* Y243F | 80 | 68 | 15 |
| SP722 + D183* G184* A186R, N195F | 79 | 67 | 14 |
| SP722 + D183* G184* H210Y | 74 | 62 | 9 |
| SP722 + D183* G184* V206L | 91 | 79 | 26 |
| SP722 + D183* G184* V213A | 87 | 75 | 22 |
| SP722 + Q174R D183* G184* E212V | 83 | 71 | 18 |
| SP722 + D183* G184* V206L E212G G304V A447V | 80 | 68 | 15 |
| SP722 + N116T G133E K142R D183* G184* Y198N V206L | 90 | 78 | 25 |

TABLE 3.1-continued

| Enzyme | Residual activity (%) | pp improvement in residual activity relative to parent | |
|---|---|---|---|
| | | SP722 | SP722 + D183* G184* |
| SP722 + G133E D183* G184* N195Y Y198N Y200F | 83 | 71 | 18 |
| SP722 + N116T D183* G184* N195Y Y198N | 79 | 67 | 14 |
| SP722 + K142R P146S G149K D183* G184* N195Y Y198N V206I | 80 | 68 | 15 |
| SP722 + D134Y D183* G184* | 72 | 60 | 7 |
| SP722 + T151R D183* G184* H210Y K320N R359I N418D | 78 | 66 | 13 |
| SP722 + G147E G149R Q169E D183* G184* Y198N Y203F V206L | 87 | 75 | 22 |
| SP722 + G133E G149R D183* G184* N195Y Y198N Y203F V206L | 91 | 79 | 26 |
| SP722 + G147E Y152H Q169E D183* G184* Y198N V206L | 90 | 78 | 25 |
| SP722 + D183* G184* N195F V206L | 98 | 86 | 33 |
| SP722 + D183* G184* N195F Y243F | 100 | 88 | 35 |
| SP722 + D183* G184* N195F H210Y | 93 | 81 | 28 |
| SP722 + D183* G184* V206L H210Y | 95 | 83 | 30 |
| SP722 + D183* G184* V213A | 93 | 81 | 28 |
| SP722 + D183* G184* S193T | 85 | 73 | 20 |
| SP722 + D183* G184* A186T N195F | 96 | 84 | 31 |
| SP722 + D183* G184* N195F V206L Y243F | 94 | 82 | 29 |
| SP722 + D183* G184* V206L Y243F | 98 | 86 | 33 |
| SP722 + D183* G184* N195Y | 93 | 81 | 28 |
| SP722 + G133D G149R D183* G184* Y198N V206L | 92 | 80 | 27 |
| SP722 + N116T G133E G147E Y152H D183* G184* Y198N Y203F V206L | 94 | 82 | 29 |
| SP722 + G147E G149R D183* G184* N195F Y198N V206L | 96 | 84 | 31 |
| SP722 + G133E K142R D183* G184* N195F Y198N | 95 | 83 | 30 |
| SP722 + G133E G149R Y152H D183* G184* N195Y Y198N V206L | 97 | 85 | 32 |
| SP722 + N116T Q129L K142R D183* G184* N195Y Y198N Y203F V206L | 101 | 89 | 36 |
| SP722 + G133E G149R Y152H D183* G184* N195Y Y198N Y203F V206L | 101 | 89 | 36 |
| SP722 + N116T G133E G149R D183* G184* Y198N Y203F V206L | 104 | 92 | 39 |
| SP722 + D183* G184* N195F V206Y Y243F | 109 | 97 | 44 |
| SP722 + D183* G184* N195F V206C Y243F | 113 | 101 | 48 |
| SP722 + D183* G184* N195F V206T Y243F | 109 | 97 | 44 |
| SP722 + D183* G184* N195F V206N Y243F | 99 | 87 | 34 |
| SP722 + D183* G184* N195F V206C | 101 | 89 | 36 |
| SP722 + D183* G184* N195F V206H | 105 | 93 | 40 |
| SP722 + D183* G184* N195F V206Y | 110 | 98 | 45 |
| SP722 + D183* G184* N195F V206L | 111 | 99 | 46 |
| SP722 + D183* G184* N195F V206G Y243F | 104 | 92 | 39 |
| SP722 + D183* G184* V206F Y243F | 104 | 92 | 39 |
| SP722 + D183* G184* N195F V206I Y243F | 105 | 93 | 40 |
| SP722 + D183* G184* N195F V206F Y243F | 92 | 80 | 27 |
| SP722 + D183* G184* N195F V206S Y243F | 104 | 92 | 39 |
| SP722 + D183* G184* A186T N195F | 103 | 91 | 38 |
| SP722 + D183* G184* N195F V206L H210Y | 102 | 90 | 37 |
| SP722 + D183* G184* S193T V206L | 101 | 89 | 36 |
| SP722 + D183* G184* S193T V213A | 108 | 96 | 43 |
| SP722 + D183* G184* S193T Y243F | 103 | 91 | 38 |
| SP722 + D183* G184* N195F V206N | 107 | 95 | 42 |

The results clearly show that the variants of the invention are considerably more resistant to the presence of strong chelating agents than the reference alpha-amylase. In a few instances the residual activity is above 100, reflecting the analytical variance of the assay.

The results show that the variants of the invention also at pH 8.0 have improved stability compared with the reference alpha-amylase, which may be SEQ ID NO: 6 (SP722) or SEQ ID NO: 6+D183* G184*, which is SEQ ID NO: 6 wherein amino acid 183 and 184 has been deleted.

Example 4: Residual Activity after Incubation with Chelating Agent at pH8 and pH10

In this example the above-described PNP-G7 assay is used to determine the residual amylase activity after incubation in the presence of the chelating agent DTPA, but the principle is the same as above for determine activity using the EnzCheck assay. In general the residual amylase activity was determined after incubation in a buffer containing a chelating agent at either pH 8 and 49° C. or pH 10 and 42° C. for 1 hour and the activity is then compared to the activity of a reference incubated at 4° C. for 1 hour as described above under "Materials and Methods".

Test of Stability of Amylase Variants after Incubation with Chelating Agent at pH8 and pH10 in Buffer Principle:

Enzyme samples were incubated in buffer pH 8.0 with 1.5% final concentration of DTPA at 49° C. for 1h and reference samples were incubated at 4° C. for 1h. In addition, enzyme samples were incubated in buffer pH10.0 with 1.5% final concentration of DTPA at 42° C. for 1h and their reference samples were incubated at 4° C. for 1 h. After incubation the residual activity was determined using the PNP-G7 amylase activity assay.

Reagents:

pH 8 buffer with DTPA: 50 mM EPPS, 0.01% TRITON™ X100, 1.875% DTPA (Diethylene triamine pentaacetic acid, cas no. 67-43-6), pH8.0 pH 10 buffer with DTPA: 50 mM EPPS, 0.01% TRITON™ X100, 1.875% DTPA (Diethylene triamine pentaacetic acid, cas no. 67-43-6), pH 10.0

Amylase solutions: 0.25 and 0.5 mg active amylase protein/mL in 5 mM EPPS, 0.01% TRITON™ X-100, pH 8.0

Procedure:

160 µL buffer (pH 8 buffer with DTPA or pH 10 buffer with DTPA) and 40 µL of the amylase solutions were transferred to a 96-well PCR microtiter plate in duplicate and the content was mixed for 1 minutes (PCR: Polymerase Chain Reaction). Final concentration of DTPA was 1.5% in each well. 20 µl from each well was transferred to a new PCR microtiter plate (PCR MTP), which was placed at 4° C. (reference sample). The PCR MTP was incubated in PCR machine for 1h at 49° C. when buffer had pH 8.0 (pH 8, 49° C. samples) and for 1h at 42° C. when buffer had pH 10.0 (pH 10, 42° C. samples).

Immediately after incubation, the samples on PCR plates were diluted ten-fold in dilution buffer and analyzed for amylase activity as described in PNP-G7 assay. It should be noted, that in order to reduce interference from the chelating agent, here DTPA, on the assay, both reference and pH8, 49° samples/pH10, 42° C. samples were diluted to the same concentration before being analyzed for residual activity. The activity of both the reference samples and the pH8, 49° samples or pH10, 42° C. samples were determined on the same 96 well plate. It was ensured that the parent amylase was included on all test microtiter plates. The residual activity was calculated as $100*V_{max}$ (pH8, 42° C. or pH10, 49° C. sample)/$V_{max}$ (reference sample) and the results are shown in table 4.1. The percentage points (pp) improvements are calculated as the residual activity of the variant minus the residual activity of the parent.

TABLE 4.1

| | pH8, 49° C. | | | pH10, 42° C. | | |
| | | pp point improvement of variant relative to parent | | | pp improvement of variant relative to parent | |
| Enzyme | Residual activity (%) | SP722 | SP722 + D183* 184* | Residual activity (%) | SP722 | SP722 + D183* 184* |
|---|---|---|---|---|---|---|
| SP722 (parent) | 1 | 0 | | 8 | 0 | |
| SP722 + D183* G184* (Parent) | 20 | — | 0 | 20 | — | 0 |
| SP722 + D183* G184* N195F V206L Y243F | 97 | 96 | 77 | 93 | 85 | 73 |
| SP722 + D183* G184* N195F V206Y Y243F | 97 | 96 | 77 | 100 | 92 | 80 |
| SP722 + D183* G184* N195F V206N Y243F | 96 | 95 | 75 | 92 | 84 | 64 |
| SP722 + D183* G184* N195F V206F Y243F | 101 | 100 | 80 | 97 | 89 | 69 |
| SP722 + D183* G184* N195F V206H | 92 | 92 | 72 | 88 | 80 | 60 |
| SP722 + D183* G184* N195F V206Y | 95 | 94 | 74 | 96 | 88 | 68 |
| SP722 + D183* G184* V206F Y243F | 87 | 86 | 66 | 89 | 81 | 61 |
| SP722 + D183* G184* N195F V206L H210Y | 98 | 97 | 77 | 96 | 88 | 68 |
| SP722 + D183* G184* S193T V206L | 79 | 78 | 58 | 73 | 65 | 45 |
| SP722 + D183* G184* G133E G149R N195Y Y203F V206L | 90 | 89 | 69 | 83 | 75 | 55 |

The results clearly show that the variants of the invention are highly stable and have high residual activity after incubation at pH8 49° C. and pH10 42° C. for 1 hour both when comparing the residual activities of the variants with that of the parent and when looking at the percentage point improvement of the variants. In comparison SP722+D183*

G184* amylase has 20% residual activity and SP722 has even less residual activity.

Example 5: Residual Activity after Incubation in Buffer with 1.5% (w/v) DTPA at pH8 and pH10

In this example the above-described PNP-G7 assay is used to determine the residual amylase activity SP722 variants after incubation in the presence of the chelating agent DTPA. In general the residual amylase activity was determined after incubation in a buffer containing a chelating agent at either pH 8 or pH 10 at the indicated temperatures and incubation times and the activity is then compared to the activity of a reference incubated at 4° C. as described above under "Materials and Methods".

Test of Stability of Amylase Variants after Incubation with Chelating Agent at pH8 and pH10 in Buffer
Principle:
Enzyme samples were incubated in buffer pH 8.0 with 1.5% (w/v) final concentration of DTPA at indicated temperature and incubation time and reference samples were incubated at 4° C. at same incubation time. In addition, enzyme samples were incubated in buffer pH10.0 with 1.5% (w/v) final concentration of DTPA at indicated temperature and incubation time and their reference samples were incubated at 4° C. at same incubation time. After incubation the residual activity was determined using the PNP-G7 amylase activity assay.
Reagents:
pH 8 buffer with DTPA: 50 mM EPPS, 0.01% (w/v) TRITON™ X100, 1.875% (w/v) DTPA (Diethylene triamine pentaacetic acid, cas no. 67-43-6), pH8.0
pH 10 buffer with DTPA: 50 mM Glycine, 0.01% (w/v) TRITON™ X100, 1.875% (w/v) DTPA (Diethylene triamine pentaacetic acid, cas no. 67-43-6), pH 10.0
Amylase solutions: 0.25 and 0.5 mg active amylase protein/mL in 5 mM EPPS, 0.01% TRITON™ X-100, pH 8.0
Procedure:
160 µL buffer (pH 8 buffer with DTPA or pH 10 buffer with DTPA) and 40 µL of the amylase solutions were transferred to a 96-well PCR microtiter plate in duplicate and the content was mixed for 1 minutes (PCR: Polymerase Chain Reaction). Final concentration of DTPA was 1.5% (w/v) in each well. 20 µl from each well was transferred to a microtiter plate (MTP), which was placed at 4° C. (reference sample). The PCR MTP (stressed sample) was incubated in PCR machine as indicated in table below.
Immediately after incubation, the samples on PCR plates were diluted ten-fold in dilution buffer and analyzed for amylase activity as described in PNP-G7 assay. It should be noted, that in order to reduce interference from the chelating agent, here DTPA, on the assay, both reference and stressed samples were diluted to the same concentration before being analyzed for residual activity. The activity of both the reference samples and the stressed were determined on the same 96 well plate. It was ensured that the parent amylase was included on all test microtiter plates. The residual activity was calculated as $100*V_{max}$ (stressed sample)/$V_{max}$ (reference sample). The percentage point (pp) improvement in the stability of the variants relative to the parent is calculated as the residual activity of the variant minus the residual activity of the parent. The results are shown in table 5.1.

TABLE 5.1

SP722 variants with DTPA chelator

| Enzyme | pH 8, 49° C., 10 minutes, 1.5% DTPA | | pH 10, 42° C., 20 minutes, 1.5% DTPA | |
|---|---|---|---|---|
| | Residual activity (%) | pp improvement in residual activity relative to parent | Residual activity (%) | pp improvement in residual activity relative to parent |
| SP722 (parent) | 29 | 0 | 25 | 0 |
| SP722 + N195F | 51 | 22 | 42 | 17 |
| SP722 + V206L | 36 | 7 | 32 | 7 |
| SP722 + V206Y | 48 | 19 | 41 | 16 |
| SP722 + Y243F | 34 | 5 | 35 | 10 |
| SP722 + N195F V206L | 68 | 39 | 62 | 37 |
| SP722 + N195F V206L Y243F | 78 | 49 | 77 | 52 |

From the residual activities it is clearly seen that the variants of SP722 is more stable in the presence of DTPA, which is also reflected in the percentage points improvements in the stability of the variant compared to the parent.

Example 6: Residual Activity after Incubation with HEDP at pH 10

In this example the above-described PNP-G7 assay is used to determine the residual amylase activity after incubation in the presence of the chelating agent HEDP. In general the residual amylase activity was determined after incubation in a buffer containing a chelating agent at pH 10 at the indicated temperatures and incubation times and the activity is then compared to the activity of a reference incubated at 4° C. as described above under Materials and Methods.
Test of Stability of Amylase Variants after Incubation with Chelating Agent at pH10 in Buffer
Principle:
Enzyme samples were incubated in buffer pH 10.0 with 1.5% (w/v) final concentration of HEDP at indicated temperature and incubation time and reference samples were incubated at 4° C. at same incubation time. After incubation the residual activity was determined using the PNP-G7 amylase activity assay.
Reagents:
pH 10 buffer with HEDP: 50 mM Glycine, 0.01% (w/v) TRITON™ X100, 1.875% (w/v) HEDP (1-Hydroxyethylidenediphosphonic acid, cas no 2809-21-4), pH 10.0
Amylase solutions: 0.25 and 0.5 mg active amylase protein/mL in 5 mM EPPS, 0.01% (w/v) TRITON™ X-100, pH 8.0
Procedure:
160 µL buffer (pH 10 buffer with HEDP) and 40 µL of the amylase solutions were transferred to a 96-well PCR microtiter plate in duplicate and the content was mixed for 1 minutes (PCR: Polymerase Chain Reaction). Final concentration of HEDP was 1.5% (w/v) in each well. 20 µl from each well was transferred to a microtiter plate (MTP), which was placed at 4° C. (reference sample). The PCR MTP (stressed sample) was incubated in PCR machine as indicated in table 6.1 below. The residual activity was calculated as 100*$V_{max}$(stressed sample)/$V_{max}$(reference sample). The percentage point (pp) improvement in the stability of the variants relative to the parent is calculated as the residual activity of the variant minus the residual activity of the parent.

TABLE 6.1

SP722 and variant thereof with HEDP

| Enzyme | pH 10, 42° C., 20 minutes, 1.5% HEDP | |
| --- | --- | --- |
| | Residual activity (%) | pp improvement relative to parent |
| SP722 (parent) | 44 | 0 |
| SP722 + N195F V206L Y243F | 76 | 32 |

The results clearly show that the variant is more stable when incubated in the presence of HEDP compared to the parent.

Example 7: Stability of SP722+D183* G184* and Variants Thereof with 1.5% (w/v) HEDP In this example the above-described PNP-G7 assay is used to determine the residual amylase activity after incubation in the presence of the chelating agent HEDP. In general the residual amylase activity was determined after incubation in a buffer containing a chelating agent at either pH 8 or pH 10 at the indicated temperatures and incubation times and the activity is then compared to the activity of a reference incubated at 4° C. as described above under Materials and Methods.

Test of Stability of Amylase Variants after Incubation with Chelating Agent at pH8 and pH10 in Buffer Principle:

Enzyme samples were incubated in buffer pH 8.0 with 1.5% (w/v) final concentration of HEDP at indicated temperature and incubation time and reference samples were incubated at 4° C. at same incubation time. In addition, enzyme samples were incubated in buffer pH10.0 with 1.5% (w/v) final concentration of HEDP at indicated temperature and incubation time and their reference samples were incubated at 4° C. at same incubation time. After incubation the residual activity was determined using the PNP-G7 amylase activity assay.

Reagents:

pH 8 buffer with HEDP: 50 mM EPPS, 0.01% (w/v) TRITON™ X100, 1.875% (w/v) HEDP (1-Hydroxyethylidenediphosphonic acid, cas no 2809-21-4), pH8.0 pH 10 buffer with HEDP: 50 mM Glycine, 0.01% (w/v) TRITON™ X100, 1.875% (w/v) HEDP (1-Hydroxyethylidenediphosphonic acid, cas no 2809-21-4), pH 10.0

Amylase solutions: 0.25 and 0.5 mg active amylase protein/mL in 5 mM EPPS, 0.01% (w/v) TRITON™ X-100, pH 8.0

Procedure:

160 µL buffer (pH 8 buffer with HEDP or pH 10 buffer with HEDP) and 40 µL of the amylase solutions were transferred to a 96-well PCR microtiter plate in duplicate and the content was mixed for 1 minutes (PCR: Polymerase Chain Reaction). Final concentration of HEDP was 1.5% (w/v) in each well. 20 µl from each well was transferred to a microtiter plate (MTP), which was placed at 4° C. (reference sample). The PCR MTP (stressed sample) was incubated in PCR machine as indicated in table 7.1 below. The residual activity was calculated as 100*$V_{max}$(stressed sample)/$V_{max}$ (reference sample). The percentage point (pp) improvement in the stability of the variants relative to the parent is calculated as the residual activity of the variant minus the residual activity of the parent.

TABLE 7-1

SP722 + D183* G184* variants with HEDP

| Enzyme | pH 8, 50° C., 210 minutes, 1.5% HEDP | | pH 10, 42° C., 60 minutes, 1.5% HEDP | |
| --- | --- | --- | --- | --- |
| | Residual activity (%) | pp improvement relative to parent | Residual activity (%) | pp improvement relative to parent |
| SP722 + D183* G184* (parent) | 16 | 0 | 16 | 0 |
| SP722 + D183* G184* N195F V206Y Y243F | 96 | 80 | 95 | 79 |
| SP722 + D183* G184* S193T V206L | 61 | 45 | 62 | 46 |
| SP722 + D183* G184* G133E G149R N195Y Y203F V206L | 82 | 66 | 74 | 58 |

The results clearly shows that the variants of SP722+D183* G184* are much more stable when incubated in the presence of HEDP as chelating agent.

Example 8: Stability of AA560 Variants in the Presence of 1.5% (w/v) DTPA or 1.5% (w/v) HEDP In this example the above-described PNP-G7 assay is used to determine the residual amylase activity after incubation in the presence of the chelating agent DTPA or HEDP. In general the residual amylase activity was determined after incubation in a buffer containing a chelating agent at either pH 8 or pH 10 at the indicated temperatures and incubation times and the activity is then compared to the activity of a reference incubated at 4° C. as described above under "Materials and Methods".

Test of Stability of Amylase Variants after Incubation with Chelating Agent at pH8 and pH10 in Buffer Principle:

Enzyme samples were incubated in buffer pH 8.0 with 1.5% (w/v) final concentration of DTPA or HEDP at indicated temperature and incubation time and reference samples were incubated at 4° C. at same incubation time. In addition, enzyme samples were incubated in buffer pH10.0 with 1.5% (w/v) final concentration of DTPA or HEDP at indicated temperature and incubation time and their reference samples were incubated at 4° C. at same incubation time. After incubation the residual activity was determined using the PNP-G7 amylase activity assay.

Reagents:

pH 8 buffer with DTPA: 50 mM EPPS, 0.01% (w/v) TRITON™ X100, 1.875% (w/v) DTPA (Diethylene triamine pentaacetic acid, cas no. 67-43-6), pH8.0 pH 10 buffer with DTPA: 50 mM Glycine, 0.01% (w/v) TRITON™ X100, 1.875% (w/v) DTPA (Diethylene triamine pentaacetic acid, cas no. 67-43-6), pH 10.0 pH 8 buffer with HEDP: 50 mM EPPS, 0.01% (w/v) TRITON™ X100, 1.875% (w/v) HEDP (1-Hydroxyethylidenediphosphonic acid, cas no 2809-21-4), pH8.0 pH 10 buffer with HEDP: 50 mM Glycine, 0.01% (w/v) TRITON™ X100, 1.875% (w/v) HEDP (1-Hydroxyethylidenediphosphonic acid, cas no 2809-21-4), pH 10.0

Amylase solutions: 0.25 and 0.5 mg active amylase protein/mL in 5 mM EPPS, 0.01% (w/v) TRITON™ X-100, pH 8.0

Procedure:

160 µL buffer (pH 8 buffer with DTPA or HEDP or pH 10 buffer with DTPA or HEDP) and 40 µL of the amylase solutions were transferred to a 96-well PCR microtiter plate in duplicate and the content was mixed for 1 minutes (PCR: Polymerase Chain Reaction). Final concentration of DTPA or HEDP was 1.5% (w/v) in each well. 20 µl from each well was transferred to a microtiter plate (MTP), which was placed at 4° C. (reference sample). The PCR MTP (stressed sample) was incubated in PCR machine as indicated in table 8.1 and 8.2 below. The residual activity was calculated as $100 * V_{max}$(stressed sample)/$V_{max}$(reference sample). The percentage point (pp) improvement in the stability of the variants relative to the parent is calculated as the residual activity of the variant minus the residual activity of the parent.

TABLE 8.1

AA560 variants with DTPA

| Enzyme | pH 8, 49° C., 150 minutes, 1.5% DTPA | | pH 10, 42° C., 60 minutes, 1.5% DTPA | |
|---|---|---|---|---|
| | Residual activity (%) | pp improvement relative to parent | Residual activity (%) | pp improvement relative to parent |
| AA560 + I18K D183* G184* N195F R320K R458K (parent) | 20 | 0 | 21 | 0 |
| Parent + I206L | 49 | 29 | 45 | 24 |
| Parent + I206Y | 77 | 57 | 78 | 57 |
| Parent + Y243F | 31 | 11 | 36 | 15 |

TABLE 8.2

AA560 variants with HEDP

| Enzyme | pH 8, 50° C., 210 minutes, 1.5% HEDP | | pH 10, 42° C., 60 minutes, 1.5% HEDP | |
|---|---|---|---|---|
| | Residual activity (%) | pp improvement relative to parent | Residual activity (%) | pp improvement relative to parent |
| AA560 + I18K D183* G184* N195F R320K R458K (parent) | 60 | 0 | 19 | 0 |
| Parent + I206L | 68 | 8 | 38 | 19 |
| Parent + I206Y | 85 | 25 | 72 | 53 |
| Parent + Y243F | 59 | −1 | 34 | 15 |

Various references are cited herein, the disclosures of which are incorporated by reference in their entireties.

Example 9: Residual Activity after Incubation in Detergent with Chelating Agent

In this example the PNP-G7 assay is used to determine the residual amylase activity after incubation in the detergent in the presence of chelating agents, as described in above under "Materials and Methods".

In general, the residual amylase activity was determined after incubation in detergent C (Table 9.1), containing chelating agents DTPMP and HEDP at pH 8.2 after 3 weeks and 6 weeks 30° C. The residual activity of the amylase is then compared to the activity of the amylase in the freshly made detergent at day zero (before incubation) as described below.

TABLE 9.1

| Detergent C Ingredient | Composition of Detergent used for stability testing Composition (wt % of composition) |
|---|---|
| $C_{11.8}$ Alkylbenzene sulfonate | 5.89 |
| Citric acid | 2.56 |
| $C_{12-18}$ fatty acid | 2.56 |
| Sodium $C_{12-14}$ alkyl ethoxy 3 sulfate | 1.96 |
| $C_{14-15}$ alkyl-7-ethoxylate | 1.94 |
| $C_{12-14}$ Alkyl-7-ethoxylate | 2.21 |
| Boric Acid | 0.5 |
| A compound having the following general structure: $bis((C_2H_5O)(C_2H_4O)n)(CH_3)$—$N^+$— $C_xH_{2x}$—$N^+$—$(CH_3)$-$bis((C_2H_5O)(C_2H_4O)n)$, wherein n = from 20 to 30, and x = from 3 to 8, or sulphated or sulphonated variants thereof | 1.46 |
| DTPMP (Diethylene triamine penta (methylene phosphonic acid) | 0.19 |
| HEDP (Hydroxyethane diphosphonic acid) | 1.6 |
| Ethanol | 1.95 |
| Propylene Glycol | 1.5 |
| Monoethanolamine | 5.15 |
| Water, Aesthetics (Dyes, perfumes), pH adjusters (sodium hydroxide) and Minors (Enzymes, solvents, structurants, brighteners) | Balance to pH 8.2 |

Test of Stability of Amylase Variants after Incubation in Detergent C with Chelating Agents at pH 8.2

Method

Detergent C, pH 8.2, samples were prepared each containing an amylase variant of the invention or the SEQ ID NO: 6 (SP722) with the following two deletions D183* +G184*—also ref to as SP722+D183* G184*. Each detergent sample was determined for the initial residual enzyme activity before incubation (reference samples).

The residual enzyme activity for each sample was determined after incubation at 30° C. for 3 weeks and 6 weeks and compared to their reference sample. The residual activity was determined using the PNP-G7 amylase activity assay.

Amylase solutions: 13.77 mg active amylase protein in 100 g detergent C, pH 8.2

Procedure:

Detergent C, 5 g pH 8.2 containing the amylase was placed in duplicate into a 7 ml glass vial with an air tight lid. The residual enzyme activity was determined for the initial samples, in duplicate, before incubation.

The samples were placed into an incubator for 3 weeks and 6 weeks at 30° C. Immediately after incubation, the samples were analysed for residual amylase activity as described in PNP-G7 assay. In this test the residual activity of 100% equals no loss of amylase activity compared to initial residual enzyme activity before incubation (reference sample). The percentage point (pp) improvement in residual activity (stability) of the variant relative to the parent is calculated as the difference between the residual activity of the variant and the residual activity of the parent.

TABLE 9.2

| | Residual activity pH 8.2, 30° C. | | pp improvement in residual activity relative to parent | |
|---|---|---|---|---|
| | 3 Weeks | 6 Weeks | 3 Weeks | 6 Weeks |
| SP722 + D183* G184* (parent) | 19 | 3 | | |
| SP722 + D183* G184* N195F | 67 | 47 | 48 | 44 |
| SP722 + D183* G184* N195F H210Y | 82 | 78 | 63 | 75 |
| SP722 + D183* G184* N195F V206L | 87 | 83 | 68 | 80 |
| SP722 + D183* G184* N195F V206Y | 98 | 97 | 79 | 94 |
| SP722 + D183* G184* N195F V206Y Y243F | 100 | 97 | 81 | 94 |

The results clearly show that the variants of the invention are highly stable and have high residual activity after incubation in detergent C at pH 8.2, 3 weeks and 6 weeks 30° C. In comparison SP722+D183* G184* amylase has 19% after 3 weeks and 3% after 6 weeks residual activity.

Various references are cited herein, the disclosures of which are incorporated by reference in their entireties.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A variant of a parent alpha-amylase comprising alterations corresponding to positions 206 and 243 of SEQ ID NO: 10, wherein the variant has alpha-amylase activity and at least 95% sequence identity to SEQ ID NO: 10.

2. The variant of claim 1, wherein the alteration is independently:
(i) an insertion of an amino acid immediately downstream and adjacent of the position, (ii) a deletion of the amino acid which occupies the position, and/or (iii) a substitution of the amino acid which occupies the position.

3. The variant of claim 2, wherein the variant comprises a substitution at position 206 selected from the group consisting of F, W, Y, N, L, I, V, H, Q, D and E.

4. The variant of claim 2, wherein the variant comprises a substitution at position 243 selected from the group consisting of F, W, Y, L, I and V.

5. The variant of claim 1, wherein the variant further comprises an alteration at one or more positions corresponding to a position of SEQ ID NO: 10 selected from the group consisting of 116, 118, 129, 133, 142, 146, 147, 149, 151, 152, 169, 174, 186, 235, 244, 303, 320, 339, 359, 418, 431, 434, 447 and 458.

6. The variant of claim 1, wherein the variant further comprises at least one, at least two, or at least three deletions in the amino acid region of positions 181, 182, 183 or 184, as set forth in SEQ ID NO: 10.

7. The variant of claim 6, comprising deletions in amino acid positions 183 and 184.

8. The variant of claim 1, wherein the variant having alpha-amylase activity has an amino acid sequence having at least 98% sequence identity with the mature polypeptide of SEQ ID NO: 10.

9. The variant of claim 1, wherein the variant has improved stability relative to the parent alpha-amylase in a composition comprising a chelating agent, and wherein said chelating agent at a concentration below 10 mM reduces the concentration of free calcium ions from 2.0 mM to 0.10 mM at 21° C. and pH 8.0.

10. The variant of claim 1, wherein the variant has at least 60% residual activity after 18 hours at pH 8 in the presence of a chelating agent, and wherein said chelating agent at a concentration below 10 mM reduces the concentration of free calcium ions from 2.0 mM to 0.10 mM at 21° C. and pH 8.0.

11. The variant of claim 1, wherein the variant has improved wash performance compared to the parent alpha-amylase when measured in an Automated Mechanical Wash Assay.

12. A composition comprising a variant of a parent alpha-amylase, wherein the variant comprises alterations corresponding to positions 206 and 243 of SEQ ID NO: 10 and further comprising at least one chelating agent, wherein said chelating agent at a concentration below 10 mM reduces the concentration of free calcium ions from 2.0 mM to 0.10 mM when measured at 21° C. and pH 8.0, and wherein the variant has alpha-amylase activity and at least 95% sequence identity to SEQ ID NO: 10.

13. The composition of claim 12, wherein the chelating agent at a concentration below 10 mM reduces the concentration of free calcium ions from 2.0 mM to 0.10 mM when measured in 80 mM potassium chloride and 49 mM EPPS at 21° C. and pH 8.0.

14. The composition of claim 12, wherein the chelating agent at a concentration below 10 mM reduces the concentration of free calcium ions from 2.0 mM to 0.10 mM.

15. The composition of claim 12, wherein the chelating agent reduces the concentration of free calcium ions from 2.0 mM to 0.10 mM at a chelator agent concentration below 8 mM.

16. The composition of claim 12, wherein the chelating agent reduces the free calcium ion concentration from 2.0 mM to 0.10 mM at a chelating agent concentration below 0.9 times the concentration of citrate that reduces the free calcium ion concentration from 2.0 mM to 0.10 mM.

17. The composition of claim 12, wherein the chelating agent is selected from the group consisting of: ethylenediaminetetraacetic acid (EDTA), methylglycinediacetic acid (MGDA), ethylene glucol-bis(beta-aminoethyl ether)-N, N, N', N'-tetraacetic acid (EGTA), diethylenetriaminepentaacetic acid (DTPA), diethylenetriamine penta(methylene phosphonic acid) (DTPMP) and 1-hydroxyethane 1,1-diphosphic acid (HEDP).

18. The composition of claim 12, wherein the variant comprises a substitution at position 206 selected from the group consisting of F, W, Y, N, L, I, V, H, Q, D and E.

19. The composition of claim 12, wherein the variant comprises a substitution at position 243 selected from the group consisting of F, W, Y, L, I and V.

20. The composition of claim 12, wherein the variant comprises substitutions at positions 206 and 243.

21. The variant of claim 12, wherein the variant further comprises an alteration at one or more positions corresponding to a position of SEQ ID NO: 10 selected from the group consisting of 116, 118, 129, 133, 142, 146, 147, 149, 151, 152, 169, 174, 186, 235, 244, 303, 320, 339, 359, 418, 431, 434, 447 and 458.

22. The variant of claim 12, wherein the variant further comprises at least one, at least two, or at least three deletions in the amino acid region of positions 181, 182, 183, or 184, as set forth in SEQ ID NO: 10.

23. The variant of claim 22, comprising deletions in amino acid positions 183 and 184.

* * * * *

```
                              SEQUENCE LISTING

<160> NUMBER OF SEQ ID NOS: 26

<210> SEQ ID NO 1
<211> LENGTH: 1440
<212> TYPE: DNA
<213> ORGANISM: Bacillus sp.
<220> FEATURE:
<221> NAME/KEY: CDS
<222> LOCATION: (1)..(1440)

<400> SEQUENCE: 1 gat gga ttg aac ggt acg atg atg cag tat tat gag tgg cat ttg gaa      48
Asp Gly Leu Asn Gly Thr Met Met Gln Tyr Tyr Glu Trp His Leu Glu
1               5                   10                  15 aac gac ggg cag cat tgg aat cgg ttg cac gat gat gcc gca gct ttg      96
Asn Asp Gly Gln His Trp Asn Arg Leu His Asp Asp Ala Ala Ala Leu
            20                  25                  30 agt gat gct ggt att aca gct att tgg att ccg cca gcc tac aaa ggt     144
Ser Asp Ala Gly Ile Thr Ala Ile Trp Ile Pro Pro Ala Tyr Lys Gly
        35                  40                  45 aat agt cag gcg gat gtt ggg tac ggt gca tac gat ctt tat gat tta     192
Asn Ser Gln Ala Asp Val Gly Tyr Gly Ala Tyr Asp Leu Tyr Asp Leu
    50                  55                  60 gga gag ttc aat caa aag ggt act gtt cga acg aaa tac gga act aag     240
Gly Glu Phe Asn Gln Lys Gly Thr Val Arg Thr Lys Tyr Gly Thr Lys
65                  70                  75                  80 gca cag ctt gaa cga gct att ggg tcc ctt aaa tct aat gat atc aat     288
Ala Gln Leu Glu Arg Ala Ile Gly Ser Leu Lys Ser Asn Asp Ile Asn
                85                  90                  95 gta tac gga gat gtc gtg atg aat cat aaa atg gga gct gat ttt acg     336
Val Tyr Gly Asp Val Val Met Asn His Lys Met Gly Ala Asp Phe Thr
            100                 105                 110 gag gca gtg caa gct gtt caa gta aat cca acg aat cgt tgg cag gat     384
Glu Ala Val Gln Ala Val Gln Val Asn Pro Thr Asn Arg Trp Gln Asp
        115                 120                 125 att tca ggt gcc tac acg att gat gcg tgg acg ggt ttc gac ttt tca     432
Ile Ser Gly Ala Tyr Thr Ile Asp Ala Trp Thr Gly Phe Asp Phe Ser
    130                 135                 140 ggg cgt aac aac gcc tat tca gat ttt aag tgg aga tgg ttc cat ttt     480
Gly Arg Asn Asn Ala Tyr Ser Asp Phe Lys Trp Arg Trp Phe His Phe
145                 150                 155                 160 aat ggt gtt gac tgg gat cag cgc tat caa gaa aat cat att ttc cgc     528
Asn Gly Val Asp Trp Asp Gln Arg Tyr Gln Glu Asn His Ile Phe Arg
                165                 170                 175 ttt gca aat acg aac tgg aac tgg cga gtg gat gaa gag aac ggt aat     576
Phe Ala Asn Thr Asn Trp Asn Trp Arg Val Asp Glu Glu Asn Gly Asn
            180                 185                 190 tat gat tac ctg tta gga tcg aat atc gac ttt agt cat cca gaa gta     624
Tyr Asp Tyr Leu Leu Gly Ser Asn Ile Asp Phe Ser His Pro Glu Val
        195                 200                 205 caa gat gag ttg aag gat tgg ggt agc tgg ttt acc gat gag tta gat     672
Gln Asp Glu Leu Lys Asp Trp Gly Ser Trp Phe Thr Asp Glu Leu Asp
    210                 215                 220 ttg gat ggt tat cgt tta gat gct att aaa cat att cca ttc tgg tat     720
Leu Asp Gly Tyr Arg Leu Asp Ala Ile Lys His Ile Pro Phe Trp Tyr
225                 230                 235                 240 aca tct gat tgg gtt cgg cat cag cgc aac gaa gca gat caa gat tta     768
Thr Ser Asp Trp Val Arg His Gln Arg Asn Glu Ala Asp Gln Asp Leu
                245                 250                 255
```

```
ttt gtc gta ggg gaa tat tgg aag gat gac gta ggt gct ctc gaa ttt     816
Phe Val Val Gly Glu Tyr Trp Lys Asp Asp Val Gly Ala Leu Glu Phe
            260                 265                 270 tat tta gat gaa atg aat tgg gag atg tct cta ttc gat gtt cca ctt     864
Tyr Leu Asp Glu Met Asn Trp Glu Met Ser Leu Phe Asp Val Pro Leu
        275                 280                 285 aat tat aat ttt tac cgg gct tca caa caa ggt gga agc tat gat atg     912
Asn Tyr Asn Phe Tyr Arg Ala Ser Gln Gln Gly Gly Ser Tyr Asp Met
    290                 295                 300 cgt aat att tta cga gga tct tta gta gaa gcg cat ccg atg cat gca     960
Arg Asn Ile Leu Arg Gly Ser Leu Val Glu Ala His Pro Met His Ala
305                 310                 315                 320 gtt acg ttt gtt gat aat cat gat act cag cca ggg gag tca tta gag    1008
Val Thr Phe Val Asp Asn His Asp Thr Gln Pro Gly Glu Ser Leu Glu
                325                 330                 335 tca tgg gtt gct gat tgg ttt aag cca ctt gct tat gcg aca att ttg    1056
Ser Trp Val Ala Asp Trp Phe Lys Pro Leu Ala Tyr Ala Thr Ile Leu
            340                 345                 350 acg cgt gaa ggt ggt tat cca aat gta ttt tac ggt gat tac tat ggg    1104
Thr Arg Glu Gly Gly Tyr Pro Asn Val Phe Tyr Gly Asp Tyr Tyr Gly
        355                 360                 365 att cct aac gat aac att tca gct aaa aaa gat atg att gat gag ctg    1152
Ile Pro Asn Asp Asn Ile Ser Ala Lys Lys Asp Met Ile Asp Glu Leu
    370                 375                 380 ctt gat gca cgt caa aat tac gca tat ggc acg cag cat gac tat ttt    1200
Leu Asp Ala Arg Gln Asn Tyr Ala Tyr Gly Thr Gln His Asp Tyr Phe
385                 390                 395                 400 gat cat tgg gat gtt gta gga tgg act agg gaa gga tct tcc tcc aga    1248
Asp His Trp Asp Val Val Gly Trp Thr Arg Glu Gly Ser Ser Ser Arg
                405                 410                 415 cct aat tca ggc ctt gcg act att atg tcg aat gga cct ggt ggt tcc    1296
Pro Asn Ser Gly Leu Ala Thr Ile Met Ser Asn Gly Pro Gly Gly Ser
            420                 425                 430 aag tgg atg tat gta gga cgt cag aat gca gga caa aca tgg aca gat    1344
Lys Trp Met Tyr Val Gly Arg Gln Asn Ala Gly Gln Thr Trp Thr Asp
        435                 440                 445 tta act ggt aat aac gga gcg tcc gtt aca att aat ggc gat gga tgg    1392
Leu Thr Gly Asn Asn Gly Ala Ser Val Thr Ile Asn Gly Asp Gly Trp
    450                 455                 460 ggc gaa ttc ttt acg aat gga gga tct gta tcc gtg tac gtg aac caa    1440
Gly Glu Phe Phe Thr Asn Gly Gly Ser Val Ser Val Tyr Val Asn Gln
465                 470                 475                 480

<210> SEQ ID NO 2
<211> LENGTH: 480
<212> TYPE: PRT
<213> ORGANISM: Bacillus sp.

<400> SEQUENCE: 2

Asp Gly Leu Asn Gly Thr Met Met Gln Tyr Tyr Glu Trp His Leu Glu
1               5                   10                  15

Asn Asp Gly Gln His Trp Asn Arg Leu His Asp Asp Ala Ala Ala Leu
            20                  25                  30

Ser Asp Ala Gly Ile Thr Ala Ile Trp Ile Pro Pro Tyr Lys Gly
        35                  40                  45

Asn Ser Gln Ala Asp Val Gly Tyr Gly Ala Tyr Asp Leu Tyr Asp Leu
    50                  55                  60

Gly Glu Phe Asn Gln Lys Gly Thr Val Arg Thr Lys Tyr Gly Thr Lys
65                  70                  75                  80
```

```
Ala Gln Leu Glu Arg Ala Ile Gly Ser Leu Lys Ser Asn Asp Ile Asn
                85                  90                  95

Val Tyr Gly Asp Val Val Met Asn His Lys Met Gly Ala Asp Phe Thr
            100                 105                 110

Glu Ala Val Gln Ala Val Gln Val Asn Pro Thr Asn Arg Trp Gln Asp
        115                 120                 125

Ile Ser Gly Ala Tyr Thr Ile Asp Ala Trp Thr Gly Phe Asp Phe Ser
130                 135                 140

Gly Arg Asn Asn Ala Tyr Ser Asp Phe Lys Trp Arg Trp Phe His Phe
145                 150                 155                 160

Asn Gly Val Asp Trp Asp Gln Arg Tyr Gln Glu Asn His Ile Phe Arg
                165                 170                 175

Phe Ala Asn Thr Asn Trp Asn Trp Arg Val Asp Glu Glu Asn Gly Asn
            180                 185                 190

Tyr Asp Tyr Leu Leu Gly Ser Asn Ile Asp Phe Ser His Pro Glu Val
        195                 200                 205

Gln Asp Glu Leu Lys Asp Trp Gly Ser Trp Phe Thr Asp Glu Leu Asp
210                 215                 220

Leu Asp Gly Tyr Arg Leu Asp Ala Ile Lys His Ile Pro Phe Trp Tyr
225                 230                 235                 240

Thr Ser Asp Trp Val Arg His Gln Arg Asn Glu Ala Asp Gln Asp Leu
                245                 250                 255

Phe Val Val Gly Glu Tyr Trp Lys Asp Asp Val Gly Ala Leu Glu Phe
            260                 265                 270

Tyr Leu Asp Glu Met Asn Trp Glu Met Ser Leu Phe Asp Val Pro Leu
        275                 280                 285

Asn Tyr Asn Phe Tyr Arg Ala Ser Gln Gln Gly Gly Ser Tyr Asp Met
290                 295                 300

Arg Asn Ile Leu Arg Gly Ser Leu Val Glu Ala His Pro Met His Ala
305                 310                 315                 320

Val Thr Phe Val Asp Asn His Asp Thr Gln Pro Gly Glu Ser Leu Glu
                325                 330                 335

Ser Trp Val Ala Asp Trp Phe Lys Pro Leu Ala Tyr Ala Thr Ile Leu
            340                 345                 350

Thr Arg Glu Gly Gly Tyr Pro Asn Val Phe Tyr Gly Asp Tyr Tyr Gly
        355                 360                 365

Ile Pro Asn Asp Asn Ile Ser Ala Lys Lys Asp Met Ile Asp Glu Leu
370                 375                 380

Leu Asp Ala Arg Gln Asn Tyr Ala Tyr Gly Thr Gln His Asp Tyr Phe
385                 390                 395                 400

Asp His Trp Asp Val Val Gly Trp Thr Arg Glu Gly Ser Ser Ser Arg
                405                 410                 415

Pro Asn Ser Gly Leu Ala Thr Ile Met Ser Asn Gly Pro Gly Gly Ser
            420                 425                 430

Lys Trp Met Tyr Val Gly Arg Gln Asn Ala Gly Gln Thr Trp Thr Asp
        435                 440                 445

Leu Thr Gly Asn Asn Gly Ala Ser Val Thr Ile Asn Gly Asp Gly Trp
450                 455                 460

Gly Glu Phe Phe Thr Asn Gly Gly Ser Val Ser Val Tyr Val Asn Gln
465                 470                 475                 480

<210> SEQ ID NO 3
<211> LENGTH: 1476
```

```
<212> TYPE: DNA
<213> ORGANISM: Bacillus circulans
<220> FEATURE:
<221> NAME/KEY: CDS
<222> LOCATION: (1)..(1476)

<400> SEQUENCE: 3 aag aga aat cat acc atg atg cag ttt ttt gaa tgg cac ctg gct gca      48
Lys Arg Asn His Thr Met Met Gln Phe Phe Glu Trp His Leu Ala Ala
1               5                   10                  15 gac gga gat cat tgg aag cga ctg gct gaa atg gcc ccg gaa ttg aaa      96
Asp Gly Asp His Trp Lys Arg Leu Ala Glu Met Ala Pro Glu Leu Lys
            20                  25                  30 gcc aaa ggc att gat acg gta tgg gtg cct cct gtg acc aaa gcc gta     144
Ala Lys Gly Ile Asp Thr Val Trp Val Pro Pro Val Thr Lys Ala Val
        35                  40                  45 tca gct gag gat aca ggt tat ggt gta tat gat ctg tat gat ttg ggt     192
Ser Ala Glu Asp Thr Gly Tyr Gly Val Tyr Asp Leu Tyr Asp Leu Gly
    50                  55                  60 gaa ttt gac caa aag ggt acc gtg cgt acc aaa tac ggc acc aag cag     240
Glu Phe Asp Gln Lys Gly Thr Val Arg Thr Lys Tyr Gly Thr Lys Gln
65                  70                  75                  80 gaa ctg ata gag gcc att gct gag tgt cag aag aac gga atc gcc gtc     288
Glu Leu Ile Glu Ala Ile Ala Glu Cys Gln Lys Asn Gly Ile Ala Val
                85                  90                  95 tat gtg gat ctg gtt atg aat cac aag gcc gga gca gat gag acg gaa     336
Tyr Val Asp Leu Val Met Asn His Lys Ala Gly Ala Asp Glu Thr Glu
            100                 105                 110 gtt ttt aaa gtg att gag gtt gat ccc aat gat cga acg aag gaa att     384
Val Phe Lys Val Ile Glu Val Asp Pro Asn Asp Arg Thr Lys Glu Ile
        115                 120                 125 tct gag ccg ttc gaa att gag ggc tgg acc aaa ttc aca ttc ccg ggt     432
Ser Glu Pro Phe Glu Ile Glu Gly Trp Thr Lys Phe Thr Phe Pro Gly
    130                 135                 140 cgc ggg gat caa tac tcc tct ttt aaa tgg aac tct gaa cac ttc aat     480
Arg Gly Asp Gln Tyr Ser Ser Phe Lys Trp Asn Ser Glu His Phe Asn
145                 150                 155                 160 ggc acg gac ttt gat gcc agg gaa gaa cga aca ggt gta ttc cgc atc     528
Gly Thr Asp Phe Asp Ala Arg Glu Glu Arg Thr Gly Val Phe Arg Ile
                165                 170                 175 gca gga gag aat aaa aaa tgg aat gag aat gtc gat gat gag ttt ggt     576
Ala Gly Glu Asn Lys Lys Trp Asn Glu Asn Val Asp Asp Glu Phe Gly
            180                 185                 190 aac tat gac tat ctg atg ttc gcc aat ata gat tat aac cac ccg gat     624
Asn Tyr Asp Tyr Leu Met Phe Ala Asn Ile Asp Tyr Asn His Pro Asp
        195                 200                 205 gtt cgg cgc gag atg atc gat tgg ggg aaa tgg ctg atc gat acc ctt     672
Val Arg Arg Glu Met Ile Asp Trp Gly Lys Trp Leu Ile Asp Thr Leu
    210                 215                 220 cag tgc ggt ggg ttc cgg ctg gat gcg att aag cat atc aac cat gaa     720
Gln Cys Gly Gly Phe Arg Leu Asp Ala Ile Lys His Ile Asn His Glu
225                 230                 235                 240 ttc att aag gag ttc gca gca gag atg atc cgc aaa cgc ggt cag gat     768
Phe Ile Lys Glu Phe Ala Ala Glu Met Ile Arg Lys Arg Gly Gln Asp
                245                 250                 255 ttc tac atc gta ggc gag ttc tgg aac tcg aac ctg gat gca tgt cgt     816
Phe Tyr Ile Val Gly Glu Phe Trp Asn Ser Asn Leu Asp Ala Cys Arg
            260                 265                 270 gaa ttc ctt gat acg gta gac tat cag atc gac ctg ttt gat gtg tct     864
Glu Phe Leu Asp Thr Val Asp Tyr Gln Ile Asp Leu Phe Asp Val Ser
        275                 280                 285
```

```
ctt cac tac aag ttg cat gag gct tcg ctt aaa ggc aga gac ttt gat        912
Leu His Tyr Lys Leu His Glu Ala Ser Leu Lys Gly Arg Asp Phe Asp
    290                 295                 300 ctc tcc aaa att ttt gat gac acc ttg gtg cag acc cat cct acc cat        960
Leu Ser Lys Ile Phe Asp Asp Thr Leu Val Gln Thr His Pro Thr His
305                 310                 315                 320 gcg gta acc ttc gta gat aac cat gac tcc caa cct cat gaa gcg ttg       1008
Ala Val Thr Phe Val Asp Asn His Asp Ser Gln Pro His Glu Ala Leu
                325                 330                 335 gaa tca tgg att ggt gat tgg ttt aag ccg agc gct tat gcg ttg acg       1056
Glu Ser Trp Ile Gly Asp Trp Phe Lys Pro Ser Ala Tyr Ala Leu Thr
            340                 345                 350 cta tta cgt cgt gat ggc tat ccg gtt gta ttt tac ggc gat tat tat       1104
Leu Leu Arg Arg Asp Gly Tyr Pro Val Val Phe Tyr Gly Asp Tyr Tyr
        355                 360                 365 ggc att ggt ggt cct gaa cct gtg gat ggc aaa aaa gaa att ctg gac       1152
Gly Ile Gly Gly Pro Glu Pro Val Asp Gly Lys Lys Glu Ile Leu Asp
    370                 375                 380 att ctg ctg tct gcc cgt tgc aac aaa gcg tat gga gag cag gaa gat       1200
Ile Leu Leu Ser Ala Arg Cys Asn Lys Ala Tyr Gly Glu Gln Glu Asp
385                 390                 395                 400 tac ttc gat cac gcc aat acg att ggc tgg gta cgt cgt ggc gta gag       1248
Tyr Phe Asp His Ala Asn Thr Ile Gly Trp Val Arg Arg Gly Val Glu
                405                 410                 415 gaa atc gaa ggt tcc ggt tgt gca gtg gtc atc tcc aac ggg gat gac       1296
Glu Ile Glu Gly Ser Gly Cys Ala Val Val Ile Ser Asn Gly Asp Asp
            420                 425                 430 ggt gag aag aga atg ttc atc gga gag cat cgt gct ggt gaa gtc tgg       1344
Gly Glu Lys Arg Met Phe Ile Gly Glu His Arg Ala Gly Glu Val Trp
        435                 440                 445 gtg gat ctg acg aag agc tgt gat gat cag att acc att gag gaa gac       1392
Val Asp Leu Thr Lys Ser Cys Asp Asp Gln Ile Thr Ile Glu Glu Asp
    450                 455                 460 ggc tgg gcc acc ttc cat gtg tgc ggt gga ggt gtc tcg gta tgg gct       1440
Gly Trp Ala Thr Phe His Val Cys Gly Gly Gly Val Ser Val Trp Ala
465                 470                 475                 480 ctt cct gaa cag aat gag gac tgc gct gac gct gag                       1476
Leu Pro Glu Gln Asn Glu Asp Cys Ala Asp Ala Glu
                485                 490

<210> SEQ ID NO 4
<211> LENGTH: 492
<212> TYPE: PRT
<213> ORGANISM: Bacillus circulans

<400> SEQUENCE: 4

Lys Arg Asn His Thr Met Met Gln Phe Phe Glu Trp His Leu Ala Ala
1               5                   10                  15

Asp Gly Asp His Trp Lys Arg Leu Ala Glu Met Ala Pro Glu Leu Lys
            20                  25                  30

Ala Lys Gly Ile Asp Thr Val Trp Val Pro Pro Val Thr Lys Ala Val
        35                  40                  45

Ser Ala Glu Asp Thr Gly Tyr Gly Val Tyr Asp Leu Tyr Asp Leu Gly
    50                  55                  60

Glu Phe Asp Gln Lys Gly Thr Val Arg Thr Lys Tyr Gly Thr Lys Gln
65                  70                  75                  80

Glu Leu Ile Glu Ala Ile Ala Glu Cys Gln Lys Asn Gly Ile Ala Val
                85                  90                  95
```

```
Tyr Val Asp Leu Val Met Asn His Lys Ala Gly Ala Asp Glu Thr Glu
                100                 105                 110
Val Phe Lys Val Ile Glu Val Asp Pro Asn Asp Arg Thr Lys Glu Ile
            115                 120                 125
Ser Glu Pro Phe Glu Ile Glu Gly Trp Thr Lys Phe Thr Phe Pro Gly
        130                 135                 140
Arg Gly Asp Gln Tyr Ser Ser Phe Lys Trp Asn Ser Glu His Phe Asn
145                 150                 155                 160
Gly Thr Asp Phe Asp Ala Arg Glu Glu Arg Thr Gly Val Phe Arg Ile
                165                 170                 175
Ala Gly Glu Asn Lys Lys Trp Asn Glu Asn Val Asp Asp Glu Phe Gly
            180                 185                 190
Asn Tyr Asp Tyr Leu Met Phe Ala Asn Ile Asp Tyr Asn His Pro Asp
        195                 200                 205
Val Arg Arg Glu Met Ile Asp Trp Gly Lys Trp Leu Ile Asp Thr Leu
210                 215                 220
Gln Cys Gly Gly Phe Arg Leu Asp Ala Ile Lys His Ile Asn His Glu
225                 230                 235                 240
Phe Ile Lys Glu Phe Ala Ala Glu Met Ile Arg Lys Arg Gly Gln Asp
                245                 250                 255
Phe Tyr Ile Val Gly Glu Phe Trp Asn Ser Asn Leu Asp Ala Cys Arg
            260                 265                 270
Glu Phe Leu Asp Thr Val Asp Tyr Gln Ile Asp Leu Phe Asp Val Ser
        275                 280                 285
Leu His Tyr Lys Leu His Glu Ala Ser Leu Lys Gly Arg Asp Phe Asp
        290                 295                 300
Leu Ser Lys Ile Phe Asp Asp Thr Leu Val Gln Thr His Pro Thr His
305                 310                 315                 320
Ala Val Thr Phe Val Asp Asn His Asp Ser Gln Pro His Glu Ala Leu
                325                 330                 335
Glu Ser Trp Ile Gly Asp Trp Phe Lys Pro Ser Ala Tyr Ala Leu Thr
            340                 345                 350
Leu Leu Arg Arg Asp Gly Tyr Pro Val Val Phe Tyr Gly Asp Tyr Tyr
        355                 360                 365
Gly Ile Gly Gly Pro Glu Pro Val Asp Gly Lys Lys Glu Ile Leu Asp
370                 375                 380
Ile Leu Leu Ser Ala Arg Cys Asn Lys Ala Tyr Gly Glu Gln Glu Asp
385                 390                 395                 400
Tyr Phe Asp His Ala Asn Thr Ile Gly Trp Val Arg Arg Gly Val Glu
                405                 410                 415
Glu Ile Glu Gly Ser Gly Cys Ala Val Val Ile Ser Asn Gly Asp Asp
            420                 425                 430
Gly Glu Lys Arg Met Phe Ile Gly Glu His Arg Ala Gly Glu Val Trp
        435                 440                 445
Val Asp Leu Thr Lys Ser Cys Asp Asp Gln Ile Thr Ile Glu Glu Asp
        450                 455                 460
Gly Trp Ala Thr Phe His Val Cys Gly Gly Val Ser Val Trp Ala
465                 470                 475                 480
Leu Pro Glu Gln Asn Glu Asp Cys Ala Asp Ala Glu
                485                 490

<210> SEQ ID NO 5
<211> LENGTH: 1455
<212> TYPE: DNA
```

```
<213> ORGANISM: Bacillus sp.
<220> FEATURE:
<221> NAME/KEY: CDS
<222> LOCATION: (1)..(1455)

<400> SEQUENCE: 5 cat cat aat ggg aca aat ggg acg atg atg caa tac ttt gaa tgg cac      48
His His Asn Gly Thr Asn Gly Thr Met Met Gln Tyr Phe Glu Trp His
1               5                   10                  15 ttg cct aat gat ggg aat cac tgg aat aga tta aga gat gat gct agt      96
Leu Pro Asn Asp Gly Asn His Trp Asn Arg Leu Arg Asp Asp Ala Ser
                20                  25                  30 aat cta aga aat aga ggt ata acc gct att tgg att ccg cct gcc tgg     144
Asn Leu Arg Asn Arg Gly Ile Thr Ala Ile Trp Ile Pro Pro Ala Trp
        35                  40                  45 aaa ggg act tcg caa aat gat gtg ggg tat gga gcc tat gat ctt tac     192
Lys Gly Thr Ser Gln Asn Asp Val Gly Tyr Gly Ala Tyr Asp Leu Tyr
    50                  55                  60 gat tta ggg gaa ttt aat caa aag ggg acg gtt cgt act aag tat ggg     240
Asp Leu Gly Glu Phe Asn Gln Lys Gly Thr Val Arg Thr Lys Tyr Gly
65                  70                  75                  80 aca cgt agt caa ttg gag tct gcc atc cat gct tta aag aat aat ggc     288
Thr Arg Ser Gln Leu Glu Ser Ala Ile His Ala Leu Lys Asn Asn Gly
                85                  90                  95 gtt caa gtt tat ggg gat gta gtg atg aac cat aaa gga gga gct gat     336
Val Gln Val Tyr Gly Asp Val Val Met Asn His Lys Gly Gly Ala Asp
                100                 105                 110 gct aca gaa aac gtt ctt gct gtc gag gtg aat cca aat aac cgg aat     384
Ala Thr Glu Asn Val Leu Ala Val Glu Val Asn Pro Asn Asn Arg Asn
        115                 120                 125 caa gaa ata tct ggg gac tac aca att gag gct tgg act aag ttt gat     432
Gln Glu Ile Ser Gly Asp Tyr Thr Ile Glu Ala Trp Thr Lys Phe Asp
    130                 135                 140 ttt cca ggg agg ggt aat aca tac tca gac ttt aaa tgg cgt tgg tat     480
Phe Pro Gly Arg Gly Asn Thr Tyr Ser Asp Phe Lys Trp Arg Trp Tyr
145                 150                 155                 160 cat ttc gat ggt gta gat tgg gat caa tca cga caa ttc caa aat cgt     528
His Phe Asp Gly Val Asp Trp Asp Gln Ser Arg Gln Phe Gln Asn Arg
                165                 170                 175 atc tac aaa ttc cga ggt gat ggc aaa gct tgg gat tgg gaa gta gat     576
Ile Tyr Lys Phe Arg Gly Asp Gly Lys Ala Trp Asp Trp Glu Val Asp
                180                 185                 190 tcg gaa aat gga aat tat gat tat tta atg tat gca gat gta gat atg     624
Ser Glu Asn Gly Asn Tyr Asp Tyr Leu Met Tyr Ala Asp Val Asp Met
        195                 200                 205 gat cat ccg gag gta gta aat gag ctt aga aga tgg gga gaa tgg tat     672
Asp His Pro Glu Val Val Asn Glu Leu Arg Arg Trp Gly Glu Trp Tyr
    210                 215                 220 aca aat aca tta aat ctt gat gga ttt agg atc gat gcg gtg aag cat     720
Thr Asn Thr Leu Asn Leu Asp Gly Phe Arg Ile Asp Ala Val Lys His
225                 230                 235                 240 att aaa tat agc ttt aca cgt gat tgg ttg acc cat gta aga aac gca     768
Ile Lys Tyr Ser Phe Thr Arg Asp Trp Leu Thr His Val Arg Asn Ala
                245                 250                 255 acg gga aaa gaa atg ttt gct gtt gct gaa ttt tgg aaa aat gat tta     816
Thr Gly Lys Glu Met Phe Ala Val Ala Glu Phe Trp Lys Asn Asp Leu
                260                 265                 270 ggt gcc ttg gag aac tat tta aat aaa aca aac tgg aat cat tct gtc     864
Gly Ala Leu Glu Asn Tyr Leu Asn Lys Thr Asn Trp Asn His Ser Val
        275                 280                 285
```

| | | | | | | | | | | | | | | | | |
|---|---|---|---|---|---|---|---|---|---|---|---|---|---|---|---|---|
| ttt | gat | gtc | ccc | ctt | cat | tat | aat | ctt | tat | aac | gcg | tca | aat | agt | gga | 912 |
| Phe | Asp | Val | Pro | Leu | His | Tyr | Asn | Leu | Tyr | Asn | Ala | Ser | Asn | Ser | Gly | |
| 290 | | | | | 295 | | | | | 300 | | | | | | |
| ggc | aac | tat | gac | atg | gca | aaa | ctt | ctt | aat | gga | acg | gtt | gtt | caa | aag | 960 |
| Gly | Asn | Tyr | Asp | Met | Ala | Lys | Leu | Leu | Asn | Gly | Thr | Val | Val | Gln | Lys | |
| 305 | | | | 310 | | | | | 315 | | | | | 320 | | |
| cat | cca | atg | cat | gcc | gta | act | ttt | gtg | gat | aat | cac | gat | tct | caa | cct | 1008 |
| His | Pro | Met | His | Ala | Val | Thr | Phe | Val | Asp | Asn | His | Asp | Ser | Gln | Pro | |
| | | | | 325 | | | | | 330 | | | | | 335 | | |
| ggg | gaa | tca | tta | gaa | tca | ttt | gta | caa | gaa | tgg | ttt | aag | cca | ctt | gct | 1056 |
| Gly | Glu | Ser | Leu | Glu | Ser | Phe | Val | Gln | Glu | Trp | Phe | Lys | Pro | Leu | Ala | |
| | | 340 | | | | | 345 | | | | | 350 | | | | |
| tat | gcg | ctt | att | tta | aca | aga | gaa | caa | ggc | tat | ccc | tct | gtc | ttc | tat | 1104 |
| Tyr | Ala | Leu | Ile | Leu | Thr | Arg | Glu | Gln | Gly | Tyr | Pro | Ser | Val | Phe | Tyr | |
| | | 355 | | | | | 360 | | | | | 365 | | | | |
| ggt | gac | tac | tat | gga | att | cca | aca | cat | agt | gtc | cca | gca | atg | aaa | gcc | 1152 |
| Gly | Asp | Tyr | Tyr | Gly | Ile | Pro | Thr | His | Ser | Val | Pro | Ala | Met | Lys | Ala | |
| 370 | | | | | 375 | | | | | 380 | | | | | | |
| aag | att | gat | cca | atc | tta | gag | gcg | cgt | caa | aat | ttt | gca | tat | gga | aca | 1200 |
| Lys | Ile | Asp | Pro | Ile | Leu | Glu | Ala | Arg | Gln | Asn | Phe | Ala | Tyr | Gly | Thr | |
| 385 | | | | | 390 | | | | | 395 | | | | | 400 | |
| caa | cat | gat | tat | ttt | gac | cat | cat | aat | ata | atc | gga | tgg | aca | cgt | gaa | 1248 |
| Gln | His | Asp | Tyr | Phe | Asp | His | His | Asn | Ile | Ile | Gly | Trp | Thr | Arg | Glu | |
| | | | | 405 | | | | | 410 | | | | | 415 | | |
| gga | aat | acc | acg | cat | ccc | aat | tca | gga | ctt | gcg | act | atc | atg | tcg | gat | 1296 |
| Gly | Asn | Thr | Thr | His | Pro | Asn | Ser | Gly | Leu | Ala | Thr | Ile | Met | Ser | Asp | |
| | | | 420 | | | | | 425 | | | | | 430 | | | |
| ggg | cca | ggg | gga | gag | aaa | tgg | atg | tac | gta | ggg | caa | aat | aaa | gca | ggt | 1344 |
| Gly | Pro | Gly | Gly | Glu | Lys | Trp | Met | Tyr | Val | Gly | Gln | Asn | Lys | Ala | Gly | |
| | | | 435 | | | | | 440 | | | | | 445 | | | |
| caa | gtt | tgg | cat | gac | ata | act | gga | aat | aaa | cca | gga | aca | gtt | acg | atc | 1392 |
| Gln | Val | Trp | His | Asp | Ile | Thr | Gly | Asn | Lys | Pro | Gly | Thr | Val | Thr | Ile | |
| | | | 450 | | | | | 455 | | | | | 460 | | | |
| aat | gca | gat | gga | tgg | gct | aat | ttt | tca | gta | aat | gga | gga | tct | gtt | tcc | 1440 |
| Asn | Ala | Asp | Gly | Trp | Ala | Asn | Phe | Ser | Val | Asn | Gly | Gly | Ser | Val | Ser | |
| 465 | | | | | 470 | | | | | 475 | | | | | 480 | |
| att | tgg | gtg | aaa | cga | | | | | | | | | | | | 1455 |
| Ile | Trp | Val | Lys | Arg | | | | | | | | | | | | |
| | | | 485 | | | | | | | | | | | | | |

<210> SEQ ID NO 6
<211> LENGTH: 485
<212> TYPE: PRT
<213> ORGANISM: Bacillus sp.

<400> SEQUENCE: 6

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
            20                  25                  30

Asn Leu Arg Asn Arg Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp

```
                100             105             110
Ala Thr Glu Asn Val Leu Ala Val Glu Val Asn Pro Asn Asn Arg Asn
            115                 120                 125

Gln Glu Ile Ser Gly Asp Tyr Thr Ile Glu Ala Trp Thr Lys Phe Asp
    130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
                180                 185                 190

Ser Glu Asn Gly Asn Tyr Asp Tyr Leu Met Tyr Ala Asp Val Asp Met
            195                 200                 205

Asp His Pro Glu Val Val Asn Glu Leu Arg Arg Trp Gly Glu Trp Tyr
            210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
            275                 280                 285

Phe Asp Val Pro Leu His Tyr Asn Leu Tyr Asn Ala Ser Asn Ser Gly
290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
            355                 360                 365

Gly Asp Tyr Tyr Gly Ile Pro Thr His Ser Val Pro Ala Met Lys Ala
370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
            435                 440                 445

Gln Val Trp His Asp Ile Thr Gly Asn Lys Pro Gly Thr Val Thr Ile
            450                 455                 460

Asn Ala Asp Gly Trp Ala Asn Phe Ser Val Asn Gly Gly Ser Val Ser
465                 470                 475                 480

Ile Trp Val Lys Arg
                485

<210> SEQ ID NO 7
<211> LENGTH: 1455
<212> TYPE: DNA
<213> ORGANISM: Bacillus sp.
```

```
<220> FEATURE:
<221> NAME/KEY: CDS
<222> LOCATION: (1)..(1455)

<400> SEQUENCE: 7 cat cat aac ggt acg aac ggg aca atg atg caa tac ttt gaa tgg tat        48
His His Asn Gly Thr Asn Gly Thr Met Met Gln Tyr Phe Glu Trp Tyr
1               5                   10                  15 cta cct aat gac gga aat cat tgg aat cga tta aac tct gat gcg agt        96
Leu Pro Asn Asp Gly Asn His Trp Asn Arg Leu Asn Ser Asp Ala Ser
            20                  25                  30 aac ctt aaa agc aaa ggg att aca gcg gtg tgg att cct cca gca tgg       144
Asn Leu Lys Ser Lys Gly Ile Thr Ala Val Trp Ile Pro Pro Ala Trp
        35                  40                  45 aag ggc gct tct caa aat gac gta gga tac gga gcc tat gac ctg tat       192
Lys Gly Ala Ser Gln Asn Asp Val Gly Tyr Gly Ala Tyr Asp Leu Tyr
    50                  55                  60 gat ctg gga gaa ttt aat caa aaa ggt acc gtc cgt aca aaa tat gga       240
Asp Leu Gly Glu Phe Asn Gln Lys Gly Thr Val Arg Thr Lys Tyr Gly
65                  70                  75                  80 aca cgt agt cag tta caa gct gcg gta acc tcc tta aaa aat aat gga       288
Thr Arg Ser Gln Leu Gln Ala Ala Val Thr Ser Leu Lys Asn Asn Gly
                85                  90                  95 att caa gta tat ggt gac gtt gtt atg aat cac aaa ggt ggc gca gac       336
Ile Gln Val Tyr Gly Asp Val Val Met Asn His Lys Gly Gly Ala Asp
            100                 105                 110 gct act gaa atg gta agg gcc gtt gaa gtg aat ccc aat aac cgt aac       384
Ala Thr Glu Met Val Arg Ala Val Glu Val Asn Pro Asn Asn Arg Asn
        115                 120                 125 caa gaa gtg act ggt gaa tat acc att gaa gct tgg act aga ttt gat       432
Gln Glu Val Thr Gly Glu Tyr Thr Ile Glu Ala Trp Thr Arg Phe Asp
    130                 135                 140 ttt cca ggg cga gga aat act cat tct agc ttt aaa tgg aga tgg tat       480
Phe Pro Gly Arg Gly Asn Thr His Ser Ser Phe Lys Trp Arg Trp Tyr
145                 150                 155                 160 cat ttt gat ggt gtg gat tgg gat cag tca cgt aga ctg aac aat cgc       528
His Phe Asp Gly Val Asp Trp Asp Gln Ser Arg Arg Leu Asn Asn Arg
                165                 170                 175 atc tat aaa ttt aga ggt cat ggc aaa gct tgg gat tgg gaa gtt gat       576
Ile Tyr Lys Phe Arg Gly His Gly Lys Ala Trp Asp Trp Glu Val Asp
            180                 185                 190 acg gaa aat ggt aat tat gat tat tta atg tac gct gat att gat atg       624
Thr Glu Asn Gly Asn Tyr Asp Tyr Leu Met Tyr Ala Asp Ile Asp Met
        195                 200                 205 gat cac cca gaa gta gta aat gaa tta aga aat tgg ggt gtt tgg tac       672
Asp His Pro Glu Val Val Asn Glu Leu Arg Asn Trp Gly Val Trp Tyr
    210                 215                 220 aca aac aca tta gga ctc gat gga ttt aga ata gat gcg gtt aaa cat       720
Thr Asn Thr Leu Gly Leu Asp Gly Phe Arg Ile Asp Ala Val Lys His
225                 230                 235                 240 ata aag tat agc ttt acg cgc gat tgg att aat cac gtt aga agt gca       768
Ile Lys Tyr Ser Phe Thr Arg Asp Trp Ile Asn His Val Arg Ser Ala
                245                 250                 255 aca ggt aaa aat atg ttt gcg gtt gct gag ttt tgg aag aat gat tta       816
Thr Gly Lys Asn Met Phe Ala Val Ala Glu Phe Trp Lys Asn Asp Leu
            260                 265                 270 ggt gca att gaa aac tat ctg cag aaa aca aac tgg aac cat tca gtc       864
Gly Ala Ile Glu Asn Tyr Leu Gln Lys Thr Asn Trp Asn His Ser Val
        275                 280                 285 ttt gat gtg ccg tta cat tat aat ctt tat aat gca tca aaa agc gga       912
```

```
                                                                              -continued Phe Asp Val Pro Leu His Tyr Asn Leu Tyr Asn Ala Ser Lys Ser Gly
            290                 295                 300 ggg aac tat gat atg cga aac ata ttt aat gga acg gtt gtt caa cga       960
Gly Asn Tyr Asp Met Arg Asn Ile Phe Asn Gly Thr Val Val Gln Arg
305                 310                 315                 320 cat cca agt cat gct gta aca ttt gtt gat aat cat gat tcg cag cct      1008
His Pro Ser His Ala Val Thr Phe Val Asp Asn His Asp Ser Gln Pro
                325                 330                 335 gaa gaa gca tta gaa tct ttt gtt gaa gaa tgg ttt aaa cca tta gcg      1056
Glu Glu Ala Leu Glu Ser Phe Val Glu Glu Trp Phe Lys Pro Leu Ala
            340                 345                 350 tat gcg ctt aca tta acg cgt gaa caa gga tac cct tct gta ttt tac      1104
Tyr Ala Leu Thr Leu Thr Arg Glu Gln Gly Tyr Pro Ser Val Phe Tyr
        355                 360                 365 gga gat tat tat ggg att cca aca cat gga gtg cca gca atg aga tca      1152
Gly Asp Tyr Tyr Gly Ile Pro Thr His Gly Val Pro Ala Met Arg Ser
370                 375                 380 aaa atc gat ccg att tta gaa gca cgt caa aag tat gca tac gga aaa      1200
Lys Ile Asp Pro Ile Leu Glu Ala Arg Gln Lys Tyr Ala Tyr Gly Lys
385                 390                 395                 400 caa aat gat tac tta gac cat cat aat atc att ggt tgg acg cgt gaa      1248
Gln Asn Asp Tyr Leu Asp His His Asn Ile Ile Gly Trp Thr Arg Glu
                405                 410                 415 ggg aat aca gca cac ccc aat tca ggt cta gct acc atc atg tct gat      1296
Gly Asn Thr Ala His Pro Asn Ser Gly Leu Ala Thr Ile Met Ser Asp
            420                 425                 430 gga gcg ggt gga agt aag tgg atg ttt gtt ggg cgt aat aag gct ggt      1344
Gly Ala Gly Gly Ser Lys Trp Met Phe Val Gly Arg Asn Lys Ala Gly
        435                 440                 445 caa gta tgg agt gat att aca gga aac cgt aca ggt acg gtt aca atc      1392
Gln Val Trp Ser Asp Ile Thr Gly Asn Arg Thr Gly Thr Val Thr Ile
450                 455                 460 aat gca gac ggt tgg ggc aat ttc tct gtg aat gga ggg tca gtt tct      1440
Asn Ala Asp Gly Trp Gly Asn Phe Ser Val Asn Gly Gly Ser Val Ser
465                 470                 475                 480 att tgg gtc aac aaa                                                   1455
Ile Trp Val Asn Lys
            485

<210> SEQ ID NO 8
<211> LENGTH: 485
<212> TYPE: PRT
<213> ORGANISM: Bacillus sp.

<400> SEQUENCE: 8

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
                20                  25                  30

Asn Leu Lys Ser Lys Gly Ile Thr Ala Val Trp Ile Pro Pro Ala Trp
            35                  40                  45

Lys Gly Ala Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110
```

```
Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
        130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
                180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
        210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
        260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
        290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Trp Phe Lys Pro Leu Ala
                340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Arg Ser
370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
                420                 425                 430

Gly Ala Gly Gly Ser Lys Trp Met Phe Val Gly Arg Asn Lys Ala Gly
        435                 440                 445

Gln Val Trp Ser Asp Ile Thr Gly Asn Arg Thr Gly Thr Val Thr Ile
        450                 455                 460

Asn Ala Asp Gly Trp Gly Asn Phe Ser Val Asn Gly Gly Ser Val Ser
465                 470                 475                 480

Ile Trp Val Asn Lys
                485
```

<210> SEQ ID NO 9
<211> LENGTH: 1458
<212> TYPE: DNA
<213> ORGANISM: Bacillus sp.
<220> FEATURE:

```
<221> NAME/KEY: CDS
<222> LOCATION: (1)..(1458)

<400> SEQUENCE: 9 cac cat aat ggt acg aac ggc aca atg atg cag tac ttt gaa tgg tat    48
His His Asn Gly Thr Asn Gly Thr Met Met Gln Tyr Phe Glu Trp Tyr
1               5                   10                  15 cta cca aat gac gga aac cat tgg aat aga tta agg tct gat gca agt    96
Leu Pro Asn Asp Gly Asn His Trp Asn Arg Leu Arg Ser Asp Ala Ser
            20                  25                  30 aac cta aaa gat aaa ggg atc tca gcg gtt tgg att cct cct gca tgg   144
Asn Leu Lys Asp Lys Gly Ile Ser Ala Val Trp Ile Pro Pro Ala Trp
        35                  40                  45 aag ggt gcc tct caa aat gat gtg ggg tat ggt gct tat gat ctg tat   192
Lys Gly Ala Ser Gln Asn Asp Val Gly Tyr Gly Ala Tyr Asp Leu Tyr
50                  55                  60 gat tta gga gaa ttc aat caa aaa gga acc att cgt aca aaa tat gga   240
Asp Leu Gly Glu Phe Asn Gln Lys Gly Thr Ile Arg Thr Lys Tyr Gly
65                  70                  75                  80 acg cgc aat cag tta caa gct gca gtt aac gcc ttg aaa agt aat gga   288
Thr Arg Asn Gln Leu Gln Ala Ala Val Asn Ala Leu Lys Ser Asn Gly
                85                  90                  95 att caa gtg tat ggc gat gtt gta atg aat cat aaa ggg gga gca gac   336
Ile Gln Val Tyr Gly Asp Val Val Met Asn His Lys Gly Gly Ala Asp
            100                 105                 110 gct acc gaa atg gtt agg gcg gtt gaa gta aac ccg aat aat aga aat   384
Ala Thr Glu Met Val Arg Ala Val Glu Val Asn Pro Asn Asn Arg Asn
        115                 120                 125 caa gaa gtg tcc ggt gaa tat aca att gag gct tgg aca aag ttt gac   432
Gln Glu Val Ser Gly Glu Tyr Thr Ile Glu Ala Trp Thr Lys Phe Asp
130                 135                 140 ttt cct gga cga ggt aat acc cat tca aac ttc aaa tgg aga tgg tat   480
Phe Pro Gly Arg Gly Asn Thr His Ser Asn Phe Lys Trp Arg Trp Tyr
145                 150                 155                 160 cac ttt gat gga gta gat tgg gat cag tca cgt aag ctg aac aat cga   528
His Phe Asp Gly Val Asp Trp Asp Gln Ser Arg Lys Leu Asn Asn Arg
                165                 170                 175 att tat aaa ttt aga ggt gat gga aaa ggg tgg gat tgg gaa gtc gat   576
Ile Tyr Lys Phe Arg Gly Asp Gly Lys Gly Trp Asp Trp Glu Val Asp
            180                 185                 190 aca gaa aac ggt aac tat gat tac cta atg tat gca gat att gac atg   624
Thr Glu Asn Gly Asn Tyr Asp Tyr Leu Met Tyr Ala Asp Ile Asp Met
        195                 200                 205 gat cac cca gag gta gtg aat gag cta aga aat tgg ggt gtt tgg tat   672
Asp His Pro Glu Val Val Asn Glu Leu Arg Asn Trp Gly Val Trp Tyr
210                 215                 220 acg aat aca tta ggc ctt gat ggt ttt aga ata gat gca gta aaa cat   720
Thr Asn Thr Leu Gly Leu Asp Gly Phe Arg Ile Asp Ala Val Lys His
225                 230                 235                 240 ata aaa tac agc ttt act cgt gat tgg atc aat cat gtt aga agt gca   768
Ile Lys Tyr Ser Phe Thr Arg Asp Trp Ile Asn His Val Arg Ser Ala
                245                 250                 255 act ggc aaa aat atg ttt gcg gtt gcg gaa ttt tgg aaa aat gat tta   816
Thr Gly Lys Asn Met Phe Ala Val Ala Glu Phe Trp Lys Asn Asp Leu
            260                 265                 270 ggt gct att gaa aac tat tta aac aaa aca aac tgg aac cat tca gtc   864
Gly Ala Ile Glu Asn Tyr Leu Asn Lys Thr Asn Trp Asn His Ser Val
        275                 280                 285 ttt gat gtt ccg ctg cac tat aac ctc tat aat gct tca aaa agc gga   912
Phe Asp Val Pro Leu His Tyr Asn Leu Tyr Asn Ala Ser Lys Ser Gly
```

```
                    290                 295                 300
ggg aat tat gat atg agg caa ata ttt aat ggt aca gtc gtg caa aga       960
Gly Asn Tyr Asp Met Arg Gln Ile Phe Asn Gly Thr Val Val Gln Arg
305                 310                 315                 320 cat cca atg cat gct gtt aca ttt gtt gat aat cat gat tcg caa cct      1008
His Pro Met His Ala Val Thr Phe Val Asp Asn His Asp Ser Gln Pro
                325                 330                 335 gaa gaa gct tta gag tct ttt gtt gaa gaa tgg ttc aaa cca tta gcg      1056
Glu Glu Ala Leu Glu Ser Phe Val Glu Glu Trp Phe Lys Pro Leu Ala
            340                 345                 350 tat gct ttg aca tta aca cgt gaa caa ggc tac cct tct gta ttt tat      1104
Tyr Ala Leu Thr Leu Thr Arg Glu Gln Gly Tyr Pro Ser Val Phe Tyr
        355                 360                 365 gga gat tat tat ggc att cca acg cat ggt gta cca gcg atg aaa tcg      1152
Gly Asp Tyr Tyr Gly Ile Pro Thr His Gly Val Pro Ala Met Lys Ser
    370                 375                 380 aaa att gac ccg att cta gaa gcg cgt caa aag tat gca tat gga aga      1200
Lys Ile Asp Pro Ile Leu Glu Ala Arg Gln Lys Tyr Ala Tyr Gly Arg
385                 390                 395                 400 caa aat gac tac tta gac cat cat aat atc att ggt tgg aca cgt gaa      1248
Gln Asn Asp Tyr Leu Asp His His Asn Ile Ile Gly Trp Thr Arg Glu
                405                 410                 415 ggg aat aca gca cac ccc aac tct ggt tta gct act atc atg tcc gat      1296
Gly Asn Thr Ala His Pro Asn Ser Gly Leu Ala Thr Ile Met Ser Asp
            420                 425                 430 gga gca gga gga aat aag tgg atg ttt gtt ggg cgt aat aaa gct ggt      1344
Gly Ala Gly Gly Asn Lys Trp Met Phe Val Gly Arg Asn Lys Ala Gly
        435                 440                 445 caa gtt tgg acc gat atc act gga aat cgt gca ggt act gtt acg att      1392
Gln Val Trp Thr Asp Ile Thr Gly Asn Arg Ala Gly Thr Val Thr Ile
    450                 455                 460 aat gct gat gga tgg ggt aat ttt tct gta aat gga gga tca gtt tct      1440
Asn Ala Asp Gly Trp Gly Asn Phe Ser Val Asn Gly Gly Ser Val Ser
465                 470                 475                 480 att tgg gta aac aaa taa                                              1458
Ile Trp Val Asn Lys
                485

<210> SEQ ID NO 10
<211> LENGTH: 485
<212> TYPE: PRT
<213> ORGANISM: Bacillus sp.

<400> SEQUENCE: 10

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110
```

```
Ala Thr Glu Met Val Arg Ala Glu Val Asn Pro Asn Asn Arg Asn
        115                 120                 125

Gln Glu Val Ser Gly Glu Tyr Thr Ile Glu Ala Trp Thr Lys Phe Asp
130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Asn Lys Trp Met Phe Val Gly Arg Asn Lys Ala Gly
        435                 440                 445

Gln Val Trp Thr Asp Ile Thr Gly Asn Arg Ala Gly Thr Val Thr Ile
450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 11
<211> LENGTH: 1455
<212> TYPE: DNA
<213> ORGANISM: Bacillus Sp
<220> FEATURE:
<221> NAME/KEY: CDS
```

<222> LOCATION: (1)..(1455)

<400> SEQUENCE: 11

| | | | | | | | | | | | | | | | | |
|---|---|---|---|---|---|---|---|---|---|---|---|---|---|---|---|---|
| cat | cat | aat | gga | aca | aat | ggt | act | atg | atg | caa | tat | ttc | gaa | tgg | tat | 48 |
| His | His | Asn | Gly | Thr | Asn | Gly | Thr | Met | Met | Gln | Tyr | Phe | Glu | Trp | Tyr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttg | cca | aat | gac | ggg | aat | cat | tgg | aac | agg | ttg | agg | gat | gac | gca | gct | 96 |
| Leu | Pro | Asn | Asp | Gly | Asn | His | Trp | Asn | Arg | Leu | Arg | Asp | Asp | Ala | Ala | |
| | | | 20 | | | | | 25 | | | | | 30 | | | |

| | | | | | | | | | | | | | | | | |
|---|---|---|---|---|---|---|---|---|---|---|---|---|---|---|---|---|
| aac | tta | aag | agt | aaa | ggg | ata | aca | gct | gta | tgg | att | cca | cct | gca | tgg | 144 |
| Asn | Leu | Lys | Ser | Lys | Gly | Ile | Thr | Ala | Val | Trp | Ile | Pro | Pro | Ala | Trp | |
| | | 35 | | | | | 40 | | | | | 45 | | | | |

| | | | | | | | | | | | | | | | | |
|---|---|---|---|---|---|---|---|---|---|---|---|---|---|---|---|---|
| aag | ggg | act | tcc | cag | aat | gat | gta | ggt | tat | gga | gcc | tat | gat | tta | tat | 192 |
| Lys | Gly | Thr | Ser | Gln | Asn | Asp | Val | Gly | Tyr | Gly | Ala | Tyr | Asp | Leu | Tyr | |
| 50 | | | | | 55 | | | | | 60 | | | | | | |

| | | | | | | | | | | | | | | | | |
|---|---|---|---|---|---|---|---|---|---|---|---|---|---|---|---|---|
| gat | ctt | gga | gag | ttt | aac | cag | aag | ggg | acg | gtt | cgt | aca | aaa | tat | gga | 240 |
| Asp | Leu | Gly | Glu | Phe | Asn | Gln | Lys | Gly | Thr | Val | Arg | Thr | Lys | Tyr | Gly | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| aca | cgc | aac | cag | ctg | cag | gct | gcc | gtg | aca | tct | tta | aaa | aat | aac | ggc | 288 |
| Thr | Arg | Asn | Gln | Leu | Gln | Ala | Ala | Val | Thr | Ser | Leu | Lys | Asn | Asn | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| att | cag | gta | tat | ggt | gat | gtc | gtc | atg | aat | cat | aaa | ggt | gga | gca | gat | 336 |
| Ile | Gln | Val | Tyr | Gly | Asp | Val | Val | Met | Asn | His | Lys | Gly | Gly | Ala | Asp | |
| | | | 100 | | | | | 105 | | | | | 110 | | | |

| | | | | | | | | | | | | | | | | |
|---|---|---|---|---|---|---|---|---|---|---|---|---|---|---|---|---|
| ggt | acg | gaa | att | gta | aat | gcg | gta | gaa | gtg | aat | cgg | agc | aac | cga | aac | 384 |
| Gly | Thr | Glu | Ile | Val | Asn | Ala | Val | Glu | Val | Asn | Arg | Ser | Asn | Arg | Asn | |
| | | 115 | | | | | 120 | | | | | 125 | | | | |

| | | | | | | | | | | | | | | | | |
|---|---|---|---|---|---|---|---|---|---|---|---|---|---|---|---|---|
| cag | gaa | acc | tca | gga | gag | tat | gca | ata | gaa | gcg | tgg | aca | aag | ttt | gat | 432 |
| Gln | Glu | Thr | Ser | Gly | Glu | Tyr | Ala | Ile | Glu | Ala | Trp | Thr | Lys | Phe | Asp | |
| 130 | | | | | 135 | | | | | 140 | | | | | | |

| | | | | | | | | | | | | | | | | |
|---|---|---|---|---|---|---|---|---|---|---|---|---|---|---|---|---|
| ttt | cct | gga | aga | gga | aat | aac | cat | tcc | agc | ttt | aag | tgg | cgc | tgg | tat | 480 |
| Phe | Pro | Gly | Arg | Gly | Asn | Asn | His | Ser | Ser | Phe | Lys | Trp | Arg | Trp | Tyr | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cat | ttt | gat | ggg | aca | gat | tgg | gat | cag | tca | cgc | cag | ctt | caa | aac | aaa | 528 |
| His | Phe | Asp | Gly | Thr | Asp | Trp | Asp | Gln | Ser | Arg | Gln | Leu | Gln | Asn | Lys | |
| | | | | 165 | | | | | 170 | | | | | 175 | | |

| | | | | | | | | | | | | | | | | |
|---|---|---|---|---|---|---|---|---|---|---|---|---|---|---|---|---|
| ata | tat | aaa | ttc | agg | gga | aca | ggc | aag | gcc | tgg | gac | tgg | gaa | gtc | gat | 576 |
| Ile | Tyr | Lys | Phe | Arg | Gly | Thr | Gly | Lys | Ala | Trp | Asp | Trp | Glu | Val | Asp | |
| | | | 180 | | | | | 185 | | | | | 190 | | | |

| | | | | | | | | | | | | | | | | |
|---|---|---|---|---|---|---|---|---|---|---|---|---|---|---|---|---|
| aca | gag | aat | ggc | aac | tat | gac | tat | ctt | atg | tat | gca | gac | gtg | gat | atg | 624 |
| Thr | Glu | Asn | Gly | Asn | Tyr | Asp | Tyr | Leu | Met | Tyr | Ala | Asp | Val | Asp | Met | |
| | | 195 | | | | | 200 | | | | | 205 | | | | |

| | | | | | | | | | | | | | | | | |
|---|---|---|---|---|---|---|---|---|---|---|---|---|---|---|---|---|
| gat | cac | cca | gaa | gta | ata | cat | gaa | ctt | aga | aac | tgg | gga | gtg | tgg | tat | 672 |
| Asp | His | Pro | Glu | Val | Ile | His | Glu | Leu | Arg | Asn | Trp | Gly | Val | Trp | Tyr | |
| 210 | | | | | 215 | | | | | 220 | | | | | | |

| | | | | | | | | | | | | | | | | |
|---|---|---|---|---|---|---|---|---|---|---|---|---|---|---|---|---|
| acg | aat | aca | ctg | aac | ctt | gat | gga | ttt | aga | ata | gat | gca | gtg | aaa | cat | 720 |
| Thr | Asn | Thr | Leu | Asn | Leu | Asp | Gly | Phe | Arg | Ile | Asp | Ala | Val | Lys | His | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ata | aaa | tat | agc | ttt | acg | aga | gat | tgg | ctt | aca | cat | gtg | cgt | aac | acc | 768 |
| Ile | Lys | Tyr | Ser | Phe | Thr | Arg | Asp | Trp | Leu | Thr | His | Val | Arg | Asn | Thr | |
| | | | | 245 | | | | | 250 | | | | | 255 | | |

| | | | | | | | | | | | | | | | | |
|---|---|---|---|---|---|---|---|---|---|---|---|---|---|---|---|---|
| aca | ggt | aaa | cca | atg | ttt | gca | gtg | gct | gag | ttt | tgg | aaa | aat | gac | ctt | 816 |
| Thr | Gly | Lys | Pro | Met | Phe | Ala | Val | Ala | Glu | Phe | Trp | Lys | Asn | Asp | Leu | |
| | | | 260 | | | | | 265 | | | | | 270 | | | |

| | | | | | | | | | | | | | | | | |
|---|---|---|---|---|---|---|---|---|---|---|---|---|---|---|---|---|
| ggt | gca | att | gaa | aac | tat | ttg | aat | aaa | aca | agt | tgg | aat | cac | tcg | gtg | 864 |
| Gly | Ala | Ile | Glu | Asn | Tyr | Leu | Asn | Lys | Thr | Ser | Trp | Asn | His | Ser | Val | |
| | | 275 | | | | | 280 | | | | | 285 | | | | |

| | | | | | | | | | | | | | | | | |
|---|---|---|---|---|---|---|---|---|---|---|---|---|---|---|---|---|
| ttt | gat | gtt | cct | ctc | cac | tat | aat | ttg | tac | aat | gca | tct | aat | agc | ggt | 912 |
| Phe | Asp | Val | Pro | Leu | His | Tyr | Asn | Leu | Tyr | Asn | Ala | Ser | Asn | Ser | Gly | |
| | | 290 | | | | | 295 | | | | | 300 | | | | |

```
ggt tat tat gat atg aga aat att tta aat ggt tct gtg gtg caa aaa    960
Gly Tyr Tyr Asp Met Arg Asn Ile Leu Asn Gly Ser Val Val Gln Lys
305                 310                 315                 320 cat cca aca cat gcc gtt act ttt gtt gat aac cat gat tct cag ccc   1008
His Pro Thr His Ala Val Thr Phe Val Asp Asn His Asp Ser Gln Pro
            325                 330                 335 ggg gaa gca ttg gaa tcc ttt gtt caa caa tgg ttt aaa cca ctt gca   1056
Gly Glu Ala Leu Glu Ser Phe Val Gln Gln Trp Phe Lys Pro Leu Ala
340                 345                 350 tat gca ttg gtt ctg aca agg gaa caa ggt tat cct tcc gta ttt tat   1104
Tyr Ala Leu Val Leu Thr Arg Glu Gln Gly Tyr Pro Ser Val Phe Tyr
        355                 360                 365 ggg gat tac tac ggt atc cca acc cat ggt gtt ccg gct atg aaa tct   1152
Gly Asp Tyr Tyr Gly Ile Pro Thr His Gly Val Pro Ala Met Lys Ser
370                 375                 380 aaa ata gac cct ctt ctg cag gca cgt caa act ttt gcc tat ggt acg   1200
Lys Ile Asp Pro Leu Leu Gln Ala Arg Gln Thr Phe Ala Tyr Gly Thr
385                 390                 395                 400 cag cat gat tac ttt gat cat cat gat att atc ggt tgg aca aga gag   1248
Gln His Asp Tyr Phe Asp His His Asp Ile Ile Gly Trp Thr Arg Glu
                405                 410                 415 gga aat agc tcc cat cca aat tca ggc ctt gcc acc att atg tca gat   1296
Gly Asn Ser Ser His Pro Asn Ser Gly Leu Ala Thr Ile Met Ser Asp
            420                 425                 430 ggt cca ggt ggt aac aaa tgg atg tat gtg ggg aaa aat aaa gcg gga   1344
Gly Pro Gly Gly Asn Lys Trp Met Tyr Val Gly Lys Asn Lys Ala Gly
        435                 440                 445 caa gtt tgg aga gat att acc gga aat agg aca ggc acc gtc aca att   1392
Gln Val Trp Arg Asp Ile Thr Gly Asn Arg Thr Gly Thr Val Thr Ile
450                 455                 460 aat gca gac gga tgg ggt aat ttc tct gtt aat gga ggg tcc gtt tcg   1440
Asn Ala Asp Gly Trp Gly Asn Phe Ser Val Asn Gly Gly Ser Val Ser
465                 470                 475                 480 gtt tgg gtg aag caa                                                1455
Val Trp Val Lys Gln
                485

<210> SEQ ID NO 12
<211> LENGTH: 485
<212> TYPE: PRT
<213> ORGANISM: Bacillus Sp

<400> SEQUENCE: 12

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Gly Thr Glu Ile Val Asn Ala Val Glu Val Asn Arg Ser Asn Arg Asn
```

```
                115                 120                 125
      Gln Glu Thr Ser Gly Glu Tyr Ala Ile Glu Ala Trp Thr Lys Phe Asp
                      130                 135                 140

Phe Pro Gly Arg Gly Asn Asn His Ser Ser Phe Lys Trp Arg Trp Tyr
      145                 150                 155                 160

His Phe Asp Gly Thr Asp Trp Asp Gln Ser Arg Gln Leu Gln Asn Lys
                          165                 170                 175

Ile Tyr Lys Phe Arg Gly Thr Gly Lys Ala Trp Asp Trp Glu Val Asp
                      180                 185                 190

Thr Glu Asn Gly Asn Tyr Asp Tyr Leu Met Tyr Ala Asp Val Asp Met
                      195                 200                 205

Asp His Pro Glu Val Ile His Glu Leu Arg Asn Trp Gly Val Trp Tyr
                      210                 215                 220

Thr Asn Thr Leu Asn Leu Asp Gly Phe Arg Ile Asp Ala Val Lys His
      225                 230                 235                 240

Ile Lys Tyr Ser Phe Thr Arg Asp Trp Leu Thr His Val Arg Asn Thr
                          245                 250                 255

Thr Gly Lys Pro Met Phe Ala Val Ala Glu Phe Trp Lys Asn Asp Leu
                      260                 265                 270

Gly Ala Ile Glu Asn Tyr Leu Asn Lys Thr Ser Trp Asn His Ser Val
                      275                 280                 285

Phe Asp Val Pro Leu His Tyr Asn Leu Tyr Asn Ala Ser Asn Ser Gly
      290                 295                 300

Gly Tyr Tyr Asp Met Arg Asn Ile Leu Asn Gly Ser Val Val Gln Lys
      305                 310                 315                 320

His Pro Thr His Ala Val Thr Phe Val Asp Asn His Asp Ser Gln Pro
                          325                 330                 335

Gly Glu Ala Leu Glu Ser Phe Val Gln Gln Trp Phe Lys Pro Leu Ala
                      340                 345                 350

Tyr Ala Leu Val Leu Thr Arg Glu Gln Gly Tyr Pro Ser Val Phe Tyr
                      355                 360                 365

Gly Asp Tyr Tyr Gly Ile Pro Thr His Gly Val Pro Ala Met Lys Ser
      370                 375                 380

Lys Ile Asp Pro Leu Leu Gln Ala Arg Gln Thr Phe Ala Tyr Gly Thr
      385                 390                 395                 400

Gln His Asp Tyr Phe Asp His His Asp Ile Ile Gly Trp Thr Arg Glu
                      405                 410                 415

Gly Asn Ser Ser His Pro Asn Ser Gly Leu Ala Thr Ile Met Ser Asp
                      420                 425                 430

Gly Pro Gly Gly Asn Lys Trp Met Tyr Val Gly Lys Asn Lys Ala Gly
                      435                 440                 445

Gln Val Trp Arg Asp Ile Thr Gly Asn Arg Thr Gly Thr Val Thr Ile
                      450                 455                 460

Asn Ala Asp Gly Trp Gly Asn Phe Ser Val Asn Gly Gly Ser Val Ser
      465                 470                 475                 480

Val Trp Val Lys Gln
                      485

<210> SEQ ID NO 13
<211> LENGTH: 1452
<212> TYPE: DNA
<213> ORGANISM: Bacillus amyloliquefaciens
<220> FEATURE:
<221> NAME/KEY: CDS
<222> LOCATION: (1)..(1449)
```

<400> SEQUENCE: 13

```
gta aat ggc acg ctg atg cag tat ttt gaa tgg tat acg ccg aac gac      48
Val Asn Gly Thr Leu Met Gln Tyr Phe Glu Trp Tyr Thr Pro Asn Asp
1               5                   10                  15 ggc cag cat tgg aaa cga ttg cag aat gat gcg gaa cat tta tcg gat      96
Gly Gln His Trp Lys Arg Leu Gln Asn Asp Ala Glu His Leu Ser Asp
            20                  25                  30 atc gga atc act gcc gtc tgg att cct ccc gca tac aaa gga ttg agc     144
Ile Gly Ile Thr Ala Val Trp Ile Pro Pro Ala Tyr Lys Gly Leu Ser
        35                  40                  45 caa tcc gat aac gga tac gga cct tat gat ttg tat gat tta gga gaa     192
Gln Ser Asp Asn Gly Tyr Gly Pro Tyr Asp Leu Tyr Asp Leu Gly Glu
    50                  55                  60 ttc cag caa aaa ggg acg gtc aga acg aaa tac ggc aca aaa tca gag     240
Phe Gln Gln Lys Gly Thr Val Arg Thr Lys Tyr Gly Thr Lys Ser Glu
65                  70                  75                  80 ctt caa gat gcg atc ggc tca ctg cat tcc cgg aac gtc caa gta tac     288
Leu Gln Asp Ala Ile Gly Ser Leu His Ser Arg Asn Val Gln Val Tyr
                85                  90                  95 gga gat gtg gtt ttg aat cat aag gct ggt gct gat gca aca gaa gat     336
Gly Asp Val Val Leu Asn His Lys Ala Gly Ala Asp Ala Thr Glu Asp
            100                 105                 110 gta act gcc gtc gaa gtc aat ccg gcc aat aga aat cag gaa act tcg     384
Val Thr Ala Val Glu Val Asn Pro Ala Asn Arg Asn Gln Glu Thr Ser
        115                 120                 125 gag gaa tat caa atc aaa gcg tgg acg gat ttt cgt ttt ccg ggc cgt     432
Glu Glu Tyr Gln Ile Lys Ala Trp Thr Asp Phe Arg Phe Pro Gly Arg
    130                 135                 140 gga aac acg tac agt gat ttt aaa tgg cat tgg tat cat ttc gac gga     480
Gly Asn Thr Tyr Ser Asp Phe Lys Trp His Trp Tyr His Phe Asp Gly
145                 150                 155                 160 gcg gac tgg gat gaa tcc cgg aag atc agc cgc atc ttt aag ttt cgt     528
Ala Asp Trp Asp Glu Ser Arg Lys Ile Ser Arg Ile Phe Lys Phe Arg
                165                 170                 175 ggg gaa gga aaa gcg tgg gat tgg gaa gta tca agt gaa aac ggc aac     576
Gly Glu Gly Lys Ala Trp Asp Trp Glu Val Ser Ser Glu Asn Gly Asn
            180                 185                 190 tat gac tat tta atg tat gct gat gtt gac tac gac cac cct gat gtc     624
Tyr Asp Tyr Leu Met Tyr Ala Asp Val Asp Tyr Asp His Pro Asp Val
        195                 200                 205 gtg gca gag aca aaa aaa tgg ggt atc tgg tat gca aat gaa ctg tca     672
Val Ala Glu Thr Lys Lys Trp Gly Ile Trp Tyr Ala Asn Glu Leu Ser
    210                 215                 220 tta gac ggc ttc cgt att gat gcc gcc aaa cat att aaa ttt tca ttt     720
Leu Asp Gly Phe Arg Ile Asp Ala Ala Lys His Ile Lys Phe Ser Phe
225                 230                 235                 240 ctg cgt gat tgg gtt cag gcg gtc aga cag gcg acg gga aaa gaa atg     768
Leu Arg Asp Trp Val Gln Ala Val Arg Gln Ala Thr Gly Lys Glu Met
                245                 250                 255 ttt acg gtt gcg gag tat tgg cag aat aat gcc ggg aaa ctc gaa aac     816
Phe Thr Val Ala Glu Tyr Trp Gln Asn Asn Ala Gly Lys Leu Glu Asn
            260                 265                 270 tac ttg aat aaa aca agc ttt aat caa tcc gtg ttt gat gtt ccg ctt     864
Tyr Leu Asn Lys Thr Ser Phe Asn Gln Ser Val Phe Asp Val Pro Leu
        275                 280                 285 cat ttc aat tta cag gcg gct tcc tca caa gga ggc gga tat gat atg     912
His Phe Asn Leu Gln Ala Ala Ser Ser Gln Gly Gly Gly Tyr Asp Met
    290                 295                 300
```

```
agg cgt ttg ctg gac ggt acc gtt gtg tcc agg cat ccg gaa aag gcg      960
Arg Arg Leu Leu Asp Gly Thr Val Val Ser Arg His Pro Glu Lys Ala
305                 310                 315                 320 gtt aca ttt gtt gaa aat cat gac aca cag ccg gga cag tca ttg gaa     1008
Val Thr Phe Val Glu Asn His Asp Thr Gln Pro Gly Gln Ser Leu Glu
                325                 330                 335 tcg aca gtc caa act tgg ttt aaa ccg ctt gca tac gcc ttt att ttg     1056
Ser Thr Val Gln Thr Trp Phe Lys Pro Leu Ala Tyr Ala Phe Ile Leu
            340                 345                 350 aca aga gaa tcc ggt tat cct cag gtg ttc tat ggg gat atg tac ggg     1104
Thr Arg Glu Ser Gly Tyr Pro Gln Val Phe Tyr Gly Asp Met Tyr Gly
        355                 360                 365 aca aaa ggg aca tcg cca aag gaa att ccc tca ctg aaa gat aat ata     1152
Thr Lys Gly Thr Ser Pro Lys Glu Ile Pro Ser Leu Lys Asp Asn Ile
    370                 375                 380 gag ccg att tta aaa gcg cgt aag gag tac gca tac ggg ccc cag cac     1200
Glu Pro Ile Leu Lys Ala Arg Lys Glu Tyr Ala Tyr Gly Pro Gln His
385                 390                 395                 400 gat tat att gac cac ccg gat gtg atc gga tgg acg agg gaa ggt gac     1248
Asp Tyr Ile Asp His Pro Asp Val Ile Gly Trp Thr Arg Glu Gly Asp
                405                 410                 415 agc tcc gcc gcc aaa tca ggt ttg gcc gct tta atc acg gac gga ccc     1296
Ser Ser Ala Ala Lys Ser Gly Leu Ala Ala Leu Ile Thr Asp Gly Pro
            420                 425                 430 ggc gga tca aag cgg atg tat gcc ggc ctg aaa aat gcc ggc gag aca     1344
Gly Gly Ser Lys Arg Met Tyr Ala Gly Leu Lys Asn Ala Gly Glu Thr
        435                 440                 445 tgg tat gac ata acg ggc aac cgt tca gat act gta aaa atc gga tct     1392
Trp Tyr Asp Ile Thr Gly Asn Arg Ser Asp Thr Val Lys Ile Gly Ser
    450                 455                 460 gac ggc tgg gga gag ttt cat gta aac gat ggg tcc gtc tcc att tat     1440
Asp Gly Trp Gly Glu Phe His Val Asn Asp Gly Ser Val Ser Ile Tyr
465                 470                 475                 480 gtt cag aaa taa                                                     1452
Val Gln Lys <210> SEQ ID NO 14
<211> LENGTH: 483
<212> TYPE: PRT
<213> ORGANISM: Bacillus amyloliquefaciens

<400> SEQUENCE: 14

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
                20                  25                  30

Ile Gly Ile Thr Ala Val Trp Ile Pro Pro Ala Tyr Lys Gly Leu Ser
            35                  40                  45

Gln Ser Asp Asn Gly Tyr Gly Pro Tyr Asp Leu Tyr Asp Leu Gly Glu
        50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
            100                 105                 110

Val Thr Ala Val Glu Val Asn Pro Ala Asn Arg Asn Gln Glu Thr Ser
        115                 120                 125
```

Glu Glu Tyr Gln Ile Lys Ala Trp Thr Asp Phe Arg Phe Pro Gly Arg
        130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                    165                 170                 175

Gly Glu Gly Lys Ala Trp Asp Trp Glu Val Ser Ser Glu Asn Gly Asn
                180                 185                 190

Tyr Asp Tyr Leu Met Tyr Ala Asp Val Asp Tyr Asp His Pro Asp Val
            195                 200                 205

Val Ala Glu Thr Lys Lys Trp Gly Ile Trp Tyr Ala Asn Glu Leu Ser
210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255

Phe Thr Val Ala Glu Tyr Trp Gln Asn Asn Ala Gly Lys Leu Glu Asn
                260                 265                 270

Tyr Leu Asn Lys Thr Ser Phe Asn Gln Ser Val Phe Asp Val Pro Leu
            275                 280                 285

His Phe Asn Leu Gln Ala Ala Ser Ser Gln Gly Gly Tyr Asp Met
290                 295                 300

Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
            355                 360                 365

Thr Lys Gly Thr Ser Pro Lys Glu Ile Pro Ser Leu Lys Asp Asn Ile
        370                 375                 380

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
                405                 410                 415

Ser Ser Ala Ala Lys Ser Gly Leu Ala Ala Leu Ile Thr Asp Gly Pro
                420                 425                 430

Gly Gly Ser Lys Arg Met Tyr Ala Gly Leu Lys Asn Ala Gly Glu Thr
            435                 440                 445

Trp Tyr Asp Ile Thr Gly Asn Arg Ser Asp Thr Val Lys Ile Gly Ser
450                 455                 460

Asp Gly Trp Gly Glu Phe His Val Asn Asp Gly Ser Val Ser Ile Tyr
465                 470                 475                 480

Val Gln Lys

<210> SEQ ID NO 15
<211> LENGTH: 1548
<212> TYPE: DNA
<213> ORGANISM: Bacillus stearothermophilus
<220> FEATURE:
<221> NAME/KEY: CDS
<222> LOCATION: (1)..(1548)

<400> SEQUENCE: 15

```
gcc gca ccg ttt aac ggc acc atg atg cag tat ttt gaa tgg tac ttg      48
Ala Ala Pro Phe Asn Gly Thr Met Met Gln Tyr Phe Glu Trp Tyr Leu
 1               5                  10                  15 ccg gat gat ggc acg tta tgg acc aaa gtg gcc aat gaa gcc aac aac      96
Pro Asp Asp Gly Thr Leu Trp Thr Lys Val Ala Asn Glu Ala Asn Asn
             20                  25                  30 tta tcc agc ctt ggc atc acc gct ctt tgg ctg ccg ccc gct tac aaa     144
Leu Ser Ser Leu Gly Ile Thr Ala Leu Trp Leu Pro Pro Ala Tyr Lys
         35                  40                  45 gga aca agc cgc agc gac gta ggg tac gga gta tac gac ttg tat gac     192
Gly Thr Ser Arg Ser Asp Val Gly Tyr Gly Val Tyr Asp Leu Tyr Asp
     50                  55                  60 ctc ggc gaa ttc aat caa aaa ggg acc gtc cgc aca aaa tac gga aca     240
Leu Gly Glu Phe Asn Gln Lys Gly Thr Val Arg Thr Lys Tyr Gly Thr
 65                  70                  75                  80 aaa gct caa tat ctt caa gcc att caa gcc gcc cac gcc gct gga atg     288
Lys Ala Gln Tyr Leu Gln Ala Ile Gln Ala Ala His Ala Ala Gly Met
                 85                  90                  95 caa gtg tac gcc gat gtc gtg ttc gac cat aaa ggc ggc gct gac ggc     336
Gln Val Tyr Ala Asp Val Val Phe Asp His Lys Gly Gly Ala Asp Gly
            100                 105                 110 acg gaa tgg gtg gac gcc gtc gaa gtc aat ccg tcc gac cgc aac caa     384
Thr Glu Trp Val Asp Ala Val Glu Val Asn Pro Ser Asp Arg Asn Gln
        115                 120                 125 gaa atc tcg ggc acc tat caa atc caa gca tgg acg aaa ttt gat ttt     432
Glu Ile Ser Gly Thr Tyr Gln Ile Gln Ala Trp Thr Lys Phe Asp Phe
    130                 135                 140 ccc ggg cgg ggc aac acc tac tcc agc ttt aag tgg cgc tgg tac cat     480
Pro Gly Arg Gly Asn Thr Tyr Ser Ser Phe Lys Trp Arg Trp Tyr His
145                 150                 155                 160 ttt gac ggc gtt gat tgg gac gaa agc cga aaa ttg agc cgc att tac     528
Phe Asp Gly Val Asp Trp Asp Glu Ser Arg Lys Leu Ser Arg Ile Tyr
                165                 170                 175 aaa ttc cgc ggc atc ggc aaa gcg tgg gat tgg gaa gta gac acg gaa     576
Lys Phe Arg Gly Ile Gly Lys Ala Trp Asp Trp Glu Val Asp Thr Glu
            180                 185                 190 aac gga aac tat gac tac tta atg tat gcc gac ctt gat atg gat cat     624
Asn Gly Asn Tyr Asp Tyr Leu Met Tyr Ala Asp Leu Asp Met Asp His
        195                 200                 205 ccc gaa gtc gtg acc gag ctg aaa aac tgg ggg aaa tgg tat gtc aac     672
Pro Glu Val Val Thr Glu Leu Lys Asn Trp Gly Lys Trp Tyr Val Asn
    210                 215                 220 aca acg aac att gat ggg ttc cgg ctt gat gcc gtc aag cat att aag     720
Thr Thr Asn Ile Asp Gly Phe Arg Leu Asp Ala Val Lys His Ile Lys
225                 230                 235                 240 ttc agt ttt ttt cct gat tgg ttg tcg tat gtg cgt tct cag act ggc     768
Phe Ser Phe Phe Pro Asp Trp Leu Ser Tyr Val Arg Ser Gln Thr Gly
                245                 250                 255 aag ccg cta ttt acc gtc ggg gaa tat tgg agc tat gac atc aac aag     816
Lys Pro Leu Phe Thr Val Gly Glu Tyr Trp Ser Tyr Asp Ile Asn Lys
            260                 265                 270 ttg cac aat tac att acg aaa aca gac gga acg atg tct ttg ttt gat     864
Leu His Asn Tyr Ile Thr Lys Thr Asp Gly Thr Met Ser Leu Phe Asp
        275                 280                 285 gcc ccg tta cac aac aaa ttt tat acc gct tcc aaa tca ggg ggc gca     912
Ala Pro Leu His Asn Lys Phe Tyr Thr Ala Ser Lys Ser Gly Gly Ala
    290                 295                 300 ttt gat atg cgc acg tta atg acc aat act ctc atg aaa gat caa ccg     960
Phe Asp Met Arg Thr Leu Met Thr Asn Thr Leu Met Lys Asp Gln Pro
305                 310                 315                 320
```

```
aca ttg gcc gtc acc ttc gtt gat aat cat gac acc gaa ccc ggc caa      1008
Thr Leu Ala Val Thr Phe Val Asp Asn His Asp Thr Glu Pro Gly Gln
                325                 330                 335 gcg ctg cag tca tgg gtc gac cca tgg ttc aaa ccg ttg gct tac gcc      1056
Ala Leu Gln Ser Trp Val Asp Pro Trp Phe Lys Pro Leu Ala Tyr Ala
                340                 345                 350 ttt att cta act cgg cag gaa gga tac ccg tgc gtc ttt tat ggt gac      1104
Phe Ile Leu Thr Arg Gln Glu Gly Tyr Pro Cys Val Phe Tyr Gly Asp
                355                 360                 365 tat tat ggc att cca caa tat aac att cct tcg ctg aaa agc aaa atc      1152
Tyr Tyr Gly Ile Pro Gln Tyr Asn Ile Pro Ser Leu Lys Ser Lys Ile
            370                 375                 380 gat ccg ctc ctc atc gcg cgc agg gat tat gct tac gga acg caa cat      1200
Asp Pro Leu Leu Ile Ala Arg Arg Asp Tyr Ala Tyr Gly Thr Gln His
385                 390                 395                 400 gat tat ctt gat cac tcc gac atc atc ggg tgg aca agg gaa ggg ggc      1248
Asp Tyr Leu Asp His Ser Asp Ile Ile Gly Trp Thr Arg Glu Gly Gly
                405                 410                 415 act gaa aaa cca gga tcc gga ctg gcc gca ctg atc acc gat ggg ccg      1296
Thr Glu Lys Pro Gly Ser Gly Leu Ala Ala Leu Ile Thr Asp Gly Pro
                420                 425                 430 gga gga agc aaa tgg atg tac gtt ggc aaa caa cac gct gga aaa gtg      1344
Gly Gly Ser Lys Trp Met Tyr Val Gly Lys Gln His Ala Gly Lys Val
                435                 440                 445 ttc tat gac ctt acc ggc aac cgg agt gac acc gtc acc atc aac agt      1392
Phe Tyr Asp Leu Thr Gly Asn Arg Ser Asp Thr Val Thr Ile Asn Ser
            450                 455                 460 gat gga tgg ggg gaa ttc aaa gtc aat ggc ggt tcg gtt tcg gtt tgg      1440
Asp Gly Trp Gly Glu Phe Lys Val Asn Gly Gly Ser Val Ser Val Trp
465                 470                 475                 480 gtt cct aga aaa acg acc gtt tct acc atc gct cgg ccg atc aca acc      1488
Val Pro Arg Lys Thr Thr Val Ser Thr Ile Ala Arg Pro Ile Thr Thr
                485                 490                 495 cga ccg tgg act ggt gaa ttc gtc cgt tgg acc gaa cca cgg ttg gtg      1536
Arg Pro Trp Thr Gly Glu Phe Val Arg Trp Thr Glu Pro Arg Leu Val
                500                 505                 510 gca tgg cct tga                                                      1548
Ala Trp Pro
        515

<210> SEQ ID NO 16
<211> LENGTH: 515
<212> TYPE: PRT
<213> ORGANISM: Bacillus stearothermophilus

<400> SEQUENCE: 16

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95
```

```
Gln Val Tyr Ala Asp Val Phe Asp His Lys Gly Gly Ala Asp Gly
            100                 105                 110

Thr Glu Trp Val Asp Ala Val Glu Val Asn Pro Ser Asp Arg Asn Gln
            115                 120                 125

Glu Ile Ser Gly Thr Tyr Gln Ile Gln Ala Trp Thr Lys Phe Asp Phe
            130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
            195                 200                 205

Pro Glu Val Val Thr Glu Leu Lys Asn Trp Gly Lys Trp Tyr Val Asn
            210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asp Gly Thr Met Ser Leu Phe Asp
            275                 280                 285

Ala Pro Leu His Asn Lys Phe Tyr Thr Ala Ser Lys Ser Gly Gly Ala
            290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
            370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Gly
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
            450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
```

<210> SEQ ID NO 17
<211> LENGTH: 1455
<212> TYPE: DNA
<213> ORGANISM: Bacillus sp.
<220> FEATURE:
<221> NAME/KEY: CDS
<222> LOCATION: (1)..(1455)

<400> SEQUENCE: 17

| | | | | | | | | | | | | | | | | |
|---|---|---|---|---|---|---|---|---|---|---|---|---|---|---|---|---|
| cat | cat | aat | ggg | acg | aat | ggg | acc | atg | atg | cag | tat | ttt | gaa | tgg | cat | 48 |
| His | His | Asn | Gly | Thr | Asn | Gly | Thr | Met | Met | Gln | Tyr | Phe | Glu | Trp | His | |
| 1 | | | | 5 | | | | | 10 | | | | | 15 | | |
| ttg | cca | aat | gac | ggg | aac | cac | tgg | aac | agg | tta | cga | gat | gac | gca | gct | 96 |
| Leu | Pro | Asn | Asp | Gly | Asn | His | Trp | Asn | Arg | Leu | Arg | Asp | Asp | Ala | Ala | |
| | | | 20 | | | | | 25 | | | | | 30 | | | |
| aac | tta | aag | agt | aaa | ggg | att | acc | gct | gtt | tgg | att | cct | cct | gca | tgg | 144 |
| Asn | Leu | Lys | Ser | Lys | Gly | Ile | Thr | Ala | Val | Trp | Ile | Pro | Pro | Ala | Trp | |
| | | 35 | | | | | 40 | | | | | 45 | | | | |
| aag | ggg | act | tcg | caa | aat | gat | gtt | ggg | tat | ggt | gcc | tat | gat | ttg | tac | 192 |
| Lys | Gly | Thr | Ser | Gln | Asn | Asp | Val | Gly | Tyr | Gly | Ala | Tyr | Asp | Leu | Tyr | |
| 50 | | | | | 55 | | | | | 60 | | | | | | |
| gat | ctt | ggt | gag | ttt | aac | caa | aag | gga | acc | gtc | cgt | aca | aaa | tat | ggc | 240 |
| Asp | Leu | Gly | Glu | Phe | Asn | Gln | Lys | Gly | Thr | Val | Arg | Thr | Lys | Tyr | Gly | |
| 65 | | | | | 70 | | | | | 75 | | | | | 80 | |
| aca | agg | agt | cag | ttg | caa | ggt | gcc | gtg | aca | tct | ttg | aaa | aat | aac | ggg | 288 |
| Thr | Arg | Ser | Gln | Leu | Gln | Gly | Ala | Val | Thr | Ser | Leu | Lys | Asn | Asn | Gly | |
| | | | | 85 | | | | | 90 | | | | | 95 | | |
| att | caa | gtt | tat | ggg | gat | gtc | gtg | atg | aat | cat | aaa | ggt | gga | gca | gac | 336 |
| Ile | Gln | Val | Tyr | Gly | Asp | Val | Val | Met | Asn | His | Lys | Gly | Gly | Ala | Asp | |
| | | | | 100 | | | | | 105 | | | | | 110 | | |
| ggg | aca | gag | atg | gta | aat | gcg | gtg | gaa | gtg | aac | cga | agc | aac | cga | aac | 384 |
| Gly | Thr | Glu | Met | Val | Asn | Ala | Val | Glu | Val | Asn | Arg | Ser | Asn | Arg | Asn | |
| | | | | 115 | | | | | 120 | | | | | 125 | | |
| caa | gaa | ata | tca | ggt | gaa | tac | acc | att | gaa | gca | tgg | acg | aaa | ttt | gat | 432 |
| Gln | Glu | Ile | Ser | Gly | Glu | Tyr | Thr | Ile | Glu | Ala | Trp | Thr | Lys | Phe | Asp | |
| | | 130 | | | | | 135 | | | | | 140 | | | | |
| ttc | cct | gga | aga | gga | aat | acc | cat | tcc | aac | ttt | aaa | tgg | cgc | tgg | tat | 480 |
| Phe | Pro | Gly | Arg | Gly | Asn | Thr | His | Ser | Asn | Phe | Lys | Trp | Arg | Trp | Tyr | |
| 145 | | | | | 150 | | | | | 155 | | | | | 160 | |
| cat | ttt | gat | ggg | aca | gat | tgg | gat | cag | tca | cgt | cag | ctt | cag | aac | aaa | 528 |
| His | Phe | Asp | Gly | Thr | Asp | Trp | Asp | Gln | Ser | Arg | Gln | Leu | Gln | Asn | Lys | |
| | | | | 165 | | | | | 170 | | | | | 175 | | |
| ata | tat | aaa | ttc | aga | ggt | acc | gga | aag | gca | tgg | gac | tgg | gaa | gta | gat | 576 |
| Ile | Tyr | Lys | Phe | Arg | Gly | Thr | Gly | Lys | Ala | Trp | Asp | Trp | Glu | Val | Asp | |
| | | | 180 | | | | | 185 | | | | | 190 | | | |
| ata | gag | aac | ggc | aac | tat | gat | tac | ctt | atg | tat | gca | gac | att | gat | atg | 624 |
| Ile | Glu | Asn | Gly | Asn | Tyr | Asp | Tyr | Leu | Met | Tyr | Ala | Asp | Ile | Asp | Met | |
| | | 195 | | | | | 200 | | | | | 205 | | | | |
| gat | cat | cca | gaa | gta | atc | aat | gaa | ctt | aga | aat | tgg | gga | gtt | tgg | tat | 672 |
| Asp | His | Pro | Glu | Val | Ile | Asn | Glu | Leu | Arg | Asn | Trp | Gly | Val | Trp | Tyr | |
| | 210 | | | | | 215 | | | | | 220 | | | | | |
| aca | aat | aca | ctt | aat | cta | gat | gga | ttt | aga | atc | gat | gct | gtg | aaa | cat | 720 |
| Thr | Asn | Thr | Leu | Asn | Leu | Asp | Gly | Phe | Arg | Ile | Asp | Ala | Val | Lys | His | |
| 225 | | | | | 230 | | | | | 235 | | | | | 240 | |
| att | aaa | tac | agc | tat | acg | aga | gat | tgg | cta | aca | cat | gtg | cgt | aac | acc | 768 |
| Ile | Lys | Tyr | Ser | Tyr | Thr | Arg | Asp | Trp | Leu | Thr | His | Val | Arg | Asn | Thr | |
| | | | | 245 | | | | | 250 | | | | | 255 | | |
| aca | ggt | aaa | cca | atg | ttt | gca | gtt | gca | gaa | ttt | tgg | aaa | aat | gac | ctt | 816 |
| Thr | Gly | Lys | Pro | Met | Phe | Ala | Val | Ala | Glu | Phe | Trp | Lys | Asn | Asp | Leu | |

```
                   260                 265                 270
gct gca atc gaa aac tat tta aat aaa aca agt tgg aat cac tcc gtg      864
Ala Ala Ile Glu Asn Tyr Leu Asn Lys Thr Ser Trp Asn His Ser Val
            275                 280                 285 ttc gat gtt cct ctt cat tat aat ttg tac aat gca tct aat agt ggt      912
Phe Asp Val Pro Leu His Tyr Asn Leu Tyr Asn Ala Ser Asn Ser Gly
    290                 295                 300 ggc tat ttt gat atg aga aat att tta aat ggt tct gtc gta caa aaa      960
Gly Tyr Phe Asp Met Arg Asn Ile Leu Asn Gly Ser Val Val Gln Lys
305                 310                 315                 320 cac cct ata cat gca gtc aca ttt gtt gat aac cat gac tct cag cca     1008
His Pro Ile His Ala Val Thr Phe Val Asp Asn His Asp Ser Gln Pro
                325                 330                 335 gga gaa gca ttg gaa tcc ttt gtt caa tcg tgg ttc aaa cca ctg gca     1056
Gly Glu Ala Leu Glu Ser Phe Val Gln Ser Trp Phe Lys Pro Leu Ala
            340                 345                 350 tat gca ttg att ctg aca agg gag caa ggt tac cct tcc gta ttt tac     1104
Tyr Ala Leu Ile Leu Thr Arg Glu Gln Gly Tyr Pro Ser Val Phe Tyr
    355                 360                 365 ggt gat tac tac ggt ata cca act cat ggt gtt cct tcg atg aaa tct     1152
Gly Asp Tyr Tyr Gly Ile Pro Thr His Gly Val Pro Ser Met Lys Ser
370                 375                 380 aaa att gat cca ctt ctg cag gca cgt caa acg tat gcc tac gga acc     1200
Lys Ile Asp Pro Leu Leu Gln Ala Arg Gln Thr Tyr Ala Tyr Gly Thr
385                 390                 395                 400 caa cat gat tat ttt gat cat cat gat att atc ggc tgg acg aga gaa     1248
Gln His Asp Tyr Phe Asp His His Asp Ile Ile Gly Trp Thr Arg Glu
                405                 410                 415 ggg gac agc tcc cac cca aat tca gga ctt gca act att atg tcc gat     1296
Gly Asp Ser Ser His Pro Asn Ser Gly Leu Ala Thr Ile Met Ser Asp
            420                 425                 430 ggg cca ggg ggt aat aaa tgg atg tat gtc ggg aaa cat aaa gct ggc     1344
Gly Pro Gly Gly Asn Lys Trp Met Tyr Val Gly Lys His Lys Ala Gly
    435                 440                 445 caa gta tgg aga gat atc acc gga aat agg tct ggt acc gtc acc att     1392
Gln Val Trp Arg Asp Ile Thr Gly Asn Arg Ser Gly Thr Val Thr Ile
450                 455                 460 aat gca gat ggt tgg ggg aat ttc act gta aac gga ggg gca gtt tcg     1440
Asn Ala Asp Gly Trp Gly Asn Phe Thr Val Asn Gly Gly Ala Val Ser
465                 470                 475                 480 gtt tgg gtg aag caa                                                 1455
Val Trp Val Lys Gln
                485

<210> SEQ ID NO 18
<211> LENGTH: 485
<212> TYPE: PRT
<213> ORGANISM: Bacillus sp.

<400> SEQUENCE: 18

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
```

-continued

Thr Arg Ser Gln Leu Gln Gly Ala Val Thr Ser Leu Lys Asn Asn Gly
 65                  70                  75                  80

Ile Gln Val Tyr Gly Asp Val Val Met Asn His Lys Gly Gly Ala Asp
             85                  90                  95

Gly Thr Glu Met Val Asn Ala Val Glu Val Asn Arg Ser Asn Arg Asn
        100                 105                 110

Gln Glu Ile Ser Gly Glu Tyr Thr Ile Glu Ala Trp Thr Lys Phe Asp
    115                 120                 125

Phe Pro Gly Arg Gly Asn Thr His Ser Asn Phe Lys Trp Arg Trp Tyr
130                 135                 140

His Phe Asp Gly Thr Asp Trp Asp Gln Ser Arg Gln Leu Gln Asn Lys
145                 150                 155                 160

Ile Tyr Lys Phe Arg Gly Thr Gly Lys Ala Trp Asp Trp Glu Val Asp
                165                 170                 175

Ile Glu Asn Gly Asn Tyr Asp Tyr Leu Met Tyr Ala Asp Ile Asp Met
            180                 185                 190

Asp His Pro Glu Val Ile Asn Glu Leu Arg Asn Trp Gly Val Trp Tyr
        195                 200                 205

Thr Asn Thr Leu Asn Leu Asp Gly Phe Arg Ile Asp Ala Val Lys His
    210                 215                 220

Ile Lys Tyr Ser Tyr Thr Arg Asp Trp Leu Thr His Val Arg Asn Thr
225                 230                 235                 240

Thr Gly Lys Pro Met Phe Ala Val Ala Glu Phe Trp Lys Asn Asp Leu
                245                 250                 255

Ala Ala Ile Glu Asn Tyr Leu Asn Lys Thr Ser Trp Asn His Ser Val
            260                 265                 270

Phe Asp Val Pro Leu His Tyr Asn Leu Tyr Asn Ala Ser Asn Ser Gly
        275                 280                 285

Gly Tyr Phe Asp Met Arg Asn Ile Leu Asn Gly Ser Val Val Gln Lys
    290                 295                 300

His Pro Ile His Ala Val Thr Phe Val Asp Asn His Asp Ser Gln Pro
305                 310                 315                 320

Gly Glu Ala Leu Glu Ser Phe Val Gln Ser Trp Phe Lys Pro Leu Ala
                325                 330                 335

Tyr Ala Leu Ile Leu Thr Arg Glu Gln Gly Tyr Pro Ser Val Phe Tyr
            340                 345                 350

Gly Asp Tyr Tyr Gly Ile Pro Thr His Gly Val Pro Ser Met Lys Ser
        355                 360                 365

Lys Ile Asp Pro Leu Leu Gln Ala Arg Gln Thr Tyr Ala Tyr Gly Thr
    370                 375                 380

Gln His Asp Tyr Phe Asp His His Asp Ile Ile Gly Trp Thr Arg Glu
385                 390                 395                 400

Gly Asp Ser Ser His Pro Asn Ser Gly Leu Ala Thr Ile Met Ser Asp
                405                 410                 415

Gly Pro Gly Gly Asn Lys Trp Met Tyr Val Gly Lys His Lys Ala Gly
            420                 425                 430

Gln Val Trp Arg Asp Ile Thr Gly Asn Arg Ser Gly Thr Val Thr Ile
        435                 440                 445

Asn Ala Asp Gly Trp Gly Asn Phe Thr Val Asn Gly Gly Ala Val Ser
    450                 455                 460

Val Trp Val Lys Gln
465                 470                 475                 480

485

<210> SEQ ID NO 19
<211> LENGTH: 1452
<212> TYPE: DNA
<213> ORGANISM: Bacillus licheniformis
<220> FEATURE:
<221> NAME/KEY: CDS
<222> LOCATION: (1)..(1452)

<400> SEQUENCE: 19

| | | |
|---|---|---|
| gca aat ctt aat ggg acg ctg atg cag tat ttt gaa tgg tac atg ccc<br>Ala Asn Leu Asn Gly Thr Leu Met Gln Tyr Phe Glu Trp Tyr Met Pro<br>1               5                   10                  15 | 48 |
| aat gac ggc caa cat tgg agg cgt ttg caa aac gac tcg gca tat ttg<br>Asn Asp Gly Gln His Trp Arg Arg Leu Gln Asn Asp Ser Ala Tyr Leu<br>            20                  25                  30 | 96 |
| gct gaa cac ggt att act gcc gtc tgg att ccc ccg gca tat aag gga<br>Ala Glu His Gly Ile Thr Ala Val Trp Ile Pro Pro Ala Tyr Lys Gly<br>        35                  40                  45 | 144 |
| acg agc caa gcg gat gtg ggc tac ggt gct tac gac ctt tat gat tta<br>Thr Ser Gln Ala Asp Val Gly Tyr Gly Ala Tyr Asp Leu Tyr Asp Leu<br>    50                  55                  60 | 192 |
| ggg gag ttt cat caa aaa ggg acg gtt cgg aca aag tac ggc aca aaa<br>Gly Glu Phe His Gln Lys Gly Thr Val Arg Thr Lys Tyr Gly Thr Lys<br>65                  70                  75                  80 | 240 |
| gga gag ctg caa tct gcg atc aaa agt ctt cat tcc cgc gac att aac<br>Gly Glu Leu Gln Ser Ala Ile Lys Ser Leu His Ser Arg Asp Ile Asn<br>                85                  90                  95 | 288 |
| gtt tac ggg gat gtg gtc atc aac cac aaa ggc ggc gct gat gcg acc<br>Val Tyr Gly Asp Val Val Ile Asn His Lys Gly Gly Ala Asp Ala Thr<br>            100                 105                 110 | 336 |
| gaa gat gta acc gcg gtt gaa gtc gat ccc gct gac cgc aac cgc gta<br>Glu Asp Val Thr Ala Val Glu Val Asp Pro Ala Asp Arg Asn Arg Val<br>        115                 120                 125 | 384 |
| att tca gga gaa cac cta att aaa gcc tgg aca cat ttt cat ttt ccg<br>Ile Ser Gly Glu His Leu Ile Lys Ala Trp Thr His Phe His Phe Pro<br>    130                 135                 140 | 432 |
| ggg cgc ggc agc aca tac agc gat ttt aaa tgg cat tgg tac cat ttt<br>Gly Arg Gly Ser Thr Tyr Ser Asp Phe Lys Trp His Trp Tyr His Phe<br>145                 150                 155                 160 | 480 |
| gac gga acc gat tgg gac gag tcc cga aag ctg aac cgc atc tat aag<br>Asp Gly Thr Asp Trp Asp Glu Ser Arg Lys Leu Asn Arg Ile Tyr Lys<br>                165                 170                 175 | 528 |
| ttt caa gga aag gct tgg gat tgg gaa gtt tcc aat gaa aac ggc aac<br>Phe Gln Gly Lys Ala Trp Asp Trp Glu Val Ser Asn Glu Asn Gly Asn<br>            180                 185                 190 | 576 |
| tat gat tat ttg atg tat gcc gac atc gat tat gac cat cct gat gtc<br>Tyr Asp Tyr Leu Met Tyr Ala Asp Ile Asp Tyr Asp His Pro Asp Val<br>        195                 200                 205 | 624 |
| gca gca gaa att aag aga tgg ggc act tgg tat gcc aat gaa ctg caa<br>Ala Ala Glu Ile Lys Arg Trp Gly Thr Trp Tyr Ala Asn Glu Leu Gln<br>    210                 215                 220 | 672 |
| ttg gac ggt ttc cgt ctt gat gct gtc aaa cac att aaa ttt tct ttt<br>Leu Asp Gly Phe Arg Leu Asp Ala Val Lys His Ile Lys Phe Ser Phe<br>225                 230                 235                 240 | 720 |
| ttg cgg gat tgg gtt aat cat gtc agg gaa aaa acg ggg aag gaa atg<br>Leu Arg Asp Trp Val Asn His Val Arg Glu Lys Thr Gly Lys Glu Met<br>                245                 250                 255 | 768 |
| ttt acg gta gct gaa tat tgg cag aat gac ttg ggc gcg ctg gaa aac<br>Phe Thr Val Ala Glu Tyr Trp Gln Asn Asp Leu Gly Ala Leu Glu Asn<br>            260                 265                 270 | 816 |

```
tat ttg aac aaa aca aat ttt aat cat tca gtg ttt gac gtg ccg ctt      864
Tyr Leu Asn Lys Thr Asn Phe Asn His Ser Val Phe Asp Val Pro Leu
            275                 280                 285 cat tat cag ttc cat gct gca tcg aca cag gga ggc ggc tat gat atg      912
His Tyr Gln Phe His Ala Ala Ser Thr Gln Gly Gly Gly Tyr Asp Met
        290                 295                 300 agg aaa ttg ctg aac ggt acg gtc gtt tcc aag cat ccg ttg aaa tcg      960
Arg Lys Leu Leu Asn Gly Thr Val Val Ser Lys His Pro Leu Lys Ser
305                 310                 315                 320 gtt aca ttt gtc gat aac cat gat aca cag ccg ggg caa tcg ctt gag     1008
Val Thr Phe Val Asp Asn His Asp Thr Gln Pro Gly Gln Ser Leu Glu
                325                 330                 335 tcg act gtc caa aca tgg ttt aag ccg ctt gct tac gct ttt att ctc     1056
Ser Thr Val Gln Thr Trp Phe Lys Pro Leu Ala Tyr Ala Phe Ile Leu
            340                 345                 350 aca agg gaa tct gga tac cct cag gtt ttc tac ggg gat atg tac ggg     1104
Thr Arg Glu Ser Gly Tyr Pro Gln Val Phe Tyr Gly Asp Met Tyr Gly
        355                 360                 365 acg aaa gga gac tcc cag cgc gaa att cct gcc ttg aaa cac aaa att     1152
Thr Lys Gly Asp Ser Gln Arg Glu Ile Pro Ala Leu Lys His Lys Ile
    370                 375                 380 gaa ccg atc tta aaa gcg aga aaa cag tat gcg tac gga gca cag cat     1200
Glu Pro Ile Leu Lys Ala Arg Lys Gln Tyr Ala Tyr Gly Ala Gln His
385                 390                 395                 400 gat tat ttc gac cac cat gac att gtc ggc tgg aca agg gaa ggc gac     1248
Asp Tyr Phe Asp His His Asp Ile Val Gly Trp Thr Arg Glu Gly Asp
                405                 410                 415 agc tcg gtt gca aat tca ggt ttg gcg gca tta ata aca gac gga ccc     1296
Ser Ser Val Ala Asn Ser Gly Leu Ala Ala Leu Ile Thr Asp Gly Pro
            420                 425                 430 ggt ggg gca aag cga atg tat gtc ggc cgg caa aac gcc ggt gag aca     1344
Gly Gly Ala Lys Arg Met Tyr Val Gly Arg Gln Asn Ala Gly Glu Thr
        435                 440                 445 tgg cat gac att acc gga aac cgt tcg gag ccg gtt gtc atc aat tcg     1392
Trp His Asp Ile Thr Gly Asn Arg Ser Glu Pro Val Val Ile Asn Ser
    450                 455                 460 gaa ggc tgg gga gag ttt cac gta aac ggc ggg tcg gtt tca att tat     1440
Glu Gly Trp Gly Glu Phe His Val Asn Gly Gly Ser Val Ser Ile Tyr
465                 470                 475                 480 gtt caa aga tag                                                     1452
Val Gln Arg
```

<210> SEQ ID NO 20
<211> LENGTH: 483
<212> TYPE: PRT
<213> ORGANISM: Bacillus licheniformis

<400> SEQUENCE: 20

```
Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80
```

```
Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
    290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
    370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
        435                 440                 445

Trp His Asp Ile Thr Gly Asn Arg Ser Glu Pro Val Val Ile Asn Ser
    450                 455                 460

Glu Gly Trp Gly Glu Phe His Val Asn Gly Gly Ser Val Ser Ile Tyr
465                 470                 475                 480

Val Gln Arg

<210> SEQ ID NO 21
```

```
<211> LENGTH: 1455
<212> TYPE: DNA
<213> ORGANISM: Bacillus sp.
<220> FEATURE:
<221> NAME/KEY: CDS
<222> LOCATION: (1)..(1455)

<400> SEQUENCE: 21 cac cat aat ggc aca aat gga aca atg atg caa tat ttt gaa tgg tat     48
His His Asn Gly Thr Asn Gly Thr Met Met Gln Tyr Phe Glu Trp Tyr
1               5                   10                  15 ttg cca aat gac ggt aat cat tgg aat aga tta aga tca gat gca agt     96
Leu Pro Asn Asp Gly Asn His Trp Asn Arg Leu Arg Ser Asp Ala Ser
            20                  25                  30 aat ctt aaa gat aaa ggg att aca gcg gtt tgg att cca cct gct tgg    144
Asn Leu Lys Asp Lys Gly Ile Thr Ala Val Trp Ile Pro Pro Ala Trp
        35                  40                  45 aaa ggg gct tct caa aat gat gta ggg tat gga gcc tat gat ctg tat    192
Lys Gly Ala Ser Gln Asn Asp Val Gly Tyr Gly Ala Tyr Asp Leu Tyr
50                  55                  60 gat tta gga gaa ttc aat caa aaa gga acc gta cgt aca aag tac gga    240
Asp Leu Gly Glu Phe Asn Gln Lys Gly Thr Val Arg Thr Lys Tyr Gly
65                  70                  75                  80 acc cgt aat caa tta caa gct gca gta acc gcc tta aaa agt aat ggt    288
Thr Arg Asn Gln Leu Gln Ala Ala Val Thr Ala Leu Lys Ser Asn Gly
                85                  90                  95 att caa gta tac gga gat gtc gta atg aat cat aag ggt gga gcg gat    336
Ile Gln Val Tyr Gly Asp Val Val Met Asn His Lys Gly Gly Ala Asp
            100                 105                 110 gcc act gag tgg gtt cga gcg gtt gaa gtg aac cca agt aat cgt aat    384
Ala Thr Glu Trp Val Arg Ala Val Glu Val Asn Pro Ser Asn Arg Asn
        115                 120                 125 caa gaa gtc tct ggt gat tat acg att gag gct tgg act aag ttt gat    432
Gln Glu Val Ser Gly Asp Tyr Thr Ile Glu Ala Trp Thr Lys Phe Asp
130                 135                 140 ttt cct ggt cga ggt aat acc cac tct aac ttt aaa tgg aga tgg tat    480
Phe Pro Gly Arg Gly Asn Thr His Ser Asn Phe Lys Trp Arg Trp Tyr
145                 150                 155                 160 cat ttc gat ggt gta gat tgg gat cag tca cgt caa ttg cag aat cga    528
His Phe Asp Gly Val Asp Trp Asp Gln Ser Arg Gln Leu Gln Asn Arg
                165                 170                 175 atc tat aaa ttc aga gga gat gga aaa ggt tgg gac tgg gaa gtt gat    576
Ile Tyr Lys Phe Arg Gly Asp Gly Lys Gly Trp Asp Trp Glu Val Asp
            180                 185                 190 aca gag aac gga aac tat gac tat cta atg tac gcg gat att gat atg    624
Thr Glu Asn Gly Asn Tyr Asp Tyr Leu Met Tyr Ala Asp Ile Asp Met
        195                 200                 205 gat cac cct gaa gta gtg aat gaa ctc aga aac tgg ggt gta tgg tat    672
Asp His Pro Glu Val Val Asn Glu Leu Arg Asn Trp Gly Val Trp Tyr
210                 215                 220 acc aat aca ctg ggg cta gac ggg ttc aga ata gat gcg gta aaa cat    720
Thr Asn Thr Leu Gly Leu Asp Gly Phe Arg Ile Asp Ala Val Lys His
225                 230                 235                 240 ata aaa tat agc ttt act cgt gat tgg ctt act cac gtt aga aat acg    768
Ile Lys Tyr Ser Phe Thr Arg Asp Trp Leu Thr His Val Arg Asn Thr
                245                 250                 255 aca ggt aaa aat atg ttt gca gtt gca gag ttc tgg aag aat gac ata    816
Thr Gly Lys Asn Met Phe Ala Val Ala Glu Phe Trp Lys Asn Asp Ile
            260                 265                 270 ggt gca att gaa aat tac tta agt aaa aca aat tgg aat cat tca gtt    864
Gly Ala Ile Glu Asn Tyr Leu Ser Lys Thr Asn Trp Asn His Ser Val
```

```
                275                 280                 285
ttt gat gtg ccc ctg cat tat aac ctt tat aat gca tcg aga agt ggt       912
Phe Asp Val Pro Leu His Tyr Asn Leu Tyr Asn Ala Ser Arg Ser Gly
290                 295                 300 ggc aat tat gat atg agg caa ata ttt aat gga aca gtt gtt cag aga       960
Gly Asn Tyr Asp Met Arg Gln Ile Phe Asn Gly Thr Val Val Gln Arg
305                 310                 315                 320 cat cct aca cat gct gta aca ttt gtt gat aac cat gat tca cag ccg      1008
His Pro Thr His Ala Val Thr Phe Val Asp Asn His Asp Ser Gln Pro
            325                 330                 335 gaa gaa gcc cta gag tca ttt gtt gaa gag tgg ttc aaa ccg tta gcg      1056
Glu Glu Ala Leu Glu Ser Phe Val Glu Glu Trp Phe Lys Pro Leu Ala
                340                 345                 350 tat gct ctc aca cta aca cgt gat caa gga tat cct tcc gtt ttt tat      1104
Tyr Ala Leu Thr Leu Thr Arg Asp Gln Gly Tyr Pro Ser Val Phe Tyr
                355                 360                 365 gga gat tat tat ggg att ccg acg cat ggt gta cca gca atg aaa tct      1152
Gly Asp Tyr Tyr Gly Ile Pro Thr His Gly Val Pro Ala Met Lys Ser
370                 375                 380 aag att gat ccg att tta gaa gca cgt caa aag tat gcg tac gga aaa      1200
Lys Ile Asp Pro Ile Leu Glu Ala Arg Gln Lys Tyr Ala Tyr Gly Lys
385                 390                 395                 400 caa aat gat tat ttg gat cac cat aat atg att ggc tgg acg cgt gaa      1248
Gln Asn Asp Tyr Leu Asp His His Asn Met Ile Gly Trp Thr Arg Glu
            405                 410                 415 ggt aat aca gca cat ccc aac tca gga cta gca act att atg tcg gat      1296
Gly Asn Thr Ala His Pro Asn Ser Gly Leu Ala Thr Ile Met Ser Asp
                420                 425                 430 ggc cca gga gga aat aaa tgg atg tat gtt ggg cgt aat aag gct gga      1344
Gly Pro Gly Gly Asn Lys Trp Met Tyr Val Gly Arg Asn Lys Ala Gly
                435                 440                 445 caa gtt tgg aga gat att aca gga aat cgc tca ggt acg gtg acg att      1392
Gln Val Trp Arg Asp Ile Thr Gly Asn Arg Ser Gly Thr Val Thr Ile
450                 455                 460 aac gca gat ggg tgg ggt aat ttt tct gta aat ggt ggg tct gta tct      1440
Asn Ala Asp Gly Trp Gly Asn Phe Ser Val Asn Gly Gly Ser Val Ser
465                 470                 475                 480 ata tgg gta aat aat                                                   1455
Ile Trp Val Asn Asn
            485

<210> SEQ ID NO 22
<211> LENGTH: 485
<212> TYPE: PRT
<213> ORGANISM: Bacillus sp.

<400> SEQUENCE: 22

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95
```

```
Ile Gln Val Tyr Gly Asp Val Met Asn His Lys Gly Gly Ala Asp
                100                 105                 110
Ala Thr Glu Trp Val Arg Ala Val Glu Val Asn Pro Ser Asn Arg Asn
            115                 120                 125
Gln Glu Val Ser Gly Asp Tyr Thr Ile Glu Ala Trp Thr Lys Phe Asp
        130                 135                 140
Phe Pro Gly Arg Gly Asn Thr His Ser Asn Phe Lys Trp Arg Trp Tyr
145                 150                 155                 160
His Phe Asp Gly Val Asp Trp Asp Gln Ser Arg Gln Leu Gln Asn Arg
                165                 170                 175
Ile Tyr Lys Phe Arg Gly Asp Gly Lys Gly Trp Asp Trp Glu Val Asp
            180                 185                 190
Thr Glu Asn Gly Asn Tyr Asp Tyr Leu Met Tyr Ala Asp Ile Asp Met
        195                 200                 205
Asp His Pro Glu Val Val Asn Glu Leu Arg Asn Trp Gly Val Trp Tyr
    210                 215                 220
Thr Asn Thr Leu Gly Leu Asp Gly Phe Arg Ile Asp Ala Val Lys His
225                 230                 235                 240
Ile Lys Tyr Ser Phe Thr Arg Asp Trp Leu Thr His Val Arg Asn Thr
                245                 250                 255
Thr Gly Lys Asn Met Phe Ala Val Ala Glu Phe Trp Lys Asn Asp Ile
            260                 265                 270
Gly Ala Ile Glu Asn Tyr Leu Ser Lys Thr Asn Trp Asn His Ser Val
        275                 280                 285
Phe Asp Val Pro Leu His Tyr Asn Leu Tyr Asn Ala Ser Arg Ser Gly
    290                 295                 300
Gly Asn Tyr Asp Met Arg Gln Ile Phe Asn Gly Thr Val Val Gln Arg
305                 310                 315                 320
His Pro Thr His Ala Val Thr Phe Val Asp Asn His Asp Ser Gln Pro
                325                 330                 335
Glu Glu Ala Leu Glu Ser Phe Val Glu Trp Phe Lys Pro Leu Ala
            340                 345                 350
Tyr Ala Leu Thr Leu Thr Arg Asp Gln Gly Tyr Pro Ser Val Phe Tyr
        355                 360                 365
Gly Asp Tyr Tyr Gly Ile Pro Thr His Gly Val Pro Ala Met Lys Ser
    370                 375                 380
Lys Ile Asp Pro Ile Leu Glu Ala Arg Gln Lys Tyr Ala Tyr Gly Lys
385                 390                 395                 400
Gln Asn Asp Tyr Leu Asp His His Asn Met Ile Gly Trp Thr Arg Glu
                405                 410                 415
Gly Asn Thr Ala His Pro Asn Ser Gly Leu Ala Thr Ile Met Ser Asp
            420                 425                 430
Gly Pro Gly Gly Asn Lys Trp Met Tyr Val Gly Arg Asn Lys Ala Gly
        435                 440                 445
Gln Val Trp Arg Asp Ile Thr Gly Asn Arg Ser Gly Thr Val Thr Ile
    450                 455                 460
Asn Ala Asp Gly Trp Gly Asn Phe Ser Val Asn Gly Gly Ser Val Ser
465                 470                 475                 480
Ile Trp Val Asn Asn
                485

<210> SEQ ID NO 23
<211> LENGTH: 1452
```

```
<212> TYPE: DNA
<213> ORGANISM: Bacillus sp
<220> FEATURE:
<221> NAME/KEY: CDS
<222> LOCATION: (1)..(1452)

<400> SEQUENCE: 23 gga agt gtg ccg gta aat ggc aca atg atg caa tat ttc gaa tgg tac      48
Gly Ser Val Pro Val Asn Gly Thr Met Met Gln Tyr Phe Glu Trp Tyr
1               5                   10                  15 ctt cca gac gat gga aca cta tgg acg aaa gta gca aat aac gct caa      96
Leu Pro Asp Asp Gly Thr Leu Trp Thr Lys Val Ala Asn Asn Ala Gln
            20                  25                  30 tct tta gcg aat ctt ggc att act gcc ctt tgg ctt ccc cct gcc tat     144
Ser Leu Ala Asn Leu Gly Ile Thr Ala Leu Trp Leu Pro Pro Ala Tyr
        35                  40                  45 aaa gga aca agc agc agt gac gtt gga tat ggc gtt tat gat tta tat     192
Lys Gly Thr Ser Ser Ser Asp Val Gly Tyr Gly Val Tyr Asp Leu Tyr
50                  55                  60 gac ctt gga gag ttt aat caa aaa gga act gtc cga aca aaa tac ggg     240
Asp Leu Gly Glu Phe Asn Gln Lys Gly Thr Val Arg Thr Lys Tyr Gly
65                  70                  75                  80 aca aaa aca caa tat atc caa gca atc caa gcg gcg cat aca gca ggg     288
Thr Lys Thr Gln Tyr Ile Gln Ala Ile Gln Ala Ala His Thr Ala Gly
                85                  90                  95 atg caa gta tat gca gat gtc gtc ttt aac cat aaa gcc ggt gca gat     336
Met Gln Val Tyr Ala Asp Val Val Phe Asn His Lys Ala Gly Ala Asp
            100                 105                 110 gga aca gaa cta gtc gat gca gta gaa gta aat cct tct gac cgc aat     384
Gly Thr Glu Leu Val Asp Ala Val Glu Val Asn Pro Ser Asp Arg Asn
        115                 120                 125 caa gaa ata tca gga aca tat caa atc caa gcg tgg aca aaa ttt gat     432
Gln Glu Ile Ser Gly Thr Tyr Gln Ile Gln Ala Trp Thr Lys Phe Asp
    130                 135                 140 ttt cct ggt cgt gga aac acc tat tct agt ttt aaa tgg cgt tgg tat     480
Phe Pro Gly Arg Gly Asn Thr Tyr Ser Ser Phe Lys Trp Arg Trp Tyr
145                 150                 155                 160 cat ttc gat gga acg gac tgg gat gag agt aga aaa cta aat cgt att     528
His Phe Asp Gly Thr Asp Trp Asp Glu Ser Arg Lys Leu Asn Arg Ile
                165                 170                 175 tac aag ttc cgc ggc acg gga aaa gca tgg gat tgg gaa gta gat aca     576
Tyr Lys Phe Arg Gly Thr Gly Lys Ala Trp Asp Trp Glu Val Asp Thr
            180                 185                 190 gaa aac ggg aat tat gac tat ctc atg tat gca gat tta gat atg gat     624
Glu Asn Gly Asn Tyr Asp Tyr Leu Met Tyr Ala Asp Leu Asp Met Asp
        195                 200                 205 cat cca gag gtt gta tcc gaa cta aaa aat tgg gga aag tgg tat gta     672
His Pro Glu Val Val Ser Glu Leu Lys Asn Trp Gly Lys Trp Tyr Val
    210                 215                 220 acc aca acc aat atc gac gga ttc cgt ctg gat gca gtg aag cat att     720
Thr Thr Thr Asn Ile Asp Gly Phe Arg Leu Asp Ala Val Lys His Ile
225                 230                 235                 240 aaa tat agc ttt ttc ccg gac tgg cta tcg tac gta cga acc caa aca     768
Lys Tyr Ser Phe Phe Pro Asp Trp Leu Ser Tyr Val Arg Thr Gln Thr
                245                 250                 255 caa aag cct ctt ttt gcc gtt ggg gaa ttt tgg agc tat gac att agc     816
Gln Lys Pro Leu Phe Ala Val Gly Glu Phe Trp Ser Tyr Asp Ile Ser
            260                 265                 270 aag ttg cac aac tat att aca aag acg aac ggc tct atg tcc cta ttc     864
Lys Leu His Asn Tyr Ile Thr Lys Thr Asn Gly Ser Met Ser Leu Phe
        275                 280                 285
```

| | | | | | | | | | | | | | | | |
|---|---|---|---|---|---|---|---|---|---|---|---|---|---|---|---|
| gat | gcc | ccg | ctg | cat | aac | aat | ttt | tat | ata | gca | tcg | aaa | tca | ggc | ggt | 912 |
| Asp | Ala | Pro | Leu | His | Asn | Asn | Phe | Tyr | Ile | Ala | Ser | Lys | Ser | Gly | Gly | |
| 290 | | | | 295 | | | | | 300 | | | | | | | |

```
gat gcc ccg ctg cat aac aat ttt tat ata gca tcg aaa tca ggc ggt      912
Asp Ala Pro Leu His Asn Asn Phe Tyr Ile Ala Ser Lys Ser Gly Gly
    290             295                 300 tat ttt gat atg cgc aca tta ctc aac aac aca ttg atg aaa gat cag      960
Tyr Phe Asp Met Arg Thr Leu Leu Asn Asn Thr Leu Met Lys Asp Gln
305             310                 315                 320 cct aca tta gca gtc aca tta gtg gat aat cac gat act gag cca ggg     1008
Pro Thr Leu Ala Val Thr Leu Val Asp Asn His Asp Thr Glu Pro Gly
                325                 330                 335 caa tct ctg cag tca tgg gtc gag cca tgg ttt aaa ccg tta gct tac     1056
Gln Ser Leu Gln Ser Trp Val Glu Pro Trp Phe Lys Pro Leu Ala Tyr
            340                 345                 350 gca ttt atc ttg acc cgc caa gaa ggt tat cct tgc gtc ttt tat gga     1104
Ala Phe Ile Leu Thr Arg Gln Glu Gly Tyr Pro Cys Val Phe Tyr Gly
                355                 360                 365 gat tac tat ggt att cca aaa tac aac att cct gcg ctg aaa agc aaa     1152
Asp Tyr Tyr Gly Ile Pro Lys Tyr Asn Ile Pro Ala Leu Lys Ser Lys
370                 375                 380 ctt gat ccg ctg tta att gcc aga aga gat tat gcc tat gga aca cag     1200
Leu Asp Pro Leu Leu Ile Ala Arg Arg Asp Tyr Ala Tyr Gly Thr Gln
385                 390                 395                 400 cac gac tat att gac agt gcg gat att atc ggt tgg acg cgg gaa gga     1248
His Asp Tyr Ile Asp Ser Ala Asp Ile Ile Gly Trp Thr Arg Glu Gly
                405                 410                 415 gtg gct gaa aaa gca aat tca gga ctg gct gca ctc att acc gac ggg     1296
Val Ala Glu Lys Ala Asn Ser Gly Leu Ala Ala Leu Ile Thr Asp Gly
            420                 425                 430 cct ggc gga agc aaa tgg atg tat gtt gga aaa caa cac gct ggc aaa     1344
Pro Gly Gly Ser Lys Trp Met Tyr Val Gly Lys Gln His Ala Gly Lys
                435                 440                 445 acg ttt tat gat tta acc ggc aat cga agt gat aca gtg aca atc aat     1392
Thr Phe Tyr Asp Leu Thr Gly Asn Arg Ser Asp Thr Val Thr Ile Asn
        450                 455                 460 gct gat gga tgg gga gaa ttt aaa gtc aat gga ggg tct gta tcc ata     1440
Ala Asp Gly Trp Gly Glu Phe Lys Val Asn Gly Gly Ser Val Ser Ile
465                 470                 475                 480 tgg gtt cca aaa                                                     1452
Trp Val Pro Lys
```

<210> SEQ ID NO 24
<211> LENGTH: 484
<212> TYPE: PRT
<213> ORGANISM: Bacillus sp

<400> SEQUENCE: 24

```
Gly Ser Val Pro Val Asn Gly Thr Met Met Gln Tyr Phe Glu Trp Tyr
1               5                   10                  15

Leu Pro Asp Asp Gly Thr Leu Trp Thr Lys Val Ala Asn Asn Ala Gln
            20                  25                  30

Ser Leu Ala Asn Leu Gly Ile Thr Ala Leu Trp Leu Pro Pro Ala Tyr
        35                  40                  45

Lys Gly Thr Ser Ser Ser Asp Val Gly Tyr Gly Val Tyr Asp Leu Tyr
    50                  55                  60

Asp Leu Gly Glu Phe Asn Gln Lys Gly Thr Val Arg Thr Lys Tyr Gly
65                  70                  75                  80

Thr Lys Thr Gln Tyr Ile Gln Ala Ile Gln Ala Ala His Thr Ala Gly
                85                  90                  95

Met Gln Val Tyr Ala Asp Val Val Phe Asn His Lys Ala Gly Ala Asp
```

```
                100             105             110
Gly Thr Glu Leu Val Asp Ala Val Glu Val Asn Pro Ser Asp Arg Asn
            115                 120                 125

Gln Glu Ile Ser Gly Thr Tyr Gln Ile Gln Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Thr Gly Lys Ala Trp Asp Trp Glu Val Asp Thr
            180                 185                 190

Glu Asn Gly Asn Tyr Asp Tyr Leu Met Tyr Ala Asp Leu Asp Met Asp
        195                 200                 205

His Pro Glu Val Val Ser Glu Leu Lys Asn Trp Gly Lys Trp Tyr Val
    210                 215                 220

Thr Thr Thr Asn Ile Asp Gly Phe Arg Leu Asp Ala Val Lys His Ile
225                 230                 235                 240

Lys Tyr Ser Phe Phe Pro Asp Trp Leu Ser Tyr Val Arg Thr Gln Thr
                245                 250                 255

Gln Lys Pro Leu Phe Ala Val Gly Glu Phe Trp Ser Tyr Asp Ile Ser
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Ile Ala Ser Lys Ser Gly Gly
    290                 295                 300

Tyr Phe Asp Met Arg Thr Leu Leu Asn Asn Thr Leu Met Lys Asp Gln
305                 310                 315                 320

Pro Thr Leu Ala Val Thr Leu Val Asp Asn His Asp Thr Glu Pro Gly
                325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
        355                 360                 365

Asp Tyr Tyr Gly Ile Pro Lys Tyr Asn Ile Pro Ala Leu Lys Ser Lys
    370                 375                 380

Leu Asp Pro Leu Leu Ile Ala Arg Arg Asp Tyr Ala Tyr Gly Thr Gln
385                 390                 395                 400

His Asp Tyr Ile Asp Ser Ala Asp Ile Ile Gly Trp Thr Arg Glu Gly
                405                 410                 415

Val Ala Glu Lys Ala Asn Ser Gly Leu Ala Ala Leu Ile Thr Asp Gly
            420                 425                 430

Pro Gly Gly Ser Lys Trp Met Tyr Val Gly Lys Gln His Ala Gly Lys
        435                 440                 445

Thr Phe Tyr Asp Leu Thr Gly Asn Arg Ser Asp Thr Val Thr Ile Asn
    450                 455                 460

Ala Asp Gly Trp Gly Glu Phe Lys Val Asn Gly Gly Ser Val Ser Ile
465                 470                 475                 480

Trp Val Pro Lys

<210> SEQ ID NO 25
<211> LENGTH: 1455
<212> TYPE: DNA
<213> ORGANISM: Bacillus sp.
<220> FEATURE:
```

<221> NAME/KEY: CDS
<222> LOCATION: (1)..(1455)

<400> SEQUENCE: 25

| | | | | | | | | | | | | | | | | |
|---|---|---|---|---|---|---|---|---|---|---|---|---|---|---|---|---|
| gct | aat | act | gca | cct | att | aac | gaa | aca | atg | atg | caa | tat | ttt | gaa | tgg | 48 |
| Ala | Asn | Thr | Ala | Pro | Ile | Asn | Glu | Thr | Met | Met | Gln | Tyr | Phe | Glu | Trp | |
| 1 | | | | 5 | | | | | 10 | | | | | 15 | | |
| gat | tta | ccg | aac | gat | gga | acc | ctt | tgg | aca | aag | gtg | aaa | aat | gaa | gcc | 96 |
| Asp | Leu | Pro | Asn | Asp | Gly | Thr | Leu | Trp | Thr | Lys | Val | Lys | Asn | Glu | Ala | |
| | | | 20 | | | | | 25 | | | | | 30 | | | |
| gca | aat | ctt | tct | tcg | ctc | ggt | att | aca | gcg | tta | tgg | ctt | cct | cca | gcg | 144 |
| Ala | Asn | Leu | Ser | Ser | Leu | Gly | Ile | Thr | Ala | Leu | Trp | Leu | Pro | Pro | Ala | |
| | | 35 | | | | | 40 | | | | | 45 | | | | |
| tat | aaa | gga | aca | agt | caa | agc | gat | gtc | gga | tac | ggc | gtg | tac | gat | tta | 192 |
| Tyr | Lys | Gly | Thr | Ser | Gln | Ser | Asp | Val | Gly | Tyr | Gly | Val | Tyr | Asp | Leu | |
| | 50 | | | | | 55 | | | | | 60 | | | | | |
| tat | gac | ctt | ggg | gaa | ttt | aat | caa | aaa | gga | acg | att | cga | aca | aaa | tac | 240 |
| Tyr | Asp | Leu | Gly | Glu | Phe | Asn | Gln | Lys | Gly | Thr | Ile | Arg | Thr | Lys | Tyr | |
| 65 | | | | | 70 | | | | | 75 | | | | | 80 | |
| gga | aca | aaa | aca | caa | tat | att | caa | gcc | atc | caa | gct | gcc | aaa | gcc | gca | 288 |
| Gly | Thr | Lys | Thr | Gln | Tyr | Ile | Gln | Ala | Ile | Gln | Ala | Ala | Lys | Ala | Ala | |
| | | | | 85 | | | | | 90 | | | | | 95 | | |
| ggg | atg | caa | gta | tat | gca | gat | gtt | gtc | ttt | aat | cat | aag | gcg | gga | gct | 336 |
| Gly | Met | Gln | Val | Tyr | Ala | Asp | Val | Val | Phe | Asn | His | Lys | Ala | Gly | Ala | |
| | | | 100 | | | | | 105 | | | | | 110 | | | |
| gac | ggc | aca | gaa | ttt | gtc | gat | gcg | gtt | gag | gta | gac | cct | tct | aat | cga | 384 |
| Asp | Gly | Thr | Glu | Phe | Val | Asp | Ala | Val | Glu | Val | Asp | Pro | Ser | Asn | Arg | |
| | | 115 | | | | | 120 | | | | | 125 | | | | |
| aat | caa | gaa | aca | tct | gga | aca | tat | caa | att | caa | gca | tgg | aca | aaa | ttt | 432 |
| Asn | Gln | Glu | Thr | Ser | Gly | Thr | Tyr | Gln | Ile | Gln | Ala | Trp | Thr | Lys | Phe | |
| | 130 | | | | | 135 | | | | | 140 | | | | | |
| gat | ttt | ccc | ggt | cgg | ggg | aac | aca | tac | tcg | agt | ttt | aaa | tgg | cgt | tgg | 480 |
| Asp | Phe | Pro | Gly | Arg | Gly | Asn | Thr | Tyr | Ser | Ser | Phe | Lys | Trp | Arg | Trp | |
| 145 | | | | | 150 | | | | | 155 | | | | | 160 | |
| tat | cat | ttt | gac | ggt | acc | gat | tgg | gat | gaa | agc | cga | aaa | tta | aat | cgg | 528 |
| Tyr | His | Phe | Asp | Gly | Thr | Asp | Trp | Asp | Glu | Ser | Arg | Lys | Leu | Asn | Arg | |
| | | | | 165 | | | | | 170 | | | | | 175 | | |
| att | tac | aaa | ttc | cgc | agt | aca | gga | aaa | gca | tgg | gac | tgg | gaa | gtc | gat | 576 |
| Ile | Tyr | Lys | Phe | Arg | Ser | Thr | Gly | Lys | Ala | Trp | Asp | Trp | Glu | Val | Asp | |
| | | | 180 | | | | | 185 | | | | | 190 | | | |
| aca | gaa | aac | gga | aac | tat | gat | tat | tta | atg | ttc | gct | gat | tta | gat | atg | 624 |
| Thr | Glu | Asn | Gly | Asn | Tyr | Asp | Tyr | Leu | Met | Phe | Ala | Asp | Leu | Asp | Met | |
| | | 195 | | | | | 200 | | | | | 205 | | | | |
| gat | cac | cct | gag | gtt | gtg | aca | gaa | tta | aaa | aac | tgg | gga | acg | tgg | tac | 672 |
| Asp | His | Pro | Glu | Val | Val | Thr | Glu | Leu | Lys | Asn | Trp | Gly | Thr | Trp | Tyr | |
| | 210 | | | | | 215 | | | | | 220 | | | | | |
| gtc | aat | act | aca | aat | atc | gat | gga | ttc | cgc | tta | gat | gcc | gta | aaa | cat | 720 |
| Val | Asn | Thr | Thr | Asn | Ile | Asp | Gly | Phe | Arg | Leu | Asp | Ala | Val | Lys | His | |
| 225 | | | | | 230 | | | | | 235 | | | | | 240 | |
| att | aaa | tac | agc | ttt | ttc | cct | gac | tgg | cta | aca | tat | gta | cgt | aat | caa | 768 |
| Ile | Lys | Tyr | Ser | Phe | Phe | Pro | Asp | Trp | Leu | Thr | Tyr | Val | Arg | Asn | Gln | |
| | | | | 245 | | | | | 250 | | | | | 255 | | |
| aca | gga | aaa | aat | tta | ttt | gcc | gtt | ggg | gaa | ttt | tgg | agc | tat | gac | gtc | 816 |
| Thr | Gly | Lys | Asn | Leu | Phe | Ala | Val | Gly | Glu | Phe | Trp | Ser | Tyr | Asp | Val | |
| | | | 260 | | | | | 265 | | | | | 270 | | | |
| aat | aag | ctg | cat | aat | tac | att | aca | aaa | aca | aat | gga | tcg | atg | tca | tta | 864 |
| Asn | Lys | Leu | His | Asn | Tyr | Ile | Thr | Lys | Thr | Asn | Gly | Ser | Met | Ser | Leu | |
| | | 275 | | | | | 280 | | | | | 285 | | | | |
| ttt | gat | gca | cct | ttg | cat | aac | aac | ttt | tat | acc | gct | tcc | aaa | tcg | agt | 912 |
| Phe | Asp | Ala | Pro | Leu | His | Asn | Asn | Phe | Tyr | Thr | Ala | Ser | Lys | Ser | Ser | |

```
                290                 295                 300
gga tat ttt gac atg cgt tat tta ttg aat aat aca tta atg aaa gat      960
Gly Tyr Phe Asp Met Arg Tyr Leu Leu Asn Asn Thr Leu Met Lys Asp
305                 310                 315                 320 caa cct tca ctc gct gtg aca ctt gtc gat aac cac gac acg caa cca     1008
Gln Pro Ser Leu Ala Val Thr Leu Val Asp Asn His Asp Thr Gln Pro
                325                 330                 335 ggg caa tct tta cag tca tgg gtc gaa cct tgg ttt aaa cca ctt gct     1056
Gly Gln Ser Leu Gln Ser Trp Val Glu Pro Trp Phe Lys Pro Leu Ala
            340                 345                 350 tac gcc ttt att tta acg aga caa gag gga tat cct tgc gta ttt tac     1104
Tyr Ala Phe Ile Leu Thr Arg Gln Glu Gly Tyr Pro Cys Val Phe Tyr
        355                 360                 365 ggt gac tat tat gga atc ccg aaa tac aat att cca gga tta aaa agc     1152
Gly Asp Tyr Tyr Gly Ile Pro Lys Tyr Asn Ile Pro Gly Leu Lys Ser
    370                 375                 380 aaa atc gac ccg ctt tta att gct cgt cgg gac tat gcc tat gga aca     1200
Lys Ile Asp Pro Leu Leu Ile Ala Arg Arg Asp Tyr Ala Tyr Gly Thr
385                 390                 395                 400 caa cgt gat tac att gac cat caa gac att att gga tgg aca cgc gaa     1248
Gln Arg Asp Tyr Ile Asp His Gln Asp Ile Ile Gly Trp Thr Arg Glu
                405                 410                 415 ggc att gat aca aaa cca aac tct gga ctg gcg gct tta att acc gac     1296
Gly Ile Asp Thr Lys Pro Asn Ser Gly Leu Ala Ala Leu Ile Thr Asp
            420                 425                 430 ggc cct ggc gga agc aaa tgg atg tat gtc ggt aaa aaa cat gct gga     1344
Gly Pro Gly Gly Ser Lys Trp Met Tyr Val Gly Lys Lys His Ala Gly
        435                 440                 445 aaa gta ttt tat gat tta acc gga aac cga agt gac aca gta acg att     1392
Lys Val Phe Tyr Asp Leu Thr Gly Asn Arg Ser Asp Thr Val Thr Ile
    450                 455                 460 aat gcg gat ggt tgg gga gaa ttt aaa gta aac gga ggc tcc gtt tcg     1440
Asn Ala Asp Gly Trp Gly Glu Phe Lys Val Asn Gly Gly Ser Val Ser
465                 470                 475                 480 att tgg gtg gct aaa                                                 1455
Ile Trp Val Ala Lys
                485

<210> SEQ ID NO 26
<211> LENGTH: 485
<212> TYPE: PRT
<213> ORGANISM: Bacillus sp.

<400> SEQUENCE: 26

Ala Asn Thr Ala Pro Ile Asn Glu Thr Met Gln Tyr Phe Glu Trp
1               5                   10                  15

Asp Leu Pro Asn Asp Gly Thr Leu Trp Thr Lys Val Lys Asn Glu Ala
                20                  25                  30

Ala Asn Leu Ser Ser Leu Gly Ile Thr Ala Leu Trp Leu Pro Pro Ala
            35                  40                  45

Tyr Lys Gly Thr Ser Gln Ser Asp Val Gly Tyr Gly Val Tyr Asp Leu
        50                  55                  60

Tyr Asp Leu Gly Glu Phe Asn Gln Lys Gly Thr Ile Arg Thr Lys Tyr
65                  70                  75                  80

Gly Thr Lys Thr Gln Tyr Ile Gln Ala Ile Gln Ala Ala Lys Ala Ala
                85                  90                  95

Gly Met Gln Val Tyr Ala Asp Val Val Phe Asn His Lys Ala Gly Ala
            100                 105                 110
```

```
Asp Gly Thr Glu Phe Val Asp Ala Val Glu Val Asp Pro Ser Asn Arg
            115                 120                 125
Asn Gln Glu Thr Ser Gly Thr Tyr Gln Ile Gln Ala Trp Thr Lys Phe
        130                 135                 140
Asp Phe Pro Gly Arg Gly Asn Thr Tyr Ser Ser Phe Lys Trp Arg Trp
145                 150                 155                 160
Tyr His Phe Asp Gly Thr Asp Trp Asp Glu Ser Arg Lys Leu Asn Arg
                165                 170                 175
Ile Tyr Lys Phe Arg Ser Thr Gly Lys Ala Trp Asp Trp Glu Val Asp
            180                 185                 190
Thr Glu Asn Gly Asn Tyr Asp Tyr Leu Met Phe Ala Asp Leu Asp Met
        195                 200                 205
Asp His Pro Glu Val Val Thr Glu Leu Lys Asn Trp Gly Thr Trp Tyr
    210                 215                 220
Val Asn Thr Thr Asn Ile Asp Gly Phe Arg Leu Asp Ala Val Lys His
225                 230                 235                 240
Ile Lys Tyr Ser Phe Phe Pro Asp Trp Leu Thr Tyr Val Arg Asn Gln
            245                 250                 255
Thr Gly Lys Asn Leu Phe Ala Val Gly Glu Phe Trp Ser Tyr Asp Val
        260                 265                 270
Asn Lys Leu His Asn Tyr Ile Thr Lys Thr Asn Gly Ser Met Ser Leu
    275                 280                 285
Phe Asp Ala Pro Leu His Asn Asn Phe Tyr Thr Ala Ser Lys Ser Ser
290                 295                 300
Gly Tyr Phe Asp Met Arg Tyr Leu Leu Asn Asn Thr Leu Met Lys Asp
305                 310                 315                 320
Gln Pro Ser Leu Ala Val Thr Leu Val Asp Asn His Asp Thr Gln Pro
            325                 330                 335
Gly Gln Ser Leu Gln Ser Trp Val Glu Pro Trp Phe Lys Pro Leu Ala
        340                 345                 350
Tyr Ala Phe Ile Leu Thr Arg Gln Glu Gly Tyr Pro Cys Val Phe Tyr
            355                 360                 365
Gly Asp Tyr Tyr Gly Ile Pro Lys Tyr Asn Ile Pro Gly Leu Lys Ser
370                 375                 380
Lys Ile Asp Pro Leu Leu Ile Ala Arg Arg Asp Tyr Ala Tyr Gly Thr
385                 390                 395                 400
Gln Arg Asp Tyr Ile Asp His Gln Asp Ile Ile Gly Trp Thr Arg Glu
                405                 410                 415
Gly Ile Asp Thr Lys Pro Asn Ser Gly Leu Ala Ala Leu Ile Thr Asp
            420                 425                 430
Gly Pro Gly Gly Ser Lys Trp Met Tyr Val Gly Lys Lys His Ala Gly
        435                 440                 445
Lys Val Phe Tyr Asp Leu Thr Gly Asn Arg Ser Asp Thr Val Thr Ile
    450                 455                 460
Asn Ala Asp Gly Trp Gly Glu Phe Lys Val Asn Gly Gly Ser Val Ser
465                 470                 475                 480
Ile Trp Val Ala Lys
            485
```